United States Patent
Wu et al.

(10) Patent No.: US 12,129,262 B2
(45) Date of Patent: Oct. 29, 2024

(54) CDK INHIBITORS AND THEIR USE AS PHARMACEUTICALS

(71) Applicant: Prelude Therapeutics, Incorporated, Wilmington, DE (US)

(72) Inventors: Xiaowei Wu, Wilmington, DE (US); Andrew W. Buesking, Wilmington, DE (US); Andrew Paul Combs, Kenneth Square, PA (US); Ryan Holmes, Wilmington, DE (US); Sarah Pawley, Landenberg, PA (US); Katarina Rohlfing, Conshohocken, PA (US)

(73) Assignee: Prelude Therapeutics Incorporated, Wilmington, DE (US)

( * ) Notice: Subject to any disclaimer, the term of this patent is extended or adjusted under 35 U.S.C. 154(b) by 0 days.

(21) Appl. No.: 17/554,284

(22) Filed: Dec. 17, 2021

(65) Prior Publication Data
US 2022/0267345 A1  Aug. 25, 2022

Related U.S. Application Data

(60) Provisional application No. 63/127,853, filed on Dec. 18, 2020.

(51) Int. Cl.
C07D 495/04 (2006.01)

(52) U.S. Cl.
CPC .................. C07D 495/04 (2013.01)

(58) Field of Classification Search
CPC .................................... C07D 495/04
See application file for complete search history.

(56) References Cited

U.S. PATENT DOCUMENTS

| | | |
|---|---|---|
| 3,657,744 A | 4/1972 | Ersek |
| 4,739,762 A | 4/1988 | Palmaz |
| 4,992,445 A | 2/1991 | Lawter |
| 5,001,139 A | 3/1991 | Lawter |
| 5,023,252 A | 6/1991 | Hseih |
| 5,040,548 A | 8/1991 | Yock |
| 5,061,273 A | 10/1991 | Yock |
| 5,195,984 A | 3/1993 | Schatz |
| 5,292,331 A | 3/1994 | Boneau |
| 5,451,233 A | 9/1995 | Yock |
| 5,496,346 A | 5/1996 | Horzewski |
| 5,674,278 A | 10/1997 | Boneau |
| 5,879,382 A | 3/1999 | Boneau |
| 6,344,053 B1 | 2/2002 | Boneau |
| 2019/0048014 A1 | 2/2019 | Lin et al. |
| 2019/0284193 A1 | 5/2019 | Luengo et al. |
| 2020/0148692 A1 | 1/2020 | Lin et al. |
| 2020/0165239 A1 | 5/2020 | Lei et al. |

FOREIGN PATENT DOCUMENTS

| | | |
|---|---|---|
| WO | 2009040399 A1 | 4/2009 |
| WO | 202007260 A1 | 10/2020 |
| WO | WO-2022038563 A1 * | 2/2022 |

OTHER PUBLICATIONS

Lindvall "3D Pharmacophore Model-Assisted Discovery of Novel CDC7 Inhibitors" ACS Med. Chem. Lett. 2011, 2, 720-723.*
&Nbsp;Bronner "Design of a brain-penetrant CDK4/6 inhibitor for glioblastoma" Bioorganic & Medicinal Chemistry Letters vol. 29, Issue 16, Aug. 15, 2019, pp. 2294-2301.*
Dick "Structural Basis for the Activation and Target Site Specificity of CDC7 Kinase" Structure 28, 954-962, Aug. 4, 2020.*

* cited by examiner

*Primary Examiner* — David K O'Dell
(74) *Attorney, Agent, or Firm* — BakerHostetler

(57) ABSTRACT

The disclosure is directed to compounds of Formula I

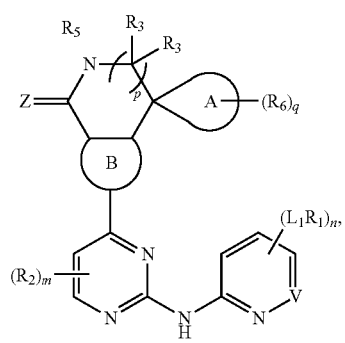

pharmaceutical compositions comprising compounds of Formula I, as well as methods of their use and preparation, are also described.

29 Claims, No Drawings

CDK INHIBITORS AND THEIR USE AS PHARMACEUTICALS

TECHNICAL FIELD

The disclosure is directed to CDK inhibitors and methods of their use.

BACKGROUND

Cyclin-dependent kinases (CDKs) are a family of conserved serine/threonine kinases that play critical roles in cell cycle and gene transcription regulation (Malumbres 2014). Among the cell cycle CDK subfamily, CDK4 and CDK6 are the master regulators that control entry of cells from the first gap phase (G1) to the DNA synthesis phase (S). During this process, cyclin D protein levels increase, complex with CDK4/6 and activate their kinase activities. Activated CDK4/6 complexes phosphorylate retinoblastoma protein (RB1) and other RB1-like proteins, reduce their binding affinities and release RB1-containing transcription repressor complexes from E2F transcription factors, resulting in activation of E2F controlled cell cycle genes and progression of cell cycle (Lapenna and Giordano 2009, Asghar, Witkiewicz et al. 2015).

Given the central roles CDK4/6 play in cell cycle regulation, dysfunction of which is a hallmark of cancer (Hanahan and Weinberg 2011), dysregulation of CDK4/6 pathway has been frequently observed in cancer, such as (epi)genetic inactivation of endogenous CDK4/6 inhibitor p16INK4A and amplification/overexpression of CDK4/6 as well as cyclin D proteins (Lapenna and Giordano 2009, Malumbres and Barbacid 2009, Asghar, Witkiewicz et al. 2015, O'Leary, Finn et al. 2016). CDK4/6 have been intensively investigated as potential therapeutic targets for cancer treatment and the recent approval of CDK4/6 selective inhibitors, namely, palbociclib (U.S. Food & Drug Administration. 2017), ribociclib (U.S. Food & Drug Administration. 2017), and abemaciclib (U.S. Food & Drug Administration. 2018), in combination with endocrine therapies, to treat hormone receptor (HR) positive and human epidermal growth factor receptor 2 (HER2) negative metastatic breast cancer further validated this thesis.

Central nervous system (CNS) diseases such as glioblastoma (GBM) and brain metastases are challenging malignancies with urgent unmet needs. GBM is the most common and aggressive primary brain cancer in adults with overall 5-year survival rate less than 6% (Ostrom, Gittleman et al. 2016). Large scale genomic studies revealed that the cyclin D-CDK4/6-RB1 pathway is alternated in majority of gliomas and represents one of the most perturbed pathways (Cancer Genome Atlas Research 2008, Brennan, Verhaak et al. 2013), suggesting CDK4/6 may be good targets for GBM. Brain metastases, on the other hand, may arise from an estimated of 20% of all cancer patients but still lacks effective treatments (Achrol, Rennert et al. 2019). Interestingly, genomic studies also identified CDK pathway as one of three most altered and actionable genetic alternations in brain metastases (Brastianos, Carter et al. 2015, Valiente, Ahluwalia et al. 2018). However, despite positive preclinical data supporting targeting CDK4/6 to treat GBM (Yin, Li et al. 2018, Bronner, Merrick et al. 2019), and initial signs of brain penetration of Abemaciclib in patients (Patnaik, Rosen et al. 2016, Sahebjam, Rhun et al. 2016), clinical development of CDK4/6 inhibitors in the clinic for GBM or brain metastases are still in early stage or unsuccessful (Anders, Rhun et al. 2019, Nguyen, Searle et al. 2019, Sahebjam, Le Rhun et al. 2019), likely due to their inability to penetrate the blood-brain barrier (BBB) (de Gooijer, Zhang et al. 2015, Parrish, Pokorny et al. 2015, Raub, Wishart et al. 2015).

Additional small molecule CDK4/6 inhibitors are needed.

SUMMARY OF THE INVENTION

The disclosure is directed to compounds of Formula I:

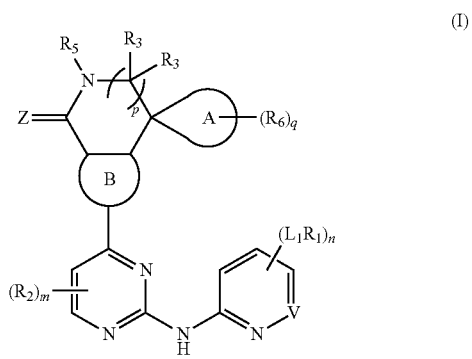

(I)

or a pharmaceutically acceptable salt thereof, wherein
ring A is a 3-8-membered cycloalkyl or heterocycloalkyl ring;
ring B is a 6-membered aryl or 5-6-membered heteroaryl, wherein ring B is optionally substituted with 1, 2 or 3 $R_4$ substituents;
Z is O, S, $NR^b$, $NOR^b$ or N—CN,
V is $CL_1R_1$ or N
n is 1 or 2 or 3;
m is 1 or 2;
p is 0, 1, or 2;
q is 0, 1, 2, 3, 4, 5, 6;
each $L_1$ is independently a bond, O, —C(O), S, NR, $C_2$-$C_6$ alkylyne or $C_1$-$C_6$ alkylene, wherein R is H or $C_1$-$C_6$alkyl;
each $R_1$ is independently H, D, halogen, —OH, —CN, —$NO_2$, —$C_1$-$C_6$alkyl, $C_{1-6}$alkoxide, —$C_2$-$C_6$alkenyl, —$C_2$-$C_6$alkynyl, aryl, heteroaryl, cycloalkyl, cycloalkenyl, heterocycloalkyl, or heterocycloalkenyl, —$OR^a$, —$SR^a$, —$NR^cR^d$, —$NR^aR^c$, —$C(O)R^b$, —$OC(O)R^b$, —$C(O)OR^b$, —$C(O)NR^cR^d$, —$S(O)R^b$, —$S(O)_2NR^cR^d$, —$S(O)(=NR^b)R^b$, —$SF_5$, —$P(O)R^bR^b$, —$P(O)(OR^b)(OR^b)$, —$B(OR^c)(OR^d)$ or —$S(O)_2R^b$;
each $R_2$ is independently H, D, halogen, $C_1$-$C_8$ alkoxide, $C_1$-$C_8$ alkyl, haloalkyl, or CN;
each $R_3$ is independently H, D, halogen, —OH, —CN, —$NO_2$, —$C_1$-$C_6$alkyl, —$C_2$-$C_6$alkenyl, —$C_2$-$C_6$alkynyl, $C_0$-$C_1$alk-aryl, $C_0$-$C_1$alk-heteroaryl, cycloalkyl, cycloalkenyl, heterocycloalkyl, heterocycloalkenyl, —$OR^a$, —$SR^b$, —$NR^cR^d$, —$NR^aR^c$, —$C(O)R^b$, —$OC(O)R^b$, —$C(O)OR^b$, —$C(O)NR^cR^d$, or —$B(OR^d)(OR^c)$;
each $R_4$ is independently H, D, halogen, $C_1$-$C_8$ alkoxide, $C_1$-$C_8$ alkyl, haloalkyl or CN;
each $R^a$ is independently H, D, —$C(O)R^b$, —$C(O)OR^c$, —$C(O)NR^cR^d$, —$C(=NR^b)NR^bR^c$, $C(NOR^b)NR^bR^c$, —$C(=NCN)NR^bR^c$, —$P(OR^c)_2$, —$P(O)OR^cOR^b$, —$S(O)_2R^b$, —$S(O)_2NR^cR^d$, $SiR^b_3$, —$C_1$-$C_{10}$alkyl, —$C_2$-$C_{10}$ alkenyl, —$C_2$-$C_{10}$ alkynyl, $C_0$-$C_1$alk-aryl, cycloalkyl, cycloalkenyl, $C_0$-$C_1$alk-heteroaryl, heterocycloalkyl, or heterocycloalkenyl;

each $R^b$, is independently H, D, —$C_1$-$C_6$ alkyl, —$C_2$-$C_6$ alkenyl, —$C_2$-$C_6$ alkynyl, $C_0$-$C_1$alk-aryl, cycloalkyl, cycloalkenyl, $C_0$-$C_1$alk-heteroaryl, heterocycloalkyl, or heterocycloalkenyl;

each $R^c$ or $R^d$ is independently H, D, —$C_1$-$C_{10}$ alkyl, —$C_2$-$C_6$ alkenyl, —$C_2$-$C_6$ alkynyl, —$OC_1$-$C_6$alkyl, —O-cycloalkyl, aryl, $C_1$alk-aryl, heteroaryl, cycloalkyl, cycloalkenyl, $C_1$alk-heteroaryl, heterocycloalkyl, or heterocycloalkenyl;

or $R^c$ and $R^d$, together with the atom to which they are both attached, form a monocyclic or multicyclic heterocycloalkyl, or a monocyclic or multicyclic heterocyclo-alkenyl group;

$R_5$ is H, D, $OR^b$, $C_{1-4}$alkyl, wherein the $C_{1-4}$alkyl may be substituted with at least one of halogen, —OH, —CN or an amine, or cycloalkyl; and $R_6$ is independently H, D, halogen, —OH, —CN, —$NO_2$, —$C_1$-$C_6$alkyl, —$C_2$-$C_6$alkenyl, —$C_2$-$C_6$alkynyl, aryl, heteroaryl, cycloalkyl, cycloalkenyl, heterocycloalkyl, or heterocycloalkenyl, —$OR^a$, —$SR^a$, —$NR^cR^d$, —$NR^aR^c$, —$C(O)R^b$, —$OC(O)R^b$, —$C(O)OR^b$, —$C(O)NR^cR^d$, —$S(O)R^b$, —$S(O)_2NR^cR^d$, —$S(O)(=NR)R^b$, —$SF_5$, —$P(O)R^bR^b$, —$P(O)(OR^b)(OR^b)$, —$B(OR^c)(OR^d)$ or —$S(O)_2R^b$.

Stereoisomers of the compounds of Formula I, and the pharmaceutical salts and solvates thereof, are also contemplated, described, and encompassed herein. Methods of using compounds of Formula I are described, as well as pharmaceutical compositions including the compounds of Formula I.

DETAILED DESCRIPTION OF ILLUSTRATIVE EMBODIMENTS

The disclosure may be more fully appreciated by reference to the following description, including the following definitions and examples. Certain features of the disclosed compositions and methods which are described herein in the context of separate aspects, may also be provided in combination in a single aspect. Alternatively, various features of the disclosed compositions and methods that are, for brevity, described in the context of a single aspect, may also be provided separately or in any subcombination.

At various places in the present specification, substituents of compounds of the invention are disclosed in groups or in ranges. It is specifically intended that the invention include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl. "$C_0$ alkyl" refers to a covalent bond.

It is further intended that the compounds of the invention are stable. As used herein "stable" refers to a compound that is sufficiently robust to survive isolation to a useful degree of purity from a reaction mixture, and preferably capable of formulation into an efficacious therapeutic agent.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable sub-combination.

The term "alkyl," when used alone or as part of a substituent group, refers to a straight- or branched-chain hydrocarbon group having from 1 to 12 carbon atoms ("$C_1$-$C_{12}$"), preferably 1 to 6 carbons atoms ("$C_1$-$C_6$"), in the group. Examples of alkyl groups include methyl (Me, $C_1$alkyl), ethyl (Et, $C_2$alkyl), n-propyl ($C_3$alkyl), isopropyl ($C_3$alkyl), butyl ($C_4$alkyl), isobutyl ($C_4$alkyl), sec-butyl ($C_4$alkyl), tert-butyl ($C_4$alkyl), pentyl ($C_5$alkyl), isopentyl ($C_5$alkyl), tert-pentyl ($C_5$alkyl), hexyl ($C_6$alkyl), isohexyl ($C_6$alkyl), and the like. Alkyl groups of the disclosure can be unsubstituted or substituted. In those embodiments wherein the alkyl group is substituted, the alkyl group can be substituted with 1, 2, or 3 substituents independently selected from —OH, —CN, amino, halo, $C_1$-$C_6$alkyl, $C_1$-$C_6$alkoxy, $C_1$-$C_6$haloalkyl, and $C_1$-$C_6$haloalkoxy. Additional substitutents include —$C(O)NH(C_1$-$C_6$alkyl), —$C(O)N(C_1$-$C_6$alkyl$)_2$, —$OC(O)NH(C_1$-$C_6$alkyl), —$OC(O)N(C_1$-$C_6$alkyl$)_2$, —$S(O)_2NH(C_1$-$C_6$alkyl), and —$S(O)_2N(C_1$-$C_6$alkyl$)_2$.

The term "alkoxide" refers to the conjugate base of an alcohol and includes an organic group bonded to a negatively charged oxygen atom.

The term "halo" or halogen, refers to chloro, fluoro, bromo, or iodo.

The term "haloalkyl" refers to any alkyl radical having one or more hydrogen atoms replaced by a halogen atom.

The term "cycloalkyl" when used alone or as part of a substituent group refers to cyclic-containing, non-aromatic hydrocarbon groups having from 3 to 10 carbon atoms ("$C_3$-$C_{10}$"), preferably from 3 to 6 carbon atoms ("$C_3$-$C_6$"). Cycloalkyl groups of the disclosure include monocyclic groups, as well as multicyclic groups such as bicyclic and tricyclic groups. In those embodiments having at least one multicyclic cycloalkyl group, the cyclic groups can share one common atom (i.e., spirocyclic). In other embodiments having at least one multicyclic cycloalkyl group, the cyclic groups share two common atoms. Examples of cycloalkyl groups include, for example, cyclopropyl ($C_3$), cyclobutyl ($C_4$), cyclopropylmethyl ($C_4$), cyclopentyl ($C_5$), cyclohexyl ($C_6$), 1-methylcyclopropyl ($C_4$), 2-methylcyclopentyl ($C_4$), adamantanyl ($C_{10}$), spiro[3.3]heptanyl, bicyclo[3.3.0]octanyl, and the like. Cycloalkyl groups of the disclosure can be unsubstituted or substituted. In those embodiments wherein the cycloalkyl group is substituted, the cycloalkyl group can be substituted with 1, 2, or 3 substituents independently selected from —OH, —CN, amino, halo, $C_1$-$C_6$alkyl, $C_1$-$C_6$alkoxy, $C_1$-$C_6$haloalkyl, and $C_1$-$C_6$haloalkoxy. Additional substitutents include —$C(O)NH(C_1$-$C_6$alkyl), —$C(O)N(C_1$-$C_6$alkyl$)_2$, —$OC(O)NH(C_1$-$C_6$alkyl), —$OC(O)N(C_1$-$C_6$alkyl$)_2$, —$S(O)_2NH(C_1$-$C_6$alkyl), and —$S(O)_2N(C_1$-$C_6$alkyl$)_2$.

The term "cycloalkenyl" refer to cyclic, non-aromatic hydrocarbon groups having from 3 to 10 carbon atoms ("$C_3$-$C_{10}$"), preferably from 3 to 6 carbon atoms ("$C_3$-$C_6$") and containing at least one carbon-carbon double bond. For example, cycloalkenyl groups include, but are not limited to cyclopropenyl, cyclobutenyl, and the like.

The term "heterocycloalkyl" when used alone or as part of a substituent group refers to any three to ten membered monocyclic or bicyclic, saturated ring structure containing at least one heteroatom selected from the group consisting of O, N and S. Heterocycloalkyl groups of the disclosure include monocyclic groups, as well as multicyclic groups such as bicyclic and tricyclic groups. In those embodiments having at least one multicyclic heterocycloalkyl group, the cyclic groups can share one common atom (i.e., spirocyclic). In other embodiments having at least one multicyclic heterocycloalkyl group, the cyclic groups share two common atoms. The term —$C_3$-$C_6$ heterocycloalkyl refers to a heterocycloalkyl group having between three and six carbon ring atoms. The term —$C_3$-$C_{10}$ heterocycloalkyl refers to a heterocycloalkyl group having between three and 10 ring atoms. The heterocycloalkyl group may be attached at any heteroatom or carbon atom of the ring such that the result is a stable structure. Examples of suitable heterocycloalkyl groups include, but are not limited to, azepanyl, aziridinyl, azetidinyl, pyrrolidinyl, dioxolanyl, imidazolidinyl, pyrazolidinyl, piperazinyl, piperidinyl, dioxanyl, morpholinyl, dithianyl, thiomorpholinyl, oxazepanyl, oxiranyl, oxetanyl, quinuclidinyl, tetrahydrofuranyl, tetrahydropyranyl, piperazinyl, azepanyl, diazepanyl, oxepanyl, dioxepanyl, azocanyl diazocanyl, oxocanyl, dioxocanyl, azaspiro[2.2]pentanyl, oxaazaspiro[3.3]heptanyl, oxaspiro[3.3]heptanyl, dioxaspiro[3.3]heptanyl, and the like. Heteroycloalkyl groups of the disclosure can be unsubstituted or substituted. In those embodiments wherein the heterocycloalkyl group is substituted, the heterocycloalkyl group can be substituted with 1, 2, or 3 substituents independently selected from —OH, —CN, amino, halo, $C_1$-$C_6$alkyl, $C_1$-$C_6$alkoxy, $C_1$-$C_6$haloalkyl, and $C_1$-$C_6$haloalkoxy. Additional substitutents include —C(O)NH($C_1$-$C_6$alkyl), —C(O)N($C_1$-$C_6$alkyl)$_2$, —OC(O)NH($C_1$-$C_6$alkyl), —OC(O)N($C_1$-$C_6$alkyl)$_2$, —S(O)$_2$NH($C_1$-$C_6$alkyl), and —S(O)$_2$N($C_1$-$C_6$alkyl)$_2$.

The term "heterocycloalkenyl" when used alone or as part of a substituent group refers to any three to ten membered monocyclic or bicyclic, partially saturated ring structure containing at least one heteroatom selected from the group consisting of O, N and S. Heterocycloalkenyl groups of the disclosure include monocyclic groups, as well as multicyclic groups such as bicyclic and tricyclic groups. In those embodiments having at least one multicyclic heterocycloalkyenyl group, the cyclic groups can share one common atom (i.e., spirocyclic). In other embodiments having at least one multicyclic heterocycloalkenyl group, the cyclic groups share two common atoms. The term —$C_3$-$C_6$ heterocycloalkenyl refers to a heterocycloalkenyl group having between three and six carbon atoms. The term —$C_3$-$C_{10}$ heterocycloalkenyl refers to a heterocycloalkenyl group having between three and ten ring atoms. The heterocycloalkenyl group may be attached at any heteroatom or carbon atom of the ring such that the result is a stable structure. Heteroycloalkenyl groups of the disclosure can be unsubstituted or substituted. In those embodiments wherein the heterocycloalkenyl group is substituted, the heterocycloalkenyl group can be substituted with 1, 2, or 3 substituents independently selected from —OH, —CN, amino, halo, $C_1$-$C_6$alkyl, $C_1$-$C_6$alkoxy, $C_1$-$C_6$haloalkyl, and $C_1$-$C_6$haloalkoxy. Additional substituents include —C(O)NH($C_1$-$C_6$alkyl), —C(O)N($C_1$-$C_6$alkyl)$_2$, —OC(O)NH($C_1$-$C_6$alkyl), —OC(O)N($C_1$-$C_6$alkyl)$_2$, —S(O)$_2$NH($C_1$-$C_6$alkyl), and —S(O)$_2$N($C_1$-$C_6$alkyl)$_2$.

The term "heteroaryl" when used alone or as part of a substituent group refers to a mono- or bicyclic-aromatic ring structure including carbon atoms as well as up to five heteroatoms selected from nitrogen, oxygen, and sulfur. Heteroaryl rings can include a total of 5, 6, 7, 8, 9, or 10 ring atoms. The term —$C_5$-$C_{10}$ heteroaryl refers to a heteroaryl group containing five to ten ring atoms. Examples of heteroaryl groups include but are not limited to, pyrrolyl, furyl, thiophenyl (thienyl), oxazolyl, imidazolyl, pyrazolyl, isoxazolyl, isothiazolyl, triazolyl, thiadiazolyl, pyrazolyl, pyridinyl, pyridazinyl, pyrimidinyl, pyrazinyl, pyranyl, furazanyl, indolizinyl, indolyl, and the like. Heteroaryl groups of the disclosure can be unsubstituted or substituted. In those embodiments wherein the heteroaryl group is substituted, the heteroaryl group can be substituted with 1, 2, or 3 substituents independently selected from —OH, —CN, amino, halo, $C_1$-$C_6$alkyl, $C_1$-$C_6$alkoxy, $C_1$-$C_6$haloalkyl, and $C_1$-$C_6$haloalkoxy. Additional substituents include —C(O)NH($C_1$-$C_6$alkyl), —C(O)N($C_1$-$C_6$alkyl)$_2$, —OC(O)NH($C_1$-$C_6$alkyl), —OC(O)N($C_1$-$C_6$alkyl)$_2$, —S(O)$_2$NH($C_1$-$C_6$alkyl), and —S(O)$_2$N($C_1$-$C_6$alkyl)$_2$.

The term "aryl" when used alone or as part of a substituent group refers to a mono- or bicyclic-aromatic carbon ring structure. Aryl rings can include a total of 6, 7, 8, 9, or 10 ring atoms. Examples of aryl groups include but are not limited to, phenyl, napthyl, and the like. Aryl groups of the disclosure can be unsubstituted or substituted. In those embodiments wherein the aryl group is substituted, the aryl group can be substituted with 1, 2, or 3 substituents independently selected from —OH, —CN, amino, halo, $C_1$-$C_6$alkyl, $C_1$-$C_6$alkoxy, $C_1$-$C_6$haloalkyl, and $C_1$-$C_6$haloalkoxy. Additional substituents include —C(O)NH($C_1$-$C_6$alkyl), —C(O)N($C_1$-$C_6$alkyl)$_2$, —OC(O)NH($C_1$-$C_6$alkyl), —OC(O)N($C_1$-$C_6$alkyl)$_2$, —S(O)$_2$NH($C_1$-$C_6$alkyl), and —S(O)$_2$N($C_1$-$C_6$alkyl)$_2$.

The term "alkenyl" refers to $C_2$-$C_{12}$ alkyl group that contains at least one carbon-carbon double bond. In some embodiments, the alkenyl group is optionally substituted. In some embodiments, the alkenyl group is a $C_2$-$C_6$ alkenyl.

The term "alkynyl" refers to $C_2$-$C_{12}$ alkyl group that contains at least one carbon-carbon triple bond. In some embodiments, the alkenyl group is optionally substituted. In some embodiments, the alkynyl group is a $C_2$-$C_6$ alkynyl.

The term "alkylyne" refers to a straight or branched $C_2$-$C_{12}$ chain divalent hydrocarbon radical having one or more carbon-carbon triple bonds. In some embodiments, the alkylyne group is a $C_2$-$C_6$ alkylyne group.

The term "alkylene" refers to a bivalent saturated $C_2$-$C_{12}$ aliphatic radical regarded as derived from an alkene by opening of the double bond or from an alkane by removal of two hydrogen atoms from different carbon atoms. In some embodiments, the alkylene group is a $C_2$-$C_6$ alkylene group.

When a range of carbon atoms is used herein, for example, $C_1$-$C_6$, all ranges, as well as individual numbers of carbon atoms are encompassed, for example, "$C_{1-3}$" includes $C_{1-3}$, $C_{1-2}$, $C_{2-3}$, $C_1$, $C_2$, and $C_3$. The term "$C_{1-6}$alk" refers to an aliphatic linker having 1, 2, 3, 4, 5, or 6 carbon atoms and includes, for example, —CH$_2$—, —CH(CH$_3$)—, —CH(CH$_3$)—CH$_2$—, and —C(CH$_3$)$_2$—. The term "—$C_0$alk-" refers to a bond.

The term "$C_0$-$C_6$alk" when used alone or as part of a substituent group refers to an aliphatic linker having 0, 1, 2, 3, 4, 5 or 6 carbon atoms. The term "—$C_1$alk-", for example, refers to a —CH$_2$—. The term "—$C_0$alk-" refers to a bond.

As used herein, each —$C_1$-$C_6$alkyl, —$C_1$-$C_{10}$ alkyl, —$C_2$-$C_6$alkenyl, —$C_2$-$C_{10}$alkenyl, —$C_2$-$C_6$alkynyl, —$C_2$-$C_{10}$alkynyl, aryl, heteroaryl, cycloalkyl, cycloalkenyl, heterocycloalkenyl, and heterocycloalkyl can be optionally substituted with 1, 2, or 3 substituents independently selected from —OH, —CN, amino, halo, $C_1$-$C_6$alkyl, $C_1$-$C_6$alkoxy, $C_1$-$C_6$haloalkyl, and $C_1$-$C_6$haloalkoxy. Additional substituents include —C(O)NH($C_1$-$C_6$alkyl), —C(O)N($C_1$-$C_6$alkyl)$_2$, —OC(O)NH($C_1$-$C_6$alkyl), —OC(O)N($C_1$-$C_6$alkyl)$_2$, —S(O)$_2$NH($C_1$-$C_6$alkyl), and —S(O)$_2$N($C_1$-$C_6$alkyl)$_2$.

As used herein, "alkoxy" refers to an —O-alkyl group. Example alkoxy groups include methoxy, ethoxy, propoxy (e.g., n-propoxy and isopropoxy), t-butoxy, and the like.

As used herein, "hydroxylalkyl" refers to an alkyl group substituted by OH.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Geometric isomers of olefins, C=N double bonds, and the like can also be present in the compounds described herein, and all such stable isomers are contemplated in the present invention. Geometric isomers of the compounds of the present invention are described and may be isolated as a mixture of isomers or as separated isomeric forms.

Compounds of the invention may also include tautomeric forms. All tautomeric forms are encompassed.

In some embodiments, the compounds of the present invention may exist as rotational isomers. In some embodiments, the compounds of the present invention exist as mixtures of rotational isomers in any proportion. In other embodiments, the compounds of the present invention exist as particular rotational isomers, substantially free of other rotational isomers.

Compounds of the invention can also include all isotopes of atoms occurring in the intermediates or final compounds. Isotopes include those atoms having the same atomic number but different mass numbers. For example, isotopes of hydrogen include tritium and deuterium.

In some embodiments, the compounds of the invention, and salts thereof, are substantially isolated. By "substantially isolated" is meant that the compound is at least partially or substantially separated from the environment in which is was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418 and *Journal of Pharmaceutical Science*, 66, 2 (1977), each of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

A "solvate" refers to a physical association of a compound of Formula I with one or more solvent molecules.

"Subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Compounds of the present disclosure," and equivalent expressions, are meant to embrace compounds of Formula I as described herein, as well as its subgenera, which expression includes the stereoisomers (e.g., enantiomers, diastereomers) and constitutional isomers (e.g., tautomers) of compounds of Formula I as well as the pharmaceutically acceptable salts, where the context so permits.

As used herein, the term "isotopic variant" refers to a compound that contains proportions of isotopes at one or more of the atoms that constitute such compound that is greater than natural abundance. For example, an "isotopic variant" of a compound can be radiolabeled, that is, contain one or more radioactive isotopes, or can be labeled with non-radioactive isotopes such as for example, deuterium ($^{2}$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^{2}$H/D, any carbon may be $^{13}$C, or any nitrogen may be $^{15}$N, and that the presence and placement of such atoms may be determined within the skill of the art.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers," for example, diastereomers, enantiomers, and atropisomers. The compounds of this disclosure may possess one or more asymmetric centers; such compounds can therefore be produced as individual (R)- or (S)-stereoisomers at each asymmetric center, or as mixtures thereof. Unless indicated otherwise, the description or naming of a particular compound in the specification and claims is intended to include all stereoisomers and mixtures, racemic or otherwise, thereof. Where one chiral center exists in a structure, but no specific stereochemistry is shown for that center, both enantiomers, individually or as a mixture of enantiomers, are encompassed by that structure. Where more than one chiral center exists in a structure, but no specific stereochemistry is shown for the centers, all enantiomers and diastereomers, individually or as a mixture, are encompassed by that structure. The methods for the determination of stereochemistry and the separation of stereoisomers are well-known in the art.

The disclosure is directed to compounds of Formula I.

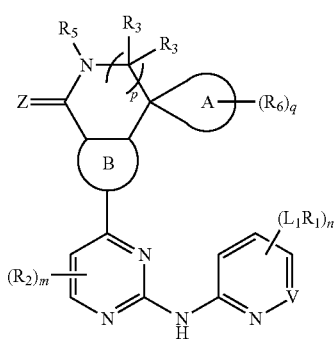

(I)

or a pharmaceutically acceptable salt or solvate or N-oxide thereof, wherein
  ring A is a 3-8-membered cycloalkyl or heterocycloalkyl ring;
  ring B is a 6-membered aryl or 5-6-membered heteroaryl, wherein ring B is optionally substituted with 1, 2 or 3 $R_4$ substituents;
  Z is O, S, $NR^b$, $NOR^b$ or N—CN,
  V is $CL_1R_1$ or N
  n is 1 or 2 or 3;
  m is 1 or 2;
  p is 0, 1, or 2;
  q is 0, 1, 2, 3, 4, 5, 6;
  each $L_1$ is independently a bond, O, —C(O), S, NR, $C_2$-$C_6$ alkylyne or $C_1$-$C_6$ alkylene, wherein R is H or $C_1$-$C_6$alkyl;
  each $R_1$ is independently H, D, halogen, —OH, —CN, —$NO_2$, —$C_1$-$C_6$alkyl, $C_{1-6}$alkoxide, —$C_2$-$C_6$alkenyl, —$C_2$-$C_6$alkynyl, aryl, heteroaryl, cycloalkyl, cycloalkenyl, heterocycloalkyl, or heterocycloalkenyl, —$OR^a$, —$SR^a$, —$NR^cR^d$, —$NR^aR^c$, —$C(O)R^b$, —$OC(O)R^b$, —$C(O)OR^b$, —$C(O)NR^cR^d$, —$S(O)R^b$, —$S(O)_2NR^cR^d$, —$S(O)(=NR^b)R^b$, —$SF_5$, —$P(O)R^bR^b$, —$P(O)(OR^b)(OR)$, —$B(OR^c)(OR^d)$ or —$S(O)_2R^b$;
  each $R_2$ is independently H, D, halogen, $C_1$-$C_8$ alkoxide, $C_1$-$C_8$ alkyl, haloalkyl, or CN;
  each $R_3$ is independently H, D, halogen, —OH, —CN, —$NO_2$, —$C_1$-$C_6$alkyl, —$C_2$-$C_6$alkenyl, —$C_2$-$C_6$alkynyl, $C_0$-$C_1$alk-aryl, $C_0$-$C_1$alk-heteroaryl, cycloalkyl, cycloalkenyl, heterocycloalkyl, heterocycloalkenyl, —$OR^a$, —$SR^b$, —$NR^cR^d$, —$NR^aR^c$, —$C(O)R^b$, —$OC(O)R^b$, —$C(O)OR^b$, —$C(O)NR^cR^d$, or —$B(OR^d)(OR^c)$;
  each $R_4$ is independently H, D, halogen, $C_1$-$C_8$ alkoxide, $C_1$-$C_8$ alkyl, haloalkyl or CN;
  each $R^a$ is independently H, D, —$C(O)R^b$, —$C(O)OR^c$, —$C(O)NR^cR^d$, —$C(=NR^b)NR^bR^c$, —$C(=NOR^b)$ $NR^bR^c$, —$C(=NCN)NR^bR^c$, —$P(OR^c)_2$, —$P(O)$ $OR^cOR^b$, —$S(O)_2R^b$, —$S(O)_2NR^cR^d$, $SiR^b_3$, —$C_1$-

$C_{10}$alkyl, —$C_2$-$C_{10}$ alkenyl, —$C_2$-$C_{10}$ alkynyl, $C_0$-$C_1$alk-aryl, cycloalkyl, cycloalkenyl, $C_0$-$C_1$alk-heteroaryl, heterocycloalkyl, or heterocycloalkenyl;
  each $R^b$, is independently H, D, —$C_1$-$C_6$ alkyl, —$C_2$-$C_6$ alkenyl, —$C_2$-$C_6$ alkynyl, $C_0$-$C_1$alk-aryl, cycloalkyl, cycloalkenyl, $C_0$-$C_1$alk-heteroaryl, heterocycloalkyl, or heterocycloalkenyl;
  each $R^c$ or $R^d$ is independently H, D, —$C_1$-$C_{10}$ alkyl, —$C_2$-$C_6$ alkenyl, —$C_2$-$C_6$ alkynyl, —$OC_1$-$C_6$alkyl, —O-cycloalkyl, aryl, $C_1$alk-aryl, heteroaryl, cycloalkyl, cycloalkenyl, $C_1$alk-heteroaryl, heterocycloalkyl, or heterocycloalkenyl;
  or $R^c$ and $R^d$, together with the atom to which they are both attached, form a monocyclic or multicyclic heterocycloalkyl, or a monocyclic or multicyclic heterocyclo-alkenyl group;
  $R_5$ is H, D, $OR^b$, $C_{1-4}$alkyl, wherein the $C_{1-4}$alkyl may be substituted with at least one of halogen, —OH, —CN or an amine, or cycloalkyl; and
  $R_6$ is independently H, D, halogen, —OH, —CN, —$NO_2$, —$C_1$-$C_6$alkyl, —$C_2$-$C_6$alkenyl, —$C_2$-$C_6$alkynyl, aryl, heteroaryl, cycloalkyl, cycloalkenyl, heterocycloalkyl, or heterocycloalkenyl, —$OR^a$, —$SR^a$, —$NR^cR^d$, —$NR^aR^c$, —$C(O)R^b$, —$OC(O)R^b$, —$C(O)OR^b$, —$C(O)NR^cR^d$, —$S(O)R^b$, —$S(O)_2NR^cR^d$, —$S(O)$ $(=NR)R^b$, —$SF_5$, —$P(O)R^bR^b$, —$P(O)(OR^b)(OR)$, —$B(OR^c)(OR^d)$ or —$S(O)_2R^b$.

In some embodiments, ring A in Formula (I) is a 3-8-membered cycloalkyl ring or heterocycloalkyl ring.

In some embodiments, ring A in Formula (I) is a 3-8-membered cycloalkyl ring. In some embodiments, ring A is a 3-membered cycloalkyl ring. In other embodiments, ring A is a 4-membered cycloalkyl ring. In yet other embodiments, ring A is a 5-membered cycloalkyl ring. In yet other embodiments, ring A is a 6-membered cycloalkyl ring. In yet other embodiments, ring A is a 7-membered cycloalkyl ring. In yet other embodiments, ring A is an 8-membered cycloalkyl ring.

In some embodiments, ring A in Formula (I) is a 3-8-membered heterocycloalkyl ring. In some embodiments, ring A in Formula (I) is a 3-8-membered heterocycloalkyl ring. In some embodiments, ring A is a 3-membered heterocycloalkyl ring. In other embodiments, ring A is a 4-membered heterocycloalkyl ring. In yet other embodiments, ring A is a 5-membered heterocycloalkyl ring. In yet other embodiments, ring A is a 6-membered heterocycloalkyl ring. In yet other embodiments, ring A is a 7-membered heterocycloalkyl ring. In yet other embodiments, ring A is an 8-membered heterocycloalkyl ring.

In some embodiments, ring A in Formula (I) is a cyclopropane, an oxirane or an aziridine. In some embodiments, ring A in Formula (I) is a cyclobutane, an oxetane or an azetidine. In some embodiments, ring A in Formula (I) is a cyclopentane, a tetrahydrofuran or a pyrrolidine.

In some embodiments, ring B is a 6-membered aryl or 5-6-membered heteroaryl, wherein ring B is optionally substituted with 1, 2 or 3 $R_4$ substituents. In some embodiments, ring B in Formula (I) is a phenyl ring. In some embodiments, ring B in Formula (I) is a 5-6-membered heteroaryl ring. In some embodiments, ring B in Formula (I) is substituted with one $R_4$ substituent. In some embodiments, ring B in Formula (I) is substituted with two $R_4$ substituents. In some embodiments, ring B in Formula (I) is substituted with three $R_4$ substituents.

In some embodiments, $R_4$ in Formula I is independently H, D, halogen, $C_1$-$C_8$ alkoxide, $C_1$-$C_8$ alkyl, haloalkyl and —CN. In some embodiments, $R_4$ in Formula I is H. In some embodiments, $R_4$ in Formula I is D. In some embodiments, $R_4$ in Formula I is halogen. In some embodiments, $R_4$ in Formula I is —$C_1$-$C_8$ alkoxide. In other embodiments, $R_4$ in Formula I is —$C_1$-$C_8$ alkyl. In other embodiments, $R_4$ in Formula I is methyl. In other embodiments, $R_4$ is haloalkyl. In other embodiments, $R_4$ in Formula I is —CN.

In some embodiments, Z in Formula (I) is O, S, $NR^b$, $NOR^b$ or N—CN. In some embodiments, Z is O. In some embodiments, Z is S. In some embodiments, Z is $NR^b$. In some embodiments, Z is $NOR^b$. In some embodiments, Z is N—CN.

In some embodiments, ring B in Formula (I) is a 5-6-membered heteroaryl ring. In some embodiments, ring B is a 5-membered heteroaryl ring. In some embodiments, ring B is a 6-membered heteroaryl ring. In other embodiments, ring B is a thiophene group.

In some embodiments, V in Formula (I) is N or $CL_1R_1$. In some embodiments, V is N. In other embodiments, V is $CL_1R_1$. In other embodiments, V is CH.

In some embodiments, n in Formula (I) is 1, 2 or 3. In some embodiments, n is 1. In other embodiments, n is 2. In yet other embodiments, n is 3. In some embodiments, m in Formula (I) is 1 or 2. In some embodiments, m is 1. In other embodiments, m is 2.

In some embodiments, p in Formula (I) is 0, 1 or 2. In some embodiments, p is 0. In other embodiments, p is 1. In some embodiments, p is 2.

In some embodiments, q in Formula (I) is 0, 1, 2, 3, 4, 5 or 6. In some embodiments, q is 0. In some embodiments, q is 1. In some embodiments, q is 2. In other embodiments, q is 3. In other embodiments, q is 4. In other embodiments, q is 5. In other embodiments, q is 6.

In some embodiments, each $L_1$ in Formula I is independently a bond, O, —C(O), S, NR, $C_2$-$C_6$ alkylyne or $C_1$-$C_6$ alkylene, wherein R is H or $C_1$-$C_6$alkyl.

In some embodiments, $L_1$ is a bond. In some embodiments, $L_1$ is O. In some embodiments, $L_1$ is —C(O). In some embodiments, $L_1$ is S. In some embodiments, $L_1$ is NR. In some embodiments, $L_1$ is $C_1$-$C_6$ alkylene. In some embodiments, $L_1$ is methylene. In some embodiments, $L_1$ is $C_2$-$C_6$ alkylyne.

In some embodiments, R is H. In some embodiments, R is $C_1$-$C_6$alkyl. In some embodiments, R is methyl.

In some embodiments, each $R_1$ in Formula I is independently H, D, halogen, —OH, —CN, —$NO_2$, —$C_1$-$C_6$alkyl, $C_{1-6}$alkoxide, —$C_2$-$C_6$alkenyl, —$C_2$-$C_6$alkynyl, aryl, heteroaryl, cycloalkyl, cycloalkenyl, heterocycloalkyl, or heterocycloalkenyl, —$OR^a$, —$SR^a$, —$NR^cR^d$, —$NR^aR^c$, —$C(O)R^b$, —$OC(O)R^b$, —$C(O)OR^b$, —$C(O)NR^cR^d$, —$S(O)R^b$, —$S(O)_2NR^cR^d$, —$S(O)(=NR^b)R^b$, —$SF_5$, —$P(O)R^bR^b$, —$P(O)(OR^b)(OR^b)$, —$B(OR^c)(OR^d)$ or —$S(O)_2R^b$. In some embodiments, $R_1$ is H. In some embodiments, $R_1$ is D. In some embodiments, $R_1$ is halogen. In some embodiments, $R_1$ is —OH. In some embodiments, $R_1$ is —CN. In some embodiments, $R_1$ is $NO_2$. In some embodiments, $R_1$ is —$C_1$-$C_6$alkyl. In some embodiments, $R_1$ is $C_{1-6}$alkoxide. In some embodiments, $R_1$ is —$C_2$-$C_6$alkenyl. In some embodiments, $R_1$ is —$C_2$-$C_6$alkynyl. In some embodiments, $R_1$ is aryl. In some embodiments, $R_1$ is heteroaryl. In some embodiments, $R_1$ is cycloalkyl. In some embodiments, $R_1$ is cycloalkenyl. In some embodiments, $R_1$ is heterocycloalkenyl. In some embodiments, $R_1$ is —$OR^a$, —$SR^a$, —$NR^cR^d$, —$NR^aR^c$, —$C(O)R^b$, —$OC(O)R^b$, —$C(O)OR^b$, —$C(O)NR^cR^d$, —$S(O)R^b$, —$S(O)_2NR^cR^d$, —$S(O)(=NR^b)R^b$, —$SF_5$, —$P(O)R^bR^b$, —$P(O)(OR^b)(OR^b)$, —$B(OR^c)(OR^d)$, —$S(O)_2R^b$ and the like.

In other embodiments, $R_1$ is heterocycloalkyl. In other embodiments, $R_1$ is a 6-membered heterocyclalkyl. In some embodiments, $R_1$ is a piperazine. In yet other embodiments, $R_1$ is a 7-membered heterocyclalkyl. In yet other embodiments, $R_1$ is a spiro-fused group. In yet other embodiments, $R_1$ is a diazaspiroheptane.

In yet other embodiments, at least one $R_1$ is a group of formula Y:

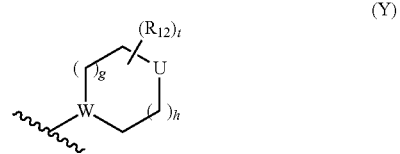

wherein

∼∼ is a point of attachment to $L_1$;
W is $CR_{11}$ or N;
U is $C(R_{11})_2$, $NR_{10}$, or O;
$R_{10}$ is H, D, or $C_{1-6}$alkyl;
$R_{11}$ is H, D, fluoro, $C_{1-6}$alkyl, or $C_{1-6}$alkoxide;
$R_{12}$ is H, D, fluoro, $C_{1-6}$alkyl, or $C_{1-6}$alkoxide;
t is 0, 1, 2, 3, 4, 5, or 6 and
each g and h is independently 0, 1, 2 or 3.

In some embodiments, W of Formula Y is $CR_{11}$. In other embodiments, W of Formula Y is N.

In some embodiments, U of Formula Y is $C(R_{11})_2$. In other embodiments, U of Formula Y is $NR_{10}$. In yet other embodiments, U of Formula Y is O.

In some embodiments, $R_{11}$ of Formula Y is H. In some embodiments, $R_{11}$ of Formula Y is D. In some embodiments, $R_{11}$ of Formula Y is fluoro. In some embodiments, $R_{11}$ of Formula Y is $C_{1-6}$alkyl. In other embodiments, $R_{11}$ of Formula Y is methyl or ethyl. In some embodiments, $R_{11}$ of Formula Y is $C_{1-6}$alkoxide.

In some embodiments, $R_{10}$ of Formula Y is H. In some embodiments, $R_{10}$ of Formula Y is D. In some embodiments, $R_{10}$ of Formula Y is $C_{1-6}$alkyl. In other embodiments, $R_{10}$ of Formula Y is methyl or ethyl.

In some embodiments, when U of Formula Y is $C(R_{11})_2$, each $R_{11}$ is H. In some embodiments, when U of Formula Y is $C(R_{11})_2$, each $R_{11}$ is methyl. In some embodiments, when U of Formula Y is $C(R_{11})_2$, one $R_{11}$ is methyl and one $R_{11}$ is hydrogen. In some embodiments, when U of Formula Y is $C(R_{11})_2$, each $R_{10}$ is halogen. In some embodiments, when U of Formula Y is $C(R_{11})_2$, one $R_{11}$ is halogen and one $R_{11}$ is hydrogen. In other embodiments, when U of Formula Y is $C(R_{11})_2$, each $R_{11}$ is fluoro. In other embodiments, when U of Formula Y is $C(R_{11})_2$, one $R_{11}$ is fluoro and one $R_{11}$ is hydrogen.

In some embodiments, U of Formula Y is $NCH_3$. In other embodiments, U of Formula Y is $NCH_2CH_3$.

In some embodiments, g in Formula Y is 0, 1, 2 or 3. In some embodiments, g in Formula Y is 0. In some embodiments, g in Formula Y is 1. In other embodiments, g in Formula Y is 2. In other embodiments, g in Formula Y is 3.

In some embodiments, h in Formula Y is 0, 1, 2 or 3. In some embodiments, h in Formula Y is 0. In some embodiments, h in Formula Y is 1. In other embodiments, h in Formula Y is 2. In other embodiments, h in Formula Y is 3.

In some embodiments, $R_{12}$ of Formula Y is H, D, fluoro, $C_{1-6}$alkyl, or $C_{1-6}$alkoxide. In some embodiments, $R_{12}$ of Formula Y is H. In some embodiments, $R_{12}$ of Formula Y is D. In some embodiments, $R_{12}$ of Formula Y is fluoro. In some embodiments, $R_{12}$ of Formula Y is $C_{1-6}$alkyl. In other embodiments, $R_{12}$ of Formula Y is methyl or ethyl. In some embodiments, $R_{12}$ of Formula Y is $C_{1-6}$alkoxide.

In some embodiments, t in Formula Y is 0, 1, 2, 3, 4, 5 or 6. In some embodiments, t in Formula Y is 0. In some embodiments, t in Formula Y is 1. In other embodiments, t in Formula Y is 2. In other embodiments, t in Formula Y is 3. In some embodiments, t in Formula Y is 4. In other embodiments, t in Formula Y is 5. In other embodiments, t in Formula Y is 6.

In some embodiments, at least one $R_1$ is a group chosen from:

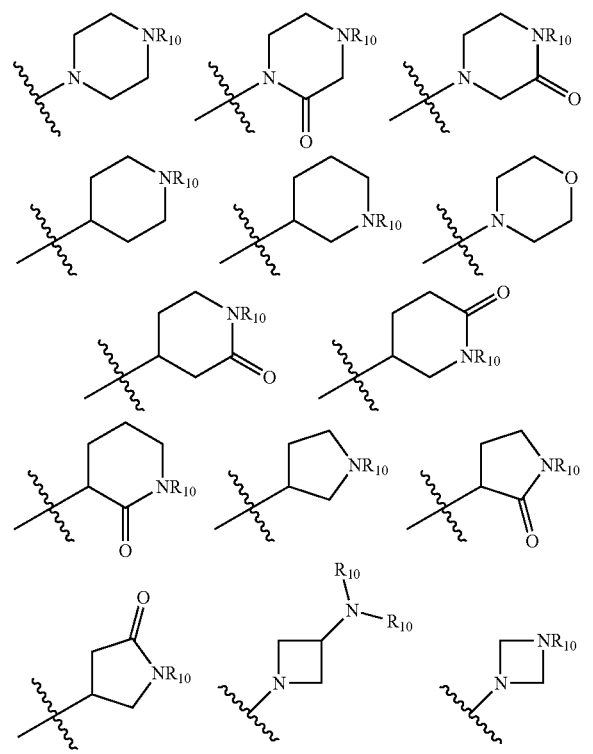

wherein $R_{10}$ is H or $C_{1-6}$alkyl.

In some embodiments, at least one $R_1$ is

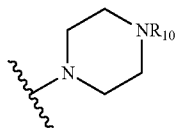

wherein $R_{10}$ is H or $C_{1-6}$alkyl.

In some embodiments, at least one $R_1$ is

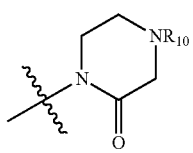

wherein $R_{10}$ is H or $C_{1-6}$alkyl.

In some embodiments, at least one $R_1$ is

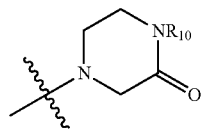

wherein $R_{10}$ is H or $C_{1-6}$alkyl.

In some embodiments, at least one $R_1$ is

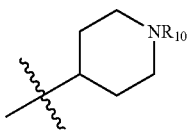

wherein $R_{10}$ is H or $C_{1-6}$alkyl.

In some embodiments, at least one $R_1$ is

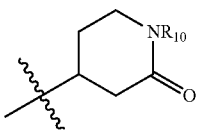

wherein $R_{10}$ is H or $C_{1-6}$alkyl.

In some embodiments, at least one $R_1$ is

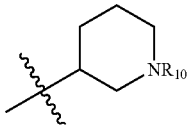

wherein $R_{10}$ is H or $C_{1-6}$alkyl.

In some embodiments, at least one $R_1$ is

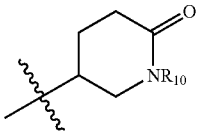

wherein $R_{10}$ is H or $C_{1-6}$alkyl.

In some embodiments, at least one $R_1$ is

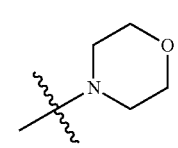

wherein $R_{10}$ is H or $C_{1-6}$alkyl.

In some embodiments, at least one $R_1$ is

[structure: pyrrolidine with $NR_{10}$]

wherein $R_{10}$ is H or $C_{1-6}$alkyl.

In some embodiments, at least one $R_1$ is

[structure: pyrrolidinone with $NR_{10}$]

wherein $R_{10}$ is H or $C_{1-6}$alkyl.

In some embodiments, at least one $R_1$ is

[structure: piperidinone with $NR_{10}$]

wherein $R_{10}$ is H or $C_{1-6}$alkyl.

In some embodiments, at least one $R_1$ is

[structure: pyrrolidinone with $NR_{10}$]

wherein $R_{10}$ is H or $C_{1-6}$alkyl.

In some embodiments, at least one $R_1$ is

[structure: azetidine with $NR_{10}R_{10}$]

wherein $R_{10}$ is H or $C_{1-6}$alkyl.

In some embodiments, at least one $R_1$ is

[structure: azetidine with $NR_{10}$]

wherein $R_{10}$ is H or $C_{1-6}$alkyl.

In other embodiments, at least one R1is is a piperazine. In other embodiments, at least one $R_1$ is a piperdine.

In some embodiments, at least one $R_1$ is a group of formula Z:

[structure (Z)]

wherein

⌇⌇⌇ is a point of attachment to $L_1$;

W is $CR_{11}$ or N;

U is $C(R_{11})_2$, $NR_{10}$, or O;

$R_{10}$ is H or $C_{1-6}$alkyl;

$R_{11}$ is H, D, fluoro, $C_{1-6}$alkyl, or $C_{1-6}$alkoxide;

$R_{12}$ is H, D, fluoro, $C_{1-6}$alkyl, or $C_{1-6}$alkoxide;

t is 0, 1, 2, 3, 4, 5, or 6; and each g, h, j and k is independently 0, 1, 2 or 3.

In some embodiments, W of Formula Z is $CR_{11}$. In other embodiments, W of Formula Z is N.

In some embodiments, U of Formula Z is $C(R_{11})_2$. In other embodiments, U of Formula Z is $NR_{10}$. In yet other embodiments, U of Formula Z is O.

In some embodiments, $R_{11}$ of Formula Z is H. In some embodiments, $R_{11}$ of Formula Z is fluoro. In some embodiments, $R_{11}$ of Formula Z is $C_{1-6}$alkyl. In other embodiments, $R_{11}$ of Formula Z is methyl or ethyl. In some embodiments, $R_{11}$ of Formula Z is $C_{1-6}$alkoxide.

In some embodiments, $R_{10}$ of Formula Z is H. In some embodiments, $R_{10}$ of Formula Z is $C_{1-6}$alkyl. In other embodiments, $R_{10}$ of Formula Z is methyl or ethyl.

In some embodiments, when U of Formula Z is $C(R_{11})_2$, each $R_{11}$ is H. In some embodiments, when U of Formula Z is $C(R_{11})_2$, each $R_{11}$ is methyl. In some embodiments, when U of Formula Z is $C(R_{11})_2$, one $R_{11}$ is methyl and one $R_{11}$ is hydrogen. In some embodiments, when U of Formula Z is $C(R_{11})_2$, each $R_{10}$ is halogen. In some embodiments, when U of Formula Z is $C(R_{11})_2$, one $R_{11}$ is halogen and one $R_{11}$ is hydrogen. In other embodiments, when U of Formula Z is $C(R_{11})_2$, each $R_{11}$ is fluoro. In other embodiments, when U of Formula Z is $C(R_{11})_2$, one $R_{11}$ is fluoro and one $R_{11}$ is hydrogen.

In some embodiments, U of Formula Z is $NCH_3$. In other embodiments, U of Formula Z is $NCH_2CH_3$.

In some embodiments, g in Formula Z is 0, 1, 2 or 3. In some embodiments, g in Formula Z is 0. In some embodiments, g in Formula Z is 1. In other embodiments, g in Formula Y is 2. In other embodiments, g in Formula Z is 3.

In some embodiments, h in Formula Z is 0, 1, 2 or 3. In some embodiments, h in Formula XIII is 0. In some embodiments, h in Formula Z is 1. In other embodiments, h in Formula Z is 2. In other embodiments, h in Formula Z is 3.

In some embodiments, j in Formula Z is 0, 1, 2 or 3. In some embodiments, j in Formula Z is 0. In some embodiments, j in Formula Z is 1. In other embodiments, j in Formula Z is 2. In other embodiments, j in Formula Z is 3.

In some embodiments, k in Formula Z is 0, 1, 2 or 3. In some embodiments, k in Formula Z is 0. In some embodiments, k in Formula Z is 1. In other embodiments, k in Formula Z is 2. In other embodiments, k in Formula Z is 3.

In some embodiments, $R_{12}$ of Formula Z is H, D, fluoro, $C_{1-6}$alkyl, or $C_{1-6}$alkoxide. In some embodiments, $R_{12}$ of Formula Z is H. In some embodiments, $R_{12}$ of Formula Z is D. In some embodiments, $R_{12}$ of Formula Z is fluoro. In some embodiments, $R_{12}$ of Formula Z is $C_{1-6}$alkyl. In other embodiments, $R_{12}$ of Formula Z is methyl or ethyl. In some embodiments, $R_{12}$ of Formula Z is $C_{1-6}$alkoxide.

In some embodiments, t in Formula Z is 0, 1, 2, 3, 4, 5 or 6. In some embodiments, t in Formula Z is 0. In some embodiments, t in Formula Z is 1. In other embodiments, t in Formula Z is 2. In other embodiments, t in Formula Z is 3. In some embodiments, t in Formula Z is 4. In other embodiments, t in Formula Z is 5. In other embodiments, t in Formula Z is 6.

In other embodiments, at least one R is a group chosen from:

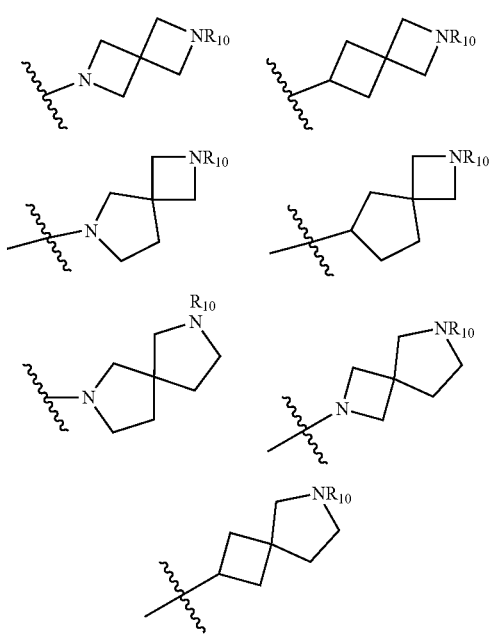

wherein $R_{10}$ is H or $C_{1-6}$alkyl.

In other embodiments, at least one $R_1$ is

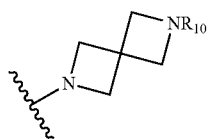

wherein $R_{10}$ is H or $C_{1-6}$alkyl.

In other embodiments, at least one $R_1$ is

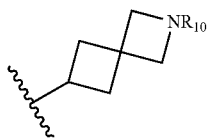

wherein $R_{10}$ is H or $C_{1-6}$alkyl.

In other embodiments, at least one $R_1$ is

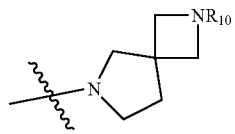

wherein $R_{10}$ is H or $C_{1-6}$alkyl.

In other embodiments, at least one $R_1$ is

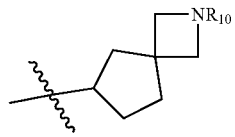

wherein $R_{10}$ is H or $C_{1-6}$alkyl.

In other embodiments, at least one $R_1$ is

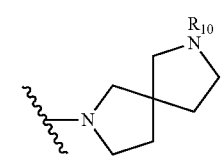

wherein $R_{10}$ is H or $C_{1-6}$alkyl.

In other embodiments, at least one $R_1$ is

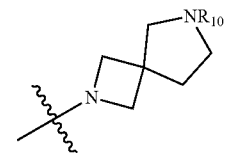

wherein $R_{10}$ is H or $C_{1-6}$alkyl.

In other embodiments, at least one $R_1$ is

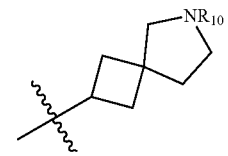

wherein $R_{10}$ is H or $C_{1-6}$alkyl.

In other embodiments, at least one $R_1$ is

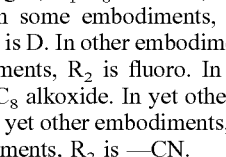

wherein $R_{10}$ is H or $C_{1-6}$alkyl.

In other embodiments, at least one $R_1$ is

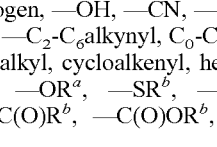

wherein $R_{10}$ is H or $C_{1-6}$alkyl.

In some embodiments, each $R_2$ in Formula I is independently H, D, halogen, $C_1$-$C_8$ alkoxide, $C_1$-$C_8$ alkyl, haloalkyl, or —CN. In some embodiments, $R_2$ is H. In some embodiments, $R_2$ is D. In other embodiments, $R_2$ is halogen. In other embodiments, $R_2$ is fluoro. In yet other embodiments, $R_2$ is $C_1$-$C_8$ alkoxide. In yet other embodiments, $R_2$ is $C_1$-$C_8$ alkyl. In yet other embodiments, $R_2$ is haloalkyl. In yet other embodiments, $R_2$ is —CN.

In some embodiments, each $R_3$ in Formula I is independently H, D, halogen, —OH, —CN, —NO$_2$, —C$_1$-C$_6$alkyl, —C$_2$-C$_6$alkenyl, —C$_2$-C$_6$alkynyl, C$_0$-C$_1$alk-aryl, C$_0$-C$_1$alk-heteroaryl, cycloalkyl, cycloalkenyl, heterocycloalkyl, heterocycloalkenyl, —OR$^a$, —SR$^b$, —NR$^c$R$^d$, —NR$^a$R$^c$, —C(O)R$^b$, —OC(O)R$^b$, —C(O)OR$^b$, —C(O)NR$^c$R$^d$, or —B(OR$^d$)(OR$^c$).

In some embodiments of the disclosure, at least one $R_3$ moiety will be directly bonded to the remainder of the compound of Formula (I) via a carbon atom. In particularly preferred aspects of these embodiments, each $R_3$ bonded through a carbon atom is independently H, D, halogen, —OH, —CN, —NO$_2$, —C$_1$-C$_6$alkyl, —C$_2$-C$_6$alkenyl, —C$_2$-C$_6$alkynyl, C$_0$-C$_1$alk-aryl, C$_0$-C$_1$alk-heteroaryl, cycloalkyl, cycloalkenyl, heterocycloalkyl, heterocycloalkenyl, —OR$^a$, —SR$^b$, —NR$^c$R$^d$, —NR$^a$R$^c$, —C(O)R$^b$, —OC(O)R$^b$, —C(O)OR$^b$, —C(O)NR$^c$R$^d$, or —B(OR$^d$)(OR).

In some embodiments, $R_3$ is H. In some embodiments, $R_3$ is D. In some embodiments, $R_3$ is halogen. In some embodiments, $R_3$ is —OH. In some embodiments, $R_3$ is —CN. In some embodiments, $R_3$ is NO$_2$. In some embodiments, $R_3$ is —C$_1$-C$_6$alkyl. In some embodiments, $R_3$ is —C$_2$-C$_6$alkenyl. In some embodiments, $R_3$ is —C$_2$-C$_6$alkynyl. In other embodiments, $R_3$ is C$_0$-C$_1$alk-aryl. In other embodiments, $R_3$ is C$_0$-C$_1$alk-heteroaryl. In other embodiments, $R_3$ is cycloalkyl. In other embodiments, $R_3$ is C$_{3-10}$cycloalkyl. In other embodiments, $R_3$ is cycloalkenyl. In other embodiments, $R_3$ is heterocycloalkyl. In other embodiments, $R_3$ is heterocycloalkenyl. In yet other embodiments, $R_3$ is —OR$^a$, —SR$^b$, —NR$^c$R$^d$, —NR$^a$R$^c$, —C(O)R$^b$, —OC(O)R$^b$, —C(O)OR$^b$, —C(O)NR$^c$R$^d$, or —B(OR$^d$)(OR$^c$) and the like. In other aspects, at least one $R_3$ is hydroxyalkyl. In other aspects, $R_3$ is C$_1$-C$_6$alkyl, for example, isopropyl. In other aspects, $R_3$ is oxo. In other aspects, $R_3$ is oxo bound to a nitrogen atom. In some aspects $R_3$ is OR$^a$.

In some embodiments, each $R^a$ in Formula I is independently H, D, —C(O)R$^b$, —C(O)OR$^c$, —C(O)NR$^c$R$^d$, —C(=NR$^b$)NR$^b$R$^c$, —C(=NOR$^b$)NR$^b$R$^c$, —C(=NCN)NR$^b$R$^c$, —P(OR$^c$)$_2$, —P(O)OR$^c$OR$^b$, —S(O)$_2$R$^b$, —S(O)$_2$NR$^c$R$^d$, SiR$^b{}_3$, —C$_1$-C$_{10}$alkyl, —C$_2$-C$_{10}$ alkenyl, —C$_2$-C$_{10}$ alkynyl, C$_0$-C$_1$alk-aryl, cycloalkyl, cycloalkenyl, C$_0$-C$_1$alk-heteroaryl, heterocycloalkyl, or heterocycloalkenyl.

In some embodiments, $R^a$ is H. In some embodiments, $R^a$ is D. In some embodiments, $R^a$ is —C(O)R$^b$. In some embodiments, $R^a$ is —C(O)OR$^c$. In some embodiments, $R^a$ is —C(O)NR$^c$R$^d$. In some embodiments, $R^a$ is —C(=NR$^b$)NR$^b$R$^c$. In some embodiments, $R^a$ is C(=NOR$^b$)NR$^b$R$^c$. In some embodiments, $R^a$ is —C(=NCN)NR$^b$R$^c$.

In other embodiments, $R^a$ is P(OR$^c$)$_2$, —P(O)OR$^c$OR$^b$, —S(O)$_2$R$^b$, —S(O)$_2$NR$^c$R$^d$, SiR$^b{}_3$, and the like. In yet other embodiments, $R^a$ is —C$_1$-C$_{10}$alkyl, —C$_2$-C$_{10}$ alkenyl, —C$_2$-C$_{10}$ alkynyl, C$_0$-C$_1$alk-aryl, cycloalkyl, cycloalkenyl, C$_0$-C$_1$alk-heteroaryl, heterocycloalkyl, or heterocycloalkenyl, and the like.

In some embodiments, each $R^b$ in Formula I is independently H, D, —C$_1$-C$_6$ alkyl, —C$_2$-C$_6$ alkenyl, —C$_2$-C$_6$ alkynyl, C$_0$-C$_1$alk-aryl, cycloalkyl, cycloalkenyl, C$_0$-C$_1$alk-heteroaryl, heterocycloalkyl, or heterocycloalkenyl. In some embodiments, $R^b$ is H. In some embodiments, $R^b$ is D. In some embodiments, $R^b$ is —C$_1$-C$_6$ alkyl. In some embodiments, $R^b$ is —C$_2$-C$_6$ alkenyl. In some embodiments, $R^b$ is —C$_2$-C$_6$ alkynyl. In other embodiments, $R^b$ is C$_0$-C$_1$alk-aryl. In other embodiments, $R^b$ is cycloalkyl. In other embodiments, $R^b$ is cycloalkenyl. In other embodiments, $R^b$ is C$_0$-C$_1$alk-heteroaryl. In other embodiments, $R^b$ is heterocycloalkyl. In other embodiments, $R^b$ is heterocycloalkenyl.

In some embodiments, each $R^c$ or $R^d$ in Formula I is independently H, D, —C$_1$-C$_6$ alkyl, —C$_2$-C$_6$ alkenyl, —C$_2$-C$_6$ alkynyl, aryl, C$_1$alk-aryl, cycloalkyl, cycloalkenyl, C$_1$alk-heteroaryl, heteroaryl, heterocycloalkyl, or heterocycloalkenyl. In some embodiments, $R^c$ or $R^d$ is H. In some embodiments, $R^c$ or $R^d$ is D. In some embodiments, $R^c$ or $R^d$ is —C$_1$-C$_{10}$ alkyl. In some embodiments, $R^c$ or $R^d$ is —C$_2$-C$_6$ alkenyl. In some embodiments, $R^c$ or $R^d$ is —C$_2$-C$_6$ alkynyl. In other embodiments, $R^c$ or $R^d$ is —OC$_1$-C$_6$alkyl. In other embodiments, $R^c$ or $R^d$ is —O-cycloalkyl. In other embodiments, $R^c$ or $R^d$ is aryl. In other embodiments, $R^c$ or $R^d$ is C$_1$alk-aryl. In other embodiments, $R^c$ or $R^d$ is cycloalkyl. In other embodiments, $R^c$ or $R^d$ is cycloalkenyl. In other embodiments, $R^c$ or $R^d$ is C$_1$alk-heteroaryl. In other embodiments, $R^c$ or $R^d$ is heteroaryl. In other embodiments, $R^c$ or $R^d$ is heterocycloalkyl. In other embodiments, $R^c$ or $R^d$ is heterocycloalkenyl.

In yet other embodiments, $R^c$ and $R^d$, together with the atom to which they are both attached, form a monocyclic or multicyclic heterocycloalkyl, or a monocyclic or multicyclic heterocyclo-alkenyl group. In yet other embodiments, $R^c$ and $R^d$ form a monocyclic heterocycloalkyl. In yet other embodiments, $R^c$ and $R^d$ form a multicyclic heterocycloalkyl. In yet other embodiments, $R^c$ and $R^d$ form a monocyclic heterocyclo-alkenyl group. In yet other embodiments, $R^c$ and $R^d$ form a multicyclic heterocyclo-alkenyl group.

In some embodiments, each $R_5$ in Formula I is independently H, D, —OR$^b$, C$_{1-4}$alkyl, wherein the C$_{1-4}$alkyl may be substituted with at least one of halogen, —OH, —CN or an amine, or cycloalkyl. In some embodiments, $R_5$ is H. In some embodiments, $R_5$ is D. In some embodiments, $R_5$ is —OR$^b$. In some embodiments, $R_5$ is C$_{1-4}$alkyl. In other embodiments, C$_{1-4}$alkyl group of $R_5$ substituted with at least one halogen. In other embodiments, C$_{1-4}$alkyl group of $R_5$ substituted with at least one —OH. In other embodiments, C$_{1-4}$alkyl group of $R_5$ substituted with at least one —CN. In other embodiments, C$_{1-4}$alkyl group of $R_5$ substituted with at least one amine. In other embodiments, $R_5$ is cycloalkyl.

In some embodiments, each $R_6$ in Formula I is independently H, D, halogen, —OH, —CN, —NO$_2$, —C$_1$-C$_6$alkyl, —C$_2$-C$_6$alkenyl, —C$_2$-C$_6$alkynyl, aryl, heteroaryl, cycloalkyl, cycloalkenyl, heterocycloalkyl, or heterocycloalkenyl, —OR$^a$, —SR$^a$, —NR$^c$R$^d$, —NR$^a$R$^c$, —C(O)R$^b$, —OC(O)R$^b$, —C(O)OR$^b$, —C(O)NR$^c$R$^d$, —S(O)R$^b$, —S(O)$_2$NR$^c$R$^d$, —S(O)(=NR$^b$)R$^b$, —SF$_5$, —P(O)R$^b$R$^b$, —P(O)(OR$^b$)(OR$^b$), —B(OR$^c$)(OR$^d$) or —S(O)$_2$R$^b$.

In some embodiments, $R_6$ is H. In some embodiments, $R_6$ is D. In some embodiments, $R_6$ is halogen. In some embodiments, $R_6$ is —OH. In some embodiments, $R_6$ is —CN. In some embodiments, $R_6$ is NO$_2$. In some embodiments, $R_6$ is —C$_1$-C$_6$alkyl. In some embodiments, $R_6$ is —C$_2$-C$_6$alkenyl. In some embodiments, $R_6$ is —C$_2$-C$_6$alkynyl. In other embodiments, $R_6$ is aryl. In other embodiments, $R_6$ is heteroaryl. In other embodiments, $R_6$ is cycloalkyl. In other embodiments, $R_6$ is cycloalkenyl. In other embodiments, $R_6$ is heterocycloalkyl. In other embodiments, $R_6$ is heterocycloalkenyl. In other embodiments, $R_6$ is —OR$^a$, —SR$^a$, —NR$^c$R$^d$, —NR$^a$R$^c$, —C(O)R$^b$, —OC(O)R$^b$, —C(O)OR$^b$, —C(O)NR$^c$R$^d$, —S(O)R$^b$, —S(O)$_2$NR$^c$R$^d$, —S(O)(=NR$^b$)R$^b$, —SF$_5$, —P(O)R$^b$R$^b$, —P(O)(OR$^b$)(OR$^b$), —B(OR$^c$)(OR$^d$) or —S(O)$_2$R$^b$.

In some embodiments, the compounds of Formula (I) are the pharmaceutically acceptable salts. In some embodiments, the compounds of Formula (I) are solvates. In some embodiments, the compounds of Formula (I) are N-oxides of the compounds of Formula (I).

In some embodiments, the compounds of Formula (I) are represented by compounds of Formula II, Formula IIa and Formula IIb

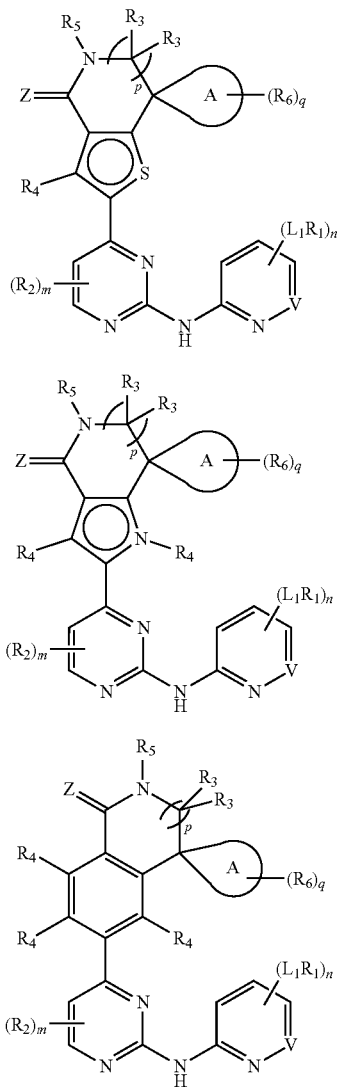

(II)

(IIa)

(IIb)

or a pharmaceutically acceptable salt thereof, wherein each $(L_1R_1)_n$, $(R_2)_m$, $R_3$, $R_4$, $R_5$, $(R_6)_q$, Z, V, ring A and p are defined with respect to Formula (I).

In some embodiments, the compounds of Formula (I) are represented by compounds of Formula III

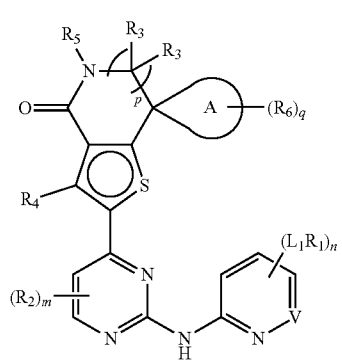

(III)

or a pharmaceutically acceptable salt thereof, wherein each $(L_1R_1)_n$, $(R_2)_m$, $R_3$, $R_4$, $R_5$, $(R_6)_q$, V, ring A and p are defined with respect to Formula (I).

In some embodiments, the compounds of Formula (I) are represented by compounds of Formula IV

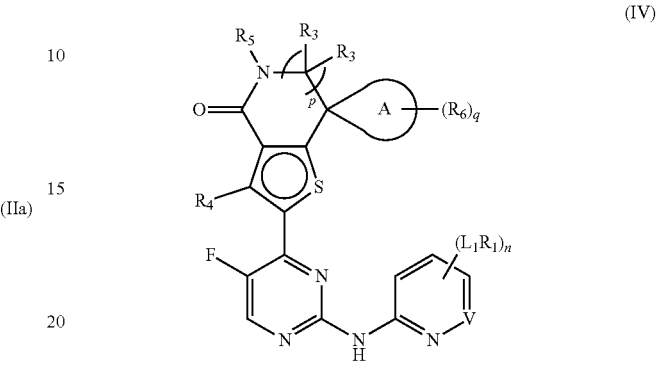

(IV)

or a pharmaceutically acceptable salt thereof, wherein each $(L_1R_1)_n$, $R_3$, $R_4$, $R_5$, $(R_6)_q$, V, ring A and p are defined with respect to Formula (I).

In some embodiments, the compounds of Formula (I) are represented by compounds of Formula V

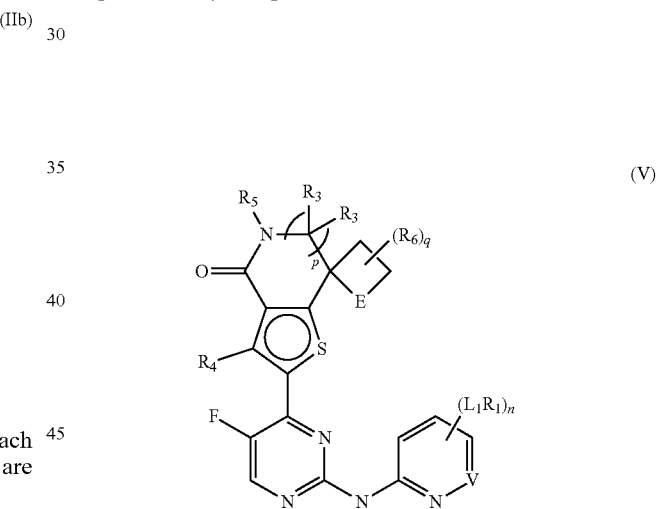

(V)

or a pharmaceutically acceptable salt thereof, wherein E is a bond, —O—, —S—, $C(R^a)_2$, —C(=O)NR$^a$— or NR$^a$; and wherein each $(L_1R_1)_n$, $R_3$, $R_4$, $R_5$, $(R_6)_q$, V and p are defined with respect to Formula (I).

In some embodiments, E in Formula V is a bond, —O—, —S—, $C(R^a)_2$, —C(=O)NR$^a$— or NR$^a$. In some embodiments, E in Formula V is a bond. In some embodiments, E in Formula V is —O—. In some embodiments, E in Formula V is —S—. In some embodiments, E in Formula V is $C(R^a)_2$. In some embodiments, E in Formula V is —C(=O)NR—. In some embodiments, E in Formula V is NR$^a$.

In some embodiments, the compounds of Formula (I) are represented by compounds of Formula VI

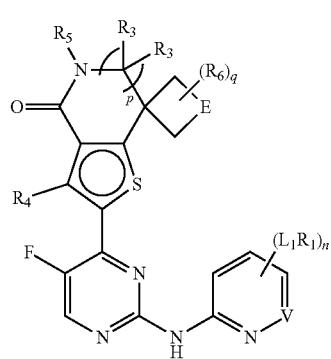

(VI)

or a pharmaceutically acceptable salt thereof, wherein E is a bond, —O—, —S—, $C(R^a)_2$, —C(=O)$NR^a$— or $NR^a$; and wherein each $(L_1R_1)_n$, $R_3$, $R_4$, $R_5$, $(R_6)_q$, V and p are defined with respect to Formula (I).

In some embodiments, E in Formula VI is a bond, —O—, —S—, $C(R^a)_2$, —C(=O)NR— or $NR^a$. In some embodiments, E in Formula VI is a bond. In some embodiments, E in Formula VI is —O—. In some embodiments, E in Formula VI is —S—. In some embodiments, E in Formula VI is $C(R^a)_2$. In some embodiments, E in Formula VI is —C(=O)NR—. In some embodiments, E in Formula VI is $NR^a$.

In some embodiments, the compounds of Formula (I) are represented by compounds of Formula VII

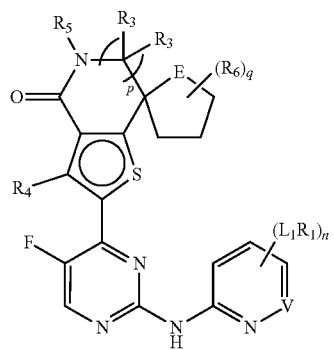

(VII)

or a pharmaceutically acceptable salt thereof, wherein E is a bond, —O—, —S—, $C(R^a)_2$, —C(=O)$NR^a$— or $NR^a$; and wherein each $(L_1R_1)_n$, $R_3$, $R_4$, $R_5$, $(R_6)_q$, V and p are defined with respect to Formula (I).

In some embodiments, E in Formula VII is a bond, —O—, —S—, $C(R^a)_2$, —C(=O)NR— or $NR^a$. In some embodiments, E in Formula VII is a bond. In some embodiments, E in Formula VII is —O—. In some embodiments, E in Formula VII is —S—. In some embodiments, E in Formula VII is $C(R^a)_2$. In some embodiments, E in Formula VII is —C(=O)NR—. In some embodiments, E in Formula VII is $NR^a$.

In some embodiments, the compounds of Formula (I) are represented by compounds of Formula VIII

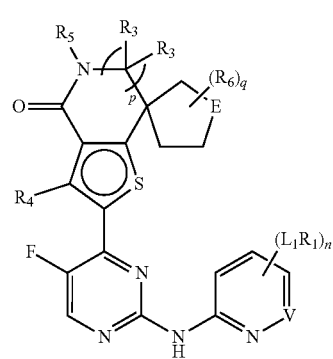

(VIII)

or a pharmaceutically acceptable salt thereof, wherein E is a bond, —O—, —S—, $C(R^a)_2$, —C(=O)$NR^a$— or $NR^a$; and wherein each $(L_1R_1)_n$, $R_3$, $R_4$, $R_5$, $(R_6)_q$, V and p are defined with respect to Formula (I).

In some embodiments, E in Formula VIII is a bond, —O—, —S—, $C(R^a)_2$, —C(=O)NR— or $NR^a$. In some embodiments, E in Formula VIII is a bond. In some embodiments, E in Formula VIII is —O—. In some embodiments, E in Formula VIII is —S—. In some embodiments, E in Formula VIII is $C(R^a)_2$. In some embodiments, E in Formula VIII is —C(=O)NR—. In some embodiments, E in Formula VIII is $NR^a$.

In some embodiments, the compounds of Formula (I) are represented by compounds of Formula IX

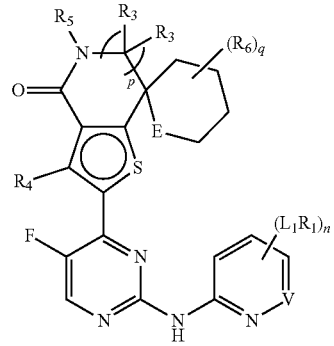

(IX)

or a pharmaceutically acceptable salt thereof, wherein E is a bond, —O—, —S—, $C(R^a)_2$, —C(=O)$NR^a$— or $NR^a$; and wherein each $(L_1R_1)_n$, $R_3$, $R_4$, $R_5$, $(R_6)_q$, V and p are defined with respect to Formula (I).

In some embodiments, E in Formula IX is a bond, —O—, —S—, $C(R^a)_2$, —C(=O)NR— or $NR^a$. In some embodiments, E in Formula IX is a bond. In some embodiments, E in Formula IX is —O—. In some embodiments, E in Formula IX is —S—. In some embodiments, E in Formula IX is $C(R^a)_2$. In some embodiments, E in Formula IX is —C(=O)NR—. In some embodiments, E in Formula IX is $NR^a$.

In some embodiments, the compounds of Formula (I) are represented by compounds of Formula X

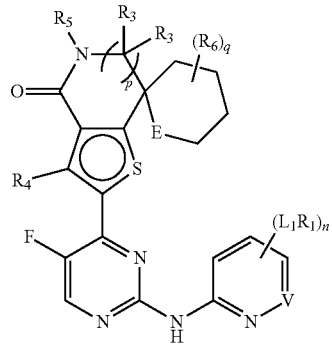

(X)

or a pharmaceutically acceptable salt thereof, wherein E is a bond, —O—, —S—, $C(R^a)_2$, —C(=O)$NR^a$— or $NR^a$; and wherein each $(L_1R_1)_n$, $R_3$, $R_4$, $R_5$, $(R_6)_q$, V and p are defined with respect to Formula (I).

In some embodiments, E in Formula X is a bond, —O—, —S—, $C(R^a)_2$, —C(=O)NR— or $NR^a$. In some embodiments, E in Formula X is a bond. In some embodiments, E in Formula X is —O—. In some embodiments, E in Formula X is —S—. In some embodiments, E in Formula X is $C(R^a)_2$. In some embodiments, E in Formula X is —C(=O)NR—. In some embodiments, E in Formula X is $NR^a$.

In some embodiments, the compounds of Formula (I) are represented by compounds of Formula XI

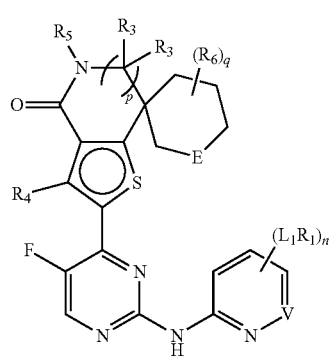

(XI)

or a pharmaceutically acceptable salt thereof, wherein E is a bond, —O—, —S—, $C(R^a)_2$, —C(=O)$NR^a$— or $NR^a$; and wherein each $(L_1R_1)_n$, $R_3$, $R_4$, $R_5$, $(R_6)_q$, V and p are defined with respect to Formula (I).

In some embodiments, E in Formula XI is a bond, —O—, —S—, $C(R^a)_2$, —C(=O)NR— or $NR^a$. In some embodiments, E in Formula XI is a bond. In some embodiments, E in Formula XI is —O—. In some embodiments, E in Formula XI is —S—. In some embodiments, E in Formula XI is $C(R^a)_2$. In some embodiments, E in Formula XI is —C(=O)NR—. In some embodiments, E in Formula XI is $NR^a$.

In some embodiments, the compounds of Formula (I) are represented by compounds of Formula XII

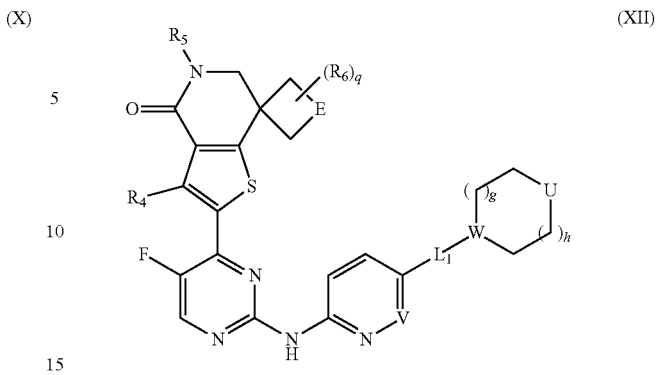

(XII)

or a pharmaceutically acceptable salt thereof, wherein
E is a bond, —O—, —S—, $C(R^a)_2$, —C(=O)$NR^a$— or $NR^a$;
$(R_6)_q$ is defined with respect to Formula (I);
$L_1$ is a bond, —$CH_2$—, or C=O;
V is $CR_{11}$ or N;
W is $CR_{11}$ or N;
U is $C(R_{11})_2$, $NR_{10}$, or O;
$R_{10}$ is H, D, $C_{1-6}$alkyl or haloalkyl;
$R_{11}$ is H, D, fluoro, $C_{1-6}$alkyl, or $C_{1-6}$alkoxide;
$R_4$ is H, D, Me or haloalkyl;
$R_5$ is H, D, Me or haloalkyl; and
each g and h is independently 0, 1, 2 or 3.

In some embodiments, E in Formula XII is a bond, —O—, —S—, $C(R^a)_2$, —C(=O)NR— or $NR^a$. In some embodiments, E in Formula XII is a bond. In some embodiments, E in Formula XII is —O—. In some embodiments, E in Formula XII is —S—. In some embodiments, E in Formula XII is $C(R^a)_2$. In some embodiments, E in Formula XII is —C(=O)NR—. In some embodiments, E in Formula XII is $NR^a$.

In some embodiments, $L_1$ of Formula XII is a bond. In some embodiments, $L_1$ of Formula XII is —$CH_2$—. In some embodiments, $L_1$ of Formula XII is C=O.

In some embodiments, V of Formula XII is $CR_{11}$. In other embodiments, V of Formula XII is N.

In some embodiments, W of Formula XII is $CR_{11}$. In other embodiments, W of Formula XII is N.

In some embodiments, U of Formula XII is $C(R_{11})_2$. In other embodiments, U of Formula XII is $NR_{10}$. In yet other embodiments, U of Formula XII is O.

In some embodiments, $R_4$ of Formula XII is H. In some embodiments, $R_4$ of Formula XII is D. In some embodiments, $R_4$ of Formula XII is methyl. In some embodiments, $R_4$ of Formula XII is haloalkyl.

In some embodiments, $R_5$ of Formula XII is H. In some embodiments, $R_5$ of Formula XII is D. In some embodiments, $R_5$ of Formula XII is methyl. In some embodiments, $R_5$ of Formula XII is haloalkyl.

In some embodiments, $R_{11}$ of Formula XII is H. In some embodiments, $R_{11}$ of Formula XII is D. In some embodiments, $R_{11}$ of Formula XII is fluoro. In some embodiments, $R_{11}$ of Formula XII is $C_{1-6}$alkyl. In other embodiments, $R_{11}$ of Formula XII is methyl or ethyl. In some embodiments, $R_{11}$ of Formula XII is $C_{1-6}$alkoxide.

In some embodiments, $R_{10}$ of Formula XII is H. In some embodiments, $R_{10}$ of Formula XII is D. In some embodiments, $R_{10}$ of Formula XXIV is $C_{1-6}$alkyl. In other embodiments, $R_{10}$ of Formula XII is methyl or ethyl. In some embodiments, $R_{10}$ of Formula XII is haloalkyl.

In some embodiments, when U of Formula XII is C(R$_{11}$)$_2$, each R$_{11}$ is H. In some embodiments, when U of Formula XII is C(R$_{11}$)$_2$, each R$_{11}$ is methyl. In some embodiments, when U of Formula XII is C(R$_{11}$)$_2$, one R$_{11}$ is methyl and one R$_{11}$ is hydrogen. In some embodiments, when U of Formula XII is C(R$_{11}$)$_2$, each R$_{10}$ is halogen. In some embodiments, when U of Formula XII is C(R$_{11}$)$_2$, one R$_{11}$ is halogen and one R$_{11}$ is hydrogen. In other embodiments, when U of Formula XII is C(R$_{11}$)$_2$, each R$_{11}$ is fluoro. In other embodiments, when U of Formula XII is C(R$_{11}$)$_2$, one R$_{11}$ is fluoro and one R$_{11}$ is hydrogen.

In some embodiments, U of Formula XII is NCH$_3$. In other embodiments, U of Formula XII is NCH$_2$CH$_3$.

In some embodiments, g in Formula XII is 0, 1, 2 or 3. In some embodiments, g in Formula XII is 0. In some embodiments, g in Formula XII is 1. In other embodiments, g in Formula XII is 2. In other embodiments, g in Formula XII is 3.

In some embodiments, h in Formula XII is 0, 1, 2 or 3. In some embodiments, h in Formula XII is 0. In some embodiments, h in Formula XII is 1. In other embodiments, h in Formula XII is 2. In other embodiments, h in Formula XII is 3.

In some embodiments, the compounds of Formula (I) are represented by compounds of Formula XIII

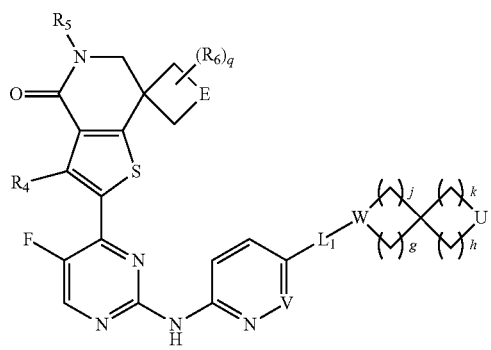

(XIII)

or a pharmaceutically acceptable salt thereof, wherein
E is a bond, —O—, —S—, C(R$^a$)$_2$, —C(=O)NR$^a$— or NR$^a$;
(R$_6$)$_q$ is defined with respect to Formula (I);
L$_1$ is a bond, —CH$_2$—, or C=O;
V is CR$_{11}$ or N;
W is CR$_{11}$ or N;
U is C(R$_{11}$)$_2$, NR$_{10}$, or O;
R$_4$ is H, D, Me or haloalkyl;
R$_5$ is H, D, Me or haloalkyl;
R$_{10}$ is H, D, C$_{1-6}$alkyl or haloalkyl;
R$_{11}$ is H, D, fluoro, C$_{1-6}$alkyl, or C$_{1-6}$alkoxide; and
each g, h, j and k is independently 0, 1, 2 or 3.

In some embodiments, E in Formula XIII is a bond, —O—, —S—, C(R$^a$)$_2$, —C(=O)NR— or NR$^a$. In some embodiments, E in Formula XIII is a bond. In some embodiments, E in Formula XIII is —O—. In some embodiments, E in Formula XIII is —S—. In some embodiments, E in Formula XIII is C(R$^a$)$_2$. In some embodiments, E in Formula XIII is —C(=O)NR—. In some embodiments, E in Formula XIII is NR$^a$.

In some embodiments, L$_1$ of Formula XIII is a bond. In some embodiments, L$_1$ of Formula XIII is —CH$_2$—. In some embodiments, L$_1$ of Formula XIII is C=O.

In some embodiments, V of Formula XIII is CR$_{11}$. In other embodiments, V of Formula XIII is N.

In some embodiments, W of Formula XIII is CR$_{11}$. In other embodiments, W of Formula XIII is N.

In some embodiments, U of Formula XIII is C(R$_{11}$)$_2$. In other embodiments, U of Formula XIII is NR$_{10}$. In yet other embodiments, U of Formula XIII is O.

In some embodiments, R$_{11}$ of Formula XIII is H. In some embodiments, R$_{11}$ of Formula XII is D. In some embodiments, R$_{11}$ of Formula XIII is fluoro. In some embodiments, R$_{11}$ of Formula XIII is C$_{1-6}$alkyl. In other embodiments, R$_{11}$ of Formula XIII is methyl or ethyl. In some embodiments, R$_{11}$ of Formula XIII is C$_{1-6}$alkoxide.

In some embodiments, R$_{10}$ of Formula XIII is H. In some embodiments, R$_{10}$ of Formula XIII is D. In some embodiments, R$_{10}$ of Formula XIII is C$_{1-6}$alkyl. In other embodiments, R$_{10}$ of Formula XIII is methyl or ethyl. In some embodiments, R$_{10}$ of Formula XIII is haloalkyl.

In some embodiments, when U of Formula XIII is C(R$_{11}$)$_2$, each R$_{11}$ is H. In some embodiments, when U of Formula XIII is C(R$_{11}$)$_2$, each R$_{11}$ is methyl. In some embodiments, when U of Formula XIII is C(R$_{11}$)$_2$, one R$_{11}$ is methyl and one R$_{11}$ is hydrogen. In some embodiments, when U of Formula XIII is C(R$_{11}$)$_2$, each R$_{10}$ is halogen. In some embodiments, when U of Formula XIII is C(R$_{11}$)$_2$, one R$_{11}$ is halogen and one R$_{11}$ is hydrogen. In other embodiments, when U of Formula XIII is C(R$_{11}$)$_2$, each R$_{11}$ is fluoro. In other embodiments, when U of Formula XIII is C(R$_{11}$)$_2$, one R$_{11}$ is fluoro and one R$_{11}$ is hydrogen.

In some embodiments, U of Formula XIII is NCH$_3$. In other embodiments, U of Formula XIII is NCH$_2$CH$_3$.

In some embodiments, R$_4$ of Formula XIII is H. In some embodiments, R$_4$ of Formula XIII is D. In some embodiments, R$_4$ of Formula XIII is methyl. In some embodiments, R$_4$ of Formula XIII is haloalkyl.

In some embodiments, R$_5$ of Formula XIII is H. In some embodiments, R$_5$ of Formula XIII is D. In some embodiments, R$_5$ of Formula XIII is methyl. In some embodiments, R$_5$ of Formula XIII is haloalkyl.

In some embodiments, g in Formula XIII is 0, 1, 2 or 3. In some embodiments, g in Formula XIII is 0. In some embodiments, g in Formula XIII is 1. In other embodiments, g in Formula XIII is 2. In other embodiments, g in Formula XIII is 3.

In some embodiments, h in Formula XIII is 0, 1, 2 or 3. In some embodiments, h in Formula XIII is 0. In some embodiments, h in Formula XIII is 1. In other embodiments, h in Formula XIII is 2. In other embodiments, h in Formula XIII is 3.

In some embodiments, j in Formula XIII is 0, 1, 2 or 3. In some embodiments, j in Formula XIII is 0. In some embodiments, j in Formula XIII is 1. In other embodiments, j in Formula XIII is 2. In other embodiments, j in Formula XIII is 3.

In some embodiments, k in Formula XIII is 0, 1, 2 or 3. In some embodiments, k in Formula XIII is 0. In some embodiments, k in Formula XIII is 1. In other embodiments, k in Formula XIII is 2. In other embodiments, k in Formula XIII is 3.

In some embodiments, the compounds of Formula (I) are represented by compounds of Formula XIV

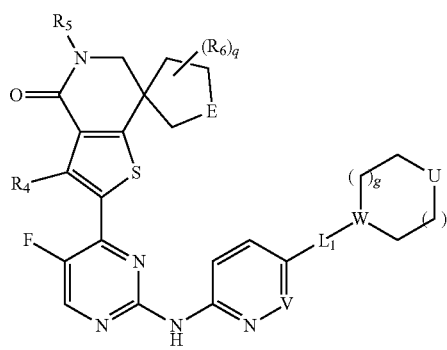

(XIV)

or a pharmaceutically acceptable salt thereof, wherein
E is a bond, —O—, —S—, C($R^a$)$_2$, —C(=O)N$R^a$— or N$R^a$;
($R_6$)$_q$ is defined with respect to Formula (I);
$L_1$ is a bond, —CH$_2$—, or C=O;
V is C$R_{11}$ or N;
W is C$R_{11}$ or N;
U is C($R_{11}$)$_2$, N$R_{10}$, or O;
$R_{10}$ is H, D, C$_{1-6}$alkyl or haloalkyl;
$R_{11}$ is H, D, fluoro, C$_{1-6}$alkyl, or C$_{1-6}$alkoxide;
$R_4$ is H, D, Me or haloalkyl;
$R_5$ is H, D, Me or haloalkyl; and
each g and h is independently 0, 1, 2 or 3.

In some embodiments, E in Formula XIV is a bond, —O—, —S—, C($R^a$)$_2$, —C(=O)NR— or N$R^a$. In some embodiments, E in Formula XIV is a bond. In some embodiments, E in Formula XIV is —O—. In some embodiments, E in Formula XIV is —S—. In some embodiments, E in Formula XIV is C($R^a$)$_2$. In some embodiments, E in Formula XIV is —C(=O)NR—. In some embodiments, E in Formula XIV is N$R^a$.

In some embodiments, $L_1$ of Formula XIV is a bond. In some embodiments, $L_1$ of Formula XIV is —CH$_2$—. In some embodiments, $L_1$ of Formula XIV is C=O.

In some embodiments, V of Formula XIV is C$R_{11}$. In other embodiments, V of Formula XIV is N.

In some embodiments, W of Formula XIV is C$R_{11}$. In other embodiments, W of Formula XIV is N.

In some embodiments, U of Formula XIV is C($R_{11}$)$_2$. In other embodiments, U of Formula XIV is N$R_{10}$. In yet other embodiments, U of Formula XIV is O.

In some embodiments, $R_{11}$ of Formula XIV is H. In some embodiments, $R_{11}$ of Formula XIV is D. In some embodiments, $R_{11}$ of Formula XIV is fluoro. In some embodiments, $R_{11}$ of Formula XIV is C$_{1-6}$alkyl. In other embodiments, $R_{11}$ of Formula XIV is methyl or ethyl. In some embodiments, $R_{11}$ of Formula XIV is C$_{1-6}$alkoxide.

In some embodiments, $R_{10}$ of Formula XIV is H. In some embodiments, $R_{10}$ of Formula XIV is D. In some embodiments, $R_{10}$ of Formula XIV is C$_{1-6}$alkyl. In other embodiments, $R_{10}$ of Formula XIV is methyl or ethyl. In some embodiments, $R_{10}$ of Formula XIV is haloalkyl.

In some embodiments, when U of Formula XIV is C($R_{11}$)$_2$, each $R_{11}$ is H. In some embodiments, when U of Formula XIV is C($R_{11}$)$_2$, each $R_{11}$ is methyl. In some embodiments, when U of Formula XIV is C($R_{11}$)$_2$, one $R_{11}$ is methyl and one $R_{11}$ is hydrogen. In some embodiments, when U of Formula XIV is C($R_{11}$)$_2$, each $R_{10}$ is halogen. In some embodiments, when U of Formula XIV is C($R_{11}$)$_2$, one $R_{11}$ is halogen and one $R_{11}$ is hydrogen. In other embodiments, when U of Formula XIV is C($R_{11}$)$_2$, each $R_{11}$ is fluoro. In other embodiments, when U of Formula XIV is C($R_{11}$)$_2$, one $R_{11}$ is fluoro and one $R_{11}$ is hydrogen.

In some embodiments, U of Formula XIV is NCH$_3$. In other embodiments, U of Formula XIV is NCH$_2$CH$_3$.

In some embodiments, $R_4$ of Formula XIV is H. In some embodiments, $R_4$ of Formula XIV is D. In some embodiments, $R_4$ of Formula XIV is methyl. In some embodiments, $R_4$ of Formula XIV is haloalkyl.

In some embodiments, $R_5$ of Formula XIV is H. In some embodiments, $R_5$ of Formula XIV is D. In some embodiments, $R_5$ of Formula XIV is methyl. In some embodiments, $R_5$ of Formula XIV is haloalkyl.

In some embodiments, g in Formula XIV is 0, 1, 2 or 3. In some embodiments, g in Formula XIV is 0. In some embodiments, g in Formula XIV is 1. In other embodiments, g in Formula XIV is 2. In other embodiments, g in Formula XIV is 3.

In some embodiments, h in Formula XIV is 0, 1, 2 or 3. In some embodiments, h in Formula XIV is 0. In some embodiments, h in Formula XIV is 1. In other embodiments, h in Formula XIV is 2. In other embodiments, h in Formula XIV is 3.

In some embodiments, the compounds of Formula (I) are represented by compounds of Formula XV

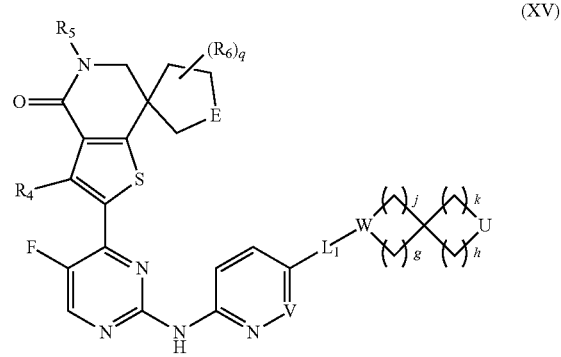

(XV)

or a pharmaceutically acceptable salt thereof, wherein
E is a bond, —O—, —S—, C($R^a$)$_2$, —C(=O)N$R^a$— or N$R^a$;
($R_6$)$_q$ is defined with respect to Formula (I);
$L_1$ is a bond, —CH$_2$—, or C=O;
V is C$R_{11}$ or N;
W is C$R_{11}$ or N;
U is C($R_{11}$)$_2$, N$R_{10}$, or O;
$R_{10}$ is H, D, C$_{1-6}$alkyl or haloalkyl;
$R_{11}$ is H, D, fluoro, C$_{1-6}$alkyl, or C$_{1-6}$alkoxide;
$R_4$ is H, D, Me or haloalkyl;
$R_5$ is H, D, Me or haloalkyl; and
each g, h, j and k is independently 0, 1, 2 or 3.

In some embodiments, E in Formula XV is a bond, —O—, —S—, C($R^a$)$_2$, —C(=O)NR— or N$R^a$. In some embodiments, E in Formula XV is a bond. In some embodiments, E in Formula XV is —O—. In some embodiments, E in Formula XV is —S—. In some embodiments, E in Formula XV is C($R^a$)$_2$. In some embodiments, E in Formula XV is —C(=O)NR—. In some embodiments, E in Formula XV is N$R^a$.

In some embodiments, $L_1$ of Formula XV is a bond. In some embodiments, $L_1$ of Formula XV is —CH$_2$—. In some embodiments, $L_1$ of Formula XV is C=O.

In some embodiments, V of Formula XV is C$R_{11}$. In other embodiments, V of Formula XV is N.

In some embodiments, W of Formula XV is $CR_{11}$. In other embodiments, W of Formula XV is N.

In some embodiments, U of Formula XV is $C(R_{11})_2$. In other embodiments, U of Formula XV is $NR_{10}$. In yet other embodiments, U of Formula XV is O.

In some embodiments, $R_{11}$ of Formula XV is H. In some embodiments, $R_{11}$ of Formula XV is D. In some embodiments, $R_{11}$ of Formula XV is fluoro. In some embodiments, $R_{11}$ of Formula XV is $C_{1-6}$alkyl. In other embodiments, $R_{11}$ of Formula XV is methyl or ethyl. In some embodiments, $R_{11}$ of Formula XV is $C_{1-6}$alkoxide.

In some embodiments, $R_{10}$ of Formula XV is H. In some embodiments, $R_{10}$ of Formula XV is D. In some embodiments, $R_{10}$ of Formula XV is $C_{1-6}$alkyl. In other embodiments, $R_{10}$ of Formula XV is methyl or ethyl. In some embodiments, $R_{10}$ of Formula XV is haloalkyl.

In some embodiments, when U of Formula XV is $C(R_{11})_2$, each $R_{11}$ is H. In some embodiments, when U of Formula XV is $C(R_{11})_2$, each $R_{11}$ is methyl. In some embodiments, when U of Formula XV is $C(R_{11})_2$, one $R_{11}$ is methyl and one $R_{11}$ is hydrogen. In some embodiments, when U of Formula XV is $C(R_{11})_2$, each $R_{10}$ is halogen. In some embodiments, when U of Formula XV is $C(R_{11})_2$, one $R_{11}$ is halogen and one $R_{11}$ is hydrogen. In other embodiments, when U of Formula XV is $C(R_{11})_2$, each $R_{11}$ is fluoro. In other embodiments, when U of Formula XV is $C(R_{11})_2$, one $R_{11}$ is fluoro and one $R_{11}$ is hydrogen.

In some embodiments, U of Formula XV is $NCH_3$. In other embodiments, U of Formula XV is $NCH_2CH_3$.

In some embodiments, $R_4$ of Formula XV is H. In some embodiments, $R_4$ of Formula XV is D. In some embodiments, $R_4$ of Formula XV is methyl. In some embodiments, $R_4$ of Formula XV is haloalkyl.

In some embodiments, $R_5$ of Formula XV is H. In some embodiments, $R_5$ of Formula XV is D. In some embodiments, $R_5$ of Formula XV is methyl. In some embodiments, $R_5$ of Formula XV is haloalkyl.

In some embodiments, g in Formula XV is 0, 1, 2 or 3. In some embodiments, g in Formula XV is 0. In some embodiments, g in Formula XV is 1. In other embodiments, g in Formula XV is 2. In other embodiments, g in Formula XV is 3.

In some embodiments, h in Formula XV is 0, 1, 2 or 3. In some embodiments, h in Formula XV is 0. In some embodiments, h in Formula XV is 1. In other embodiments, h in Formula XV is 2. In other embodiments, h in Formula XV is 3.

In some embodiments, j in Formula XV is 0, 1, 2 or 3. In some embodiments, j in Formula XV is 0. In some embodiments, j in Formula XV is 1. In other embodiments, j in Formula XV is 2. In other embodiments, j in Formula XV is 3.

In some embodiments, k in Formula XV is 0, 1, 2 or 3. In some embodiments, k in Formula XV is 0. In some embodiments, k in Formula XV is 1. In other embodiments, k in Formula XV is 2. In other embodiments, k in Formula XV is 3.

In some embodiments, the compounds of Formula (I) are represented by compounds of Formula XVI

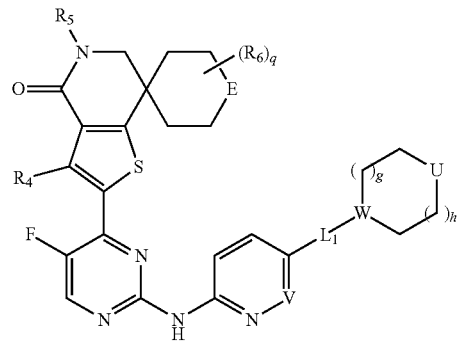

(XVI)

or a pharmaceutically acceptable salt thereof, wherein
E is a bond, —O—, —S—, $C(R^a)_2$, —C(=O)$NR^a$— or $NR^a$;
$(R_6)_q$ is defined with respect to Formula (I);
$L_1$ is a bond, —$CH_2$—, or C=O;
V is $CR_{11}$ or N;
W is $CR_{11}$ or N;
U is $C(R_{11})_2$, $NR_{10}$, or O;
$R_{10}$ is H, D, $C_{1-6}$alkyl or haloalkyl;
$R_{11}$ is H, D, fluoro, $C_{1-6}$alkyl, or $C_{1-6}$alkoxide;
$R_4$ is H, D, Me or haloalkyl;
$R_5$ is H, D, Me or haloalkyl; and
each g and h is independently 0, 1, 2 or 3.

In some embodiments, E in Formula XVI is a bond, —O—, —S—, $C(R^a)_2$, —C(=O)NR— or $NR^a$. In some embodiments, E in Formula XVI is a bond. In some embodiments, E in Formula XVI is —O—. In some embodiments, E in Formula XVI is —S—. In some embodiments, E in Formula XVI is $C(R^a)_2$. In some embodiments, E in Formula XVI is —C(=O)NR—. In some embodiments, E in Formula XVI is $NR^a$.

In some embodiments, $L_1$ of Formula XVI is a bond. In some embodiments, $L_1$ of Formula XVI is —$CH_2$—. In some embodiments, $L_1$ of Formula XVI is C=O.

In some embodiments, V of Formula XVI is $CR_{11}$. In other embodiments, V of Formula XVI is N.

In some embodiments, W of Formula XVI is $CR_{11}$. In other embodiments, W of Formula XVI is N.

In some embodiments, U of Formula XVI is $C(R_{11})_2$. In other embodiments, U of Formula XVI is $NR_{10}$. In yet other embodiments, U of Formula XVI is O.

In some embodiments, $R_{11}$ of Formula XVI is H. In some embodiments, $R_{11}$ of Formula XVI is D. In some embodiments, $R_{11}$ of Formula XVI is fluoro. In some embodiments, $R_{11}$ of Formula XVI is $C_{1-6}$alkyl. In other embodiments, $R_{11}$ of Formula XVI is methyl or ethyl. In some embodiments, $R_{11}$ of Formula XVI is $C_{1-6}$alkoxide.

In some embodiments, $R_{10}$ of Formula XVI is H. In some embodiments, $R_{10}$ of Formula XVI is D. In some embodiments, $R_{10}$ of Formula XVI is $C_{1-6}$alkyl. In other embodiments, $R_{10}$ of Formula XVI is methyl or ethyl. In some embodiments, $R_{10}$ of Formula XVI is haloalkyl.

In some embodiments, when U of Formula XVI is $C(R_{11})_2$, each $R_{11}$ is H. In some embodiments, when U of Formula XVI is $C(R_{11})_2$, each $R_{11}$ is methyl. In some embodiments, when U of Formula XVI is $C(R_{11})_2$, one $R_{11}$ is methyl and one $R_{11}$ is hydrogen. In some embodiments, when U of Formula XVI is $C(R_{11})_2$, each $R_{10}$ is halogen. In some embodiments, when U of Formula XVI is $C(R_{11})_2$, one $R_{11}$ is halogen and one $R_{11}$ is hydrogen. In other embodiments, when U of Formula XVI is $C(R_{11})_2$, each $R_{11}$ is fluoro. In other embodiments, when U of Formula XVI is $C(R_{11})_2$, one $R_{11}$ is fluoro and one $R_{11}$ is hydrogen.

In some embodiments, U of Formula XVI is $NCH_3$. In other embodiments, U of Formula XVI is $NCH_2CH_3$.

In some embodiments, $R_4$ of Formula XVI is H. In some embodiments, $R_4$ of Formula XVI is D. In some embodiments, $R_4$ of Formula XVI is methyl. In some embodiments, $R_4$ of Formula XVI is haloalkyl.

In some embodiments, $R_5$ of Formula XVI is H. In some embodiments, $R_5$ of Formula XVI is D. In some embodiments, $R_5$ of Formula XVI is methyl. In some embodiments, $R_5$ of Formula XVI is haloalkyl.

In some embodiments, g in Formula XVI is 0, 1, 2 or 3. In some embodiments, g in Formula XVI is 0. In some embodiments, g in Formula XVI is 1. In other embodiments, g in Formula XVI is 2. In other embodiments, g in Formula XVI is 3.

In some embodiments, h in Formula XVI is 0, 1, 2 or 3. In some embodiments, h in Formula XVI is 0. In some embodiments, h in Formula XVI is 1. In other embodiments, h in Formula XVI is 2. In other embodiments, h in Formula XVI is 3.

In some embodiments, the compounds of Formula (I) are represented by compounds of Formula XVII

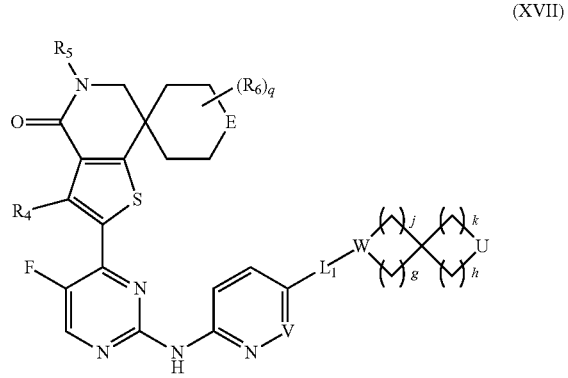

(XVII)

or a pharmaceutically acceptable salt thereof, wherein

E is a bond, —O—, —S—, $C(R^a)_2$, —C(=O)$NR^a$— or $NR^a$;

$(R_6)_q$ is defined with respect to Formula (I);

$L_1$ is a bond, —$CH_2$—, or C=O;

V is $CR_{11}$ or N;

W is $CR_{11}$ or N;

U is $C(R_{11})_2$, $NR_{10}$, or O;

$R_{10}$ is H, D, $C_{1-6}$alkyl or haloalkyl;

$R_{11}$ is H, D, fluoro, $C_{1-6}$alkyl, or $C_{1-6}$alkoxide;

$R_4$ is H, D, Me or haloalkyl;

$R_5$ is H, D, Me or haloalkyl; and each g, h, j and k is independently 0, 1, 2 or 3.

In some embodiments, E in Formula XVII is a bond, —O—, —S—, $C(R^a)_2$, —C(=O)NR— or $NR^a$. In some embodiments, E in Formula XVII is a bond. In some embodiments, E in Formula XVII is —O—. In some embodiments, E in Formula XVII is —S—. In some embodiments, E in Formula XVII is $C(R^a)_2$. In some embodiments, E in Formula XVII is —C(=O)NR—. In some embodiments, E in Formula XVII is $NR^a$.

In some embodiments, $L_1$ of Formula XVII is a bond. In some embodiments, $L_1$ of Formula XVII is —$CH_2$—. In some embodiments, $L_1$ of Formula XVII is C=O.

In some embodiments, V of Formula XVII is $CR_{11}$. In other embodiments, V of Formula XVII is N.

In some embodiments, W of Formula XVII is $CR_{11}$. In other embodiments, W of Formula XVII is N.

In some embodiments, U of Formula XVII is $C(R_{11})_2$. In other embodiments, U of Formula XVII is $NR_{10}$. In yet other embodiments, U of Formula XVII is O.

In some embodiments, $R_{11}$ of Formula XVII is H. In some embodiments, $R_{11}$ of Formula XVII is D. In some embodiments, $R_{11}$ of Formula XVII is fluoro. In some embodiments, $R_{11}$ of Formula XVII is $C_{1-6}$alkyl. In other embodiments, $R_{11}$ of Formula XVII is methyl or ethyl. In some embodiments, $R_{11}$ of Formula XVII is $C_{1-6}$alkoxide.

In some embodiments, $R_{10}$ of Formula XVII is H. In some embodiments, $R_{10}$ of Formula XVII is D. In some embodiments, $R_{10}$ of Formula XVII is $C_{1-6}$alkyl. In other embodiments, $R_{10}$ of Formula XVII is methyl or ethyl. In some embodiments, $R_{10}$ of Formula XVII is haloalkyl.

In some embodiments, when U of Formula XVII is $C(R_{11})_2$, each $R_{11}$ is H. In some embodiments, when U of Formula XVII is $C(R_{11})_2$, each $R_{11}$ is methyl. In some embodiments, when U of Formula XVII is $C(R_{11})_2$, one $R_{11}$ is methyl and one $R_{11}$ is hydrogen. In some embodiments, when U of Formula XVII is $C(R_{11})_2$, each $R_{10}$ is halogen. In some embodiments, when U of Formula XVII is $C(R_{11})_2$, one $R_{11}$ is halogen and one $R_{11}$ is hydrogen. In other embodiments, when U of Formula XVII is $C(R_{11})_2$, each $R_{11}$ is fluoro. In other embodiments, when U of Formula XVII is $C(R_{11})_2$, one $R_{11}$ is fluoro and one $R_{11}$ is hydrogen.

In some embodiments, U of Formula XVII is $NCH_3$. In other embodiments, U of Formula XVII is $NCH_2CH_3$.

In some embodiments, $R_4$ of Formula XVII is H. In some embodiments, $R_4$ of Formula XVII is D. In some embodiments, $R_4$ of Formula XVII is methyl. In some embodiments, $R_4$ of Formula XVII is haloalkyl.

In some embodiments, $R_5$ of Formula XVII is H. In some embodiments, $R_5$ of Formula XVII is D. In some embodiments, $R_5$ of Formula XVII is methyl. In some embodiments, $R_5$ of Formula XVII is haloalkyl.

In some embodiments, g in Formula XVII is 0, 1, 2 or 3. In some embodiments, g in Formula XVII is 0. In some embodiments, g in Formula XVII is 1. In other embodiments, g in Formula XVII is 2. In other embodiments, g in Formula XVII is 3.

In some embodiments, h in Formula XVII is 0, 1, 2 or 3. In some embodiments, h in Formula XVII is 0. In some embodiments, h in Formula XVII is 1. In other embodiments, h in Formula XVII is 2. In other embodiments, h in Formula XVII is 3.

In some embodiments, j in Formula XVII is 0, 1, 2 or 3. In some embodiments, j in Formula XVII is 0. In some embodiments, j in Formula XVII is 1. In other embodiments, j in Formula XVII is 2. In other embodiments, j in Formula XVII is 3.

In some embodiments, k in Formula XVII is 0, 1, 2 or 3. In some embodiments, k in Formula XVII is 0. In some embodiments, k in Formula XVII is 1. In other embodiments, k in Formula XVII is 2. In other embodiments, k in Formula XVII is 3.

In some embodiments, the compounds of Formula (I) are represented by compounds of Formula XVIII (XVIII)

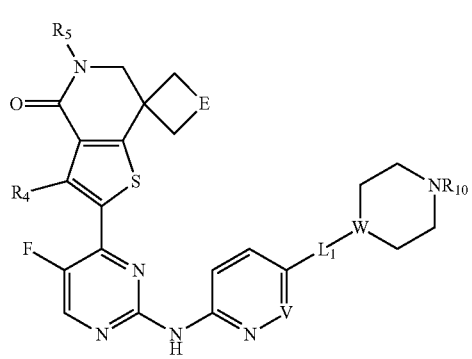

(XIX)

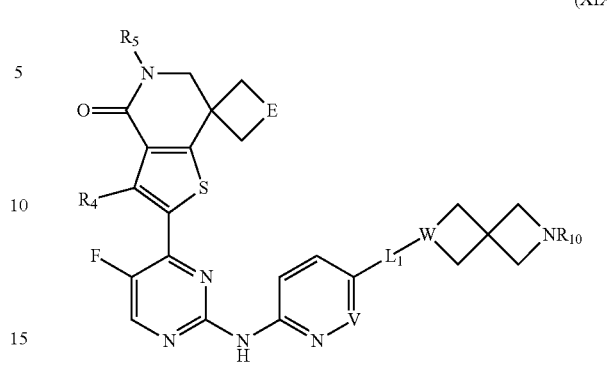

or a pharmaceutically acceptable salt thereof, wherein

E is a bond, —O—, —S—, $C(R^a)_2$, —C(=O)$NR^a$— or $NR^a$;

$L_1$ is a bond, —$CH_2$—, or C=O;

V is $CR_{11}$ or N;

W is $CR_{11}$ or N;

$R_4$ is H, D, Me or haloalkyl;

$R_5$ is H, D, Me or haloalkyl;

$R_{11}$ is H, D, fluoro, $C_{1-6}$alkyl, or $C_{1-6}$alkoxide and $R_{10}$ is H, D, $C_{1-6}$alkyl or haloalkyl.

In some embodiments, E in Formula XVIII is a bond, —O—, —S—, $C(R^a)_2$, —C(=O)NR— or $NR^a$. In some embodiments, E in Formula XVIII is a bond. In some embodiments, E in Formula XVIII is —O—. In some embodiments, E in Formula XVIII is —S—. In some embodiments, E in Formula XVIII is $C(R^a)_2$. In some embodiments, E in Formula XVIII is —C(=O)NR—. In some embodiments, E in Formula XVIII is $NR^a$.

In some embodiments, $L_1$ of Formula XVIII is a bond. In some embodiments, $L_1$ of Formula XVIII is —$CH_2$—. In some embodiments, $L_1$ of Formula XVIII is C=O.

In some embodiments, V of Formula XVIII is $CR_{11}$. In other embodiments, V of Formula XVIII is N.

In some embodiments, W of Formula XVIII is $CR_{11}$. In other embodiments, W of Formula XVIII is N.

In some embodiments, $R_4$ of Formula XVIII is H. In some embodiments, $R_4$ of Formula XVIII is D. In some embodiments, $R_4$ of Formula XVIII is methyl. In some embodiments, $R_4$ of Formula XVIII is haloalkyl.

In some embodiments, $R_5$ of Formula XVIII is H. In some embodiments, $R_5$ of Formula XVIII is D. In some embodiments, $R_5$ of Formula XVIII is methyl. In some embodiments, $R_5$ of Formula XVIII is haloalkyl.

In some embodiments, $R_{10}$ of Formula XVIII is H. In some embodiments, $R_{10}$ of Formula XVIII is D. In some embodiments, $R_{10}$ of Formula XVIII is $C_{1-6}$alkyl. In other embodiments, $R_{10}$ of Formula XVIII is methyl or ethyl. In some embodiments, $R_{10}$ of Formula XVIII is haloalkyl.

In some embodiments, $R_{11}$ of Formula XVIII is H. In some embodiments, $R_{11}$ of Formula XVIII is D. In some embodiments, $R_{11}$ of Formula XVIII is fluoro. In some embodiments, $R_{11}$ of Formula XVIII is $C_{1-6}$alkyl. In other embodiments, $R_{11}$ of Formula XVIII is methyl or ethyl. In some embodiments, $R_{11}$ of Formula XVIII is $C_{1-6}$alkoxide.

In some embodiments, the compounds of Formula (I) are represented by compounds of Formula XIX or a pharmaceutically acceptable salt thereof, wherein E is a bond, —O—, —S—, $C(R^a)_2$, —C(=O)$NR^a$— or $NR^a$;

$L_1$ is a bond, —$CH_2$—, or C=O;

V is $CR_{11}$ or N; and $R_4$ is H, D, Me or haloalkyl;

$R_5$ is H, D, Me or haloalkyl;

$R_{10}$ is H or $C_{1-6}$alkyl; and $R_{11}$ is H, D, fluoro, $C_{1-6}$alkyl, or $C_{1-6}$alkoxide.

In some embodiments, E in Formula XIX is a bond, —O—, —S—, $C(R^a)_2$, —C(=O)NR— or $NR^a$. In some embodiments, E in Formula XIX is a bond. In some embodiments, E in Formula XIX is —O—. In some embodiments, E in Formula XIX is —S—. In some embodiments, E in Formula XIX is $C(R^a)_2$. In some embodiments, E in Formula XIX is —C(=O)NR—. In some embodiments, E in Formula XIX is $NR^a$.

In some embodiments, $L_1$ of Formula XIX is a bond. In some embodiments, $L_1$ of Formula XIX is —$CH_2$—. In some embodiments, $L_1$ of Formula XIX is C=O.

In some embodiments, V of Formula XIX is $CR_{11}$. In other embodiments, V of Formula XIX is N.

In some embodiments, $R_4$ of Formula XIX is H. In some embodiments, $R_4$ of Formula XIX is D. In some embodiments, $R_4$ of Formula XIX is methyl. In some embodiments, $R_4$ of Formula XIX is haloalkyl.

In some embodiments, $R_5$ of Formula XIX is H. In some embodiments, $R_5$ of Formula XIX is D. In some embodiments, $R_5$ of Formula XIX is methyl. In some embodiments, $R_5$ of Formula XIX is haloalkyl.

In some embodiments, $R_{10}$ of Formula XIX is H. In some embodiments, $R_{10}$ of Formula XIX is D. In some embodiments, $R_{10}$ of Formula XIX is $C_{1-6}$alkyl. In other embodiments, $R_{10}$ of Formula XIX is methyl or ethyl. In some embodiments, $R_{10}$ of Formula XIX is haloalkyl.

In some embodiments, $R_{11}$ of Formula XIX is H. In some embodiments, $R_{11}$ of Formula XIX is D. In some embodiments, $R_{11}$ of Formula XIX is fluoro. In some embodiments, $R_{11}$ of Formula XIX is $C_{1-6}$alkyl. In other embodiments, $R_{11}$ of Formula XIX is methyl or ethyl. In some embodiments, $R_{11}$ of Formula XIX is $C_{1-6}$alkoxide.

In some embodiments, the compounds of Formula (I) are represented by compounds of Formula XX

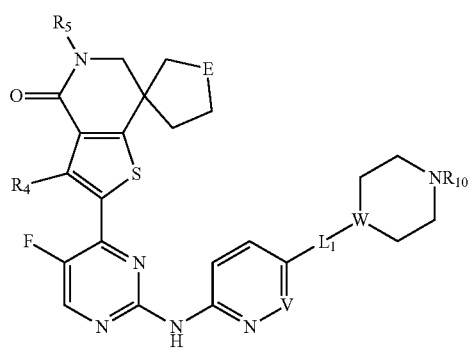 (XX)

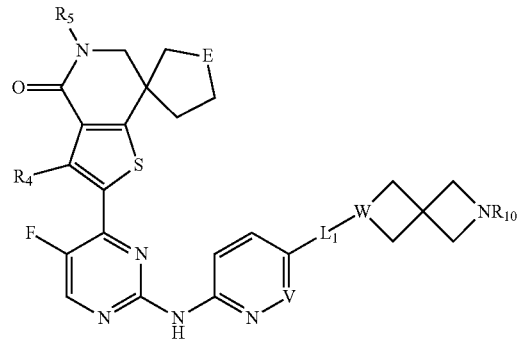 (XXI)

or a pharmaceutically acceptable salt thereof, wherein

E is a bond, —O—, —S—, $C(R^a)_2$, —C(=O)$NR^a$— or $NR^a$;

$L_1$ is a bond, —$CH_2$—, or C=O;

V is $CR_{11}$ or N;

W is $CR_{11}$ or N;

$R_4$ is H, D, Me or haloalkyl;

$R_5$ is H, D, Me or haloalkyl; $R_{11}$ is H, D, fluoro, $C_{1-6}$alkyl, or $C_{1-6}$alkoxide; and $R_{10}$ is H, D, $C_{1-6}$alkyl.

In some embodiments, E in Formula XX is a bond, —O—, —S—, $C(R^a)_2$, —C(=O)NR— or $NR^a$. In some embodiments, E in Formula XX is a bond. In some embodiments, E in Formula XX is —O—. In some embodiments, E in Formula XX is —S—. In some embodiments, E in Formula XX is $C(R^a)_2$. In some embodiments, E in Formula XX is —C(=O)NR—. In some embodiments, E in Formula XX is $NR^a$.

In some embodiments, $L_1$ of Formula XX is a bond. In some embodiments, $L_1$ of Formula XX is —$CH_2$—. In some embodiments, $L_1$ of Formula XX is C=O.

In some embodiments, V of Formula XX is $CR_{11}$. In other embodiments, V of Formula XX is N.

In some embodiments, W of Formula XX is $CR_{11}$. In other embodiments, W of Formula XX is N.

In some embodiments, $R_4$ of Formula XX is H. In some embodiments, $R_4$ of Formula XX is D. In some embodiments, $R_4$ of Formula XX is methyl. In some embodiments, $R_4$ of Formula XX is haloalkyl.

In some embodiments, $R_5$ of Formula XX is H. In some embodiments, $R_5$ of Formula XX is D. In some embodiments, $R_5$ of Formula XX is methyl. In some embodiments, $R_5$ of Formula XX is haloalkyl.

In some embodiments, $R_{10}$ of Formula XX is H. In some embodiments, $R_{10}$ of Formula XX is D. In some embodiments, $R_{10}$ of Formula XVIII is $C_{1-6}$alkyl. In other embodiments, $R_{10}$ of Formula XX is methyl or ethyl. In some embodiments, $R_{10}$ of Formula XX is haloalkyl.

In some embodiments, $R_{11}$ of Formula XX is H. In some embodiments, $R_{11}$ of Formula XX is D. In some embodiments, $R_{11}$ of Formula XX is fluoro. In some embodiments, $R_{11}$ of Formula XX is $C_{1-6}$alkyl. In other embodiments, $R_{11}$ of Formula XX is methyl or ethyl. In some embodiments, $R_{11}$ of Formula XX is $C_{1-6}$alkoxide.

In some embodiments, the compounds of Formula (I) are represented by compounds of Formula XXI or a pharmaceutically acceptable salt thereof, wherein E is a bond, —O—, —S—, $C(R^a)_2$, —C(=O)$NR^a$— or $NR^a$;

$L_1$ is a bond, —$CH_2$—, or C=O;

V is $CR_{11}$ or N;

$R_4$ is H, D, Me or haloalkyl;

$R_5$ is H, D, Me or haloalkyl;

$R_{10}$ is H or $C_{1-6}$alkyl; and $R_{11}$ is H, D, fluoro, $C_{1-6}$alkyl, or $C_{1-6}$alkoxide.

In some embodiments, E in Formula XXI is a bond, —O—, —S—, $C(R^a)_2$, —C(=O)NR— or $NR^a$. In some embodiments, E in Formula XXI is a bond. In some embodiments, E in Formula XXI is —O—. In some embodiments, E in Formula XXI is —S—. In some embodiments, E in Formula XXI is $C(R^a)_2$. In some embodiments, E in Formula XXI is —C(=O)NR—. In some embodiments, E in Formula XXI is $NR^a$.

In some embodiments, $L_1$ of Formula XXI is a bond. In some embodiments, $L_1$ of Formula XXI is —$CH_2$—. In some embodiments, $L_1$ of Formula XXI is C=O.

In some embodiments, V of Formula XXI is $CR_{11}$. In other embodiments, V of Formula XXI is N.

In some embodiments, $R_4$ of Formula XXI is H. In some embodiments, $R_4$ of Formula XXI is D. In some embodiments, $R_4$ of Formula XXI is methyl. In some embodiments, $R_4$ of Formula XXI is haloalkyl.

In some embodiments, $R_5$ of Formula XXI is H. In some embodiments, $R_5$ of Formula XXI is D. In some embodiments, $R_5$ of Formula XXI is methyl. In some embodiments, $R_5$ of Formula XXI is haloalkyl.

In some embodiments, $R_{10}$ of Formula XXI is H. In some embodiments, $R_{10}$ of Formula XXI is D. In some embodiments, $R_{10}$ of Formula XXI is $C_{1-6}$alkyl. In other embodiments, $R_{10}$ of Formula XXI is methyl or ethyl. In some embodiments, $R_{10}$ of Formula XXI is haloalkyl.

In some embodiments, $R_{11}$ of Formula XXI is H. In some embodiments, $R_{11}$ of Formula XXI is D. In some embodiments, $R_{11}$ of Formula XXI is fluoro. In some embodiments, $R_{11}$ of Formula XXI is $C_{1-6}$alkyl. In other embodiments, $R_{11}$ of Formula XXI is methyl or ethyl. In some embodiments, $R_{11}$ of Formula XXI is $C_{1-6}$alkoxide.

In some embodiments, the compounds of Formula (I) are represented by compounds of Formula XXII

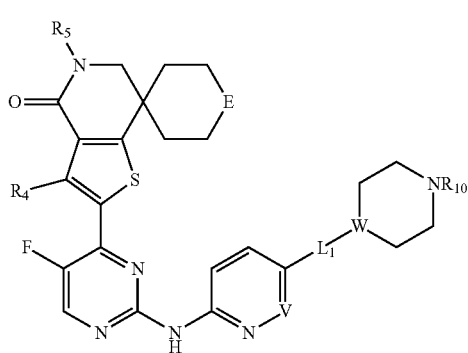

(XXII)

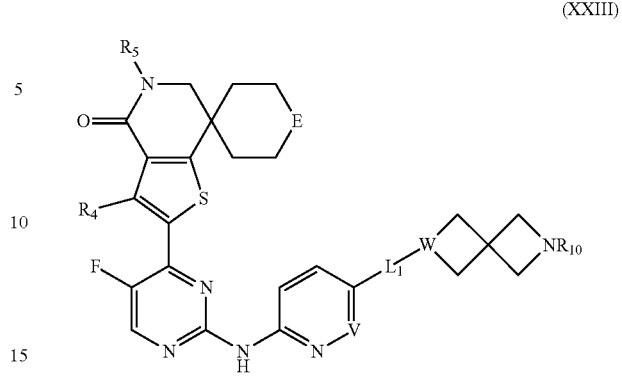

(XXIII)

or a pharmaceutically acceptable salt thereof, wherein

E is a bond, —O—, —S—, C(R$^a$)$_2$, —C(=O)Na— or NR$^a$;

L$_1$ is a bond, —CH$_2$—, or C=O;

V is CR$_{11}$ or N;

W is CR$_{11}$ or N;

R$_4$ is H, D, Me or haloalkyl;

R$_5$ is H, D, Me or haloalkyl;

R$_1$ is H, D, fluoro, C$_{1-6}$alkyl, or C$_{1-6}$alkoxide; and

R$_{10}$ is H, D, C$_{1-6}$alkyl or haloalkyl.

In some embodiments, E in Formula XXII is a bond, —O—, —S—, C(R$^a$)$_2$, —C(=O)NR— or NR$^a$. In some embodiments, E in Formula XXII is a bond. In some embodiments, E in Formula XXII is —O—. In some embodiments, E in Formula XXII is —S—. In some embodiments, E in Formula XXII is C(R$^a$)$_2$. In some embodiments, E in Formula XXII is —C(=O)NR—. In some embodiments, E in Formula XXII is NR$^a$.

In some embodiments, L$_1$ of Formula XXII is a bond. In some embodiments, L$_1$ of Formula XXII is —CH$_2$—. In some embodiments, L$_1$ of Formula XXII is C=O.

In some embodiments, V of Formula XXII is CR$_{11}$. In other embodiments, V of Formula XXII is N.

In some embodiments, W of Formula XXII is CR$_{11}$. In other embodiments, W of Formula XXII is N.

In some embodiments, R$_4$ of Formula XXII is H. In some embodiments, R$_4$ of Formula XXII is D. In some embodiments, R$_4$ of Formula XXII is methyl. In some embodiments, R$_4$ of Formula XXII is haloalkyl.

In some embodiments, R$_5$ of Formula XXII is H. In some embodiments, R$_5$ of Formula XXII is D. In some embodiments, R$_5$ of Formula XXII is methyl. In some embodiments, R$_5$ of Formula XXII is haloalkyl.

In some embodiments, R$_{10}$ of Formula XXII is H. In some embodiments, R$_{10}$ of Formula XXII is D. In some embodiments, R$_{10}$ of Formula XXII is C$_{1-6}$alkyl. In other embodiments, R$_{10}$ of Formula XXII is methyl or ethyl. In some embodiments, R$_{10}$ of Formula XXII is haloalkyl.

In some embodiments, R$_{11}$ of Formula XXII is H. In some embodiments, R$_{11}$ of Formula XXII is D. In some embodiments, R$_{11}$ of Formula XXII is fluoro. In some embodiments, R$_{11}$ of Formula XXII is C$_{1-6}$alkyl. In other embodiments, R$_{11}$ of Formula XXII is methyl or ethyl. In some embodiments, R$_{11}$ of Formula XXII is C$_{1-6}$alkoxide.

In some embodiments, the compounds of Formula (I) are represented by compounds of Formula XXIII or a pharmaceutically acceptable salt thereof, wherein E is a bond, —O—, —S—, C(R$^a$)$_2$, —C(=O)NR$^a$— or NR$^a$;

L$_1$ is a bond, —CH$_2$—, or C=O;

V is CR$_{11}$ or N;

R$_4$ is H, D, Me or haloalkyl;

R$_5$ is H, D, Me or haloalkyl;

R$_{10}$ is H, D, C$_{1-6}$alkyl or haloalkyl; and

R$_{11}$ is H, D, fluoro, C$_{1-6}$alkyl, or C$_{1-6}$alkoxide.

In some embodiments, E in Formula XXIII is a bond, —O—, —S—, C(R$^a$)$_2$, —C(=O)NR— or NR$^a$. In some embodiments, E in Formula XXIII is a bond. In some embodiments, E in Formula XXIII is —O—. In some embodiments, E in Formula XXIII is —S—. In some embodiments, E in Formula XXIII is C(R$^a$)$_2$. In some embodiments, E in Formula XXIII is —C(=O)NR—. In some embodiments, E in Formula XXIII is NR$^a$.

In some embodiments, L$_1$ of Formula XXIII is a bond. In some embodiments, L$_1$ of Formula XXIII is —CH$_2$—. In some embodiments, L$_1$ of Formula XXIII is C=O.

In some embodiments, V of Formula XXIII is CR$_{11}$. In other embodiments, V of Formula XXIII is N. In some embodiments, R$_4$ of Formula XXIII is H. In some embodiments, R$_4$ of Formula XXIII is D. In some embodiments, R$_4$ of Formula XXIII is methyl. In some embodiments, R$_4$ of Formula XXIII is haloalkyl.

In some embodiments, R$_5$ of Formula XXIII is H. In some embodiments, R$_5$ of Formula XXIII is D. In some embodiments, R$_5$ of Formula XXIII is methyl. In some embodiments, R$_5$ of Formula XXIII is haloalkyl.

In some embodiments, R$_{10}$ of Formula XXIII is H. In some embodiments, R$_{10}$ of Formula XXIII is D. In some embodiments, R$_{10}$ of Formula XXIII is C$_{1-6}$alkyl. In other embodiments, R$_{10}$ of Formula XXIII is methyl or ethyl.

In some embodiments, R$_{11}$ of Formula XXIII is H. In some embodiments, R$_{11}$ of Formula XXIII is D. In some embodiments, R$_{11}$ of Formula XXIII is fluoro. In some embodiments, R$_{11}$ of Formula XXIII is C$_{1-6}$alkyl. In other embodiments, R$_{11}$ of Formula XXIII is methyl or ethyl. In some embodiments, R$_{11}$ of Formula XXIII is C$_{1-6}$alkoxide.

In yet further embodiments, the compounds of Formula (I) are:

2'-(2-((5-(6-Ethyl-2,6-diazaspiro[3.3]heptan-2-yl)pyridin-2-yl)amino)-5-fluoropyrimidin-4-yl)-5'-methyl-5',6'-dihydro-4'H-spiro[cyclopentane-1,7'-thieno[3,2-c]pyridin]-4'-one;

2'-(5-Fluoro-2-((5-(1-methylpiperidin-4-yl)pyridin-2-yl)amino)pyrimidin-4-yl)-5'-methyl-5',6'-dihydro-4'H-spiro[cyclopentane-1,7'-thieno[3,2-c]pyridin]-4'-one;

2'-(2-((5-(4-Ethylpiperazin-1-yl)pyridin-2-yl)amino)-5-fluoropyrimidin-4-yl)-5'-methyl-5',6'-dihydro-4'H-spiro[cyclopentane-1,7'-thieno[3,2-c]pyridin]-4'-one;

2'-(2-((5-(6-Ethyl-2,6-diazaspiro[3.3]heptan-2-yl)pyridin-2-yl)amino)-5-fluoropyrimidin-4-yl)-5'-methyl-5',6'-dihydro-4'H-spiro[cyclohexane-1,7'-thieno[3,2-c]pyridin]-4'-one 2'-(5-Fluoro-2-((5-(1-methylpiperidin-4-yl)pyridin-2-yl)amino)pyrimidin-4-yl)-5'-methyl-5',6'-dihydro-4'H-spiro[cyclohexane-1,7'-thieno[3,2-c]pyridin]-4'-one;

or a pharmaceutically acceptable salt thereof.

In yet further embodiments, the compounds of Formula (I) are:

2'-(5-Fluoro-2-((5-(1-methylpiperidin-4-yl)pyridin-2-yl)amino) pyrimidin-4-yl)-3',5'-dimethylspiro[cyclopropane-1,6'-thieno[2,3-c]pyrrol]-4'(5'H)-one;

5'-Ethyl-2'-(5-fluoro-2-((5-(1-methylpiperidin-4-yl)pyridin-2-yl)amino) pyrimidin-4-yl)-3'-methylspiro[cyclopropane-1,6'-thieno[2,3-c]pyrrol]-4'(5'H)-one;

2'-(5-Fluoro-2-((5-(1-methylpiperidin-4-yl)pyridin-2-yl)amino) pyrimidin-4-yl)-5'-methyl-spiro[cyclopropane-1,6'-thieno[2,3-c]pyrrol]-4'(5'H)-one;

3'-chloro-2'-(5-Fluoro-2-((5-(1-methylpiperidin-4-yl)pyridin-2-yl) amino)pyrimidin-4-yl)-5'-methylspiro[cyclopropane-1,6'-thieno[2,3-c]pyrrol]-4'(5'H)-one;

2'-(5-Fluoro-2-((5-(1-methyl-piperidin-4-yl)pyridin-2-yl) amino) pyrimidin-4-yl)-5'-methyl-3'-(trifluoromethyl)spiro [cyclopropane-1,6'-thieno[2,3-c] pyrrol]-4'(5'H)-one;

2'-(5-Chloro-2-((5-(1-methyl-piperidin-4-yl)pyridin-2-yl) amino) pyrimidin-4-yl)-5'-ethyl-3'-methylspiro[cyclopropane-1,6'-thieno[2,3-c]pyrrol]-4'(5'H)-one;

2'-(2-((5-(6-Ethyl-2,6-diazaspiro[3.3]heptan-2-yl)pyridin-2-yl)amino)-5-fluoropyrimidin-4-yl)-3',5'-dimethylspiro[cyclopropane-1,6'-thieno [2,3-c]pyrrol]-4'(5'H)-one;

2'-(2-((5-((4-Ethylpiperazin-1-yl)methyl)pyridin-2-yl)amino)-5-fluoro-pyrimidin-4-yl)-3',5'-dimethylspiro[cyclopropane-1,6'-thieno[2,3-c] pyrrol]-4'(5'H)-one;

2'-(5-Fluoro-2-((5-(6-methyl-2,6-diazaspiro[3.4]octan-2-yl)pyridin-2-yl)amino)pyrimidin-4-yl)-3',5'-dimethylspiro[cyclopropane-1,6'-thieno [2,3-c]pyrrol]-4'(5'H)-one;

2'-(5-Fluoro-2-((5-(1-methylpiperidin-3-yl)pyridin-2-yl)amino) pyrimidin-4-yl)-3',5'-dimethylspiro[cyclopropane-1,6'-thieno[2,3-c] pyrrol]-4'(5'H)-one;

2'-(5-Fluoro-2-((5-(1-isopropylpyrrolidin-3-yl)pyridin-2-yl)amino) pyrimidin-4-yl)-3',5'-dimethylspiro[cyclopropane-1,6'-thieno[2,3-c] pyrrol]-4'(5'H)-one;

5'-Ethyl-2'-(5-methyl-2-((5-((3aR,6aS)-5-methylhexahydropyrrolo[3,4-c]pyrrol-2(1H)-yl)pyridin-2-yl)amino)pyrimidin-4-yl)spiro [cyclopropane-1,6'-thieno[2,3-c]pyrrol]-4'(5'H)-one;

5'-Ethyl-2'-[5-methyl-2-[[5-(1-methylpiperidin-3-yl)pyridin-2-yl] amino]pyrimidin-4-yl]spiro[cyclopropane-1,6'-thieno[2,3-c]pyrrole]-4'-one;

5'-Ethyl-2'-[5-methyl-2-[[5-(1-methylpiperidin-4-yl)pyridin-2-yl] amino]pyrimidin-4-yl]spiro[cyclopropane-1,6'-thieno[2,3-c]pyrrole]-4'-one;

2'-(5-Fluoro-2-((5-(1-methylpiperidin-4-yl)pyridin-2-yl)amino) pyrimidin-4-yl)-5'-methyl-spiro[cyclopentane-1,6'-thieno[2,3-c]pyrrol]-4'(5'H)-one;

5'-Ethyl-2'-(2-((5-(6-ethyl-2,6-diazaspiro[3.3]heptan-2-yl)pyridin-2-yl)amino)-5-fluoro-pyrimidin-4-yl)spiro[cyclopentane-1,6'-thieno[2,3-c]pyrrol]-4'(5'H)-one;

5'-Ethyl-2'-(5-fluoro-2-((5-(1-methylpiperidin-4-yl)pyridin-2-yl)amino) pyrimidin-4-yl)spiro [cyclopentane-1,6'-thieno[2,3-c]pyrrol]-4'(5'H)-one;

2'-(2-((5-(1-Ethylpiperidin-4-yl)pyridin-2-yl)amino)-5-fluoro-pyrimidin-4-yl)-5'-methylspiro [cyclopentane-1,6'-thieno[2,3-c]pyrrol]-4'(5'H)-one;

2'-(2-((5-(6-Ethyl-2,6-diazaspiro [3.3]heptan-2-yl)pyridin-2-yl)amino)-5-fluoropyrimidin-4-yl)-5'-methylspiro[cyclopentane-1,6'-thieno[2,3-c]pyrrol]-4'(5'H)-one;

2'-(5-Fluoro-2-((5-(1-methylpiperidin-4-yl)pyridin-2-yl) amino) pyrimidin-4-yl)-3',5'-dimethylspiro[cyclopentane-1,6'-thieno[2,3-c]pyrrol]-4'(5'H)-one;

2'-(5-Fluoro-2-((5-(1-methylpiperidin-4-yl)pyridin-2-yl) amino) pyrimidin-4-yl)-5'-methyl-3'-(trifluoromethyl)spiro [cyclopentane-1,6'-thieno[2,3-c]pyrrol]-4'(5'H)-one;

3'-Chloro-2'-(5-fluoro-2-((5-(1-methylpiperidin-4-yl)pyridin-2-yl)amino)pyrimidin-4-yl)-5'-methylspiro[cyclopentane-1,6'-thieno[2,3-c]pyrrol]-4'(5'H)-one;

2'-(5-Fluoro-2-((5-(1-methylpiperidin-4-yl)pyridin-2-yl) amino) pyrimidin-4-yl)-3',5'-dimethyl-5',6'-dihydro-4'H-spiro[cyclopropane-1,7'-thieno[3,2-c]pyridin]-4'-one;

2'-(5-Fluoro-2-((5-(1-methyl-piperidin-4-yl)pyridin-2-yl) amino) pyrimidin-4-yl)-5'-methyl-5',6'-dihydro-4'H-spiro [cyclo-propane-1,7'-thieno[3,2-c]pyridin]-4'-one;

2'-(5-Fluoro-2-((5-(1-methyl-piperidin-3-yl)pyridin-2-yl) amino) pyrimidin-4-yl)-3',5'-dimethyl-5',6'-dihydro-4'H-spiro [cyclopropane-1,7'-thieno[3,2-c] pyridin]-4'-one;

2'-(2-((5-(1-Ethylpyrrolidin-3-yl)pyridin-2-yl)amino)-5-fluoro-pyrimidin-4-yl)-5'-methyl-5',6'-dihydro-4'H-spiro [cyclo-propane-1,7'-thieno[3,2-c]pyridin]-4'-one;

2'-(5-Fluoro-2-((5-(1-(tetrahydrofuran-3-yl)piperidin-4-yl) pyridin-2-yl)amino)pyrimidin-4-yl)-3',5'-dimethyl-5',6'-dihydro-4'H-spiro [cyclopropane-1,7'-thieno[3,2-c]pyridin]-4'-one;

2'-(5-Fluoro-2-((5-(6-methyl-3,6-diazabicyclo[3.1.1]heptan-3-yl) pyridin-2-yl)amino) pyrimidin-4-yl)-3',5'-dimethyl-5',6'-dihydro-4'H-spiro[cyclopropane-1,7'-thieno[3,2-c]pyridin]-4'-one;

2'-(5-Fluoro-2-((5-(6-isopropyl-2,6-diazaspiro[3.3]heptan-2-yl)pyridin-2-yl)amino) pyrimidin-4-yl)-3',5'-dimethyl-5',6'-dihydro-4'H-spiro [cyclopropane-1,7'-thieno[3,2-c]pyridin]-4'-one;

2'-(5-Fluoro-2-((5-(6-methyl-2,6-diazaspiro[3.4]octan-2-yl)pyridin-2-yl)amino)pyrimidin-4-yl)-3',5'-dimethyl-5',6'-dihydro-4'H-spiro [cyclopropane-1,7'-thieno[3,2-c]pyridin]-4'-one;

2'-(5-Fluoro-2-((5-(2-methyl-2,7-diazaspiro[3.5]nonan-7-yl)pyridin-2-yl)amino)pyrimidin-4-yl)-3',5'-dimethyl-5',6'-dihydro-4'H-spiro [cyclopropane-1,7'-thieno[3,2-c]pyridin]-4'-one;

2'-(5-Fluoro-2-((5-(7-methyl-2,7-diazaspiro[4.4]nonan-2-yl)pyridin-2-yl)amino)pyrimidin-4-yl)-3',5'-dimethyl-5',6'-dihydro-4'H-spiro [cyclopropane-1,7'-thieno[3,2-c]pyridin]-4'-one;

2'-(2-((5-((4-Ethylpiperazin-1-yl)methyl)pyridin-2-yl)amino)-5-fluoropyrimidin-4-yl)-3',5'-dimethyl-5',6'-dihydro-4'H-spiro [cyclopropane-1,7'-thieno[3,2-c]pyridin]-4'-one;

2'-(2-((5-((3aS,6aS)-5-Ethylhexahydropyrrolo[3,4-c]pyrrol-2(1H)-yl)pyridin-2-yl)amino)-5-fluoropyrimidin-4-yl)-3',5'-dimethyl-5',6'-dihydro-4'H-spiro[cyclopropane-1,7'-thieno[3,2-c]pyridin]-4'-one;

5-Methyl-2-[4-[[5-(1-methylpiperidin-4-yl)pyridin-2-yl]amino]-5-(trifluoromethyl) pyrimidin-2-yl]spiro[6H-thieno[3,2-c]pyridine-7,1'-cyclopropane]-4-one;

2-[2-[[5-(6-Ethyl-2,6-diazaspiro[3.3]heptan-2-yl)pyridin-2-yl]amino]-5-methylpyrimidin-4-yl]-5-methylspiro[6H-thieno[3,2-c]pyridine-7,1'-cyclopropane]-4-one;

2-[2-[[5-(6-Ethyl-2,6-diazaspiro[3.3]heptan-2-yl)pyridin-2-yl]amino]-5-methylpyrimidin-4-yl]-3,5-dimethylspiro[6H-thieno [3,2-c]pyridine-7,1'-cyclopropane]-4-one;

5-methyl-2-[5-Methyl-2-[[5-(2-methyl-2,7-diazaspiro[3.5]nonan-7-yl)pyridin-2-yl]amino]pyrimidin-4-yl]spiro[6H-thieno[3,2-c]pyridine-7,1'-cyclopropane]-4-one;

2-[5-Chloro-2-[[5-(6-ethyl-2,6-diazaspiro[3.3]heptan-2-yl)pyridin-2-yl]amino]pyrimidin-4-yl]-3,5-dimethylspiro[6H-thieno[3,2-c]pyridine-7,1'-cyclopropane]-4-one;

2-[5-Chloro-2-[[5-(6-ethyl-2,6-diazaspiro[3.3]heptan-2-yl)pyridin-2-yl]amino]pyrimidin-4-yl]-5-methylspiro[6H-thieno[3,2-c]pyridine-7,1'-cyclopropane]-4-one;

2'-(5-Fluoro-2-((5-(6-methyl-3,6-diazabicyclo[3.1.1]heptan-3-yl) pyridin-2-yl)amino) pyrimidin-4-yl)-5'-methyl-5',6'-dihydro-4'H-spiro[cyclobutane-1,7'-thieno[3,2-c]pyridin]-4'-one;

2'-(5-Fluoro-2-((5-(1-methyl-piperidin-4-yl)pyridin-2-yl)amino) pyrimidin-4-yl)-5'-methyl-5',6'-dihydro-4'H-spiro[cyclobutane-1,7'-thieno[3,2-c]pyridin]-4'-one;

2'-(5-Fluoro-2-((5-(1-methyl-piperidin-4-yl)pyridin-2-yl)amino) pyrimidin-4-yl)-3',5'-dimethyl-5',6'-dihydro-4'H-spiro[cyclobutane-1,7'-thieno[3,2-c]pyridin]-4'-one;

2'-(2-((5-(1-(2,2-difluoroethyl) piperidin-4-yl)pyridin-2-yl)amino)-5-fluoropyrimidin-4-yl)-5'-methyl-5',6'-dihydro-4'H-spiro[cyclobutane-1,7'-thieno[3,2-c]pyridin]-4'-one;

2'-(5-Fluoro-2-((5-(4-methyl-piperazin-1-yl)pyridin-2-yl)amino) pyrimidin-4-yl)-5'-methyl-5',6'-dihydro-4'H-spiro[cyclobutane-1,7'-thieno[3,2-c]pyridin]-4'-one;

2'-(2-((5-(1-Ethyl-1,6-diazaspiro [3.3]heptan-6-yl)pyridin-2-yl) amino)-5-fluoropyrimidin-4-yl)-5'-methyl-5',6'-dihydro-4'H-spiro [cyclobutane-1,7'-thieno[3,2-c]pyridin]-4'-one;

2'-(2-((5-(6-Ethyl-2,6-diazaspiro [3.3]heptan-2-yl)pyridin-2-yl) amino)-5-fluoropyrimidin-4-yl)-3',5'-dimethyl-5',6'-dihydro-4'H-spiro[cyclobutane-1,7'-thieno[3,2-c]pyridin]-4'-one;

2'-(2-((5-(1,4-diazabicyclo [3.2.2]nonan-4-yl)pyridin-2-yl)amino)-5-fluoropyrimidin-4-yl)-5'-methyl-5',6'-dihydro-4'H-spiro [cyclobutane-1,7'-thieno[3,2-c] pyridin]-4'-one;

2'-(5-Fluoro-2-((5-(6-methyl-2,6-diazaspiro[3.4]octan-2-yl)pyridin-2-yl)amino)pyrimidin-4-yl)-3',5'-dimethyl-5',6'-dihydro-4'H-spiro [cyclobutane-1,7'-thieno[3,2-c]pyridin]-4'-one;

2'-(5-Fluoro-2-((5-(7-methyl-2,7-diazaspiro[4.4]nonan-2-yl)pyridin-2-yl)amino)pyrimidin-4-yl)-3',5'-dimethyl-5',6'-dihydro-4'H-spiro [cyclobutane-1,7'-thieno[3,2-c]pyridin]-4'-one;

2'-(2-((5-((4-Ethylpiperazin-1-yl)methyl)pyridin-2-yl)amino)-5-fluoropyrimidin-4-yl)-3',5'-dimethyl-5',6'-dihydro-4'H-spiro [cyclobutane-1,7'-thieno[3,2-c]pyridin]-4'-one;

2'-(5-Fluoro-2-((5-(((3aR,6aS)-5-methylhexahydropyrrolo[3,4-c]pyrrol-2(1H)-yl)pyridin-2-yl)amino)pyrimidin-4-yl)-3',5'-dimethyl-5',6'-dihydro-4'H-spiro[cyclobutane-1,7'-thieno[3,2-c]pyridin]-4'-one;

5-Methyl-2-[4-[[5-(1-methylpiperidin-4-yl)pyridin-2-yl]amino]-5-(trifluoromethyl) pyrimidin-2-yl]spiro[6H-thieno[3,2-c]pyridine-7,1'-cyclobutane]-4-one;

5-Methyl-2-[5-methyl-2-[[5-(1-methylpiperidin-4-yl)pyridin-2-yl] amino]pyrimidin-4-yl]spiro[6H-thieno[3,2-c]pyridine-7,1'-cyclobutane]-4-one;

2-[5-Chloro-2-[[5-(1-methyl-piperidin-4-yl)pyridin-2-yl] amino] pyrimidin-4-yl]-3,5-dimethylspiro[6H-thieno[3,2-c]pyridine-7,1'-cyclobutane]-4-one;

2'-(5-Fluoro-2-((5-(6-(methyl-d3)-2,6-diazaspiro[3.3]heptan-2-yl)pyridin-2-yl)amino) pyrimidin-4-yl)-5'-(methyl-d3)-5',6'-dihydro-4'H-spiro[cyclopentane-1,7'-thieno[3,2-c]pyridin]-4'-one;

2'-(5-Fluoro-2-((5-(morpholino-pyridin-2-yl)amino)pyrimidin-4-yl)-5'-methyl-5',6'-dihydro-4'H-spiro [cyclopentane-1,7'-thieno[3,2-c] pyridin]-4'-one;

2'-(5-Fluoro-2-((5-(1-methyl-piperidin-4-yl)pyridin-2-yl) amino) pyrimidin-4-yl)-3',5'-dimethyl-5',6'-dihydro-4'H-spiro [cyclopentane-1,7'-thieno[3,2-c] pyridin]-4'-one;

2-[2-[[5-(1,4-diazabicyclo [3.2.2]nonan-4-yl)pyridin-2-yl] amino]-5-fluoropyrimidin-4-yl]-5-methylspiro[6H-thieno [3,2-c] pyridine-7,1'-cyclopentane]-4-one;

2-[5-Fluoro-2-[[5-[4-methyl-2-(trifluoromethyl)piperazin-1-yl]pyridin-2-yl]amino]pyrimidin-4-yl]-5-methylspiro[6H-thieno[3,2-c]pyridine-7,1'-cyclopentane]-4-one;

2'-[5-Fluoro-2-[[5-(1-methylpiperidin-4-yl)pyridin-2-yl] amino] pyrimidin-4-yl]-3'-methyl-5'-(trideuteriomethyl)spiro[cyclopropane-1,6'-thieno[2,3-c]pyrrole]-4'-one;

2'-[2-[[5-(1-Ethylpyrrolidin-3-yl)pyridin-2-yl]amino]-5-fluoropyrimidin-4-yl]-3',5'-dimethylspiro[cyclopropane-1,6'-thieno [2,3-c]pyrrole]-4'-one;

(E)-2'-(2-((5-(1-(But-2-en-1-yl)pyrrolidin-3-yl)pyridin-2-yl)amino)-5-fluoropyrimidin-4-yl)-3',5'-dimethylspiro [cyclopropane-1,6'-thieno [2,3-c]pyrrol]-4'(5'H)-one;

2-[5-Fluoro-2-[[5-(1-methylpiperidin-4-yl)pyridin-2-yl] amino] pyrimidin-4-yl]-3-methyl-spiro[5H-thieno[2,3-c] pyrrole-6,1'-cyclopropane]-4-one;

5'-Ethyl-2'-(2-((5-(6-ethyl-2,6-diazaspiro[3.3]heptan-2-yl)pyridin-2-yl)amino)-5-fluoropyrimidin-4-yl)-5',6'-dihydro-4'H-spiro [cyclohexane-1,7'-thieno[3,2-c]pyridin]-4'-one;

2''-(2-((5-(6-Ethyl-2,6-diazaspiro[3.3]heptan-2-yl)pyridin-2-yl)amino)-5-fluoropyrimidin-4-yl)-5''-methyl-5'',6''-dihydro-4'H-dispiro [cyclopropane-1,1'-cyclobutane-3',7''-thieno[3,2-c]pyridin]-4'''-one;

2'-(5-Fluoro-2-((5-(1-methylpiperidin-4-yl)pyridin-2-yl)amino) pyrimidin-4-yl)-5'-methyl-2,3,5,5',6,6'-hexahydro-4'H-spiro[pyran-4,7'-thieno[3,2-c]pyridin]-4'-one;

5'-Methyl-2'-(5-methyl-2-((5-(1-methylpiperidin-4-yl)pyridin-2-yl) amino)pyrimidin-4-yl)spiro[cyclopropane-1,6'-thieno[2,3-c]pyrrol]-4'(5'H)-one;

2'-(2-((5-(2-Ethyl-2-azaspiro[3.3]heptan-6-yl)pyridin-2-yl)amino)-5-fluoropyrimidin-4-yl)-3',5'-dimethylspiro[cyclopropane-1,6'-thieno [2,3-c]pyrrol]-4'(5'H)-one;

2-[2-[[6-(6-Ethyl-2,6-diazaspiro[3.3]heptan-2-yl)pyridazin-3-yl]amino]-5-fluoropyrimidin-4-yl]-5-methylspiro[6H-thieno[3,2-c]pyridine-7,1'-cyclopentane]-4-one;

2'-(5-Fluoro-2-((6-(1-isopropylpiperidin-4-yl)pyridazin-3-yl)amino) pyrimidin-4-yl)-3',5'-dimethyl-5',6'-dihydro-4'H-spiro[cyclopropane-1,7'-thieno[3,2-c]pyridin]-4'-one;

3,3-Difluoro-2'-(5-fluoro-2-((5-(1-methylpiperidin-4-yl)pyridin-2-yl)amino) pyrimidin-4-yl)-5'-methyl-5',6'-dihydro-4'H-spiro [cyclobutane-1,7'-thieno[3,2-c]pyridin]-4'-one;

2'-(2-((5-(6-Ethyl-2,6-diazaspiro[3.3]heptan-2-yl)pyridin-2-yl)amino)-5-fluoropyrimidin-4-yl)-3,3-difluoro-5'-methyl-5',6'-dihydro-4'H-spiro[cyclobutane-1,7'-thieno [3,2-c]pyridin]-4'-one 2-[2-[[5-(4-Ethyl-2-oxopiperazin-1-yl)pyridin-2-yl]amino]-5-fluoropyrimidin-4-yl]-5-methylspiro[6H-thieno[3,2-c]pyridine-7,1'-cyclopentane]-4-one;

2-[5-Fluoro-2-[[6-(1-methylpiperidin-4-yl)pyridazin-3-yl] amino] pyrimidin-4-yl]-5-methylspiro[6H-thieno[3,2-c]pyridine-7,1'-cyclopentane]-4-one; or a pharmaceutically acceptable salt thereof.

In yet further embodiments, the compounds of Formula (I) are:

6'-(2-((5-(6-Ethyl-2,6-diazaspiro[3.3]heptan-2-yl)pyridin-2-yl)amino)-5-fluoropyrimidin-4-yl)-2'-methyl-2',3'-dihydro-1'H-spiro [cyclopentane-1,4'-isoquinolin]-1'-one;

6'-(5-Fluoro-2-((5-(1-methyl-piperidin-4-yl)pyridin-2-yl) amino) pyrimidin-4-yl)-2'-methyl-2',3'-dihydro-1'H-spiro [cyclopentane-1,4'-isoquinolin]-1'-one;

6'-(2-((5-((4-Ethylpiperazin-1-yl)methyl)pyridin-2-yl) amino)-5-fluoropyrimidin-4-yl)-2'-methyl-2',3'-dihydro-1'H-spiro [cyclo-pentane-1,4'-isoquinolin]-1'-one;

6'-(2-((5-(6-Ethyl-2,6-diazaspiro [3.3]heptan-2-yl)pyridin-2-yl) amino)-5-fluoropyrimidin-4-yl)-2'-methyl-2',3'-dihydro-1'H-spiro [cyclobutane-1,4'-isoquinolin]-1'-one;

2'-(5-Fluoro-2-((5-(1-methylpiperidin-4-yl)pyridin-2-yl) amino) pyrimidin-4-yl)-1',5'-dimethyl-5',6'-dihydrospiro [cyclopentane-1,7'-pyrrolo[3,2-c]pyridin]-4'(1'H)-one;

6'-(2-((5-(6-Ethyl-2,6-diazaspiro[3.3]heptan-2-yl)pyridin-2-yl)amino)-5-fluoropyrimidin-4-yl)-2'-methylspiro[cyclopentane-1,1'-isoindolin]-3'-one;

6'-(5-Fluoro-2-((5-(1-methylpiperidin-4-yl)pyridin-2-yl) amino) pyrimidin-4-yl)-2'-methylspiro[cyclopentane-1,1'-isoindolin]-3'-one; or a pharmaceutically acceptable salt thereof.

It will be apparent that the compounds of Formula I, including all subgenera described herein, may have multiple stereogenic centers. As a result, there exist multiple stereoisomers (enantiomers and diastereomers) of the compounds of Formula I (and subgenera described herein). The present disclosure contemplates and encompasses each stereoisomer of any compound of Formula I (and subgenera described herein), as well as mixtures of said stereoisomers.

Pharmaceutically acceptable salts and solvates of the compounds of Formula I (including all subgenera described herein) are also within the scope of the disclosure.

Isotopic variants of the compounds of Formula I (including all subgenera described herein) are also contemplated by the present disclosure.

Pharmaceutical Compositions and Methods of Administration

In some embodiments, the disclosure is directed to pharmaceutical compositions comprising compounds of Formula I, or a pharmaceutically acceptable salt or solvate thereof.

The subject pharmaceutical compositions are typically formulated to provide a therapeutically effective amount of a compound of the present disclosure as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the one or more compounds of the invention and other agent(s) may be mixed into a preparation or both components may be formulated into separate preparations to use them in combination separately or at the same time.

In some embodiments, the concentration of one or more compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v or v/v.

In some embodiments, the concentration of one or more compounds of the invention is greater than 90%, 80%, 70%, 60%, 50%, 40%, 30%, 20%, 19.75%, 19.50%, 19.25%, 19%, 18.75%, 18.50%, 18.25% 18%, 17.75%, 17.50%, 17.25% 17%, 16.75%, 16.50%, 16.25%, 16%, 15.75%, 15.50%, 15.25% 15%, 14.75%, 14.50%, 14.25% 14%, 13.75%, 13.50%, 13.25%, 13%, 12.75%, 12.50%, 12.25%, 12%, 11.75%, 11.50%, 11.25% 11%, 10.75%, 10.50%, 10.25% 10%, 9.75%, 9.50%, 9.25%, 9%, 8.75%, 8.50%, 8.25% 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v, or v/v.

In some embodiments, the concentration of one or more compounds of the invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds of the invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g (or a number in the range defined by and including any two numbers above).

In some embodiments, the amount of one or more compounds of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g (or a number in the range defined by and including any two numbers above).

In some embodiments, the amount of one or more compounds of the invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

A pharmaceutical composition of the invention typically contains an active ingredient (i.e., a compound of the disclosure) of the present invention or a pharmaceutically acceptable salt and/or coordination complex thereof, and one or more pharmaceutically acceptable excipients, carriers, including but not limited to inert solid diluents and fillers, diluents, sterile aqueous solution and various organic solvents, permeation enhancers, solubilizers and adjuvants.

Described below are non-limiting exemplary pharmaceutical compositions and methods for preparing the same.

Pharmaceutical Compositions for Oral Administration.

In some embodiments, the invention provides a pharmaceutical composition for oral administration containing a compound of the invention, and a pharmaceutical excipient suitable for oral administration.

In some embodiments, the invention provides a solid pharmaceutical composition for oral administration containing: (i) an effective amount of a compound of the invention; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions.

Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof, lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof, carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-lOoleate, Tween 40, Tween 60, sucrose monostearate, sucrose mono laurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, F-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, F-caprolactone and isomers thereof, 6-valerolactone and isomers thereof, β-butyrolactone and isomers thereof, and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25% o, 50%), 100% o, or up to about 200%> by weight, based on the combined weight of the drug, and other excipients. If desired, very small amounts of solubilizer may also be used, such as 5%>, 2%>, 1%) or even less. Typically, the solubilizer may be present in an amount of about 1%> to about 100%, more typically about 5%> to about 25%> by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)-aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical (e.g. Transdermal) Delivery.

In some embodiments, the invention provides a pharmaceutical composition for transdermal delivery containing a compound of the present invention and a pharmaceutical excipient suitable for transdermal delivery.

Compositions of the present invention can be formulated into preparations in solid, semisolid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation.

Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Compositions for Inhalation.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Compositions.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins, 2000; Martindale, The Extra Pharmacopoeia, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also be administered intraadiposally or intrathecally.

The amount of the compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose.

Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention is administered in a composition that comprises one or more agents, and the agent has a shorter half-life than the compound of the invention unit dose forms of the agent and the compound of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

Methods of Use

The method typically comprises administering to a subject a therapeutically effective amount of a compound of the invention. The therapeutically effective amount of the subject combination of compounds may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

As used herein, the term "IC$_{50}$" refers to the half maximal inhibitory concentration of an inhibitor in inhibiting biological or biochemical function. This quantitative measure indicates how much of a particular inhibitor is needed to inhibit a given biological process (or component of a process, i.e. an enzyme, cell, cell receptor or microorganism) by half. In other words, it is the half maximal (50%) inhibitory concentration (IC) of a substance (50% IC, or IC50). EC50 refers to the plasma concentration required for obtaining 50%> of a maximum effect in vivo.

In some embodiments, the subject methods utilize a CDK inhibitor with an IC50 value of about or less than a predetermined value, as ascertained in an in vitro assay. In some embodiments, the CDK inhibitor inhibits CDK a with an IC50 value of about 1 nM or less, 2 nM or less, 5 nM or less, 7 nM or less, 10 nM or less, 20 nM or less, 30 nM or less, 40 nM or less, 50 nM or less, 60 nM or less, 70 nM or less, 80 nM or less, 90 nM or less, 100 nM or less, 120 nM or less, 140 nM or less, 150 nM or less, 160 nM or less, 170 nM or less, 180 nM or less, 190 nM or less, 200 nM or less, 225 nM or less, 250 nM or less, 275 nM or less, 300 nM or less, 325 nM or less, 350 nM or less, 375 nM or less, 400 nM or less, 425 nM or less, 450 nM or less, 475 nM or less, 500 nM or less, 550 nM or less, 600 nM or less, 650 nM or less, 700 nM or less, 750 nM or less, 800 nM or less, 850 nM or less, 900 nM or less, 950 nM or less, 1 µM or less, 1.1 µM or less, 1.2 µM or less, 1.3 µM or less, 1.4 µM or less, 1.5 µM or less, 1.6 µM or less, 1.7 µM or less, 1.8 µM or less, 1.9 µM or less, 2 µM or less, 5 µM or less, 10 µM or less, 15 µM or less, 20 µM or less, 25 µM or less, 30 µM or less, 40 µM or less, 50 µM, 60 µM, 70 µM, 80 µM, 90 µM, 100 µM, 200 µM, 300 µM, 400 µM, or 500 µM, or less, (or a number in the range defined by and including any two numbers above).

In some embodiments, the CDK inhibitor selectively inhibits CDK a with an IC50 value that is at least 2, 3, 4, 5, 6, 7, 8, 9, 10, 15, 20, 25, 30, 35, 40, 45, 50, 100, or 1000 times less (or a number in the range defined by and including any two numbers above) than its IC50 value against one, two, or three other CDKs.

In some embodiments, the CDK inhibitor selectively inhibits CDK a with an IC50 value that is less than about 1 nM, 2 nM, 5 nM, 7 nM, 10 nM, 20 nM, 30 nM, 40 nM, 50 nM, 60 nM, 70 nM, 80 nM, 90 nM, 100 nM, 120 nM, 140 nM, 150 nM, 160 nM, 170 nM, 180 nM, 190 nM, 200 nM, 225 nM, 250 nM, 275 nM, 300 nM, 325 nM, 350 nM, 375 nM, 400 nM, 425 nM, 450 nM, 475 nM, 500 nM, 550 nM, 600 nM, 650 nM, 700 nM, 750 nM, 800 nM, 850 nM, 900 nM, 950 nM, 1 µM, 1.1 µM, 1.2 µM, 1.3 µM, 1.4 µM, 1.5 µM, 1.6 µM, 1.7 µM, 1.8 µM, 1.9 µM, 2 µM, 5 µM, 10 µM, 15 µM, 20 µM, 25 µM, 30 µM, 40 µM, 50 µM, 60 µM, 70 µM, 80 µM, 90 µM, 100 µM, 200 µM, 300 µM, 400 µM, or 500 µM (or in the range defined by and including any two numbers above), and said IC50 value is at least 2, 3, 4, 5, 6, 7, 8, 9, 10, 15, 20, 25, 30, 35, 40, 45, 50, 100, or 1000 times less (or a number in the range defined by and including any two numbers above) than its IC50 value against one, two or three other CDKs.

The subject methods are useful for treating a disease condition associated with CDK. Any disease condition that results directly or indirectly from an abnormal activity or expression level of CDK can be an intended disease condition.

Different disease conditions associated with CDK have been reported. CDK has been implicated, for example, auto-immune diseases, neurodegeneration (such as Parkinson's disease, Alzheimer's disease and ischaemia), inflammatory diseases, viral infections and cancer such as, for example, colon cancer, breast cancer, small-cell lung cancer, non-small-cell lung cancer, bladder cancer, ovarian cancer, prostate cancer, chronic lymphoid leukemia, lymphoma, myeloma, acute myeloid leukemia, or pancreatic cancer.

Non-limiting examples of such conditions include but are not limited to Acanthoma, Acinic cell carcinoma, Acoustic neuroma, Acral lentiginous melanoma, Acrospiroma, Acute eosinophilic leukemia, Acute lymphoblastic leukemia, Acute lymphocytic leukemia, Acute megakaryoblastic leukemia, Acute monocytic leukemia, Acute myeloblasts leukemia with maturation, Acute myeloid dendritic cell leukemia, Acute myeloid leukemia, Acute myelogenous leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epidermoid cancer, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Head and Neck Cancer, Head and neck cancer, Heart cancer, Hemoglobinopathies such as b-thalassemia and sickle cell disease (SCD), Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mastocytosis, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplasia Disease, Myelodysplasia Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene onChromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or any combination thereof.

In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In other embodiments, said method is for treating a disease selected from breast cancer, lung cancer, pancreatic cancer, prostate cancer, colon cancer, ovarian cancer, uterine cancer, or cervical cancer.

In other embodiments, said method is for treating a disease selected from leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS) or epidermoid cancer.

Compounds of the disclosure, as well as pharmaceutical compositions comprising them, can be administered to treat any of the described diseases, alone or in combination with a medical therapy. Medical therapies include, for example, surgery and radiotherapy (e.g., gamma-radiation, neutron beam radiotherapy, electron beam radiotherapy, proton therapy, brachytherapy, systemic radioactive isotopes).

In other aspects, compounds of the disclosure, as well as pharmaceutical compositions comprising them, can be administered to treat any of the described diseases, alone or in combination with one or more other agents.

In other methods, the compounds of the disclosure, as well as pharmaceutical compositions comprising them, can be administered in combination with agonists of nuclear receptors agents.

In other methods, the compounds of the disclosure, as well as pharmaceutical compositions comprising them, can be administered in combination with antagonists of nuclear receptors agents.

In other methods, the compounds of the disclosure, as well as pharmaceutical compositions comprising them, can be administered in combination with an anti-proliferative agent.

In some embodiments, the disclosure is directed to methods for treating a CDK4-mediated and a CDK6-mediated disorder in a patient in need thereof, comprising administering to said patient a compound of Formula I, including all subgenera described herein, or a pharmaceutically acceptable salt thereof, or a pharmaceutical composition comprising the compound of Formula I, including all subgenera described herein.

In some embodiments, the CDK4-mediated and CDK6-mediated disorder is a cancer. In some embodiments, the cancer is breast cancer, malignant brain tumors, colon cancer, small-cell lung cancer, non-small-cell lung cancer, bladder cancer, ovarian cancer, prostate cancer, chronic lymphoid leukemia, lymphoma, myeloma, acute myeloid leukemia, secondary pancreatic cancer or secondary brain metastases.

In some embodiments, the cancer is breast cancer. In some embodiments, the cancer is malignant brain tumors. In some embodiments, the cancer is colon cancer. In some embodiments, the cancer is small-cell lung cancer. In some embodiments, the cancer is non-small-cell lung cancer. In some embodiments, the cancer is bladder cancer. In some embodiments, the cancer is ovarian cancer.

In some embodiments, the cancer is prostate cancer. In some embodiments, the cancer is chronic lymphoid leukemia. In some embodiments, the cancer is lymphoma. In some embodiments, the cancer is myeloma. In some embodiments, the cancer is acute myeloid leukemia. In some embodiments, the cancer is secondary pancreatic cancer. In some embodiments, the cancer is secondary brain metastases.

In some embodiments, the breast cancer is HR+/HER2− or HR+/HER2+ advanced or metastatic breast cancer. In some embodiments, the breast cancer is HR+/HER2− advanced breast cancer. In some embodiments, the breast cancer is HR+/HER2− metastatic breast cancer. In some embodiments, the breast cancer is HR+/HER2+ advanced breast cancer. In some embodiments, the breast cancer is HR+/HER2+ metastatic breast cancer.

In some embodiments, the malignant brain tumors are glioblastoma, astrocytoma, or pontine glioma. In some embodiments, the malignant brain tumors are a glioblastoma. In some embodiments, the malignant brain tumors are an astrocytoma. In some embodiments, the malignant brain tumors are a pontine glioma.

In some embodiments, the patient is administered a pharmaceutical composition comprising a compound of Formula I, including all subgenera described herein, or a pharmaceutically acceptable salt thereof. In some embodiments, the administration is oral administration.

Combination Therapies

For treating cancer and other proliferative diseases, the compounds of the invention can be used in combination with chemotherapeutic agents, agonists or antagonists of nuclear receptors, or other anti-proliferative agents. The compounds of the invention can also be used in combination with a medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, all-trans retinoic acid, altretamine, anastrozole, arsenic trioxide, asparaginase, azacitidine, bendamustine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panobinostat, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinstat and zoledronate.

In some embodiments, the compounds of the invention can be used in combination with a therapeutic agent that targets an epigenetic regulator. Examples of epigenetic regulators include bromodomain inhibitors, the histone lysine methyltransferase inhibitors, histone arginine methyl transferase inhibitors, histone demethylase inhibitors, histone deacetylase inhibitors, histone acetylase inhibitors, and DNA methyltransferase inhibitors. Histone deacetylase inhibitors include, e.g., vorinostat. Histone arginine methyl transferase inhibitors include inhibitors of protein arginine methyltransferases (PRMTs) such as PRMT5, PRMT1 and PRMT4. DNA methyltransferase inhibitors include inhibitors of DNMT1 and DNMT3.

For treating cancer and other proliferative diseases, the compounds of the invention can be used in combination with targeted therapies, including JAK kinase inhibitors (e.g. Ruxolitinib), PI3 kinase inhibitors including PI3K-delta selective and broad spectrum PI3K inhibitors, MEK inhibitors, Cyclin Dependent kinase inhibitors, including CDK4/6 inhibitors and CDK9 inhibitors, BRAF inhibitors, mTOR inhibitors, proteasome inhibitors (e.g. Bortezomib, Carfilzomib), HDAC inhibitors (e.g. panobinostat, vorinostat), DNA methyl transferase inhibitors, dexamethasone, bromo and extra terminal family member (BET) inhibitors, BTK inhibitors (e.g. ibrutinib, acalabrutinib), BCL2 inhibitors (e.g. venetoclax), dual BCL2 family inhibitors (e.g. BCL2/BCLxL), PARP inhibitors, FLT3 inhibitors, or LSD1 inhibitors.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), or PDR001. In some embodiments, the anti-PD-1 monoclonal antibody is nivolumab or pembrolizumab. In some embodiments, the anti-PD1 antibody is pembrolizumab. In some embodiments, the inhibitor of an immune checkpoint molecule is an inhibitor of PD-L1, e.g., an anti-PD-L1 monoclonal antibody. In some embodiments, the anti-PD-L1 monoclonal antibody is atezolizumab, durvalumab, or BMS-935559. In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

For treating autoimmune or inflammatory conditions, the compound of the invention can be administered in combination with a corticosteroid such as triamcinolone, dexamethasone, fluocinolone, cortisone, prednisolone, or flumetholone.

For treating autoimmune or inflammatory conditions, the compound of the invention can be administered in combination with an immune suppressant such as fluocinolone acetonide (Retisert®), rimexolone (AL-2178, Vexol, Alcon), or cyclosporine (Restasis®).

In some embodiments, the disclosure is directed to methods described herein, further comprising administering an additional therapeutic agent to the patient. In some embodiments, the additional therapeutic agent is a PRMT5 inhibitor, a HER2 kinase inhibitor, an aromatase inhibitor, an estrogen receptor antagonist or an alkylating agent.

In some embodiments, the additional therapeutic agent is a PRMT5 inhibitor. In some embodiments, the additional therapeutic agent is a HER2 kinase inhibitor. In other embodiments, the additional therapeutic agent is an aromatase inhibitor. In other embodiments, the additional therapeutic agent is an estrogen receptor antagonist. In yet other embodiments, the additional therapeutic agent is an alkylating agent.

In some embodiments, the aromatase inhibitor is letrozole. In some embodiments, the estrogen receptor antagonist is fulvestrant. In other embodiments, the alkylating agent is temozolomide.

In yet other embodiments, the PRMT5 inhibitor is a compound disclosed in US Published Patent Application No. 2020/0148692 (filed Jan. 16, 2020); US Published Patent Application No. 2019/0284193 (filed Apr. 5, 2019); and US Published Patent Application No. 2019/0048014 (filed Aug. 9, 2018); each of which is hereby incorporated herein in its entirety.

In some embodiments, the PRMT5 inhibitor is:
(2R,3R,4S,5S)-2-(4-amino-7H-pyrrolo[2,3-d]pyrimidin-7-yl)-5-((R)-6-chloroisochroman-1-yl)tetrahydrofuran-3,4-diol, or a pharmaceutically acceptable salt or solvate thereof;

(2R,3R,4S,5S)-2-(4-amino-7H-pyrrolo[2,3-d]pyrimidin-7-yl)-5-((R)-7-chloroisochroman-1-yl)tetrahydrofuran-3,4-diol, or a pharmaceutically acceptable salt or solvate thereof;

(2R,3R,4S,5S)-2-(4-amino-7H-pyrrolo[2,3-d]pyrimidin-7-yl)-5-((R)-5-chloroisochroman-1-yl)tetrahydrofuran-3,4-diol, or a pharmaceutically acceptable salt or solvate thereof;

(2R,3R,4S,5S)-2-(4-amino-7H-pyrrolo[2,3-d]pyrimidin-7-yl)-5-((R)-6,7-difluoroisochroman-1-yl)tetrahydrofuran-3,4-diol, or a pharmaceutically acceptable salt or solvate thereof;

(2R,3R,4S,5S)-2-(4-amino-7H-pyrrolo[2,3-d]pyrimidin-7-yl)-5-((R)-5,6-difluoroisochroman-1-yl)tetrahydrofuran-3,4-diol, or a pharmaceutically acceptable salt or solvate thereof;

(2R,3R,4S,5S)-2-(4-amino-7H-pyrrolo[2,3-d]pyrimidin-7-yl)-5-((R)-6-chloro-5-fluoroisochroman-1-yl)tetrahydrofuran-3,4-diol, or a pharmaceutically acceptable salt or solvate thereof, (2R,3R,4S,5S)-2-(4-amino-5-fluoro-7H-pyrrolo[2,3-d]pyrimidin-7-yl)-5-((R)-6-chloroisochroman-1-yl)tetrahydrofuran-3,4-diol, or a pharmaceutically acceptable salt or solvate thereof, (2R,3R,4S,5 S)-2-(4-amino-7H-pyrrolo[2,3-d]pyrimidin-7-yl)-5-((R)-6,7-dichloroisochroman-1-yl)tetrahydrofuran-3,4-diol, or a pharmaceutically acceptable salt or solvate thereof;

(2S,3S,4R,5R)-2-((R)-6-chloroisochroman-1-yl)-5-(4-methyl-7H-pyrrolo[2,3-d]pyrimidin-7-yl)tetrahydrofuran-3,4-diol, or a pharmaceutically acceptable salt or solvate thereof;

(2S,3S,4R,5R)-2-((R)-6,7-difluoroisochroman-1-yl)-5-(4-methyl-7H-pyrrolo[2,3-d]pyrimidin-7-yl)tetrahydrofuran-3,4-diol, or a pharmaceutically acceptable salt or solvate thereof;

(2S,3S,4R,5R)-2-((R)-5,6-difluoroisochroman-1-yl)-5-(4-methyl-7H-pyrrolo[2,3-d]pyrimidin-7-yl)tetrahydrofuran-3,4-diol, or a pharmaceutically acceptable salt or solvate thereof;

(2S,3S,4R,5R)-2-((R)-6-chloroisochroman-1-yl)-5-(5-fluoro-4-methyl-7H-pyrrolo[2,3-d]pyrimidin-7-yl)tetrahydrofuran-3,4-diol, or a pharmaceutically acceptable salt or solvate thereof, or (2S,3S,4R,5R)-2-((R)-6,7-dichloroisochroman-1-yl)-5-(4-methyl-7H-pyrrolo[2,3-d]pyrimidin-7-yl)tetrahydrofuran-3,4-diol, or a pharmaceutically acceptable salt or solvate thereof.

In some embodiments, the PRMT5 inhibitor is (2S,3S,4R,5R)-2-((R)-6-chloroisochroman-1-yl)-5-(4-methyl-7H-pyrrolo[2,3-d]pyrimidin-7-yl)tetrahydrofuran-3,4-diol, or a pharmaceutically acceptable salt or solvate thereof.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T.W. Greene and P.G.M. Wuts, Protective Groups in Organic Synthesis, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography.

The expressions, "ambient temperature," "room temperature," and "r.t." as used herein, are understood in the art, and refer generally to a temperature, e.g. a reaction temperature, that is about the temperature of the room in which the reaction is carried out, for example, a temperature from about 20° C. to about 30° C.

Compounds of the invention can be prepared using numerous preparatory reactions known in the literature. The Schemes below provide general guidance in connection with preparing the compounds of the invention. One skilled in the art would understand that the preparations shown in the Schemes can be modified or optimized using general knowledge of organic chemistry to prepare various compounds of the invention. Example synthetic methods for preparing compounds of the invention are provided in the Schemes below.

The following Examples are provided to illustrate some of the concepts described within this disclosure. While the Examples are considered to provide an embodiment, it should not be considered to limit the more general embodiments described herein.

EXAMPLES

General Synthetic Procedures

Compounds of Formula (I) can be prepared from optionally protected compounds 1-1 where $W^1$ is halogen (e.g., Cl, Br, or I) or pseudohalogen (e.g., OTf or OMs) as shown in Scheme I. Compounds 1-1 can be coupled with compounds 1-2 where $M^1$ is a boronic acid, boronate ester, potassium trifluoroborate, or an appropriately substituted metal, such as $Sn(Bu)_3$, $Sn(Me)_3$, or ZnCl, under standard Suzuki conditions (e.g., in the presence of a palladium catalyst, such as [1,1'-bis(diphenyl-phosphino)ferrocene]dichloropalladium (II) and a base, such as $K_3PO_4$) or standard Stille conditions (e.g., in the presence of a palladium(0) catalyst, such as tetrakis(triphenyl-phosphine)palladium(0)) or standard Negishi conditions (e.g., in the presence of a palladium catalyst, such as tetrakis (triphenylphosphine)palladium(0) or [1,1'-bis(diphenylphosphino) ferrocene]dichloropalladium(II)), to give compounds 1-3 where $W^2$ is halogen (e.g., Cl, Br, or I) or pseudohalogen (e.g., OTf or OMs). Coupling of compounds 1-3 with amines 1-4 under standard Buchwald-Hartwig amination conditions (e.g., in the presence of a palladium catalyst, such as XPhos Pd G3, and a base, such as $Cs_2CO_3$ or $K_3PO_4$) can provide compounds of Formula (I).

Alternatively, compounds 1-1 can be converted to the appropriate compounds 1-5 (e.g., $M^2$ is $B(OH)_2$, Bpin, $BF_3K$, $Sn(Me)_3$, $Sn(Bu)_3$, or ZnCl) and then coupled to compounds 1-6 where $W^3$ is halogen (e.g., Cl, Br, or I) or pseudohalogen (e.g., OTf or OMs) under standard Suzuki conditions (e.g., in the presence of a palladium catalyst, such as [1,1'-bis(diphenylphosphino) ferrocene] dichloropalladium(II), and a base, such as $K_3PO_4$) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis (triphenylphosphine)palladium(0) or [1,1'-bis(diphenylphosphino)ferrocene]dichloropalladium(II)) to give compounds 1-3, which can be used to synthesize compound of Formula (I).

Scheme I

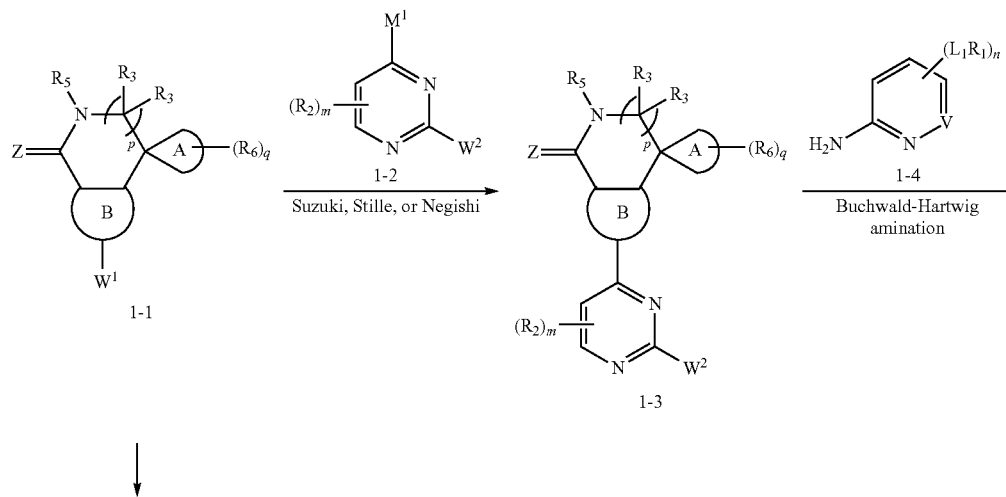

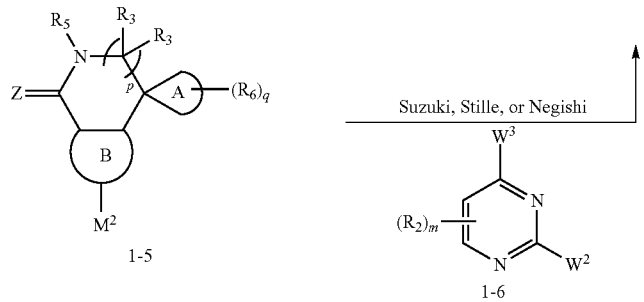

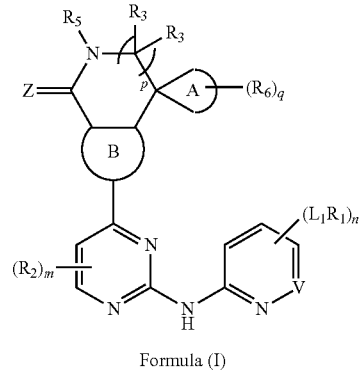

Formula (I)

Intermediates for the synthesis of compounds of Formula (I) can be prepared as described in Scheme II. Compounds 2-1 can be halogenated with suitable reagents, such as N-bromosuccinimide or N-iodosuccinimide, to provide compounds 1-1. Alternatively, compounds 2-1 can be metalated in the presence of a strong base, such as lithium diisopropylamide or butyllithium, and an appropriate reagent (e.g., 2-isopropoxy-4,4,5,5-tetramethyl-1,3,2-dioxaborolane, hexamethylditin, trimethyltin chloride, or zinc chloride) to afford compounds 1-5.

Scheme III

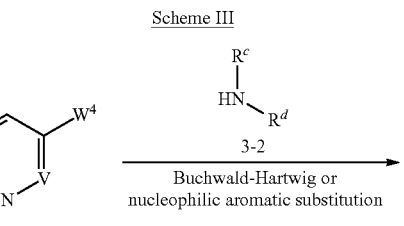

Scheme II

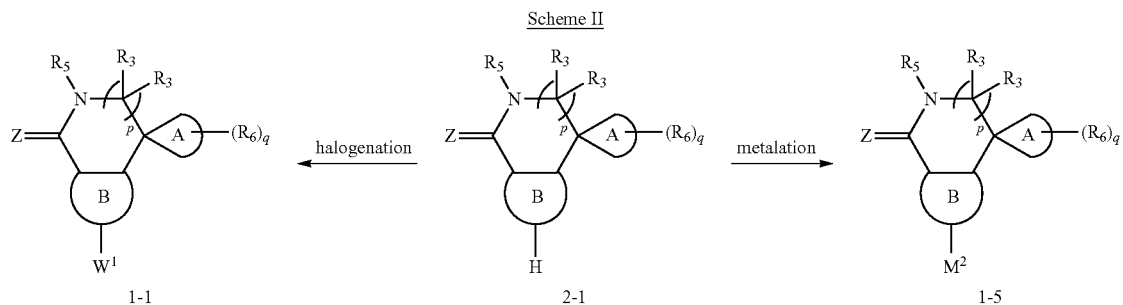

Intermediates for the synthesis of compounds of Formula (I) can be prepared as described in Scheme III. Coupling of compounds 3-1 where $W^4$ is halogen (e.g., F, Cl, Br, or I) or pseudohalogen (e.g., OTf or OMs) with amines 3-2 under either standard Buchwald-Hartwig amination conditions (e.g., in the presence of a palladium catalyst, such as XPhos Pd G2, and a base, such as $K_3PO_4$) or standard conditions for nucleophilic aromatic substitution optionally in the presence of a base (e.g., diisopropylethylamine) can provide compounds 3-3. Nitro compounds 3-3 can be reduced to amino compounds 3-4 under standard reductive conditions such as, but not limited to, $H_2$ in the presence of a transition metal catalyst (e.g., palladium on charcoal) in MeOH, Fe/$NH_4Cl$ in MeOH/$H_2O$, or sodium dithionite in EtOH/$H_2O$.

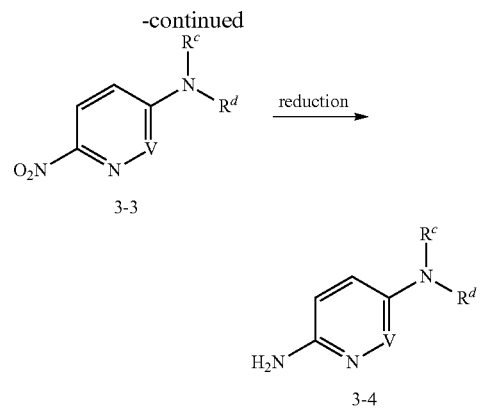

Intermediates for the synthesis of compounds of Formula (I) can be prepared as described in Scheme IV. Coupling of compounds 3-1 with compounds 4-1 where x and y are independently 0, 1, 2, or 3; where $Q^1$ is H or a protecting group, such as Boc, Cbz, Bn, PMB, Trt, acetamido, or trifluoracetamido; and where $M^3$ is a boronic acid, boronate ester, potassium trifluoroborate, or an appropriately substituted metal, such as $Sn(Bu)_3$ or ZnCl, under standard Suzuki conditions (e.g., in the presence of a palladium catalyst, such as [1,1'-bis(diphenylphosphino)ferrocene]dichloro-palladium(II) and a base, such as $K_3PO_4$ or $K_2CO_3$) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine) palladium(0) or [1,1'-bis(diphenylphosphino)ferrocene]dichloropalladium(II)), and then optional deprotection can provide compounds 4-2. Alkylation of amines 4-2 with halides 4-3 where $X^d$ is a halide (e.g., Cl, Br, or I) or pseudohalide (e.g., OTf, OTs, or OMs) and $R^x$ is a —$C_1$-$C_6$alkyl, —$C_2$-$C_6$alkenyl, —$C_2$-$C_6$alkynyl, $C_1$alk-aryl, $C_1$alk-heteroaryl, cycloalkyl, cycloalkenyl, heterocycloalkyl, or heterocycloalkenyl group under standard conditions (e.g., in the presence of a base, such as potassium carbonate) can provide compounds 4-4. Compounds 4-4 can be reduced to amines 4-5 under standard reductive conditions such as, but not limited to, $H_2$ in the presence of a transition metal catalyst (e.g., palladium on charcoal or platinum(IV) oxide).

Alternatively, reaction of amines 4-2 under standard conditions for reductive amination (e.g., in the presence of a reducing agent such as sodium triacetoxyborohydride or sodium cyanoborohydride and optionally an acid, such as acetic acid) with compounds 4-6 where $R^y$ and $R^z$ are each independently H, D, —$C_1$-$C_6$ alkyl, 5-7 membered aryl, 5-7 membered heteroaryl, cycloalkyl, or 4-, 5-, 6- or 7-membered heterocycloalkyl wherein said $C_1$-$C_5$ alkyl, 5-7 membered aryl, 5-7 membered heteroaryl, cycloalkyl, or 4-, 5-, 6- or 7-membered heterocycloalkyl may be optionally substituted and optionally $R^y$ and $R^z$, together with carbon to which they are both attached, may form a cyclic ketone can provide compounds 4-7. Compounds 4-7 can be reduced to amines 4-8 under standard reductive conditions such as, but not limited to, $H_2$ in the presence of a transition metal catalyst (e.g., palladium on charcoal or platinum(IV) oxide).

Scheme IV

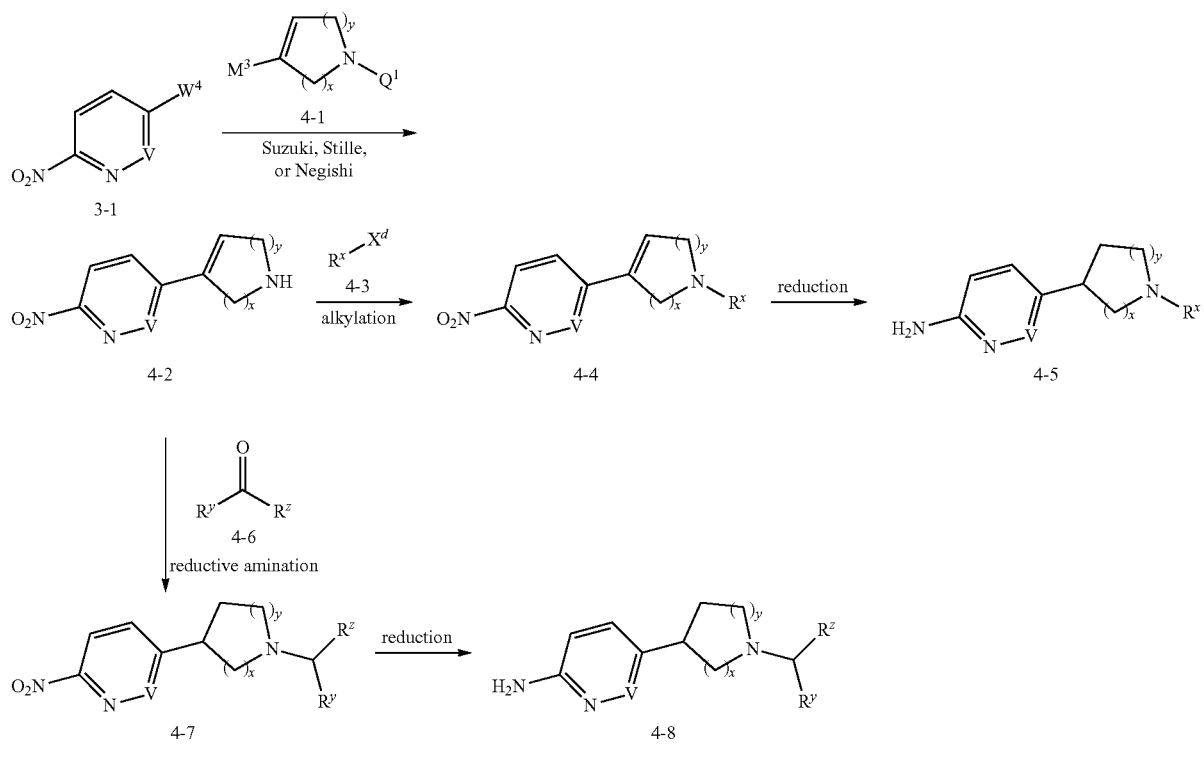

Compounds of Formula (II) can be prepared from optionally protected compounds 5-1 where $W^1$ is halogen (e.g., Cl, Br, or I) or pseudohalogen (e.g., OTf or OMs) as shown in Scheme V. Compounds 5-1 can be coupled with compounds 5-2 where $M^1$ is a boronic acid, boronate ester, potassium trifluoroborate, or an appropriately substituted metal, such as $Sn(Bu)_3$, $Sn(Me)_3$, or ZnCl under standard Suzuki conditions (e.g., in the presence of a palladium catalyst, such as [1,1'-bis (diphenylphosphino)ferrocene]dichloropalladium (II) and a base, such as $K_3PO_4$) or standard Stille conditions (e.g., in the presence of a palladium(0) catalyst, such as tetrakis(triphenylphosphine) palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium(II)), to give compounds 5-3 where $W^2$ is halogen (e.g., Cl, Br, or I) or pseudohalogen (e.g., OTf or OMs). Coupling of compounds 5-3 with amines 5-4 under standard Buchwald-Hartwig amination conditions (e.g., in the presence of a palladium catalyst, such as XPhos Pd G3, and a base, such as $Cs_2CO_3$ or $K_3PO_4$) can provide compounds of Formula (II).

Alternatively, compounds 5-1 can be converted to the appropriate compounds 5-5 (e.g., $M^2$ is $B(OH)_2$, Bpin, $BF_3K$, $Sn(Me)_3$, $Sn(Bu)_3$, or ZnCl) and then coupled to 5-6 where $W^3$ is halogen (e.g., Cl, Br, or I) or pseudohalogen (e.g., OTf or OMs) under standard Suzuki conditions (e.g., in the presence of a palladium catalyst, such as [1,1'-bis(diphenylphosphino)ferrocene]dichloropalladium(II), and a base, such as $K_3PO_4$) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine) palladium(0) or [1,1'-bis(diphenylphosphino)ferrocene]dichloropalladium(II)) to give compounds 5-3, which can be used to synthesize compound of Formula (II).

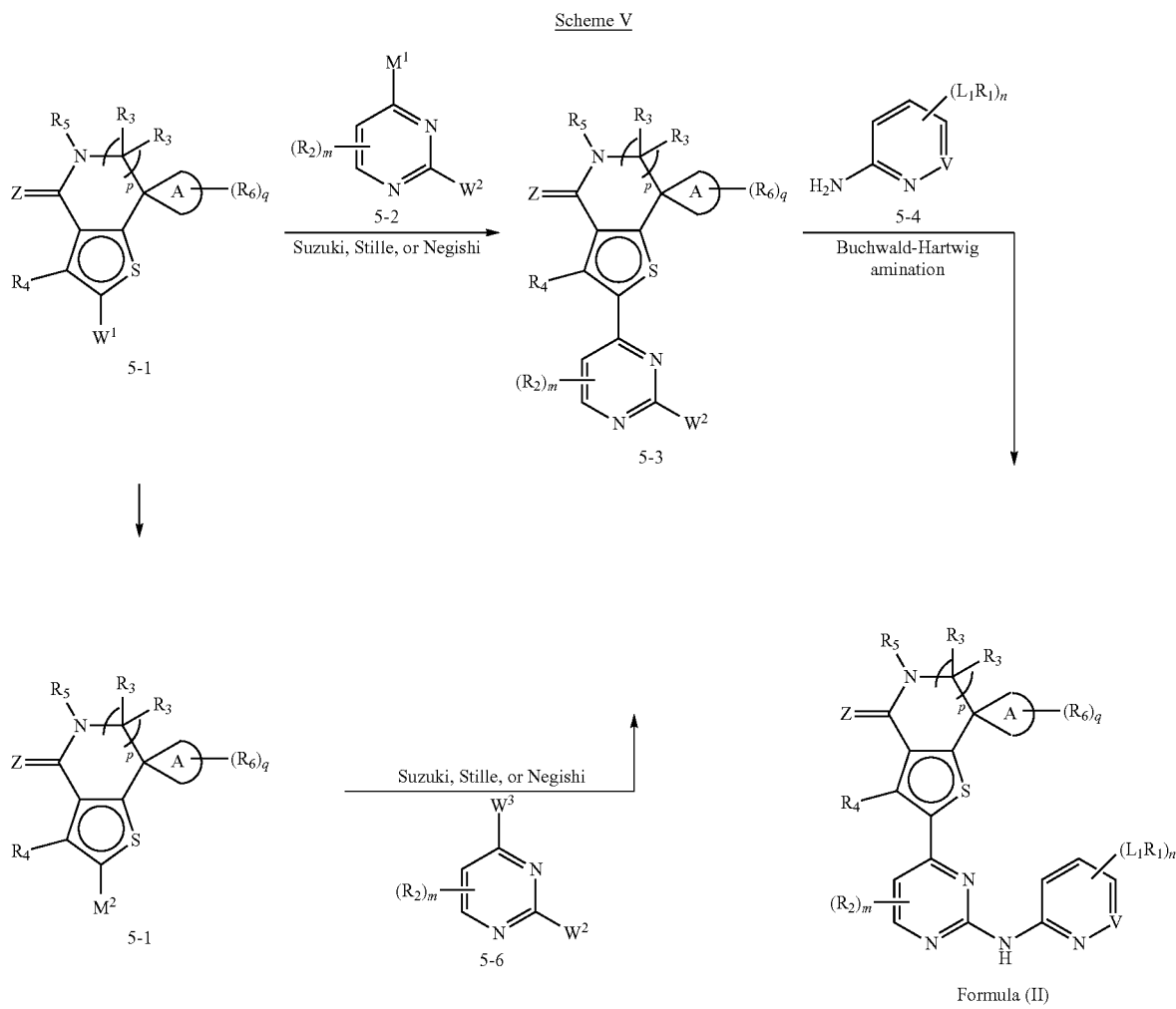

Scheme V

Intermediates for the synthesis of compounds of Formula (I) can be prepared as described in Scheme VI. Compounds 6-1 can be halogenated with suitable reagents, such as N-bromosuccinimide or N-iodosuccinimide, to provide compounds 5-1. Alternatively, compound 6-1 can be metalated in the presence of a strong base, such as lithium diisopropylamide or butyllithium, and an appropriate reagent (e.g., 2-isopropoxy-4,4,5,5-tetramethyl-1,3,2-dioxaborolane, hexamethylditin, trimethyltin chloride, or zinc chloride) to afford compounds 5-5.

Scheme VI

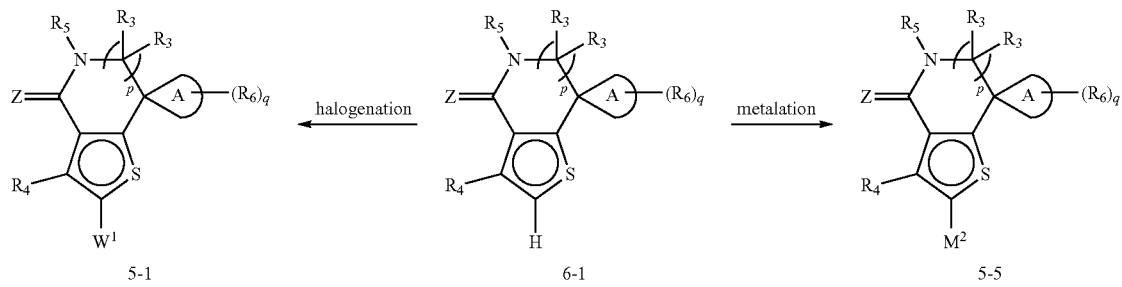

Intermediates for the synthesis of compounds of Formula (I) can be prepared as described in Scheme VII. Lithiation of thiophenes 7-1 with a strong base, such as butyllithium, and subsequent addition into ketones 7-2 where w is 0, 1, 2, or 3; and where z is 1, 2, or 3 can afford alcohols 7-3. Lactone formation under standard conditions, such as in the presence of benzenesulfonyl chloride and pyridine or in the presence of an acid (e.g., tosic acid) or in the presence of a coupling reagent (e.g., N,N'-dicyclohexylmethanediimine or HATU) and optionally an additive (e.g., 1-hydroxybenzotriazole) and optionally a base (e.g., pyridine or N,N-diisopropylethylamine) can afford lactones 7-4. Exposure of compounds 7-4 to ammonia under standard conditions, such as at elevated temperature and pressure, can provide lactams 7-5.

Alkylation of lactams 7-5 with suitable compounds 7-6 where $X^a$ is a halogen (e.g., Cl, Br, or I) or pseudohalogen (e.g., OMs, OTs, or OTf) in the presence of a base, such as NaH, can provide compounds 7-7.

Alternatively, compounds 7-3 can be dehydrated in the presence of alcohols 7-8 where $R^w$ is a $C_1$-$C_4$ alkyl group under standard conditions, such as in the presence of an acid (e.g., HCl or $H_2SO_4$) to afford compounds 7-9. Exposure of compounds 7-9 to ammonia under standard conditions at elevated temperature and pressure can provide lactams 7-5.

Scheme VII

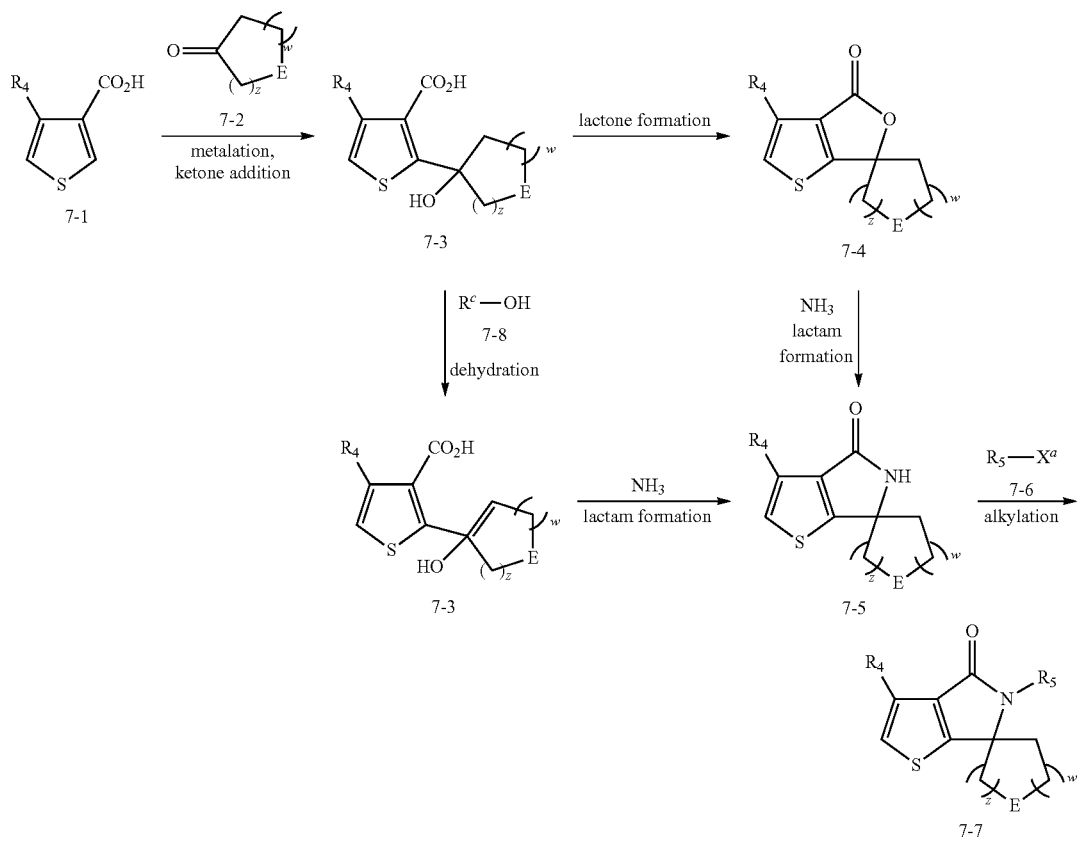

Intermediates for the synthesis of compounds of Formula (I) can be prepared as described in Scheme VIII. Alkylation of nitriles 8-1 with suitable compounds 8-2 where $X^b$ and $X^c$ are independently a halogen (e.g., Cl, Br, or I) or pseudo-halogen (e.g., OMs, OTs, or OTf) and where u and v are independently 1, 2, or 3 in the presence of a base, such as sodium hydride, can provide compounds 8-3. Reduction of nitriles 8-3 under standard conditions, such as in the presence of a reducing agent (e.g., lithium aluminumhydride or borane tetrahydrofuran complex), can provide amines 8-4. Reaction of compounds 8-4 under standard conditions, such as in the presence of a phosgene source (e.g., triphosgene) and a base (e.g., $NaHCO_3$) can afford isocyanates 8-5. Compounds 8-5 can undergo an intramolecular Friedel-Crafts acylation in the presence of a Lewis acid (e.g., aluminum trichloride) to provide lactams 8-6. Alkylation of lactams 8-6 with suitable compounds 7-6 in the presence of a base, such as NaH, can provide compounds 8-7.

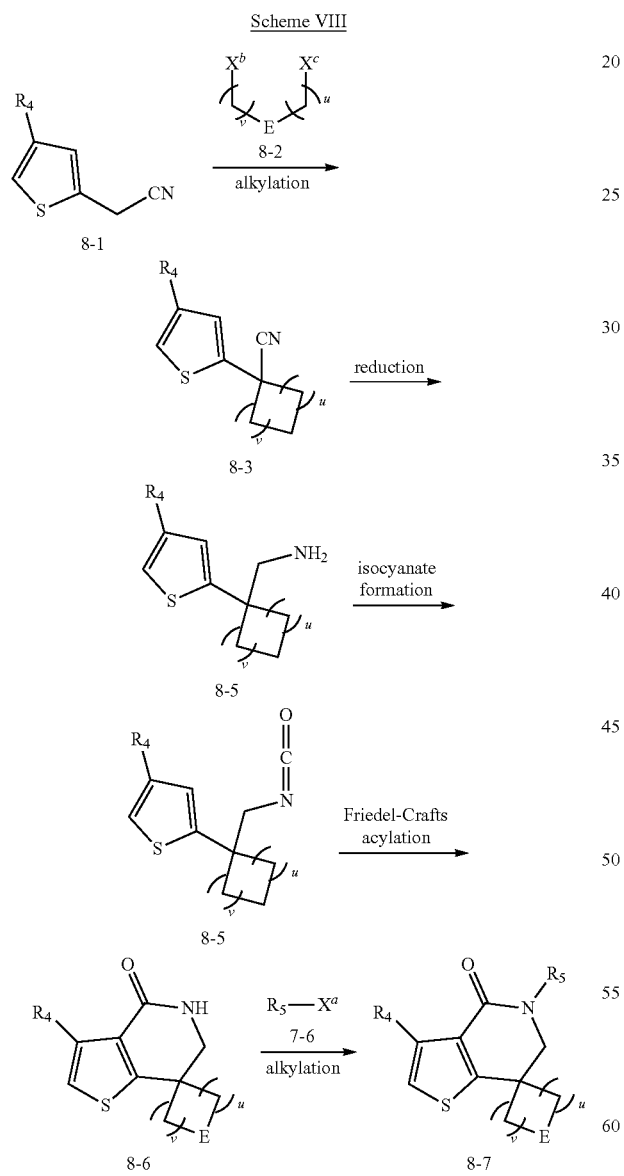

Scheme VIII

Intermediates for the synthesis of compounds of Formula (I) can be prepared as described in Scheme IX. Reduction of nitriles 8-3 under standard conditions, such as in the presence of a reducing agent (e.g., diisobutylaluminium hydride or lithium triethoxyaluminum hydride), and subsequent hydrolysis under a standard aqueous work up, such as with acid conditions (e.g. aqueous HCl), can provide aldehyde 9-1. Olefination of aldehydes 9-1 with suitable Horner-Wadsworth-Emmons reagents 9-2 where Re is a $C_1$-$C_4$ alkyl group or with Wittig reagents 9-3 where R is an aryl group and $X^-$ is a counter anion, such as halide anion (e.g., Cl— or Br—), in the presence of a base (e.g., butyllithium, lithium diisopropylamide, lithium bis(trimethylsilyl)amide, KH, methylmagnesium bromide, potassium tert-butoxide, triethylamine, or $K_2CO_3$) can afford acrylates 9-4. Conjugate reduction of acrylates 9-4 under standard conditions, such as in the presence of a hydride source (e.g., polymethylhydrosiloxane) and a catalyst (e.g., CuCl) can provide esters 9-5. Compounds 9-5 can undergo hydrolysis in aqueous media under basic conditions (e.g., LiOH, NaOH, or KOH) or acidic conditions (e.g., HCl or $H_2SO_4$) to form acid 9-6. Acids 9-6 can be converted to acyl chlorides 9-7 under standard conditions, such as in the presence of an appropriate reagent (e.g., thionyl chloride or oxalyl chloride) and optionally in the presence of a catalyst, such as DMF. Compounds 9-7 can undergo an intramolecular Friedel-Crafts acylation in the presence of a Lewis acid (e.g., aluminum trichloride) to provide cyclic ketones 9-8. Schmidt rearrangement of ketones 9-8 under standard conditions, such as in the presence of an azide source (e.g., sodium azide) and an acid (e.g., $H_2SO_4$), can afford lactams 9-9. Alkylation of lactams 9-9 with suitable compounds 7-6 in the presence of a base, such as NaH, can provide compounds 9-10.

Scheme IX

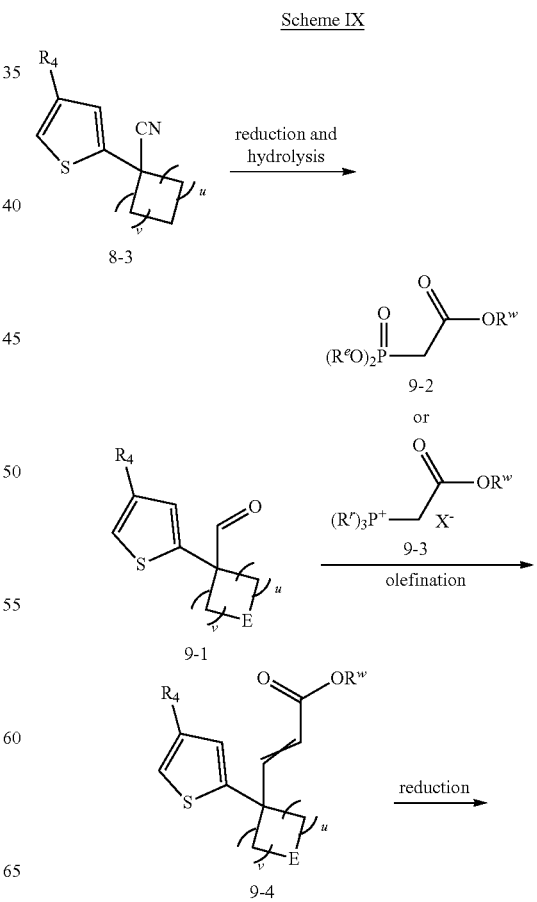

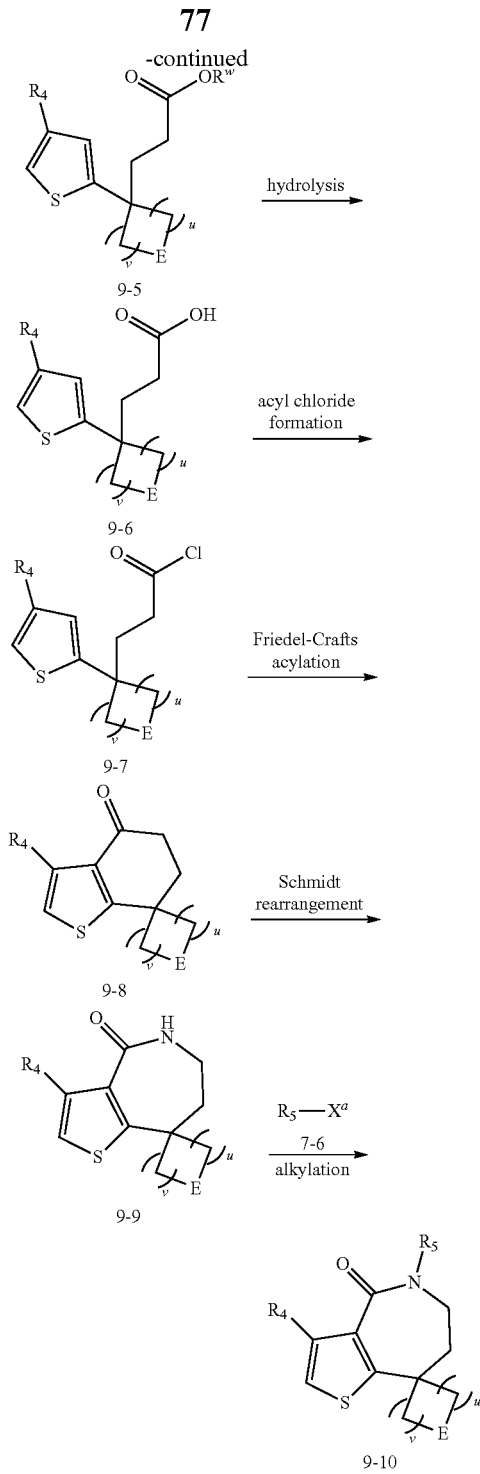

electrophile, such as methanesulfonyl chloride, p-toluenesulfonyl chloride, or triflic anhydride, and a base, such as triethylamine). Nucleophilic substitution of compounds 10-3 with cyanide salts (e.g., NaCN or KCN) can afford nitriles 8-1.

Scheme X

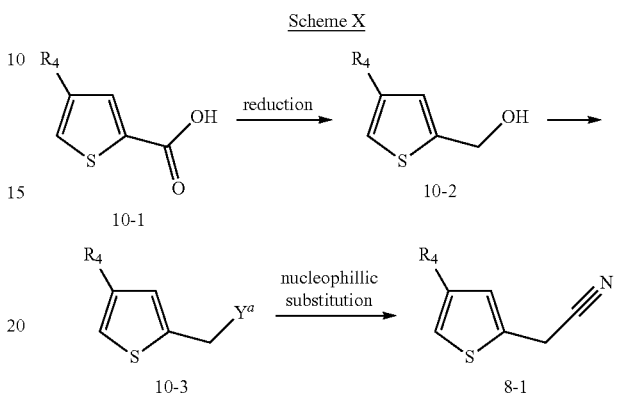

Intermediates for the synthesis of compounds of Formula (II) can be prepared as described in Scheme XI. Friedel-Crafts acylation of compounds 6-1 with acid halides 11-1 where $R^k$ is H, D, F, $C_1$-$C_8$ alkoxide, —$C_1$-$C_8$ alkyl, fluoroalkyl, or CN and $Y^9$ is a halogen (e.g., $C_1$ or Br) under standard conditions, such as in the presence of a Lewis acid (e.g., $AlCl_3$), can afford ketones 11-2. Condensation of compounds 11-2 with acetal 11-3 where $R^1$ is H, D, —$C_1$-$C_8$ alkoxide, —$C_1$-$C_8$ alkyl, fluoroalkyl, or CN can afford compounds 11-4. Subsequent condensation of compounds 11-4 with guanidine or one of its salts (e.g., guanidine hydrochloride) optionally in the presence of a base (e.g., $K_2CO_3$) can afford amino pyrimidines 11-5.

Scheme XI

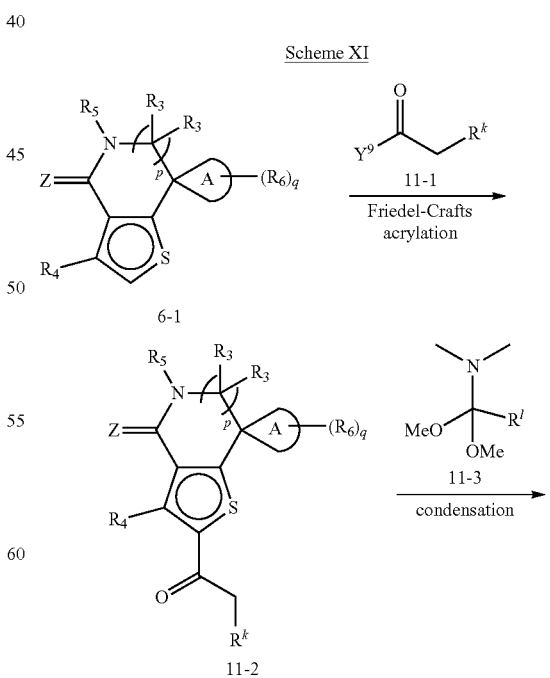

Intermediates for the synthesis of compounds of Formula (I) can be prepared as described in Scheme X. Carboxylic acids 10-1 can be reduced in the presence of a reducing agent such as lithium aluminum hydride to the primary alcohols 10-2. Alcohols 10-2 can be transformed to compounds 10-3 where $Y^a$ is a halogen (e.g., Cl, Br, or I) under standard deoxygenative halogenation conditions (e.g., in the presence of a suitable reagents, such as, thionyl chloride, phosphorous tribromide, or triphenylphosphine and iodine) or a pseudohalogen (e.g., OTf, OTs, or OMs) under sulfonylation standard conditions (e.g., in the presence of an

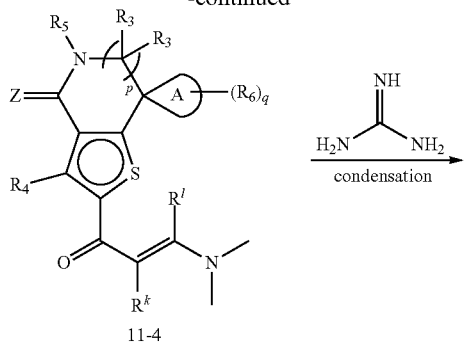
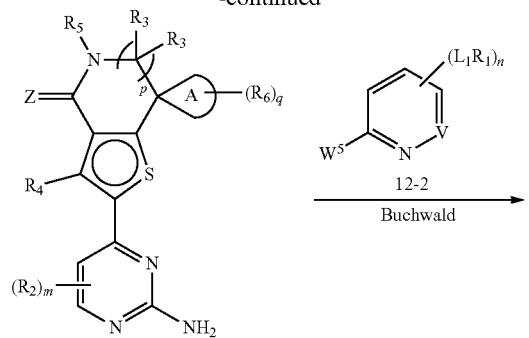

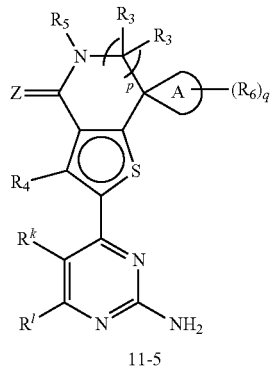

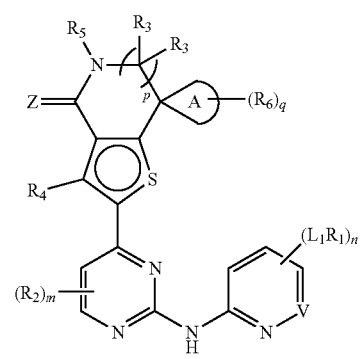

Formula (II)

Compounds of Formula (II) can be prepared from compounds 5-3 as shown in Scheme XII. Compounds 5-3 can be reacted under standard nucleophilic aromatic substitution conditions (e.g., in the presence of anhydrous $NH_3$ or $NH_4OH$ (aq.)) or standard Buchwald-Hartwig amination conditions (e.g., in the presence of an ammonia surrogate such as benzophenone imine, lithium bis(trimethylsilyl)amide, or tert-butyl carbamate; a palladium catalyst, such as $Pd_2(dba)_3$; a ligand, such as XPhos or XantPhos; and optionally base, such as $Cs_2CO_3$) or standard Ullman coupling conditions (e.g., in the presence of an ammonia source, such as $NH_3$ or ammonium bicarbonate, and a copper catalyst, such as CuO, $CuSO_4$, or CuI) to provide amino pyrimidines 12-1. Coupling of compounds 12-1 with halides 12-2 where $W^5$ is halogen (e.g., Cl, Br, or I) or pseudohalogen (e.g., OTf or OMs) under standard Buchwald-Hartwig amination conditions (e.g., in the presence of a palladium catalyst, such as XPhos Pd G2 or BrettPhos Pd G3, and a base, such as sodium tert-butoxide or $K_3PO_4$) can provide compounds of Formula (II).

Intermediates for the synthesis of compounds of Formula (II) can be prepared as described in Scheme XIII. Amide coupling of thiophenes 7-1 with a suitable amines 13-1 in the presence of a coupling reagent (e.g., N,N'-dicyclohexylcarbodiimide or HATU) and optionally an additive (e.g., 1-hydroxybenzotriazole or 4-dimethylaminopyridine) and optionally a base (e.g., pyridine or N,N-diisopropylethylamine) can provide amides 13-2. Lithiation of thiophenes 13-2 with a strong base, such as butyllithium, and subsequent addition into a formyl transfer reagent such as N,N-dimethylformamide, N-methoxy-N-methylformamide or N-formylmorpholine can afford aldehydes 13-3. Reduction of aldehydes 13-3 under standard conditions, such as in the presence of a reducing agent (e.g., sodium borohydride, lithium aluminumhydride, or borane tetrahydrofuran complex), can provide alcohols 13-4. Alcohols 13-4 can be halogenated with suitable reagents, such as thionyl chloride or phosphorus tribromide or triphenylphosphine and iodine, to provide compounds 13-5 where $X^e$ is a halogen (e.g., Cl, Br, or I). Ring closure reaction of compound 13-5 under basic conditions (e.g., in the presence of sodium hydride or lithium bis(trimethylsilyl)amide) can afford lactams 13-6. Alkylation of lactams 13-6 with compounds 8-2, in the presence of a base, such as sodium hydride or lithium diisopropylamide, can provide compounds 13-7.

Scheme XII

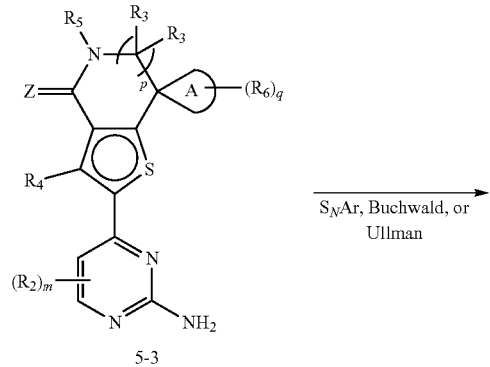

Scheme XIII

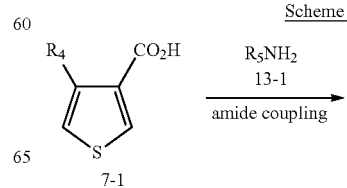

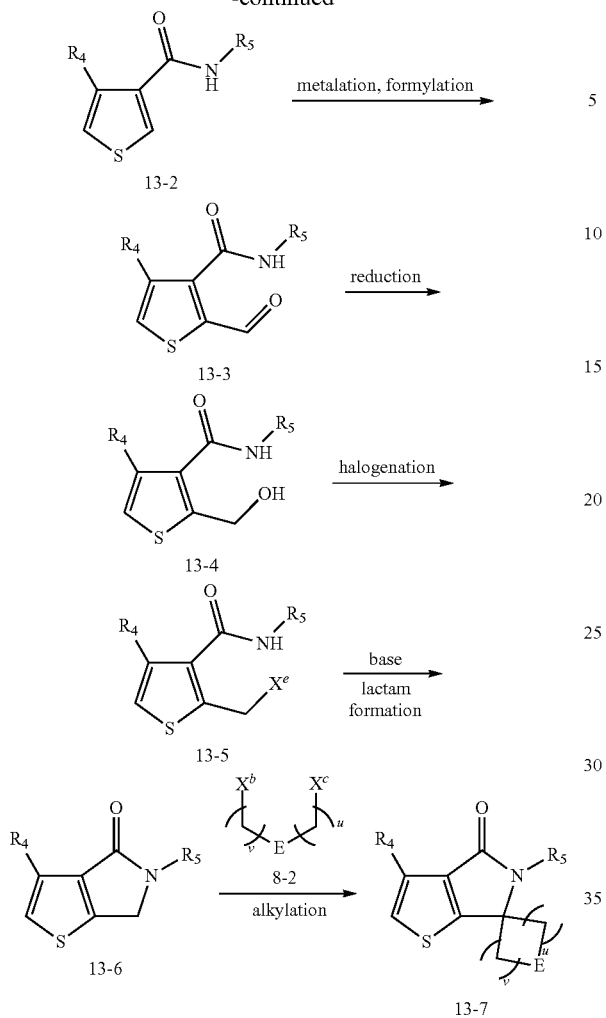

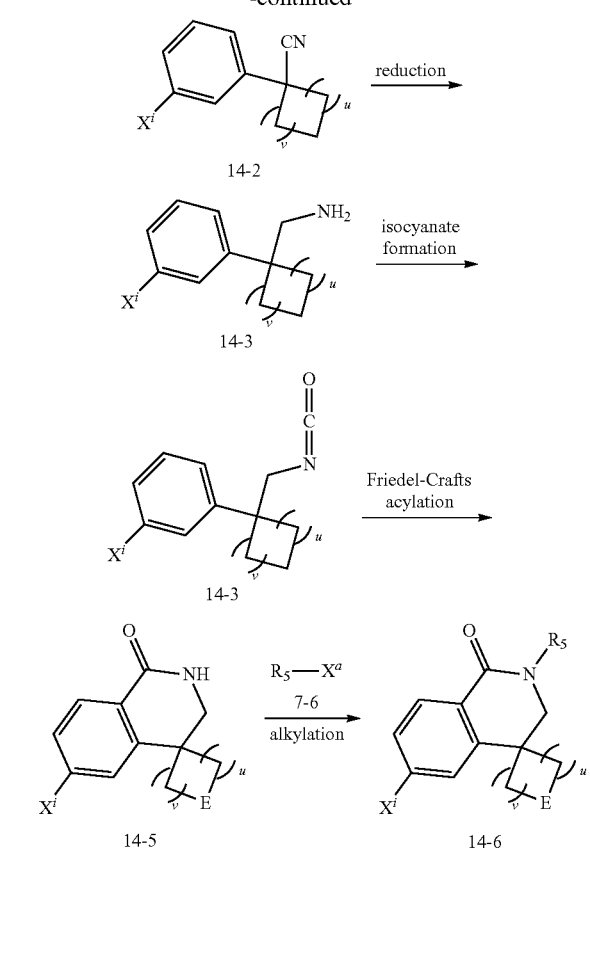

Intermediates for the synthesis of compounds of Formula (I) can be prepared as described in Scheme XIV. Alkylation of nitriles 14-1 where $X^1$ is a halogen (e.g., Cl, Br, or I) or pseudohalogen (e.g., OTf or OMs) with suitable compounds 8-2 in the presence of a base, such as sodium hydride, can provide compounds 14-2. Reduction of nitriles 14-2 under standard conditions, such as in the presence of a reducing agent (e.g., lithium aluminum hydride or borane tetrahydrofuran complex), can provide amines 14-3. Reaction of compounds 14-3 with a phosgene source (e.g., triphosgene) in the presence of a base (e.g., NaHCO$_3$) can afford isocyanates 14-4. Compounds 14-4 can undergo an intramolecular Friedel-Crafts acylation in the presence of a Lewis acid (e.g., FeCl$_3$ or AlCl$_3$) to provide lactams 14-5. Alkylation of lactams 14-5 with suitable compounds 7-6 in the presence of a base, such as NaH, can provide compounds 14-6.

Scheme XIV

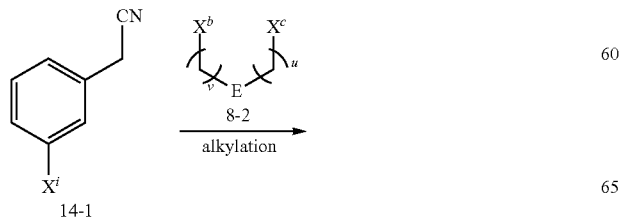

Example 1. 2'-(2-((5-(6-Ethyl-2,6-diazaspiro[3.3]heptan-2-yl)pyridin-2-yl)amino)-5-fluoropyrimidin-4-yl)-5'-methyl-5',6'-dihydro-4'H-spiro[cyclopentane-1,7'-thieno[3,2-c]pyridin]-4'-one

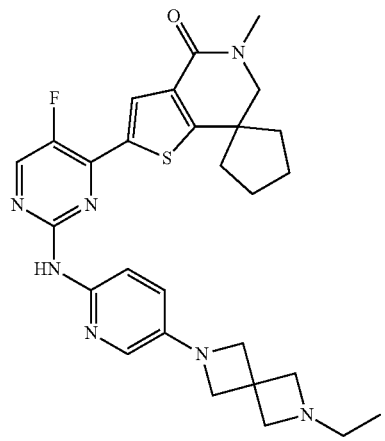 [SMILES: CCN1CC2(C1)CN(c1ccc(Nc3ncc(F)c(-c4cc5c(s4)C4(CCCC4)CN(C)C5=O)n3)nc1)C2]

Step 1. 2-(1-(Isocyanatomethyl)cyclopentyl)thiophene

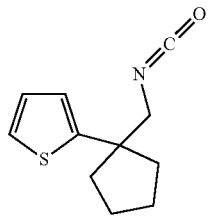 [SMILES: O=C=NCC1(c2cccs2)CCCC1]

To a vial containing triphosgene (0.15 g, 0.50 mmol) was added CH$_2$Cl$_2$ (1.5 mL). The reaction was cooled to 0° C. before 1-(2-thienyl)cyclopentanemethanamine (0.16 mL, 1.0 mmol) and sat. aq. NaHCO$_3$ (1.5 mL) were added sequentially. The reaction was stirred at rt overnight. The reaction was diluted with CH$_2$Cl$_2$ (10 mL), and the layers were separated. The organic layer was washed with brine, dried over Na$_2$SO$_4$, filtered, and used directly in next step. LCMS calc. for C$_{11}$H$_{14}$NOS [M+H]$^+$: m/z=208.1; Found: 208.0.

Step 2. 5',6'-Dihydro-4'H-spiro[cyclopentane-1,7'-thieno[3,2-c]pyridin]-4'-one

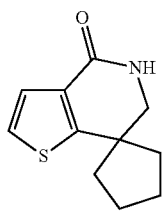 [SMILES: O=C1NCC2(CCCC2)c2sccc21]

The solution of 2-(1-(isocyanatomethyl)cyclopentyl)thiophene in CH$_2$Cl$_2$ from Step 1 was added to a vial containing AlCl$_3$ (0.13 g, 1.0 mmol). The resulting mixture was heated at 50° C. for 1 h. The reaction mixture was poured into sat. aq. NH$_4$Cl and extracted with CH$_2$Cl$_2$. The organic layer was separated, washed with brine, dried over Na$_2$SO$_4$, filtered, and concentrated in vacuo. The crude material was purified by silica gel column chromatography (50% EtOAc in hexanes) to afford the title compound (0.10 g, 0.50 mmol, 50% yield over two steps) as white solid. $^1$H NMR (400 MHz, CDCl$_3$) δ 7.41 (d, J=5.2 Hz, 1H), 7.11 (d, J=5.2 Hz, 1H), 6.42 (s, 1H), 3.43 (d, J=2.7 Hz, 2H), 2.05-1.68 (m, 8H). LCMS calc. for C$_{11}$H$_{14}$NOS [M+H]$^+$: m/z=208.1; Found: 208.0.

Step 3. 5'-Methyl-5',6'-dihydro-4'H-spiro[cyclopentane-1,7'-thieno[3,2-c]pyridin]-4'-one

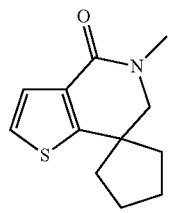

A vial was charged with 5',6'-dihydro-4'H-spiro[cyclopentane-1,7'-thieno[3,2-c]pyridin]-4'-one (80 mg, 0.39 mmol) and NaH (31 mg, 60% in mineral oil). The vial was evacuated and backfilled with N$_2$. Next, tetrahydrofuran (4 mL) was added to the vial, and the reaction mixture was stirred at rt for 5 min, before adding iodomethane (48 μL, 0.78 mmol). The reaction was stirred at rt for 4 h. The reaction was quenched with sat. aq. NH$_4$Cl, and the reaction mixture extracted with EtOAc. The organic layer was separated, washed with brine, dried over Na$_2$SO$_4$, filtered, and concentrated in vacuo. The crude material was purified by silica gel column chromatography (35% EtOAc in hexanes) to afford the title compound (66 mg, 0.30 mmol, 77% yield) as white solid. LCMS calc. for C$_{12}$H$_{16}$NOS [M+H]$^+$: m/z=222.1; Found: 222.0.

Step 4. 2'-Bromo-5'-methyl-5',6'-dihydro-4'H-spiro[cyclopentane-1,7'-thieno[3,2-c]pyridin]-4'-one

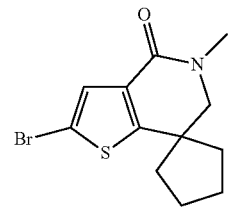

5'-Methyl-5',6'-dihydro-4'H-spiro[cyclopentane-1,7'-thieno[3,2-c]pyridin]-4'-one (66 mg, 0.30 mmol) and N-bromosuccinimide (53 mg, 0.30 mmol) were dissolved in MeCN (3 mL) and stirred at rt for 1 h. The reaction mixture was concentrated in vacuo and purified by silica gel column chromatography (20% EtOAc in hexanes) to afford the title compound (72 mg, 0.24 mmol, 80% yield) as pale yellow solid. LCMS calc. for C$_{12}$H$_{15}$BrNOS [M+H]$^+$: m/z=300.0/302.0; Found: 299.8/301.8.

Step 5. 2'-(2-Chloro-5-fluoropyrimidin-4-yl)-5'-methyl-5',6'-dihydro-4'H-spiro [cyclopentane-1,7'-thieno[3,2-c]pyridin]-4'-one

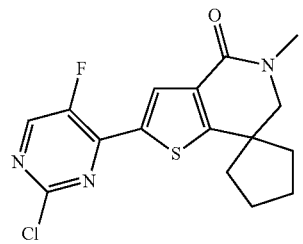 [SMILES: CN1CC2(CCCC2)c2sc(-c3nc(Cl)ncc3F)cc2C1=O]

To a vial was added 2'-bromo-5'-methyl-5',6'-dihydro-4'H-spiro[cyclopentane-1,7'-thieno[3,2-c]pyridin]-4'-one (72 mg, 0.24 mmol), 2,6-dichloro-5-fluorouracil (0.12 g, 0.73 mmol), hexamethylditin (0.10 mL, 0.49 mmol), and Pd(PPh$_3$)$_4$ (42 mg, 0.037 mmol). The vial was evacuated and backfilled with N$_2$ three times. Next, 1,4-dioxane (12 mL) was added, and the reaction mixture was heated at 100° C. for 24 h. The reaction mixture was cooled down to rt and aq. KF (9.7 mL, 0.97 mmol, 0.10 M) was added. The mixture was stirred at rt for 10 min before being filtered through Celite. The filtrate was extracted with EtOAc, washed with brine, dried over Na₂SO₄, filtered, and concentrated in vacuo. The crude material was purified by silica gel column chromatography (35% EtOAc in hexanes) to afford the title compound (26 mg, 0.074 mmol, 30% yield) as white solid. LCMS calc. for $C_{16}H_{16}ClFN_3OS$ [M+H]⁺: m/z=352.1; Found: 351.9.

Step 6. Tert-butyl 6-(6-nitropyridin-3-yl)-2,6-diazaspiro[3.3]heptane-2-carboxylate

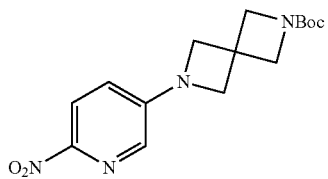 [SMILES: CC(C)(C)OC(=O)N1CC2(C1)CN(c1ccc([N+](=O)[O-])nc1)C2]

A mixture of 5-fluoro-2-nitropyridine (0.30 g, 2.1 mmol), tert-butyl 2,6-diazaspiro[3.3]heptane-2-carboxylate (0.42 g, 2.1 mmol) and DIPEA (0.36 mL, 6.3 mmol) in DMF (4 mL) was stirred at 80° C. overnight. The reaction mixture was slowly poured into ice water (30 mL). The precipitate was collected via filtration and dried to provide the title compound (0.63 g, 1.9 mmol, 92% yield) as a yellow solid. LCMS calc. for $C_{15}H_{21}N_4O_4$ [M+H]⁺: m/z=321.2; Found 321.0.

Step 7. 2-(6-Nitropyridin-3-yl)-2,6-diazaspiro[3.3]heptane

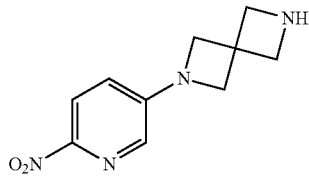 [SMILES: O=[N+]([O-])c1ccc(N2CC3(CNC3)C2)cn1]

A mixture of tert-butyl 6-(6-nitropyridin-3-yl)-2,6-diazaspiro[3.3]heptane-2-carboxylate (500 mg, 1.6 mmol) and TFA (5.0 mL, 65 mmol) in DCM (10 mL) was stirred at room temperature for 2 h. The solvent was removed under reduced pressure. The residue 2-(6-nitropyridin-3-yl)-2,6-diazaspiro[3.3]heptane (300 mg, 1.4 mmol, 87% yield) was used in the next step without further purification. LC-MS calc. for $C_{10}H_{13}N_4O_2$ [M+H]⁺: m/z=221.2; Found 220.9.

Step 8. 6-Ethyl-2-(6-nitropyridin-3-yl)-2,6-diazaspiro[3.3]heptane

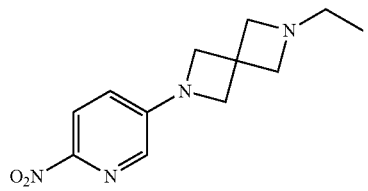 [SMILES: CCN1CC2(C1)CN(c1ccc([N+](=O)[O-])nc1)C2]

A mixture of 2-(6-nitropyridin-3-yl)-2,6-diazaspiro[3.3]heptane (500 mg, 2.3 mmol), triethylamine (0.63 mL, 4.5 mmol), acetic acid (0.010 mL, 0.23 mmol), acetaldehyde (500 mg, 11 mmol), and NaBH₃CN (713 mg, 11 mmol) in methanol (5 mL) was stirred at room temperature overnight. The solvent was removed under reduced pressure. To the resulting material was added HCl (1 N, 10 mL), and the aqueous mixture was extracted with ethyl acetate (10 mL×3). The combined organic layers were dried over Na₂SO₄, filtered, and concentrated under reduced pressure to provide the title compound (300 mg, 1.2 mmol, 53% yield), which was directly used in the next step without further purification. LC-MS calc. for $C_{12}H_{17}N_4O_2$ [M+H]⁺: m/z=249.3; Found 249.0.

Step 9. 5-(6-Ethyl-2,6-diazaspiro[3.3]heptan-2-yl)pyridin-2-amine

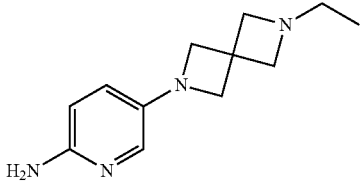

A mixture of 6-ethyl-2-(6-nitropyridin-3-yl)-2,6-diazaspiro[3.3]heptane (500 mg, 2.0 mmol) and Pd/C (50 mg, 0.047 mmol, 10%) in ethanol (10 mL) was stirred under a H₂ atmosphere overnight. The reaction mixture was filtered through Celite. The filtrate was concentrated under reduced pressure. The residue was purified by prep-HPLC on a C18 column (5-50% MeCN in 0.1% TFA (aq), pH=2) to afford the title compound (240 mg, 1.1 mmol, 55% yield). LC-MS calc. for $C_{12}H_{19}N_4$ [M+H]⁺: m/z=219.2; Found 218.9.

Step 10. 2'-(2-((5-(6-Ethyl-2,6-diazaspiro[3.3]heptan-2-yl)pyridin-2-yl)amino)-5-fluoropyrimidin-4-yl)-5'-methyl-5',6'-dihydro-4'H-spiro[cyclopentane-1,7'-thieno[3,2-c]pyridin]-4'-one A suspension of 2'-(2-chloro-5-fluoropyrimidin-4-yl)-5'-methyl-5',6'-dihydro-4'H-spiro[cyclopentane-1,7'-thieno[3,2-c]pyridin]-4'-one (20 mg, 0.057 mmol), 5-(6-ethyl-2,6-diazaspiro[3.3]heptan-2-yl)pyridin-2-amine (25 mg, 0.11 mmol), XPhos Pd G3 (7.2 mg, 0.0085 mmol), and Cs₂CO₃ (56 mg, 0.17 mmol) in 1,4-dioxane (2 mL) was heated at 100° C. under N₂ atmosphere for 18 h. The reaction mixture was cooled to rt, and TFA (0.044 mL) was added. The mixture was filtered, and the filter frit washed with MeOH. The filtrate was purified by prep-HPLC on a C18 column (6-80% MeCN in 0.1% TFA (aq), pH=2) to afford the title compound (17 mg, 0.032 mmol, 56% yield) as yellow solid. ¹H NMR (400 MHz, CD₃OD) δ 8.65 (d, J=3.1 Hz, 1H), 8.23 (s, 1H), 7.63 (d, J=9.9 Hz, 1H), 7.56-7.47 (m, 2H), 4.58-4.43 (m, 2H), 4.38-4.23 (m, 4H), 4.18 (s, 2H), 3.61 (s, 2H), 3.31-3.25 (m, 2H), 3.15 (s, 3H), 2.13-2.00 (m, 2H), 2.00-1.85 (m, 6H), 1.24 (t, J=7.2 Hz, 3H). LCMS calc. for $C_{28}H_{33}FN_7OS$ [M+H]⁺: m/z=534.2; Found: 534.1.

Example 2. 2'-(5-Fluoro-2-((5-(1-methylpiperidin-4-yl)pyridin-2-yl)amino)pyrimidin-4-yl)-5'-methyl-5',6'-dihydro-4'H-spiro[cyclopentane-1,7'-thieno[3,2-c]pyridin]-4'-one

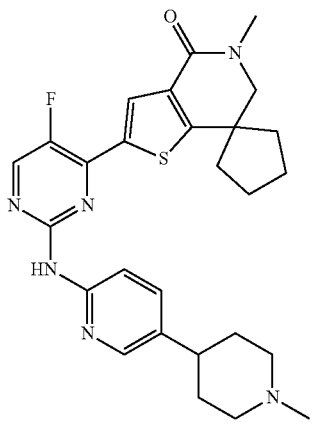 [SMILES: CN1CCC(c2ccc(Nc3ncc(F)c(-c4cc5c(s4)C4(CCCC4)CN(C)C5=O)n3)nc2)CC1]

Step 1. tert-Butyl 6-nitro-3',6'-dihydro-[3,4'-bipyridine]-1'(2'H)-carboxylate

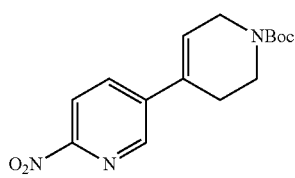 [SMILES: CC(C)(C)OC(=O)N1CC=C(c2ccc([N+](=O)[O-])nc2)CC1]

A suspension of 5-bromo-2-nitropyridine (15 g, 74 mmol), N-Boc-1,2,3,6-tetrahydropyridine-4-boronic acid pinacol ester (25 g, 81 mmol), [1,1'-bis(diphenylphosphino)ferrocene]dichloropalladium (1.6 g, 2.2 mmol) and potassium carbonate (41 g, 295 mmol) in 1,4-dioxane (160 mL) and water (40 mL) was stirred at 100° C. under N₂ atmosphere for 2 h. The reaction mixture was cooled to rt and filtered through a pad of Celite. The filtrate was diluted with water (100 mL) and extracted with EtOAc (80 mL×3). The combined organic layers were washed with brine (80 mL), dried over Na₂SO₄, filtered, and evaporated in vacuo. The residue was purified by flash chromatography on silica gel (0-100% DCM in heptanes) to give the title compound (18 g, 59 mmol, 80% yield) as yellow solid. LCMS calc. for $C_{15}H_{20}N_3O_4$ [M+H]$^+$: m/z=306.1; Found: 306.0.

Step 2. 6-Nitro-1',2',3',6'-tetrahydro-3,4'-bipyridine

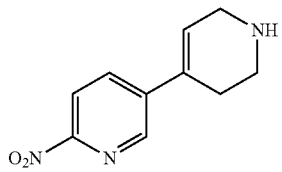 [SMILES: O=[N+]([O-])c1ccc(C2=CCNCC2)cn1]

To a solution of tert-butyl 6-nitro-3',6'-dihydro-[3,4'-bipyridine]-1'(2'H)-carboxylate (9.2 g, 30 mmol) in DCM (90 mL) at rt was slowly added TFA (90 mL). The resulting orange solution was stirred at rt for 4 h. The volatiles were evaporated in vacuo to afford the title compound (8.0 g) as TFA salt, which was used directly without further purification. LCMS calc. for $C_{10}H_{12}N_3O_2$ [M+H]$^+$: m/z=206.1; Found: 206.0.

Step 3. 1'-Methyl-6-nitro-1',2',3',6'-tetrahydro-3,4'-bipyridine

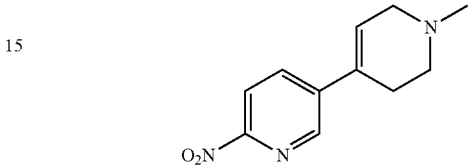

NaCNBH₃ (11 g, 180 mmol) was added in portions to a solution of 6-nitro-1',2',3',6'-tetrahydro-3,4'-bipyridine (6.2 g, 30 mmol), paraformaldehyde (5.4 g, 180 mmol) and acetic acid (11 g, 180 mmol) in methanol (60 mL) at rt over a period of 30 min. The resulting dark solution was stirred at rt for 18 h. The reaction mixture was concentrated in vacuo, and the residue was adjusted to pH 8 with 10% Na₂CO₃ (aq). The mixture was extracted with EtOAc (50 mL×3), and the combined organic layers were washed with water (50 mL) and brine (50 mL), dried over Na₂SO₄, filtered, and evaporated in vacuo. The residue was purified by flash chromatography on silica gel (0-80% MeOH in MTBE) to give the title compound (5.1 g, 23 mmol, 77% yield) as yellow solid. LCMS calc. for $C_{10}H_{14}N_3O_2$ [M+H]$^+$: m/z=220.1; Found: 220.0.

Step 4. 5-(1-Methylpiperidin-4-yl)pyridin-2-amine

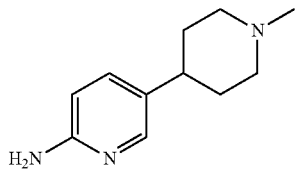

To a solution of 1'-methyl-6-nitro-1',2',3',6'-tetrahydro-3,4'-bipyridine (9.1 g, 42 mmol) in methanol (500 mL) was added 10% Pd/C (2.0 g, 19 mmol). The mixture was hydrogenated at 100 psi and 45° C. for 5 d. The reaction mixture was filtered through a pad of Celite, and the filtrate was concentrated in vacuo. The residue was purified by flash chromatography on silica gel (0-80% MeOH in MTBE) to afford the title compound (5.6 g, 29 mmol, 70% yield) as white solid. ¹H NMR (300 MHz, CD₃OD) δ 7.77 (d, J=2.3 Hz, 1H), 7.41 (dd, J=8.6, 2.4 Hz, 1H), 6.58 (d, J=8.6 Hz, 1H), 3.32-3.30 (m, 1H), 2.78-2.67 (m, 2H), 2.64 (s, 3H), 2.62-2.54 (m, 2H), 1.97-1.78 (m, 4H). LCMS calc. for $C_{11}H_{18}N_3$ [M+H]$^+$: m/z=192.2; Found: 192.2.

Step 5. 2'-(5-Fluoro-2-((5-(1-methylpiperidin-4-yl)pyridin-2-yl)amino)pyrimidin-4-yl)-5'-methyl-5',6'-dihydro-4'H-spiro[cyclopentane-1,7'-thieno[3,2-c]pyridin]-4'-one A suspension of XPhos Pd G3 (9.4 mg, 0.011 mmol), Cs₂CO₃ (72 mg, 0.22 mmol), 5-(1-methylpiperidin-4-yl)

pyridin-2-amine (28 mg, 0.15 mmol) and 2'-(2-chloro-5-fluoropyrimidin-4-yl)-5'-methyl-5',6'-dihydro-4'H-spiro[cyclopentane-1,7'-thieno[3,2-c]pyridin]-4'-one (26 mg, 0.074 mmol) in 1,4-dioxane (2 mL) was heated at 100° C. under $N_2$ atmosphere for 18 h. The reaction mixture was cooled to rt, and TFA (0.056 mL) was added. The reaction mixture was filtered, and the filter frit washed with MeOH. The filtrate was purified by prep-HPLC on a $C_{18}$ column (6-80% MeCN in 0.1% TFA (aq), pH=2) to afford the title compound (18 mg, 0.035 mmol, 47% yield) as yellow solid. $^1$H NMR (400 MHz, CD$_3$OD) δ 8.72 (d, J=3.2 Hz, 1H), 8.30-8.25 (m, 2H), 8.24 (d, J=1.7 Hz, 1H), 7.66 (d, J=9.5 Hz, 1H), 3.73-3.65 (m, 2H), 3.61 (s, 2H), 3.26-3.16 (m, 2H), 3.15 (s, 3H), 3.13-3.03 (m, 1H), 2.96 (s, 3H), 2.28-2.19 (m, 2H), 2.13-2.00 (m, 4H), 1.99-1.85 (m, 6H). LCMS calc. for $C_{27}H_{32}FN_6OS$ [M+H]$^+$: m/z=507.2; Found: 507.0.

Example 3. 2'-(2-((5-(4-Ethylpiperazin-1-yl)pyridin-2-yl)amino)-5-fluoropyrimidin-4-yl)-5'-methyl-5',6'-dihydro-4'H-spiro[cyclopentane-1,7'-thieno[3,2-c]pyridin]-4'-one

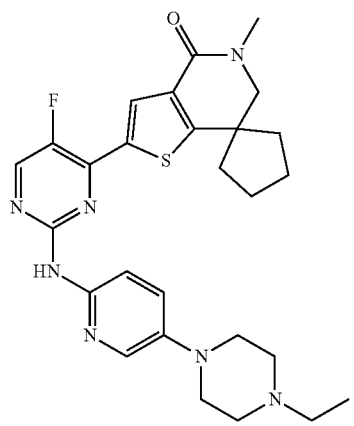 [SMILES: CCN1CCN(c2ccc(Nc3ncc(F)c(-c4cc5c(s4)C4(CCCC4)CN(C)C5=O)n3)nc2)CC1]

The title compound was synthesized by a procedure analogous to that outlined in Example 1, Step 10 substituting 5-(4-ethylpiperazin-1-yl)pyridin-2-amine for 5-(6-ethyl-ethyl-2,6-diazaspiro[3.3]heptan-2-yl)pyridin-2-amine. $^1$H NMR (400 MHz, CD$_3$OD) δ 8.68 (d, J=3.2 Hz, 1H), 8.24 (d, J=1.7 Hz, 1H), 8.17 (dd, J=9.6, 3.0 Hz, 1H), 7.94 (d, J=2.9 Hz, 1H), 7.65 (d, J=9.6 Hz, 1H), 4.04-3.62 (m, 4H), 3.61 (s, 2H), 3.46-3.16 (m, 6H), 3.15 (s, 3H), 2.14-1.85 (m, 8H), 1.43 (t, J=7.3 Hz, 3H). LC-MS calc. for $C_{27}H_{33}FN_7OS$ [M+H]$^+$: m/z=522.2; Found 522.0.

Example 4. 2'-(2-((5-(6-Ethyl-2,6-diazaspiro[3.3]heptan-2-yl)pyridin-2-yl)amino)-5-fluoropyrimidin-4-yl)-5'-methyl-5',6'-dihydro-4'H-spiro[cyclohexane-1,7'-thieno[3,2-c]pyridin]-4'-one

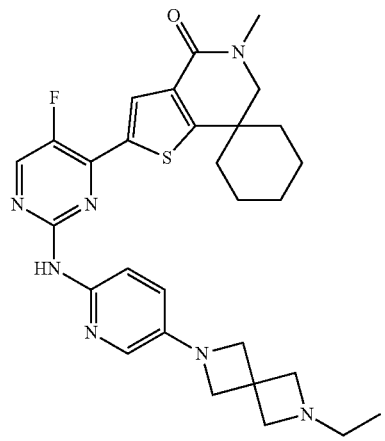 [SMILES: CCN1CC2(C1)CN(c1ccc(Nc3ncc(F)c(-c4cc5c(s4)C4(CCCCC4)CN(C)C5=O)n3)nc1)C2]

The title compound was synthesized by procedures analogous to those outlined in Example 1, Steps 1-10. LC-MS calc. for $C_{29}H_{35}FN_7OS$ [M+H]$^+$: m/z=548.3; Found 548.2.

Example 5. 2'-(5-Fluoro-2-((5-(1-methylpiperidin-4-yl)pyridin-2-yl)amino)pyrimidin-4-yl)-5'-methyl-5',6'-dihydro-4'H-spiro[cyclohexane-1,7'-thieno[3,2-c]pyridin]-4'-one

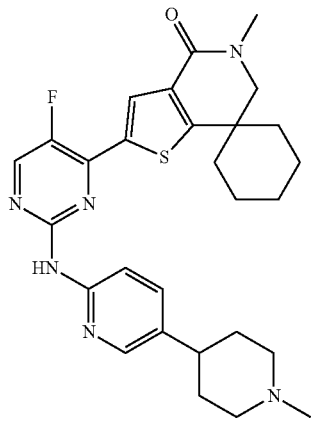 [SMILES: CN1CCC(c2ccc(Nc3ncc(F)c(-c4cc5c(s4)C4(CCCCC4)CN(C)C5=O)n3)nc2)CC1]

The title compound was synthesized by procedures analogous to those outlined in Example 1, Steps 1-5 and Example 2, Step 5. $^1$H NMR (400 MHz, CD$_3$OD) δ 8.70 (d, J=3.1 Hz, 1H), 8.26 (d, J=5.7 Hz, 2H), 8.21 (d, J=9.1 Hz, 1H), 7.75 (d, J=9.0 Hz, 1H), 3.75-3.63 (m, 4H), 3.26-3.05 (m, 3H), 3.17 (s, 3H), 2.97 (s, 3H), 2.25 (d, J=14.2 Hz, 2H), 2.08-1.86 (m, 4H), 1.83-1.47 (m, 8H). LC-MS calc. for $C_{28}H_{34}FN_6OS$ [M+H]$^+$: m/z=521.2; Found 521.1.

Example 6. 2'-(5-Fluoro-2-((5-(1-methylpiperidin-4-yl)pyridin-2-yl)amino)pyrimidin-4-yl)-3',5'-dimethylspiro[cyclopropane-1,6'-thieno[2,3-c]pyrrol]-4'(5'H)-one

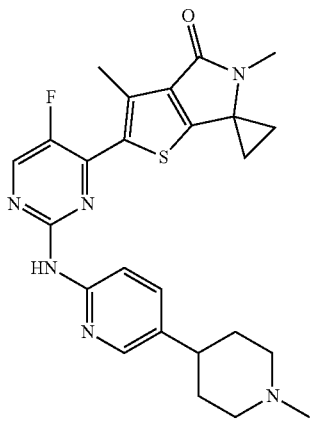 [SMILES: Cc1c(-c2nc(Nc3ccc(C4CCN(C)CC4)cn3)ncc2F)sc2c1C(=O)N(C)C21CC1]

Step 1. N,4-dimethylthiophene-3-carboxamide

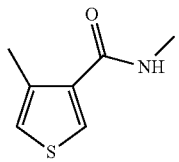

Triethylamine (13.8 mL, 99.0 mmol) was added to a solution of 4-methyl-3-thiophenecarboxylic acid (3.52 g, 24.8 mmol), HATU (10.4 g, 27.2 mmol) and methylamine hydrochloride (2.51 g, 37.1 mmol) in DCM (100 mL). The reaction was stirred at room temperature for 2 h. The reaction was diluted with water (25 mL), and the layers were separated. The organics were dried over $Na_2SO_4$, filtered, and concentrated. The crude residue was purified by silica gel chromatography (0-30% EtOAc/heptanes) to afford the title compound (3.50 g, 22.5 mmol, 91.1% yield) as a clear oil. LCMS calc. for $C_7H_{10}NOS$ [M+H]$^+$: m/z=156.1; Found: 156.0.

Step 2. 2-Formyl-N,4-dimethylthiophene-3-carboxamide

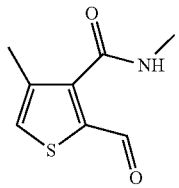

n-Butyllithium (18.0 mL, 44 mmol, 2.5 M in THF) was added dropwise over 30 min to a solution of N,4-dimethylthiophene-3-carboxamide (2.73 g, 17.6 mmol) in THF (30.0 mL) at −78° C. The reaction was stirred at −78° C. for 1 h. N,N-Dimethylformamide (6.81 mL, 87.9 mmol) was added dropwise to the reaction mixture over 15 min. The solution was warmed to room temperature and stirred for 1 h. The reaction mixture was cooled to 0° C. and diluted with sat. $NH_4Cl$ (aq.) (30.0 mL). The reaction mixture was extracted with EtOAc (2×30.0 mL) and DCM (2×30.0 mL). The combined organics were dried over $Na_2SO_4$, filtered, and concentrated to afford the title compound, which was used in the next step without additional purification. LCMS calc. for $C_8H_{10}NO_2S$ [M+H]$^+$: m/z=184.0; Found: 184.0.

Step 3. 2-(Hydroxymethyl)-N,4-dimethylthiophene-3-carboxamide

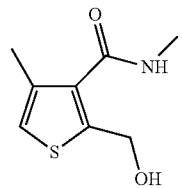

Sodium borohydride (0.666 g, 17.6 mmol) was added in portions to a solution of 2-formyl-N,4-dimethylthiophene-3-carboxamide (from Step 2) in methanol (20.0 mL) at 0° C. The reaction was stirred for 30 min. The mixture was carefully quenched with sat. $NH_4Cl$ (aq.) (35.0 mL) while stirring at 0° C. The white solid was filtered off and collected. The filtrate was extracted with EtOAc (2×20.0 mL) and DCM (2×20.0 mL). The combined organics were dried over $Na_2SO_4$, filtered, and concentrated. The crude residue was purified by silica gel chromatography (0-100% EtOAc/heptanes) to afford the title compound (1.84 g, 9.93 mmol, 56.4% yield over two steps) as a white solid. $^1$H NMR (300 MHz, DMSO-d$_6$) δ 7.87 (s, 1H), 6.95 (s, 1H), 5.51 (t, J=5.5 Hz, 1H), 4.56 (d, J=5.5 Hz, 2H), 2.67 (d, J=4.6 Hz, 3H), 2.09 (s, 3H). LCMS calc. for $C_8H_{10}NOS$ [M−OH]$^+$: m/z=168.1; Found: 167.9.

Step 4. 2-(Chloromethyl)-N,4-dimethylthiophene-3-carboxamide

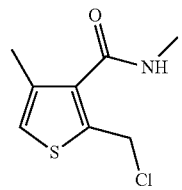

Thionyl chloride (1.08 mL, 14.9 mmol) was added dropwise to a solution of 2-(hydroxymethyl)-N,4-dimethylthiophene-3-carboxamide (1.84 g, 9.93 mmol) in DCM (30.0 mL) at 0° C. The reaction mixture was warmed to room temperature and stirred for 2 h. The reaction mixture was quenched with sat. $NaHCO_3$ (aq.) (30.0 mL) and extracted with DCM (3×30.0 mL). The combined organics were washed with brine (30.0 mL), dried over $Na_2SO_4$, filtered, and concentrated to afford the title compound, which was used directly in the next step without additional purification. LCMS calc. for $C_8H_{10}NOS$ [M−Cl]$^+$: m/z=168.1; Found: 167.9.

Step 5. 3,5-Dimethyl-5, 6-dihydro-4H-thieno[2,3-c]pyrrol-4-one

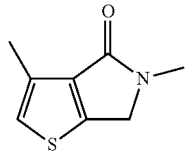

Lithium bis(trimethylsilyl)amide (11.2 mL, 11 mmol, 1.0 M in THF) was added dropwise to a solution of 2-(chloromethyl)-N,4-dimethylthiophene-3-carboxamide (from Step 4) in THF (36.0 mL) at −78° C. The reaction was stirred at −78° C. for 1 h. The reaction was quenched with sat. NaHCO$_3$ (aq.) (20.0 mL), and the reaction mixture extracted with EtOAc (3×20.0 mL). The combined organics were washed with brine (30.0 mL), dried over Na$_2$SO$_4$, filtered, and concentrated under reduced pressure. The crude residue was purified by silica gel chromatography (0-50% EtOAc/heptanes) to afford the title compound (0.605 g, 3.62 mmol, 38.8% yield over two steps) as a light-yellow oil. LCMS calc. for C$_8$H$_{10}$NOS [M+H]$^+$: m/z=168.1; Found: 168.0.

Step 6. 3',5'-Dimethylspiro[cyclopropane-1,6'-thieno[2,3-c]pyrrol]-4'(5'H)-one

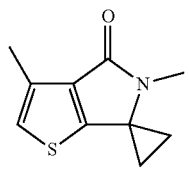

Lithium diisopropylamide (5.43 mL, 11 mmol, 2.0 M in THF) was added dropwise to a solution of 3,5-dimethyl-5,6-dihydro-4H-thieno[2,3-c]pyrrol-4-one (0.605 g, 3.62 mmol) in THF (30.0 mL) at −78° C. and stirred for 20 min. 1,2-Dibromoethane (0.627 mL, 7.24 mmol) was added, and the reaction mixture was warmed to room temperature and stirred overnight. The reaction mixture was cooled to 0° C., and the reaction quenched with sat. NH$_4$Cl (aq.). The mixture was extracted with DCM (3×30.0 mL). The combined organic layers were washed with brine (20.0 mL), dried over Na$_2$SO$_4$, filtered, and concentrated. The crude residue was purified by silica gel chromatography (0-30% EtOAc/heptanes) to afford the title compound (0.278 g, 1.44 mmol, 39.8% yield) as a light yellow solid. LCMS calc. for C$_{10}$H$_{12}$NOS [M+H]$^+$: m/z=194.1; Found: 194.1.

Step 7. 2'-Bromo-3',5'-dimethylspiro[cyclopropane-1,6'-thieno[2,3-c]pyrrol]-4'(5'H)-one

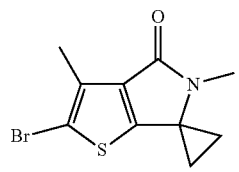

N-Bromosuccinimide (0.266 g, 1.51 mmol) was added to a solution of 3',5'-dimethylspiro[cyclopropane-1,6'-thieno[2,3-c]pyrrol]-4'(5'H)-one (0.278 g, 1.44 mmol) in acetonitrile (5.00 mL) at room temperature and stirred for 30 min. The mixture was concentrated, and the crude residue was purified by silica gel chromatography (0-40% EtOAc/heptanes) to afford the title compound (0.338 g, 1.24 mmol, 86.3% yield) as a light-yellow solid. LCMS calc. for C$_{10}$H$_{11}$BrNOS [M+H]$^+$: m/z=272.0, 274.0; Found: 271.8, 273.8.

Step 8. 2'-(2-Chloro-5-fluoropyrimidin-4-yl)-3',5'-dimethylspiro[cyclopropane-1,6'-thieno[2,3-c]pyrrol]-4'(5'H)-one

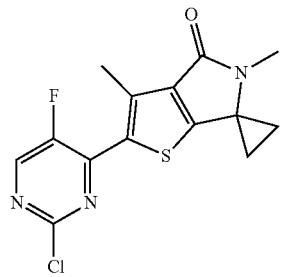 [SMILES: Cc1c(-c2nc(Cl)ncc2F)sc2c1C(=O)N(C)C21CC1]

A solution of 2'-bromo-3',5'-dimethylspiro[cyclopropane-1,6'-thieno[2,3-c]pyrrol]-4'(5'H)-one (0.306 g, 1.12 mmol), hexamethylditin (0.466 mL, 2.25 mmol) and tetrakis(triphenylphosphine)palladium(0) (0.195 g, 0.169 mmol) in 1,4-dioxane (10.0 mL) was heated at 100° C. under a nitrogen atmosphere for 3 h. The reaction mixture was cooled to room temperature, and 2,6-dichloro-5-fluororacil (0.413 g, 2.47 mmol) was added. The reaction mixture was stirred overnight at 100° C. Upon cooling to room temperature, a solution of potassium fluoride (0.261 g, 4.50 mmol) in water (30.0 mL) was added to the reaction mixture. Ethyl acetate (50.0 mL) was added, and the layers were separated. The organic layer was dried over Na$_2$SO$_4$, filtered, and concentrated. The crude residue was purified by silica gel chromatography (0-45% EtOAc/heptanes) to afford the title compound (0.220 g, 0.679 mmol, 60.4% yield) as a yellow solid. LCMS calc. for C$_{14}$H$_{12}$ClFN$_3$OS [M+H]$^+$: m/z=324.0, 326.0; Found: 323.9, 325.8.

Step 9. 2'-(5-Fluoro-2-((5-(1-methylpiperidin-4-yl)pyridin-2-yl)amino)pyrimidin-4-yl)-3',5'-dimethylspiro[cyclopropane-1,6'-thieno[2,3-c]pyrrol]-4'(5'H)-one A suspension of 2'-(2-chloro-5-fluoropyrimidin-4-yl)-3',5'-dimethylspiro[cyclopropane-1,6'-thieno[2,3-c]pyrrol]-4'(5'H)-one (0.260 g, 0.803 mmol), 5-(1-methylpiperidin-4-yl)pyridin-2-amine (0.230 g, 1.20 mmol, Example 2, Step 4), XPhos Pd G2 (0.102 g, 0.120 mmol, CAS #: 1310584-14-5), and K$_3$PO$_4$ (1.31 g, 4.02 mmol) in 1,4-dioxane (8.00 mL) was heated at 100° C. under a nitrogen atmosphere for 18 h. The reaction mixture was cooled to room temperature and TFA (2 drops) was added. The inorganic salts were filtered off, and the filtrate was purified by prep-HPLC on a C18 column (10-40% MeCN in 0.1% TFA (aq.), pH=2) to afford the title compound as a TFA salt (0.128 g, 0.181 mmol, 23%), a yellow solid. $^1$H NMR (400 MHz, CD$_3$OD) δ 8.70 (d, J=3.0 Hz, 1H), 8.24 (s, 1H), 8.15 (d, J=9.0 Hz, 1H), 7.78 (d, J=9.0 Hz, 1H), 3.71-3.63 (m, 2H), 3.24-3.15

(m, 2H), 3.10-3.00 (m, 1H), 2.95 (s, 3H), 2.87 (s, 3H), 2.75 (d, J=2.5 Hz, 3H), 2.26-2.19 (m, 2H), 2.06-1.96 (m, 2H), 1.93 (dd, J=6.2, 8.6 Hz, 2H), 1.53 (dd, J=6.0, 8.2 Hz, 2H). LCMS calc. for $C_{25}H_{28}FN_6OS$ [M+H]$^+$: m/z=479.2; Found: 479.2.

Examples 7-19

Examples 7-19 listed in Table 1 and Table 2 were synthesized according to procedures analogous to Example 6. All examples in these tables were prepared as the TFA salt unless otherwise noted.

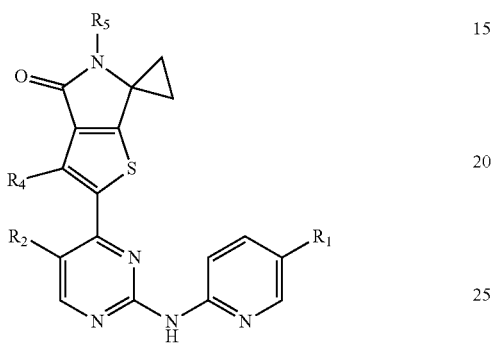

TABLE 1

Examples 7-19

| Example | R$_1$ | R$_2$ | R$_4$ | R$_5$ | LCMS [M + H]$^+$ |
|---|---|---|---|---|---|
| 7 | 1-methylpiperidin-4-yl | F | Me | Et | 493.1 |
| 8 | 1-methylpiperidin-4-yl | F | H | Me | 465.0 |
| 9 | 1-methylpiperidin-4-yl | F | Cl | Me | 499.0 |
| 10 | 1-methylpiperidin-4-yl | F | CF$_3$ | Me | 533.0 |
| 11 | 1-methylpiperidin-4-yl | Cl | Me | Et | 509.0 |

TABLE 1-continued

Examples 7-19

| Example | R₁ | R₂ | R₄ | R₅ | LCMS [M + H]⁺ |
|---|---|---|---|---|---|
| 12 | (spiro diazetidine with N-ethyl) | F | Me | Me | 506.1 |
| 13 | (N-ethylpiperazinyl-methyl) | F | Me | Me | 508.1 |
| 14 | (2,6-diazaspiro[3.4]octane N-methyl) | F | Me | Me | 506.2 |
| 15 | (1-methylpiperidin-3-yl) | F | Me | Me | 479.2 |
| 16 | (1-isopropylpyrrolidin-3-yl) | F | Me | Me | 493.2 |
| 17 | (cis-octahydropyrrolo[3,4-c]pyrrole N-methyl) | Me | H | Et | 502.2 |
| 18 | (1-methylpiperidin-3-yl) | Me | H | Et | 475.2 |
| 19 | (1-methylpiperidin-4-yl) | Me | H | Et | 475.2 |

TABLE 2

Examples 7-19

| Example | Compound name | NMR |
|---|---|---|
| 7 | 5'-Ethyl-2'-(5-fluoro-2-((5-(1-methylpiperidin-4-yl)pyridin-2-yl)amino)pyrimidin-4-yl)-3'-methylspiro[cyclopropane-1,6'-thieno[2,3-c]pyrrol]-4'(5'H)-one | ¹H NMR (400 MHz, methanol-d₄) δ 8.74 (d, J = 3.2 Hz, 1H), 8.32-8.23 (m, 2H), 7.64 (d, J = 8.8 Hz, 1H), 3.68 (d, J = 12.0 Hz, 2H), 3.30-3.27 (m, 2H), 3.24-3.15 (m, 2H), 3.15-3.02 (m, 1H), 2.95 (s, 3H), 2.78 (d, J = 2.4 Hz, 3H), 2.23 (d, J = 14.4 |

TABLE 2-continued

Examples 7-19

| Example | Compound name | NMR |
|---|---|---|
| | | Hz, 2H), 2.11-1.97 (m, 2H), 1.92 (dd, J = 8.4, 6.0, 2H), 1.55 (dd, J = 8.0, 6.0, 2H), 1.21 (t, J = 7.2 Hz, 3H). |
| 8 | 2'-(5-Fluoro-2-((5-(1-methylpiperidin-4-yl)pyridin-2-yl)amino)pyrimidin-4-yl)-5'-methylspiro[cyclopropane-1,6'-thieno[2,3-c]pyroll-4'(5'H)-one | — |
| 9 | 3'-chloro-2'-(5-Fluoro-2-((5-(1-methylpiperidin-4-yl)pyridin-2-yl)amino)pyrimidin-4-yl)-5'-methylspiro[cyclopropane-1,6'-thieno[2,3-c]pyrrol]-4'(5'H)-one | — |
| 10 | 2'-(5-Fluoro-2-((5-(1-methyl-piperidin-4-yl)pyridin-2-yl)amino)pyrimidin-4-yl)-5'-methyl-3'-(trifluoromethyl)spiro[cyclopropane-1,6'-thieno[2,3-c]pyrrol]-4'(5'H)-one | $^1$H NMR (400 MHz, methanol-d$_4$) δ 8.83 (d, J = 1.6 Hz, 1H), 8.25 (d, J = 2.0 Hz, 1H), 8.20 (dd, J = 9.2, 2.4 Hz, 1H), 7.73 (d, J = 8.8 Hz, 1H), 3.70-3.63 (m, 2H), 3.23-3.14 (m, 2H), 3.11-3.01 (m, 1H), 2.94 (s, 3H), 2.89 (s, 3H), 2.22 (d, J = 14.4 Hz, 2H), 2.09-2.01 (m, 1H), 2.00-1.95 (m, 3H), 1.63 (dd, J = 8.8, 6.4 Hz, 2H). |
| 11 | 2'-(5-Chloro-2-((5-(1-methyl-piperidin-4-yl)pyridin-2-yl)amino)pyrimidin-4-yl)-5'-ethyl-3'-methylspiro[cyclopropane-1,6'-thieno[2,3-c]pyrrol]-4'(5'H)-one | $^1$H NMR (400 MHz, methanol-d$_4$) δ 8.78 (s, 1H), 8.25 (s, 1H), 8.13-8.07 (m, 1H), 7.84 (d, J = 9.2 Hz, 1H), 3.70-3.62 (m, 2H), 3.24-3.11 (m, 3H), 3.10-2.98 (m, 2H), 2.94 (s, 3H), 2.56 (s, 3H), 2.21 (d, J = 14.0 Hz, 2H), 2.06-1.93 (m, 2H), 1.90 (dd, J = 8.4, 6.4 Hz, 2H), 1.53 (dd, J = 8.0, 6.4 Hz, 2H), 1.21 (t, J = 7.2 Hz, 3H). |
| 12 | 2'-(2-((5-(6-Ethyl-2,6-diazaspiro[3.3]heptan-2-yl)pyridin-2-yl)amino)-5-fluoropyrimidin-4-yl)-3',5'-dimethylspiro[cyclopropane-1,6'-thieno[2,3-c]pyrrol]-4'(5'H)-one | $^1$H NMR (400 MHz, methanol-d$_4$) δ 8.66 (d, J = 2.8 Hz, 1H), 7.61 (dd, J = 8.8, 2.8 Hz, 1H), 7.55 (d, J = 9.2 Hz, 1H), 7.48 (d, J = 2.8 Hz, 1H), 4.55-4.45 (m, 2H), 4.35-4.22 (m, 4H), 4.16 (s, 2H), 3.26 (q, J = 7.2 Hz, 2H), 2.86 (s, 3H), 2.75 (d, J = 2.4 Hz, 3H), 1.92 (dd, J = 8.0, 6.4 Hz, 2H), 1.53 (dd, J = 8.4, 6.0 Hz, 2H), 1.23 (t, J = 7.2 Hz, 3H). |
| 13 | 2'-(2-((5-((4-Ethylpiperazin-1-yl)methyl)pyridin-2-yl)amino)-5-fluoropyrimidin-4-yl)-3',5'-dimethylspiro[cyclopropane-1,6'-thieno[2,3-c]pyrrol]-4'(5'H)-one | $^1$H NMR (400 MHz, methanol-d$_4$) δ 8.74 (d, J = 3.2 Hz, 1H), 8.31-8.28 (m, 1H), 8.27 (d, J = 2.4 Hz, 1H), 7.68 (d, J = 9.2 Hz, 1H), 3.73 (s, 2H), 3.63-3.50 (m, 2H), 3.23 (q, J = 7.2 Hz, 2H), 3.16-3.02 (m, 4H), 2.87 (s, 3H), 2.77 (d, J = 2.4 Hz, 3H), 2.63-2.45 (m, 2H), 1.93 (dd, J = 8.4, 6.4 Hz, 2H), 1.54 (dd, J = 8.0, 6.0 Hz, 2H), 1.36 (t, J = 7.2 Hz, 3H). |
| 14 | 2'-(5-Fluoro-2-((5-(6-methyl-2,6-diazaspiro[3.4]octan-2-yl)pyridin-2-yl)amino)pyrimidin-4-yl)-3',5'-di methyl spiro[cyclopropane-1,6'-thieno[2,3-c]pyrrol]-4'(5'H)-one | $^1$H NMR (300 MHz, methanol-d$_4$) δ 8.66 (d, J = 3.3 Hz, 1H), 7.66 (dd, J = 9.3, 2.7 Hz, 1H), 7.52 (s, 1H), 7.50-7.48 (m, 1H), 4.12-3.95 (m, 5H), 3.82-3.70 (m, 1H), 3.47-3.35 (m, 1H), 3.26-3.18 (m, 1H), 2.98 (s, 3H), 2.85 (s, 3H), 2.75 (d, J = 2.4 Hz, 3H), 2.61-2.41 (m, 2H), 1.92 (dd, J = 7.7, 5.2 Hz, 2H), 1.52 (dd, J = 8.1, 6.0 Hz, 2H). |
| 15 | 2'-(5-Fluoro-2-((5-(1-methylpiperidin-3-yl)pyridin-2-yl)amino)pyrimidin-4-yl)-3',5'-dimethylspiro[cyclopropane-1,6'-thieno[2,3-c]pyrrol]-4'(5'H)-one | $^1$H NMR (300 MHz, methanol-d$_4$) δ 8.72 (d, J = 3.0 Hz, 1H), 8.34-8.21 (m, 2H), 7.71 (d, J = 8.7 Hz, 1H), 3.71-3.57 (m, 2H), 3.25-2.99 (m, 4H), 2.94 (s, 3H), 2.85 (s, 3H), 2.76 (d, J = 2.4 Hz, 3H), 2.21-1.98 (m, 3H), 1.92 (dd, J = 8.7, 6.0 Hz, 2H), 1.53 (dd, J = 8.4, 6.0 Hz, 2H). |
| 16 | 2'-(5-Fluoro-2-((5-(1-isopropylpyrrolidin-3-yl)pyridin-2-yl)amino)pyrimidin-4-yl)-3',5'-dimethylspiro[cyclopropane-1,6'-thieno[2,3-c]pyrrol]-4'(5'H)-one | $^1$H NMR (300 MHz, methanol-d$_4$) δ 8.73 (d, J = 3.0 Hz, 1H), 8.37-8.30 (m, 2H), 7.72 (d, J = 8.7 Hz, 1H), 3.88-3.75 (m, 2H), 3.62-3.51 (m, 2H), 2.86 (s, 3H), 2.77 (d, J = 2.4 Hz, 3H), 2.67-2.53 (m, 2H), 2.32-2.13 (m, 2H), 1.93 (dd, J = 8.4, 6.0 Hz, 2H), 1.53 (dd, J = 8.4, 6.0 Hz, 2H), 1.44 (d, J = 6.6 Hz, 6H). |

TABLE 2-continued

Examples 7-19

| Example | Compound name | NMR |
|---|---|---|
| 17 | 5'-Ethyl-2'-(5-methyl-2-((5-((3aR,6aS)-5-methylhexahydro-pyrrolo[3,4-c]pyrrol-2(1H)-yl)pyridin-2-yl)amino)pyrimidin-4-yl)spiro[cyclopropane-1,6'-thieno[2,3-c]pyrrol]-4'(5'H)-one | — |
| 18 | 5'-Ethyl-2'-[5-methyl-2-[[5-(1-methylpiperidin-3-yl)pyridin-2-yl]amino]pyrimidin-4-yl]spiro[cyclopropane-1,6'-thieno[2,3-c]pyrrole]-4'-one | — |
| 19 | 5'-Ethyl-2'-[5-methyl-2-[[5-(1-methylpiperidin-4-yl)pyridin-2-yl]amino]pyrimidin-4-yl]spiro[cyclopropane-1,6'-thieno[2,3-c]pyrrole]-4'-one | — |

Example 20. 2'-(5-Fluoro-2-((5-(1-methylpiperidin-4-yl)pyridin-2-yl)amino) pyrimidin-4-yl)-5'-methyl-spiro[cyclopentane-1,6'-thieno[2,3-c]pyrrol]-4'(5'H)-one

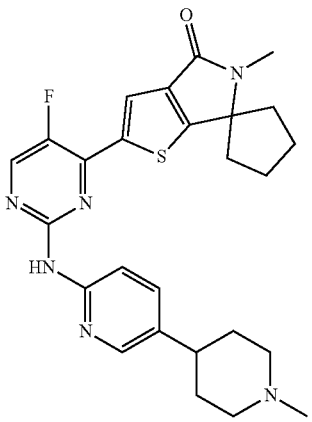 [SMILES: CN1CCC(c2ccc(Nc3ncc(F)c(-c4cc5c(s4)C4(CCCC4)N(C)C5=O)n3)nc2)CC1]

Step 1. 5-Methyl-5,6-dihydro-4H-thieno[2,3-c]pyrrol-4-one

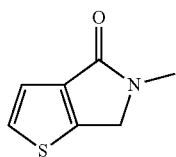

The title compound is synthesized by procedures analogous to those outlined in Example 6, Steps 1-5. LCMS calc. for $C_7H_8NOS$ [M+H]$^+$: m/z=154.0; Found: 153.9.

Step 2. 5'-Methylspiro[cyclopentane-1,6'-thieno[2,3-c]pyrrol]-4'(5'H)-one

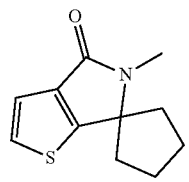

The title compound is synthesized by procedures analogous to those outlined in Example 6, Step 6, substituting 1,4-diiodobutane for 1,2-dibromoethane. LCMS calc. for $C_{11}H_{14}NOS$ [M+H]$^+$: m/z=208.1; Found: 208.0.

Step 3. 2'-(5-Fluoro-2-((5-(1-methylpiperidin-4-yl)pyridin-2-yl)amino)pyrimidin-4-yl)-5'-methylspiro[cyclopentane-1,6'-thieno[2,3-c]pyrrol]-4'(5'H)-one The title compound is synthesized by procedures analogous to those outlined in Example 6, Steps 7-9. LCMS calc. for $C_{26}H_{30}FN_6OS$ [M+H]$^+$: m/z=493.2; Found: 493.1.

Examples 21-27

Examples 21-27 listed in Table 3 and Table 4 are synthesized according to procedures analogous to Example 20. All examples in these tables were prepared as the TFA salt unless otherwise noted.

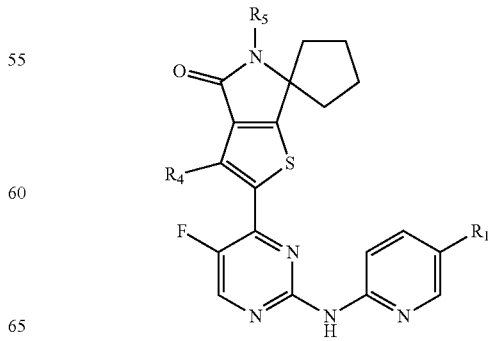

TABLE 3

Examples 21-27

| Example | R₁ | R₄ | R₅ | LCMS [M + H]⁺ |
|---|---|---|---|---|
| 21 | 2,6-diazaspiro[3.3]heptan-2-yl (N-ethyl) | H | Et | 534.2 |
| 22 | 1-methylpiperidin-4-yl | H | Et | 507.0 |
| 23 | 1-ethylpiperidin-4-yl | H | Me | 507.0 |
| 24 | 6-ethyl-2,6-diazaspiro[3.3]heptan-2-yl | H | Me | 520.1 |
| 25 | 1-methylpiperidin-4-yl | Me | Me | 507.1 |
| 26 | 1-methylpiperidin-4-yl | CF₃ | Me | 561.1 |
| 27 | 1-methylpiperidin-4-yl | Cl | Me | 527.1 |

TABLE 4

Examples 21-27

| Example | Compound name | NMR |
|---|---|---|
| 21 | 5'-Ethyl-2'-(2-((5-(6-ethyl-2,6-diazaspiro[3.3]heptan-2-yl)pyridin-2-yl)amino)-5-fluoropyrimidin-4-yl)spiro[cyclopentane-1,6'-thieno[2,3-c]pyrrol]-4'(5'H)-one | — |
| 22 | 5'-Ethyl-2'-(5-fluoro-2-((5-(1-methylpiperidin-4-yl)pyridin-2-yl)amino)pyrimidin-4-yl)spiro[cyclopentane-1,6'-thieno[2,3-c]pyrrol]-4'(5'H)-one | ¹H NMR (300 MHz, methanol-d₄) δ 8.73 (d, J = 3.0 Hz, 1H), 8.28-8.21 (m, 2H), 8.11 (d, J = 1.2 Hz, 1H), 7.68 (d, J = 8.8 Hz, 1H), 3.68 (d, J = 12.6 Hz, 2H), 3.54 (q, J = 6.9 Hz, 2H), 2.95 (s, 3H), 2.41-1.91 (m, 13H), 1.85-1.75 (m, 2H), 1.31 (t, J = 7.2 Hz, 3H). |
| 23 | 2'-(2-((5-(1-Ethylpiperidin-4-yl)pyridin-2-yl)amino)-5-fluoropyrimidin-4-yl)-5'-methylspiro[cyclopentane-1,6'-thieno[2,3-c]pyrrol]-4'(5'H)-one | — |
| 24 | 2'-(2-((5-(6-Ethyl-2,6-diazaspiro[3.3]heptan-2-yl)pyridin-2-yl)amino)-5-fluoropyrimidin-4-yl)-5'-methylspiro[cyclopentane-1,6'-thieno[2,3-c]pyrrol]-4'(5'H)-one | ¹H NMR (400 MHz, methanol-d₄) δ 8.68 (d, J = 3.2 Hz, 1H), 8.07 (d, J = 1.2 Hz, 1H), 7.65 (dd, J = 9.6, 2.8 Hz, 1H), 7.50 (s, 1H), 7.47 (d, J = 2.4 Hz, 1H), 4.51 (d, J = 10.8 Hz, 2H), 4.34-4.25 (m, 4H), 4.18 (s, 2H), 3.26 (q, J = 7.2 Hz, 2H), 3.05 (s, 3H), 2.38-2.28 (m, 2H), 2.20-1.98 (m, 4H), 1.86-1.77 (m, 2H), 1.23 (t, J = 7.2 Hz, 3H). |
| 25 | 2'-(5-Fluoro-2-((5-(1-methylpiperidin-4-yl)pyridin-2-yl)amino)pyrimidin-4-yl)-3',5'-dimethylspiro[cyclopentane-1,6'-thieno[2,3-c]pyrrol]-4'(5'H)-one | ¹H NMR (400 MHz, methanol-d₄) δ 8.75 (d, J = 2.8 Hz, 1H), 8.31-8.25 (m, 2H), 7.65 (d, J = 9.2 Hz, 1H), 3.72-3.64 (m, 2H), 3.24-3.15 (m, 2H), 3.14-3.07 (m, 1H), 3.04 (s, 3H), 2.95 (s, 3H), 2.75 (d, J = 2.4 Hz, 3H), 2.36-2.18 (m, 4H), 2.16-1.94 (m, 6H), 1.83-1.75 (m, 2H). |
| 26 | 2'-(5-Fluoro-2-((5-(1-methylpiperidin-4-yl)pyridin-2-yl)amino)pyrimidin-4-yl)-5'-methyl-3'-(trifluoromethyl)spiro | ¹H NMR (400 MHz, methanol-d₄) δ 8.84 (d, J = 1.6 Hz, 1H), 8.26 (d, J = 2.0 Hz, 1H), 8.21 (dd, J = 9.2, 2.0 Hz, 1H), 7.73 (d, J = 8.8 Hz, 1H), 3.71-3.63 (m, 2H), |

TABLE 4-continued

Examples 21-27

| Example | Compound name | NMR |
|---|---|---|
|  | [cyclopentane-1,6'-thieno[2,3-c]pyrrol]-4'(5'H)-one | 3.24-3.14 (m, 2H), 3.06 (s, 3H), 2.94 (s, 3H), 2.39-2.30 (m, 2H), 2.26-2.18 (m, 2H), 2.17-1.94 (m, 7H), 1.91-1.82 (m, 2H). |
| 27 | 3'-Chloro-2'-(5-fluoro-2-((5-(1-methylpiperidin-4-yl)pyridin-2-yl)amino)pyrimidin-4-yl)-5'-methylspiro[cyclopentane-1,6'-thieno[2,3-c]pyrrol]-4'(5'H)-one | $^1$H NMR (400 MHz, methanol-$d_4$) δ 8.80 (d, J = 2.8 Hz, 1H), 8.24 (d, J = 2.0 Hz, 1H), 8.14 (dd, J = 9.2, 2.4 Hz, 1H), 7.83 (d, J = 8.8 Hz, 1H), 3.70-3.63 (m, 2H), 3.24-3.15 (m, 2H), 3.05 (s, 3H), 2.95 (s, 3H), 2.39-2.28 (m, 2H), 2.26-2.18 (m, 2H), 2.16-2.08 (m, 2H), 2.06-1.94 (m, 5H), 1.89-1.80 (m, 2H). |

Example 28. 2'-(5-Fluoro-2-((5-(1-methylpiperidin-4-yl)pyridin-2-yl)amino)pyrimidin-4-yl)-3',5'-dimethyl-5',6'-dihydro-4'H-spiro[cyclopropane-1,7'-thieno[3,2-c]pyridin]-4'-one

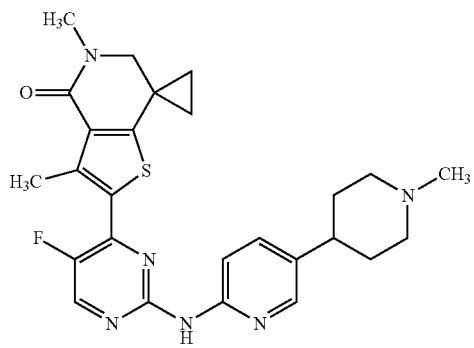 [SMILES: Cc1c(-c2nc(Nc3ccc(C4CCN(C)CC4)cn3)ncc2F)sc2c1C(=O)N(C)CC21CC1]

Step 1. (4-Methylthiophen-2-yl)methanol

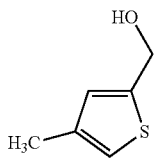

Lithium aluminum hydride (2.10 g, 55.4 mmol) was added slowly to a solution of 4-methylthiophene-2-carboxylic acid (7.50 g, 52.8 mmol) in MTBE (105 mL) while maintaining the temperature of the reaction mixture between 25-30° C. The reaction was stirred for 30 min. The reaction mixture was cooled to 0° C., and the reaction quenched by sequential addition of water (2.10 mL) and 1 N NaOH (aq.) solution (8.40 mL). The suspension was diluted with MTBE, dried with sodium sulfate, filtered, and concentrated. The crude residue containing the title compound (6.70 g), a colorless oil, was used without further purification. $^1$H NMR (400 MHz, CDCl$_3$) δ 6.85 (q, J=1.2 Hz, 1H), 6.83 (d, J=1.4 Hz, 1H), 4.77 (s, 2H), 2.24 (d, J=1.0 Hz, 3H).

Step 2. 2-(Chloromethyl)-4-methylthiophene

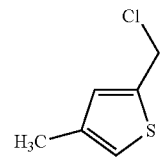

Thionyl chloride (4.56 mL, 62.7 mmol) was added dropwise to a solution of crude (4-methylthiophen-2-yl)methanol (6.70 g, from Step 1) in THF (130.0 mL) at room temperature. The reaction was heated at 50° C. for 90 min. The reaction mixture was cooled to room temperature and concentrated. The crude residue was diluted with DCM (30.0 mL), and after cooling to 0° C., sat. NaHCO$_3$ (aq.) (50.0 mL) was added. The two phases were separated, and the organic layer was dried over sodium sulfate, filtered, and concentrated. The crude residue containing the title compound (6.87 g), a yellow oil, was used without further purification. $^1$H NMR (400 MHz, CDCl$_3$) δ 6.90 (s, 1H), 6.88 (p, J=1.2 Hz, 2H), 4.75 (s, 2H), 2.23 (d, J=1.0 Hz, 3H).

Step 3. 2-(4-Methylthiophen-2-yl)acetonitrile

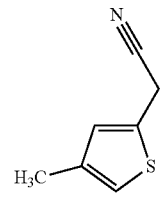

Sodium cyanide (5.12 g, 104 mmol) was added to a solution of crude 2-(chloromethyl)-4-methylthiophene (6.87 g) in DMF (105.0 mL) at room temperature. The reaction was heated at 100° C. for 1 h. The reaction mixture was cooled to room temperature and diluted with water (300 mL) and MTBE (100 mL). The two phases were separated, and the aqueous layer was extracted with MTBE (100 mL×2). The combined organic layers were washed with water (100 mL×2), dried over sodium sulfate, filtered, and concentrated. The crude residue was purified by silica gel chromatography (0-40% EtOAc/hexanes) to afford the title compound (5.15 g, 37.5 mmol, 71.8% yield over 3 steps) as a brown oil. $^1$H NMR (400 MHz, CDCl₃) δ 6.87 (s, 1H), 6.83 (t, J=1.3 Hz, 1H), 3.85 (d, J=1.1 Hz, 2H), 2.23 (d, J=1.1 Hz, 3H).

Step 4. 1-(4-Methylthiophen-2-yl)cyclopropane-1-carbonitrile

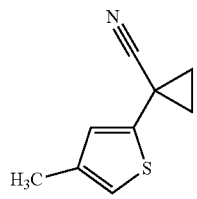

Sodium hydride (4.47 g, 112 mmol) was added portion wise to solution of 2-(4-methylthiophen-2-yl)acetonitrile (6.14 g, 44.7 mmol) in DMF (110 mL) at 0° C. The reaction mixture was stirred at 0° C. for 15 min, and then 1,2-dibromoethane (4.26 mL, 49.2 mmol) was added dropwise. The dark mixture was warmed to room temperature and stirred for 1 h. The reaction mixture was diluted with water (300 mL) and DCM (100 mL). The two phases were separated, and the aqueous layer was extracted with DCM (100 mL×4). The organic layers were combined, washed with water (100 mL×2), dried over sodium sulfate, filtered, and concentrated. The crude residue was purified by silica gel chromatography (0-40% EtOAc/hexanes) to afford the title compound (5.40 g, 33.1 mmol, 74.0% yield) as an orange oil. ¹H NMR (400 MHz, CDCl₃) δ 6.89 (d, J=1.5 Hz, 1H), 6.75 (t, J=1.3 Hz, 1H), 2.21 (d, J=1.1 Hz, 3H), 1.79-1.67 (m, 2H), 1.48-1.37 (m, 2H). LCMS calc. for $C_9H_{10}NS$ [M+H]⁺: m/z=164.1; Found: 163.8.

Step 5. (1-(4-Methylthiophen-2-yl)cyclopropyl)methanamine

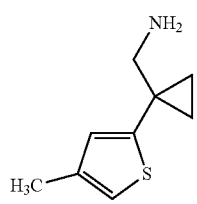

Lithium aluminum hydride (1.60 g, 42.0 mmol) was added slowly to a solution of 1-(4-methylthiophen-2-yl)cyclopropane-1-carbonitrile (6.54 g, 40.0 mmol) in THF (100 mL) at 0° C. The reaction mixture was stirred at 0° C. for 30 min. The reaction was quenched by sequential addition of water (1.60 mL) and 1 N NaOH (aq.) (6.40 mL) at 0° C. The suspension was diluted with EtOAc, dried with sodium sulfate, filtered, and concentrated. The crude residue containing the title compound (6.70 g), an orange oil, was used without further purification. LCMS calc. for $C_9H_{14}NS$ [M+H]⁺: m/z=168.1; Found 168.0.

Step 6. 2-(1-(Isocyanatomethyl)cyclopropyl)-4-methylthiophene

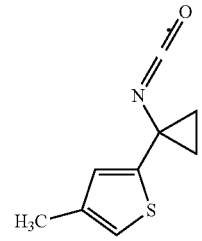

The title compound was synthesized by procedures analogous to those outlined in Example 1, Step 1. LCMS calc. for $C_{10}H_{12}NOS$ [M+H]⁺: m/z=194.1; Found 193.9.

Step 7. 3'-Methyl-5',6'-dihydro-4'H-spiro[cyclopropane-1,7'-thieno[3,2-c]pyridin]-4'-one

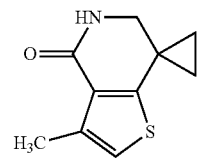

The title compound was synthesized by procedures analogous to those outlined in Example 1, Step 2. LCMS calc. for $C_{10}H_{12}NOS$ [M+H]⁺: m/z=194.1; Found 194.0.

Step 8. 3',5'-Dimethyl-5',6'-dihydro-4'H-spiro[cyclopropane-1,7'-thieno[3,2-c]pyridin]-4'-one

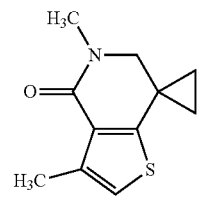

The title compound was synthesized by procedures analogous to those outlined in Example 1, Step 3. LCMS calc. for $C_{11}H_{14}NOS$ [M+H]⁺: m/z=208.1; Found 208.0.

Step 9. 2'-Bromo-3',5'-dimethyl-5',6'-dihydro-4'H-spiro[cyclopropane-1,7'-thieno[3,2-c]pyridin]-4'-one

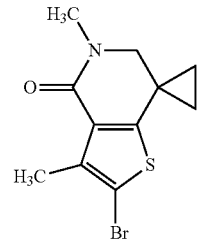

The title compound was synthesized by procedures analogous to those outlined in Example 1, Step 4. LCMS calc. for $C_{11}H_{13}BrNOS$ [M+H]$^+$: m/z=286.0, 288.0; Found 285.8, 287.8.

Step 10. 2'-(2-Chloro-5-fluoropyrimidin-4-yl)-3',5'-dimethyl-5',6'-dihydro-4'H-spiro[cyclopropane-1,7'-thieno[3,2-c]pyridin]-4'-one

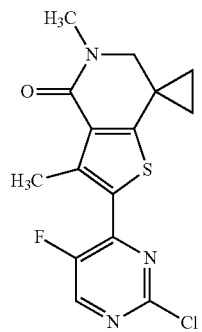 [SMILES: Cc1c(-c2nc(Cl)ncc2F)sc2c1C(=O)N(C)CC21CC1]

The title compound was synthesized by procedures analogous to those outlined in Example 1, Step 5. Purification via slurry in 1:1 EtOAc/hexanes afforded the title compound. LCMS calc. for $C_{15}H_{14}ClFN_3OS$ [M+H]$^+$: m/z=338.0, 340.0; Found 338.0, 339.9.

Step 11. 2'-(5-fluoro-2-((5-(1-methylpiperidin-4-yl)pyridin-2-yl)amino)pyrimidin-4-yl)-3',5'-dimethyl-5',6'-dihydro-4'H-spiro[cyclopropane-1,7'-thieno[3,2-c]pyridin]-4'-one The title compound was synthesized by procedures analogous to those outlined in Example 1, Step 10. It was isolated as the TFA salt. $^1$H NMR (400 MHz, DMSO-d$_6$) δ 10.54 (s, 1H), 9.57 (s, 1H), 8.73 (d, J=2.6 Hz, 1H), 8.21 (d, J=2.4 Hz, 1H), 8.01 (d, J=8.8 Hz, 1H), 7.81 (dd, J=8.9, 2.4 Hz, 1H), 3.62-3.44 (m, 4H), 3.07 (q, J=11.6 Hz, 2H), 2.97 (s, 3H), 2.89-2.75 (m, 4H), 2.55 (d, J=3.3 Hz, 3H), 2.10-1.98 (m, 2H), 1.96-1.74 (m, 2H), 1.46-1.22 (m, 2H), 1.18-0.97 (m, 2H). LCMS calc. for $C_{26}H_{30}FN_6OS$ [M+H]$^+$: m/z=493.2; Found: 493.1.

Examples 29-45

Examples 29-45 listed in Table 5 and Table 6 were synthesized according to procedures analogous to Example 28. All examples in these tables were prepared as the TFA salt unless otherwise noted.

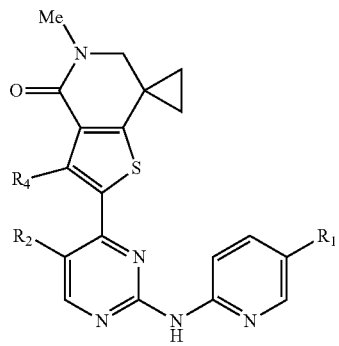

TABLE 5

Examples 29-45

| Example | R$_1$ | R$_2$ | R$_4$ | LCMS [M + H]$^+$ |
|---|---|---|---|---|
| 29 | N-methylpiperidin-4-yl | F | H | 479.0 |
| 30 | N-methylpiperidin-3-yl | F | Me | 493.1 |
| 31 | N-ethylpyrrolidin-3-yl | F | H | 479.0 |
| 32 | 1-(tetrahydrofuran-3-yl)piperidin-4-yl | F | Me | 549.1 |
| 33 | 3-methyl-3,6-diazabicyclo group | F | Me | 506.1 |
| 34 | 2-isopropyl-2,6-diazaspiro[3.3]heptan-6-yl | F | Me | 534.1 |
| 35 | 2-methyl-2,6-diazaspiro[3.4]octan-6-yl | F | Me | 520.1 |
| 36 | 2-methyl-2,7-diazaspiro[3.5]nonan-7-yl | F | Me | 534.0 |
| 37 | 2-methyl-2,7-diazaspiro[4.4]nonan-7-yl | F | Me | 534.1 |

TABLE 5-continued

Examples 29-45

| Example | R₁ | R₂ | R₄ | LCMS [M + H]⁺ |
|---|---|---|---|---|
| 38 | piperazine-N-ethyl | F | Me | 522.1 |
| 39 | octahydropyrrolo[3,4-c]pyrrole-N-ethyl | F | Me | 534.2 |
| 40 | 1-methylpiperidin-4-yl | CF₃ | H | 529.0 |
| 41 | 2-ethyl-2,6-diazaspiro[3.3]heptane | Me | H | 502.1 |
| 42 | 2-ethyl-2,6-diazaspiro[3.3]heptane | Me | Me | 516.2 |
| 43 | 2-methyl-2,7-diazaspiro[3.5]nonane | Me | H | 516.1 |
| 44 | 2-ethyl-2,6-diazaspiro[3.3]heptane | Cl | Me | 536.0 |
| 45 | 2-ethyl-2,6-diazaspiro[3.3]heptane | Cl | H | 522.0 |

TABLE 6

Examples 29-45

| Example | Compound name | NMR |
|---|---|---|
| 29 | 2'-(5-Fluoro-2-((5-(1-methyl-piperidin-4-yl)pyridin-2-yl)amino)pyrimidin-4-yl)-5'-methyl-5',6'-dihydro-4'H-spiro[cyclo-propane-1,7'-thieno[3,2-c]pyridin]-4'-one | ¹H NMR (400 MHz, methanol-d₄) δ 8.67 (d, J = 3.2 Hz, 1H), 8.36-8.17 (m, 3H), 7.68 (d, J = 9.0 Hz, 1H), 3.68 (d, J = 12.4 Hz, 2H), 3.62 (s, 2H), 3.25-3.13 (m, 2H), 3.10 (s, 3H), 3.09-3.01 (m, 1H), 2.95 (s, 3H), 2.22 (d, J = 14.2 Hz, 2H), 2.09-1.94 (m, 2H), 1.41-1.34 (m, 2H), 1.25-1.15 (m, 2H). |
| 30 | 2'-(5-Fluoro-2-((5-(1-methyl-piperidin-3-yl)pyridin-2-yl)amino)pyrimidin-4-yl)-3',5'-dimethyl-5',6'-dihydro-4'H-spiro[cyclopropane-1,7'-thieno[3,2-c]pyridin]-4'-one | — |
| 31 | 2'-(2-((5-(1-Ethylpyrrolidin-3-yl)pyridin-2-yl)amino)-5-fluoropyrimidin-4-yl)-5'-methyl-5',6'-dihydro-4'H-spiro[cyclo-propane-1,7'-thieno[3,2-c]pyridin]-4'-one | — |
| 32 | 2'-(5-Fluoro-2-((5-(1-(tetrahydrofuran-3-yl)piperidin-4-yl)pyridin-2-yl)amino)pyrimidin-4-yl)-3',5'-dimethyl-5',6'-dihydro-4'H-spiro[cyclopropane-1,7'-thieno[3,2-c]pyridin]-4'-one | — |
| 33 | 2'-(5-Fluoro-2-((5-(6-methyl-3,6-diazabicyclo[3.1.1]heptan-3-yl)pyridin-2-yl)amino)pyrimidin-4-yl)-3',5'-dimethyl-5',6'-dihydro-4'H-spiro[cyclopropane-1,7'-thieno[3,2-c]pyridin]-4'-one | — |
| 34 | 2'-(5-Fluoro-2-((5-(6-isopropyl-2,6-diazaspiro[3.3]heptan-2-yl)pyridin- | — |

TABLE 6-continued

Examples 29-45

| Example | Compound name | NMR |
|---|---|---|
| | 2-yl)amino)pyrimidin-4-yl)-3',5'-dimethyl-5',6'-dihydro-4'H-spiro[cyclopropane-1,7'-thieno[3,2-c]pyridin]-4'-one | |
| 35 | 2'-(5-Fluoro-2-((5-(6-methyl-2,6-diazaspiro[3.4]octan-2-yl)pyridin-2-yl)amino)pyrimidin-4-yl)-3',5'-dimethyl-5',6'-dihydro-4'H-spiro[cyclopropane-1,7'-thieno[3,2-c]pyridin]-4'-one | $^1$H NMR (400 MHz, DMSO-$d_6$) δ 10.45 (s, 1H), 10.13 (s, 1H), 8.68 (d, J = 2.6 Hz, 1H), 7.79 (d, J = 9.1 Hz, 1H), 7.58 (s, 1H), 7.28 (dd, J = 9.1, 2.9 Hz, 1H), 3.98-3.88 (m, 3H), 3.88-3.78 (m, 2H), 3 66-3.54 (m, 1H), 3.52 (s, 2H), 3.30 (dd, J = 12.1, 7.1 Hz, 1H), 3.21-3.05 (m, 1H), 2.97 (s, 3H), 2.85 (d, J = 4.0 Hz, 3H), 2.55 (d, J = 3.1 Hz, 3H), 2.47-2.38 (m, 1H), 2.35-2.17 (m, 1H), 1.33-1.23 (m, 2H), 1.17-1.06 (m, 2H). |
| 36 | 2'-(5-Fluoro-2-((5-(2-methyl-2,7-diazaspiro[3.5]nonan-7-yl)pyridin-2-yl)amino)pyrimidin-4-yl)-3',5'-dimethyl-5',6'-dihydro-4'H-spiro[cyclopropane-1,7'-thieno[3,2-c]pyridin]-4'-one | — |
| 37 | 2'-(5-Fluoro-2-((5-(7-methyl-2,7-diazaspiro[4.4]nonan-2-yl)pyridin-2-yl)amino)pyrimidin-4-yl)-3',5'-dimethyl-5',6'-dihydro-4'H-spiro[cyclopropane-1,7'-thieno[3,2-c]pyridin]-4'-one | — |
| 38 | 2'-(2-((5-((4-Ethylpiperazin-1-yl)methyl)pyridin-2-yl)amino)-5-fluoropyrimidin-4-yl)-3',5'-dimethyl-5',6'-dihydro-4'H-spiro[cyclopropane-1,7'-thieno[3,2-c]pyridin]-4'-one | — |
| 39 | 2'-(2-((5-((3aS,6aS)-5-Ethylhexahydropyrrolo[3,4-c]pyrrol-2(1H)-yl)pyridin-2-yl)amino)-5-fluoropyrimidin-4-yl)-3',5'-dimethyl-5',6'-dihydro-4'H-spiro[cyclopropane-1,7'-thieno[3,2-c]pyridin]-4'-one | $^1$H NMR (300 MHz, methanol-$d_4$) δ 8.66 (d, J = 2.8 Hz, 1H), 7.79 (dd, J = 9.6, 3.0 Hz, 1H), 7.57-7.21 (m, 2H), 3.92 (dd, J = 10.4, 6.0 Hz, 1H), 3.64 (dd, J = 8.6, 6.8 Hz, 2H), 3.58-3.49 (m, 4H), 3.46-3.34 (m, 2H), 3.28-3.11 (m, 2H), 3.09 (s, 3H), 2.96-2.74 (m, 2H), 2.69 (d, J = 2.9 Hz, 3H), 2.68-2.58 (m, 1H), 1.38 (t, J = 7.2 Hz, 3H), 1.34-1.25 (m, 2H), 1.19-1.08 (m, 2H). |
| 40 | 5-Methyl-2-[4-[[5-(1-methylpiperidin-4-yl)pyridin-2-yl]amino]-5-(trifluoromethyl)pyrimidin-2-yl]spiro[6H-thieno[3,2-c]pyridine-7,1'-cyclopropane]-4-one | — |
| 41 | 2-[2-[[5-(6-Ethyl-2,6-diazaspiro[3.3]heptan-2-yl)pyridin-2-yl]amino]-5-methylpyrimidin-4-yl]-5-methylspiro[6H-thieno[3,2-c]pyridine-7,1'-cyclopropane]-4-one | $^1$H NMR (400 MHz, DMSO-$d_6$) δ 10.49 (s, 1H), 9.96 (s, 1H), 8.48 (s, 1H), 7.85 (s, 1H), 7.77 (d, J = 9.2 Hz, 1H), 7.59 (d, J = 2.9 Hz, 1H), 7.39 (dd, J = 9.2, 2.9 Hz, 1H), 4.36 (dd, J = 10.9, 6.5 Hz, 2H), 4.22 (dd, J = 11.5, 5.9 Hz, 2H), 4.08 (d, J = 36.6 Hz, 4H), 3.56 (s, 2H), 3.18 (p, J = 6.9 Hz, 2H), 2.98 (s, 3H), 2.48 (s, 3H), 1.38-1.30 (m, 2H), 1.18-1.03 (m, 5H). |
| 42 | 2-[2-[[5-(6-Ethyl-2,6-diazaspiro[3.3]heptan-2-yl)pyridin-2-yl]amino]-5-methylpyrimidin-4-yl]-3,5-dimethylspiro[6H-thieno[3,2-c]pyridine-7,1'-cyclopropane]-4-one | $^1$H NMR (400 MHz, DMSO-$d_6$) δ 10.85 (s, 1H), 10.03 (s, 1H), 8.58 (s, 1H), 7.69 (d, J = 9.2 Hz, 1H), 7.59 (d, J = 2.9 Hz, 1H), 7.43 (dd, J = 9.2, 2.9 Hz, 1H), 4.35 (dd, J = 11.5, 6.0 Hz, 2H), 4.21 (dd, J = 11.6, 5.9 Hz, 2H), 4.06 (d, J = 36.9 Hz, 4H), 3.53 (s, 2H), 3.17 (p, J = 6.8 Hz, 2H), 2.97 (s, 3H), 2.31 (s, 3H), 2.16 (s, 3H), 1.38-1.22 (m, 2H), 1.15-0.98 (m, 5H). |
| 43 | 5-methyl-2-[5-Methyl-2-[[5-(2-methyl-2,7-diazaspiro[3.5]nonan-7-yl)pyridin-2-yl]amino]pyrimidin-4-yl]spiro[6H-thieno[3,2-c]pyridine-7,1'-cyclopropane]-4-one | $^1$H NMR (400 MHz, DMSO-$d_6$) δ 10.68 (s, 1H), 10.09 (s, 1H), 8.51 (s, 1H), 8.08-7.89 (m, 2H), 7.86 (s, 1H), 7.77 (d, J = 9.2 Hz, 1H), 4.03 (dd, J = 10.7, 6.4 Hz, 2H), 3.82 (dd, J = 10.7, 6.4 Hz, 2H), 3.56 (s, 2H), 3.14 (dt, J = 35.5, 5.7 Hz, 4H), 2.98 (s, 3H), 2.88 (d, J = 4.8 Hz, 3H), 2.49 (s, 3H), 1.92 (q, J = 6.5 Hz, 4H), 1.51-1.30 (m, 2H), 1.19-1.09 (m, 2H). |

TABLE 6-continued

Examples 29-45

| Example | Compound name | NMR |
|---|---|---|
| 44 | 2-[5-Chloro-2-[[5-(6-ethyl-2,6-diazaspiro[3.3]heptan-2-yl)pyridin-2-yl]amino]pyrimidin-4-yl]-3,5-dimethylspiro[6H-thieno[3,2-c]pyridine-7,1'-cyclopropane]-4-one | — |
| 45 | 2-[5-Chloro-2-[[5-(6-ethyl-2,6-diazaspiro[3.3]heptan-2-yl)pyridin-2-yl]amino]pyrimidin-4-yl]-5-methylspiro[6H-thieno[3,2-c]pyridine-7,1'-cyclopropane]-4-one | — |

Example 46. 2'-(5-Fluoro-2-((5-(6-methyl-3,6-diazabicyclo[3.1.1]heptan-3-yl)pyridin-2-yl)amino)pyrimidin-4-yl)-5'-methyl-5',6'-dihydro-4'H-spiro[cyclobutane-1,7'-thieno[3,2-c]pyridin]-4'-one

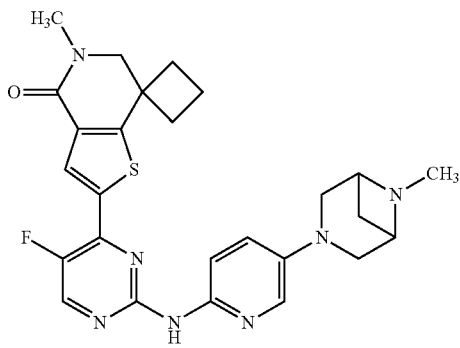 [SMILES: CN1CC2(CCC2)c2sc(-c3nc(Nc4ccc(N5CC6CC(C5)N6C)cn4)ncc3F)cc2C1=O]

Step 1. 1-(Thiophen-2-yl)cyclobutane-1-carbonitrile

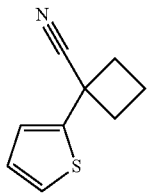 [SMILES: N#CC1(c2cccs2)CCC1]

Sodium hydride (60 wt %, 4.87 g, 122 mmol) was added portion wise to solution of 2-thiopheneacetonitrile (6.00 g, 48.7 mmol) in THF (25.0 mL), and the mixture was stirred at room temperature for 15 min. Then 1,3-diiodopropane (6.15 mL, 53.6 mmol) was added dropwise. The dark mixture was stirred for 2 h. The reaction was quenched with water (50.0 mL), and the mixture diluted with MTBE (50.0 mL). The two phases were separated, and the aqueous layer was extracted with MTBE (50.0 mL×2). The organic layers were combined, dried over sodium sulfate, filtered, and concentrated. The crude residue was purified by silica gel chromatography (0-20% EtOAc/hexanes) to afford the title compound (6.80 g, 41.7 mmol, 85.5% yield) as a dark oil. $^1$H NMR (400 MHz, CDCl$_3$) δ 7.28 (dd, J=5.1, 1.2 Hz, 1H), 7.09 (dd, J=3.6, 1.2 Hz, 1H), 6.98 (dd, J=5.1, 3.6 Hz, 1H), 3.00-2.83 (m, 2H), 2.78-2.57 (m, 2H), 2.47-2.28 (m, 1H), 2.25-2.07 (m, 1H).

Step 2. (1-(Thiophen-2-yl)cyclobutyl)methanamine

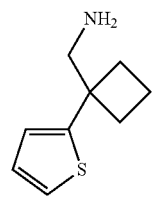 [SMILES: NCC1(c2cccs2)CCC1]

The title compound was synthesized by procedures analogous to those outlined in Example 28, Step 5. LCMS calc. for C$_9$H$_{14}$NS [M+H]$^+$: m/z=168.1; Found 168.0.

Step 3. 5-(6-Methyl-3,6-diazabicyclo[3.1.1]heptan-3-yl)pyridin-2-amine

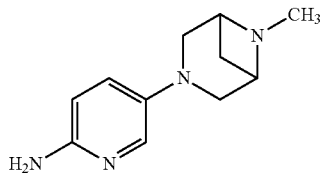

The title compound was synthesized by procedures analogous to those outlined in Example 1, Steps 6-9 as the TFA salt. $^1$H NMR (400 MHz, DMSO-d$_6$) δ 7.49 (d, J=3.0 Hz, 1H), 6.98 (dd, J=8.9, 3.1 Hz, 1H), 6.45 (d, J=8.6 Hz, 1H), 5.03 (s, 2H), 3.55 (d, J=5.8 Hz, 2H), 3.33 (d, J=11.1 Hz, 3H), 3.19 (d, J=10.9 Hz, 2H), 2.47-2.32 (m, 1H), 1.97 (s, 3H), 1.55 (d, J=8.1 Hz, 1H).

Step 4. 2'-(5-Fluoro-2-((5-(6-methyl-3,6-diazabicyclo[3.1.1]heptan-3-yl)pyridin-2-yl)amino)pyrimidin-4-yl)-5'-methyl-5',6'-dihydro-4'H-spiro[cyclobutane-1,7'-thieno[3,2-c]pyridin]-4'-one The title compound was synthesized by procedures analogous to those outlined in Example 1, Step 1-5 and 10. It was isolated as the TFA salt. $^1$H NMR (400 MHz, DMSO-d$_6$) δ 10.42 (s, 0.5H), 10.17-9.99 (m, 1H), 9.08 (s, 0.5H), 8.67 (d, J=3.2 Hz, 1H), 8.00 (dd, J=9.2, 5.4 Hz, 1H), 7.93 (d, J=1.9 Hz, 1H), 7.90 (d, J=3.1 Hz, 1H), 7.53-7.42 (m, 1H), 4.56-4.47 (m, 1H), 4.37 (d, J=6.3 Hz, 1H), 3.90 (dd, J=19.3, 12.1 Hz, 2H), 3.82-3.66 (m, 4H), 3.43-3.29 (m, 0.5H), 3.05 (d, J=5.2 Hz, 1.5H), 3.04 (s, 3H), 2.91-2.79 (m, 0.5H), 2.53 (d, J=3.8 Hz, 1.5H), 2.38-2.21 (m, 4H), 2.20-2.11 (m, 1H), 2.09-1.93 (m, 2H). LCMS calc. for $C_{26}H_{29}FN_7OS$ [M+H]$^+$: m/z=506.2; Found: 506.1.

Examples 47-60

Examples 47-60 listed in Table 7 and Table 8 were synthesized according to procedures analogous to Example 46. All examples in these tables were prepared as the TFA salt unless otherwise noted.

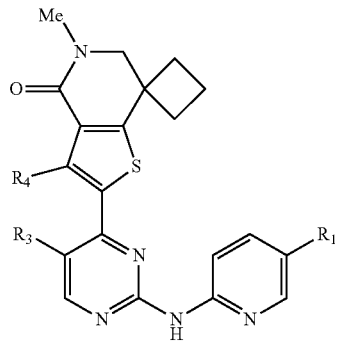

TABLE 7

Examples 47-60

| Example | R$_1$ | R$_2$ | R$_4$ | LCMS [M + H]$^+$ |
|---|---|---|---|---|
| 47 | N-methylpiperidin-4-yl | F | H | 493.1 |
| 48 | N-methylpiperidin-4-yl | F | Me | 507.1 |
| 49 | 1-(2,2-difluoroethyl)piperidin-4-yl | F | H | 543.1 |
| 50 | 4-methylpiperazin-1-yl | F | H | 494.1 |
| 51 | 2-ethyl-2,6-diazaspiro[3.3]heptan-6-yl | F | H | 520.1 |
| 52 | 2-ethyl-2,6-diazaspiro[3.3]heptan-6-yl | F | Me | 534.1 |
| 53 | 3,8-diazabicyclo[3.2.1]octan-8-yl | F | H | 520.1 |
| 54 | 2-methyl-2,6-diazaspiro[3.4]octan-6-yl | F | Me | 534.1 |
| 55 | 2-methyl-2,7-diazaspiro[4.4]nonan-7-yl | F | Me | 548.1 |
| 56 | 4-ethylpiperazin-1-ylmethyl | F | Me | 536.1 |
| 57 | 5-methyloctahydropyrrolo[3,4-c]pyrrol-2-yl | F | Me | 534.1 |
| 58 | N-methylpiperidin-4-yl | CF$_3$ | H | 543.0 |
| 59 | N-methylpiperidin-4-yl | Me | H | 489.1 |
| 60 | N-methylpiperidin-4-yl | Cl | Me | 523.0 |

TABLE 8

Examples 47-60

| Example | Compound name | NMR |
|---|---|---|
| 47 | 2'-(5-Fluoro-2-((5-(1-methyl-piperidin-4-yl)pyridin-2-yl)amino)pyrimidin-4-yl)-5'-methyl-5',6'-dihydro-4'H-spiro[cyclobutane-1,7'-thieno[3,2-c]pyridin]-4'-one | $^1$H NMR (400 MHz, methanol-$d_4$) δ 8.71 (d, J = 3.1 Hz, 1H), 8.39-8.17 (m, 3H), 7.65 (d, J = 9.3 Hz, 1H), 3.82 (s, 2H), 3.68 (d, J = 12.4 Hz, 2H), 3.26-3.02 (m, 6H), 2.95 (s, 3H), 2.46-2.31 (m, 4H), 2.29-2.10 (m, 4H), 2.11-1.95 (m, 2H). |
| 48 | 2'-(5-Fluoro-2-((5-(1-methyl-piperidin-4-yl)pyridin-2-yl)amino)pyrimidin-4-yl)-3',5'-dimethyl-5',6'-dihydro-4'H-spiro[cyclobutane-1,7'-thieno[3,2-c]pyridin]-4'-one | $^1$H NMR (400 MHz, methanol-$d_4$) δ 8.75 (d, J = 2.7 Hz, 1H), 8.32-8.22 (m, 2H), 7.68-7.60 (m, 1H), 3.77 (s, 2H), 3.70-3.63 (m, 2H), 3.25-3.03 (m, 6H), 2.95 (s, 3H), 2.68 (d, J = 2.8 Hz, 3H), 2.39-2.30 (m, 4H), 2.27-2.17 (m, 3H), 2.14-1.97 (m, 3H). |
| 49 | 2'-(2-((5-(1-(2,2-Difluoroethyl)piperidin-4-yl)pyridin-2-yl)amino)-5-fluoropyrimidin-4-yl)-5'-methyl-5',6'-dihydro-4'H-spiro[cyclobutane-1,7'-thieno[3,2-c]pyridin]-4'-one | — |
| 50 | 2'-(5-Fluoro-2-((5-(4-methyl-piperazin-1-yl)pyridin-2-yl)amino)pyrimidin-4-yl)-5'-methyl-5',6'-dihydro-4'H-spiro[cyclobutane-1,7'-thieno[3,2-c]pyridin]-4'-one | $^1$H NMR (400 MHz, DMSO-$d_6$) δ 10.29 (s, 1H), 9.99 (s, 1H), 8.69 (d, J = 3.0 Hz, 1H), 8.06 (d, J = 2.9 Hz, 1H), 8.01 (d, J = 9.2 Hz, 1H), 7.92 (s, 1H), 7.73 (dd, J = 9.5, 2.9 Hz, 1H), 3.85 (d, J = 13.1 Hz, 2H), 3.76 (s, 2H), 3.56 (d, J = 12.1 Hz, 2H), 3.33-3.10 (m, 2H), 3.10-2.94 (m, 5H), 2.88 (s, 3H), 2.35-2.23 (m, 4H), 2.22-2.10 (m, 1H), 2.10-1.94 (m, 1H). |
| 51 | 2'-(2-((5-(1-Ethyl-1,6-diazaspiro[3.3]heptan-6-yl)pyridin-2-yl)amino)-5-fluoropyrimidin-4-yl)-5'-methyl-5',6'-dihydro-4'H-spiro[cyclobutane-1,7'-thieno[3,2-c]pyridin]-4'-one | — |
| 52 | 2'-(2-((5-(6-Ethyl-2,6-diazaspiro[3.3]heptan-2-yl)pyridin-2-yl)amino)-5-fluoropyrimidin-4-yl)-3',5'-dimethyl-5',6'-dihydro-4'H-spiro[cyclobutane-1,7'-thieno[3,2-c]pyridin]-4'-one | $^1$H NMR (400 MHz, DMSO-$d_6$) δ 10.26 (s, 1H), 9.84 (s, 1H), 8.68 (d, J = 2.6 Hz, 1H), 7.82 (d, J = 9.0 Hz, 1H), 7.60 (d, J = 2.9 Hz, 1H), 7.22 (dd, J = 9.1, 3.0 Hz, 1H), 4.34 (dd, J = 11.6, 6.2 Hz, 2H), 4.20 (dd, J = 11.8, 5.9 Hz, 2H), 4.09 (s, 2H), 4.00 (s, 2H), 3.72 (s, 2H), 3.17 (p, J = 7.1 Hz, 2H), 3.04 (s, 3H), 2.52 (d, J = 3.0 Hz, 3H), 2.33-2.07 (m, 5H), 2.05-1.93 (m, 1H), 1.06 (t, J = 7.2 Hz, 3H). |
| 53 | 2'-(2-((5-(1,4-Diazabicyclo[3.2.2]nonan-4-yl)pyridin-2-yl)amino)-5-fluoropyrimidin-4-yl)-5'-methyl-5',6'-dihydro-4'H-spiro[cyclobutane-1,7'-thieno[3,2-c]pyridin]-4'-one | $^1$H NMR (400 MHz, DMSO-$d_6$) δ 10.05 (s, 1H), 10.00 (s, 1H), 8.66 (d, J = 3.2 Hz, 1H), 8.01-7.95 (m, 2H), 7.93 (d, J = 1.9 Hz, 1H), 7.56 (d, J = 8.0 Hz, 1H), 4.26 (s, 1H), 3.77 (s, 2H), 3.75-3.69 (m, 3H), 3.55-3.47 (m, 2H), 3.45-3.33 (s, 3H), 3.04 (s, 3H), 2.35-2.24 (m, 4H), 2.24-2.13 (m, 3H), 2.11-1.96 (m, 3H). |
| 54 | 2'-(5-Fluoro-2-((5-(6-methyl-2,6-diazaspiro[3.4]octan-2-yl)pyridin-2-yl)amino)pyrimidin-4-yl)-3',5'-dimethyl-5',6'-dihydro-4'H-spiro[cyclobutane-1,7'-thieno[3,2-c]pyridin]-4'-one | — |
| 55 | 2'-(5-Fluoro-2-((5-(7-methyl-2,7-diazaspiro[4.4]nonan-2-yl)pyridin-2-yl)amino)pyrimidin-4-yl)-3',5'-dimethyl-5',6'-dihydro-4'H-spiro[cyclobutane-1,7'-thieno[3,2-c]pyridin]-4'-one | $^1$H NMR (400 MHz, DMSO-$d_6$) δ 10.62 (s, 1H), 10.12 (s, 1H), 8.72 (d, J = 2.6 Hz, 1H), 7.77 (d, J = 9.2 Hz, 1H), 7.59 (dd, J = 7.4, 3.0 Hz, 1H), 7.41 (t, J = 10.6 Hz, 1H), 3.72 (s, 2H), 3.70-3.59 (m, 2H), 3.42-3.30 (m, 3H), 3.27-3.06 (m, 3H), 3.04 (s, 3H), 2.88 (d, J = 4.3 Hz, 3H), 2.54 (d, J = 3.0 Hz, 3H), 2.32-2.07 (m, 8H), 2.04-1.92 (m, 2H). |
| 56 | 2'-(2-((5-((4-Ethylpiperazin-1-yl)methyl)pyridin-2-yl)amino)-5-fluoropyrimidin-4-yl)-3',5'-dimethyl-5',6'-dihydro-4'H-spiro[cyclobutane-1,7'-thieno[3,2-c]pyridin]-4'-one | — |

TABLE 8-continued

Examples 47-60

| Example | Compound name | NMR |
|---|---|---|
| 57 | 2'-(5-Fluoro-2-((5-((3aR,6aS)-5-methylhexahydropyrrolo[3,4-c]pyrrol-2(1H)-yl)pyridin-2-yl)amino)pyrimidin-4-yl)-3',5'-dimethyl-5'6'-dihydro-4'H-spiro[cyclobutane-1,7'-thieno[3,2-c]pyridin]-4'-one | — |
| 58 | 5-Methyl-2-[4-[[5-(1-methyl-piperidin-4-yl)pyridin-2-yl]amino]-5-(trifluoromethyl)pyrimidin-2-yl]spiro[6H-thieno[3,2-c]pyridine-7,1'-cyclobutane]-4-one | — |
| 59 | 5-Methyl-2-[5-methyl-2-[[5-(1-methylpiperidin-4-yl)pyridin-2-yl]amino]pyrimidin-4-yl]spiro[6H-thieno[3,2-c]pyridine-7,1'-cyclobutane]-4-one | — |
| 60 | 2-[5-Chloro-2-[[5-(1-methyl-piperidin-4-yl)pyridin-2-yl]amino]pyrimidin-4-yl]-3,5-dimethylspiro[6H-thieno[3,2-c]pyridine-7,1'-cyclobutane]-4-one | — |

Examples 61-65

Examples 61-65 listed in Table 9 and Table 10 were synthesized according to procedures analogous to Examples 1 and 2. All examples in these tables were prepared as the TFA salt unless otherwise noted.

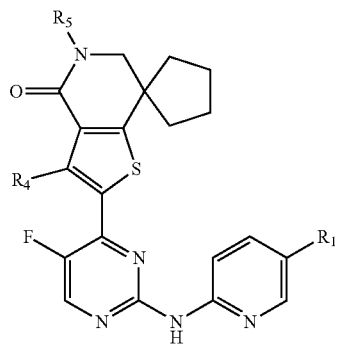

TABLE 9

Examples 61-65

| Example | $R_1$ | $R_4$ | $R_5$ | LCMS [M + H]$^+$ |
|---|---|---|---|---|
| 61 | 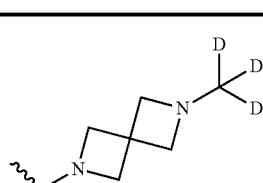 | H | $CD_3$ | 526.1 |

TABLE 9-continued

Examples 61-65

| Example | $R_1$ | $R_4$ | $R_5$ | LCMS [M + H]$^+$ |
|---|---|---|---|---|
| 62 | 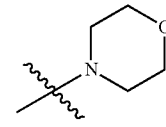 | H | Me | 495.1 |
| 63 | 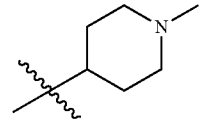 [SMILES: *C1CCN(C)CC1] | Me | Me | 521.1 |
| 64 | 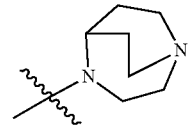 [SMILES: *N1CCN2CCC1CC2] | H | Me | 534.1 |
| 65 | 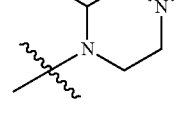 | H | Me | 576.0 |

TABLE 10

Examples 61-65

| Example | Compound name | NMR |
|---|---|---|
| 61 | 2'-(5-Fluoro-2-((5-(6-(methyl-d$_3$)-2,6-diazaspiro[3.3]heptan-2-yl)pyridin-2-yl)amino)pyrimidin-4-yl)-5,-(methyl-d3)-5',6'-dihydro-4'H-spiro[cyclopentane-1,7'-thieno[3,2-c]pyridin]-4'-one | — |
| 62 | 2'-(5-Fluoro-2-((5-morpholino-pyridin-2-yl)amino)pyrimidin-4-yl)-5'-methyl-5',6'-dihydro-4'H-spiro[cyclopentane-1,7'-thieno[3,2-c]pyridin]-4'-one | — |
| 63 | 2'-(5-Fluoro-2-((5-(1-methyl-piperidin-4-yl)pyridin-2-yl)amino)pyrimidin-4-yl)-3',5'-dimethyl-5',6'-dihydro-4'H-spiro[cyclopentane-1,7'-thieno[3,2-c]pyridin]-4'-one | $^1$H NMR (400 MHz, methanol-d$_4$) δ 8.73 (d, J = 2.7 Hz, 1H), 8.27-8.23 (m, 2H), 7.65 (d, J = 9.6 Hz, 1H), 3.68 (d, J = 12.8 Hz, 2H), 3.55 (s, 2H), 3.23-3.14 (m, 2H), 3.13 (s, 3H), 3.10-3.02 (m, 1H), 2.94 (s, 3H), 2.68 (d, J = 2.8 Hz, 3H), 2.22 (d, J = 14.4 Hz, 2H), 2.10-1.98 (m, 4H), 1.96-1.85 (m, 6H). |
| 64 | 2-[2-[[5-(1,4-Diazabicyclo[3.2.2]nonan-4-yl)pyridin-2-yl]amino]-5-fluoropyrimidin-4-yl]-5-methylspiro[6H-thieno[3,2-c]pyridine-7,1'-cyclopentane]-4-one | $^1$H NMR (400 MHz, DMSO-d$_6$) δ 10.18 (d, J = 52.8 Hz, 1H), 8.66 (d, J = 3.2 Hz, 1H), 7.97 (d, J = 3.1 Hz, 1H), 7.93 (d, J = 2.0 Hz, 1H), 7.90 (s, 1H), 7.58 (dd, J = 9.3, 3.1 Hz, 1H), 4.25 (s, 1H), 3.73 (t, J = 5.5 Hz, 2H), 3.55-3.48 (m, 4H), 3.47-3.35 (m, 4H), 3.02 (s, 3H), 2.30-1.96 (m, 7H), 1.89-1.76 (m, 6H) |
| 65 | 2-[5-Fluoro-2-[[5-[4-methyl-2-(trifluoromethyl)piperazin-1-yl]pyridin-2-yl]amino]pyrimidin-4-yl]-5-methylspiro[6H-thieno[3,2-c]pyridine-7,1'-cyclopentane]-4-one | $^1$H NMR (400 MHz, DMSO-d$_6$) δ 10.06 (s, 1H), 8.67 (d, J = 3.1 Hz, 1H), 8.14 (d, J = 3.0 Hz, 1H), 8.05 (d, J = 9.2 Hz, 1H), 7.93 (d, J = 2.0 Hz, 1H), 7.69 (d, J = 9.3 Hz, 1H), 5.39-5.14 (m, 1H), 4.05-3.68 (m, 4H), 3.02 (s, 3H), 2.89 (s, 2H), 2.15-1.94 (m, 2H), 1.92-1.74 (m, 7H). |

Example 66. 6'-(2-((5-(6-Ethyl-2,6-diazaspiro[3.3]heptan-2-yl)pyridin-2-yl)amino)-5-fluoropyrimidin-4-yl)-2'-methyl-2',3'-dihydro-1'H-spiro[cyclopentane-1,4'-isoquinolin]-1'-one

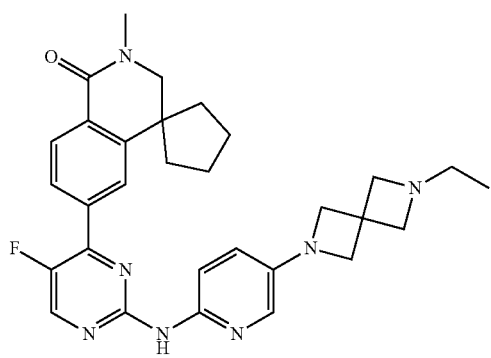 [SMILES: CCN1CC2(C1)CN(c1ccc(Nc3ncc(F)c(-c4ccc5c(c4)C4(CCCC4)CN(C)C5=O)n3)nc1)C2]

Step 1. 6'-Bromo-2',3'-dihydro-1'H-spiro[cyclopentane-1,4'-isoquinolin]-1'-one

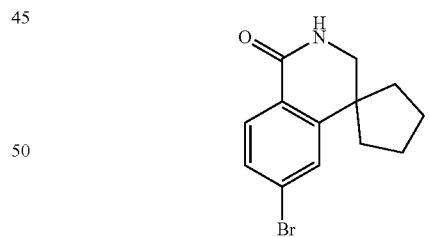

To a solution of triphosgene (222 mg, 0.750 mmol) in DCM (2.5 mL) was added 1-(3-bromophenyl)cyclopentanemethanamine (0.290 mL, 1.50 mmol) at 0° C., followed by slow addition of NaHCO$_3$ (aq.) (2.0 mL, 1.50 mmol, 0.75 M). The reaction mixture was stirred at room temperature for 2 h. The two layers were separated. The organic layer was washed with brine, dried over Na$_2$SO$_4$, and filtered. The filtrate was diluted with DCM (15 mL), and FeCl$_3$ (243 mg, 1.50 mmol) was added. The reaction mixture was heated at 50° C. for 1 h. The reaction mixture was poured into sat. NH$_4$Cl (aq.) and extracted with DCM. The organic layer was washed with brine, dried over Na$_2$SO$_4$, filtered, and concentrated. The crude was purified by silica gel chromatography (0-50% EtOAc/hexanes) to afford the title compound as a white solid (80.5 mg, 0.286 mmol, 19.1%). $^1$H NMR (400 MHz, CDCl$_3$) δ 7.95 (d, J=8.2 Hz, 1H), 7.48 (d, J=8.4 Hz, 1H), 7.44 (s, 1H), 6.58 (s, 1H), 3.37 (d, J=2.7 Hz, 2H), 2.00-1.71 (m, 8H). LCMS calc. for C$_{13}$H$_{15}$BrNO [M+H]$^+$: m/z=280.0/282.0; Found: 280.0/282.0.

Step 2. 6'-Bromo-2'-methyl-2',3'-dihydro-1'H-spiro[cyclopentane-1,4'-isoquinolin]-1'-one

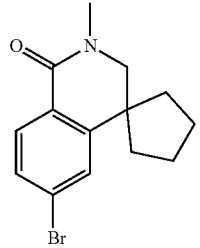 [SMILES: CN1CC2(CCCC2)c2cc(Br)ccc2C1=O]

The title compound is synthesized by procedures analogous to those outlined in Example 1, Step 3. LCMS calc. for C$_{14}$H$_{17}$BrNO [M+H]$^+$: m/z=294.0, 296.0; Found: 293.9, 295.8.

Step 3. 6'-(2-((5-(6-Ethyl-2,6-diazaspiro[3.3]heptan-2-yl)pyridin-2-yl)amino)-5-fluoropyrimidin-4-yl)-2'-methyl-2',3'-dihydro-1'H-spiro[cyclopentane-1,4'-isoquinolin]-1'-one The title compound is synthesized by procedures analogous to those outlined in Example 1, Steps 5 and 10. $^1$H NMR (400 MHz, CD$_3$OD) δ 8.64 (d, J=3.3 Hz, 1H), 8.07-7.94 (m, 3H), 7.57 (dd, J=9.3, 2.7 Hz, 1H), 7.42-7.35 (m, 2H), 4.41 (d, J=11.2 Hz, 2H), 4.21 (d, J=11.0 Hz, 2H), 4.18 (s, 2H), 4.08 (s, 2H), 3.43 (s, 2H), 3.17 (q, J=7.3 Hz, 2H), 3.10 (s, 3H), 1.92-1.73 (m, 8H), 1.13 (t, J=7.2 Hz, 3H). LCMS calc. for C$_{30}$H$_{35}$FN$_7$O [M+H]$^+$: m/z=528.3; Found: 528.1.

Examples 67-69

Examples listed in Table 11 and Table 12 were synthesized according to procedures analogous to Example 66. All examples in these tables were prepared as the TFA salt unless otherwise noted.

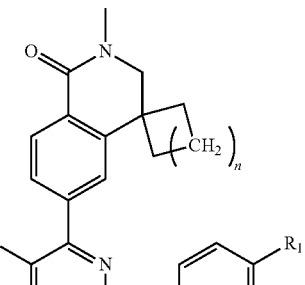

TABLE 11

Examples 67-69

| Example | n | R$_1$ | LCMS [M + H]$^+$ |
|---|---|---|---|
| 67 | 2 | (1-methylpiperidin-4-yl) | 501.2 |
| 68 | 2 | ((4-ethylpiperazin-1-yl)methyl) | 530.1 |
| 69 | 1 | (6-ethyl-2,6-diazaspiro[3.3]heptan-2-yl) | 514.1 |

TABLE 12

Examples 67-69

| Example | Compound name | NMR |
|---|---|---|
| 67 | 6'-(5-Fluoro-2-((5-(1-methyl-piperidin-4-yl)pyridin-2-yl)amino)pyrimidin-4-yl)-2'-methyl-2',3'-dihydro-1'H-spiro[cyclopentane-1,4'-isoquinolin]-1'-one | $^1$H NMR (400 MHz, methanol-d$_4$)) δ 8.80 (d, J = 3.2 Hz, 1H), 8.30-8.26 (m, 2H), 8.16-8.09 (m, 3H), 7.68-7.62 (m, 1H), 3.72-3.64 (m, 2H), 3.53 (s, 2H), 3.24-3.15 (m, 5H), 3.14-3.02 (m, 1H), 2.95 (s, 3H), 2.23 (d, J = 14.4 Hz, 2H), 2.11-1.98 (m, 3H), 1.96-1.86 (m, 7H). |
| 68 | 6'-(2-((5-((4-Ethylpiperazin-1-yl)methyl)pyridin-2-yl)amino)-5-fluoropyrimidin-4-yl)-2'-methyl-2',3'-dihydro-1'H-spiro [cyclopentane-1,4'-isoquinolin]-1'-one | $^1$H NMR (400 MHz, methanol-d$_4$)) δ 8.80 (d, J = 3.6 Hz, 1H), 8.33-8.27 (m, 2H), 8.17-8.09 (m, 3H), 7.67-7.62 (m, 1H), 3.74 (s, 2H), 3.53 (s, 3H), 3.27-3.21 (m, 2H), 3.20 (s, 3H), 3.17-2.99 (m, 3H), 2.74-2.40 (m, 3H), 2.04-1.88 (m, 9H), 1.36 (t, J = 7.2 Hz, 3H) |

TABLE 12-continued

Examples 67-69

| Example | Compound name | NMR |
|---|---|---|
| 69 | 6'-(2-((5-(6-Ethyl-2,6-diazaspiro[3.3]heptan-2-yl)pyridin-2-yl)amino)-5-fluoropyrimidin-4-yl)-2'-methyl-2',3'-dihydro-1'H-spiro[cyclobutane-1,4'-isoquinolin]-1'-one | — |

Example 70. 2'-[5-Fluoro-2-[[5-(1-methylpiperidin-4-yl)pyridin-2-yl]amino]pyrimidin-4-yl]-3'-methyl-5'-(trideuteriomethyl)spiro[cyclopropane-1,6'-thieno[2,3-c]pyrrole]-4'-one

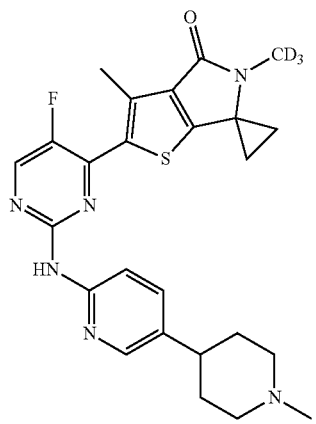 [SMILES: [2H]C([2H])([2H])N1C(=O)c2c(sc(-c3nc(Nc4ccc(C5CCN(C)CC5)cn4)ncc3F)c2C)C12CC2]

Step 1. N-[(4-Methoxyphenyl)methyl]-4-methylthiophene-3-carboxamide

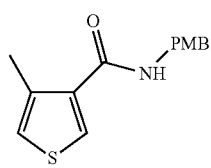

To a solution of 4-methyl-3-thiophenecarboxylic acid (15.0 g, 105 mmol) in THF (200 mL) was added 1-ethyl-3-(3'-dimethylaminopropyl)carbodiimide hydrochloride (13.9 g, 137 mmol). The mixture was stirred at room temperature for 30 min, and then 4-methoxybenzylamine (15.9 g, 116 mmol) was added dropwise at 0° C. The reaction mixture was slowly warmed to room temperature and stirred at room temperature for 2 h. The reaction mixture was poured into 1 N HCl (aq.) (100 mL) and extracted by DCM (100 mL×3). The combined organic layers were washed with brine (200 mL), dried over $Na_2SO_4$, filtered, and concentrated. The crude product was purified by silica gel chromatography (2-35% EtOAc/heptane) to afford the title compound (15.5 g, 59.3 mmol, 56.2% yield). LC-MS calc. for $C_{14}H_{16}NO_2S$ $[M+H]^+$: m/z=262.1; Found: 262.1.

Step 2. 2-Formyl-N-[(4-methoxyphenyl)methyl]-4-methylthiophene-3-carboxamide

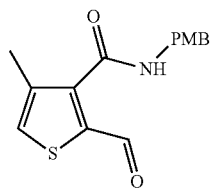

The title compound was synthesized by procedure analogous to those outlined in Example 6, Step 2. LC-MS calc. for $C_{15}H_{16}NO_3S$ $[M+H]^+$: m/z=290.1; Found: 290.0.

Step 3. 2-(Hydroxymethyl)-N-[(4-methoxyphenyl)methyl]-4-methylthiophene-3-carboxamide

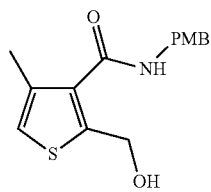

The title compound was synthesized by procedures analogous to those outlined in Example 6, Step 3. LC-MS calc. for $C_{15}H_{18}NO_3S$ $[M+Na]^+$: m/z=314.1; Found: 314.0.

Step 4. 2-(Chloromethyl)-N-[(4-methoxyphenyl)methyl]-4-methylthiophene-3-carboxamide

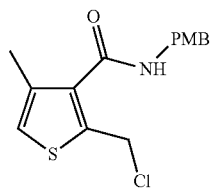

The title compound was synthesized by procedures analogous to those outlined in Example 6, Step 4. LCMS calc. for $C_{15}H_{16}NO_2S$ $[M-Cl]^+$: m/z=274.1; Found: 274.0.

Step 5. 5-[(4-Methoxyphenyl)methyl]-3-methyl-6H-thieno[2,3-c]pyrrol-4-one

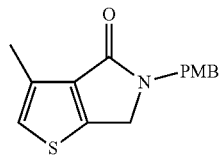

The title compound was synthesized by procedures analogous to those outlined in Example 6, Step 5. LC-MS calc. for $C_{15}H_{16}NO_2S$ [M+H]$^+$: m/z=274.1; Found 274.1.

Step 6. 3-Methyl-5,6-dihydrothieno[2,3-c]pyrrol-4-one

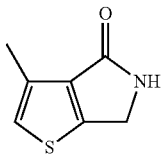

A solution of 5-[(4-methoxyphenyl)methyl]-3-methyl-6H-thieno[2,3-c]pyrrol-4-one (1.00 g, 3.66 mmol) in TFA (20 mL) was stirred at 70° C. overnight. The solvent was removed under reduced pressure. The residue was purified by prep-HPLC on a C18 column (5-50% MeCN/0.1% TFA (aq.)) to yield the title compound (215 mg, 1.40 mmol, 38.4% yield). LC-MS calc. for $C_7H_8NOS$ [M+H]$^+$: m/z=154.0; Found: 154.1.

Step 7. 3-Methyl-5-(trideuteriomethyl)-6H-thieno[2,3-c]pyrrol-4-one

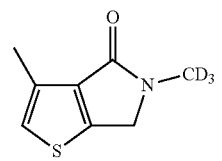

A mixture of 3-methyl-5,6-dihydrothieno[2,3-c]pyrrol-4-one (300 mg, 1.96 mmol), iodomethane-d$_3$ (0.24 mL, 3.9 mmol), and cesium carbonate (1.40 g, 4.31 mmol) in DMF (5 mL) was stirred at 70° C. overnight. The reaction was poured into brine (10 mL) and extracted with EtOAc (10 mL×3). The combined organic layers were washed with brine (20 mL), dried over Na$_2$SO$_4$, filtered, and concentrated. The residue was purified by silica gel chromatography (5-40% EtOAc/heptane) to afford the title compound (225 mg, 1.32 mmol, 67.5% yield). LC-MS calc. for $C_8H_7D_3NOS$ [M+H]$^+$: m/z=171.1; Found: 171.2.

Step 8. 3'-Methyl-5'-(trideuteriomethyl)spiro[cyclopropane-1,6'-thieno[2,3-c]pyrrole]-4'-one

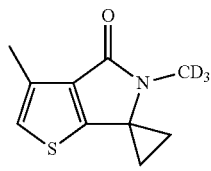 [SMILES: [2H]C([2H])([2H])N1C(=O)c2c(C)csc2C12CC2]

A solution of 3-methyl-5-(trideuteriomethyl)-6H-thieno[2,3-c]pyrrol-4-one (200 mg, 1.17 mmol) in THF (15 mL) was sparged with N$_2$ for 10 min and then cooled to −78° C. Lithium diisopropylamide (1.76 mL, 3.52 mmol, 2.0M in THF/heptane/ethylbenzene) was added dropwise. The reaction mixture was stirred at −78° C. for 20 min, and then 1-bromo-2-chloroethane (0.29 mL, 3.5 mmol) was added. The reaction mixture was slowly warmed to room temperature and stirred at room temperature for 1 h. The reaction was degassed by N$_2$ again and cooled to −78° C. An additional portion of lithium diisopropylamide (1.76 mL, 3.52 mmol, 2.0 M in THF/heptane/ethylbenzene) was added dropwise. After stirring for 20 min, 1-bromo-2-chloroethane (0.290 mL, 3.52 mmol) was added. The reaction mixture was slowly warmed to room temperature and stirred overnight. The reaction mixture was poured into cold sat. NH$_4$Cl (aq.) (10 mL) and extracted with EtOAc (10 mL×3). The combined organic layers were dried over Na$_2$SO$_4$, filtered and concentrated. The residue was purified by silica gel chromatography (2-35% EtOAc/heptane) to afford the title compound (75.1 mg, 0.382 mmol, 32.5% yield). LC-MS calc. for $C_{10}H_9D_3NOS$ [M+H]$^+$: m/z=197.1; Found: 197.2.

Step 9. 2'-Bromo-3'-methyl-5'-(trideuteriomethyl)spiro[cyclopropane-1,6'-thieno[2,3-c]pyrrole]-4'-one

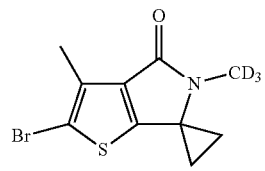 [SMILES: [2H]C([2H])([2H])N1C(=O)c2c(sc(Br)c2C)C12CC2]

The title compound was synthesized by procedures analogous to those outlined in Example 6, Step 7. LC-MS calc. for $C_{10}H_8D_3BrNOS$ [M+H]$^+$: m/z=275.0, 277.0; Found: 274.9, 276.9.

Step 10. 2'-(2-Chloro-5-fluoropyrimidin-4-yl)-3'-methyl-5'-(trideuteriomethyl)spiro [cyclopropane-1,6'-thieno[2,3-c]pyrrole]-4'-one

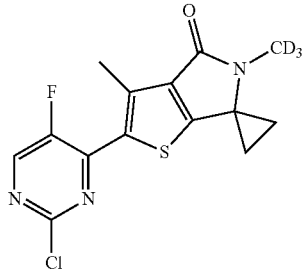 [SMILES: [2H]C([2H])([2H])N1C(=O)c2c(sc(-c3nc(Cl)ncc3F)c2C)C12CC2]

The title compound was synthesized by procedures analogous to those outlined in Example 6, Step 8. LC-MS calc. for $C_{14}H_9D_3ClFN_3OS$ [M+H]$^+$: m/z=327.1, 329.1; Found: 326.9, 328.9.

Step 11. 2'-[5-Fluoro-2-[[5-(1-methylpiperidin-4-yl)pyridin-2-yl]amino]pyrimidin-4-yl]-3'-methyl-5'-(trideuteriomethyl)spiro[cyclopropane-1,6'-thieno[2,3-c]pyrrole]-4'-one The title compound was synthesized by procedures analogous to those outlined in Example 6, Step 9. It was isolated as a TFA salt. $^1$H NMR (300 MHz, CD$_3$OD) δ 8.72 (d, J=3.0 Hz, 1H), 8.25 (s, 1H), 8.21 (dd, J=9.1, 2.1 Hz, 1H), 7.73 (d, J=9.0 Hz, 1H), 3.73-3.62 (m, 2H), 3.27-3.11 (m, 2H), 3.08-3.01 (m, 1H), 2.95 (s, 3H), 2.76 (d, J=2.5 Hz, 3H), 2.28-2.18 (m, 2H), 2.10-1.96 (m, 2H), 1.96-1.88 (m, 2H), 1.58-1.49 (m, 2H). LC-MS calc. for $C_{25}H_{25}D_3FN_6OS$ [M+H]$^+$: m/z=482.2; Found: 482.2.

Example 71. 2'-[2-[[5-(1-Ethylpyrrolidin-3-yl)pyridin-2-yl]amino]-5-fluoropyrimidin-4-yl]-3',5'-dimethylspiro[cyclopropane-1,6'-thieno[2,3-c]pyrrole]-4'-one

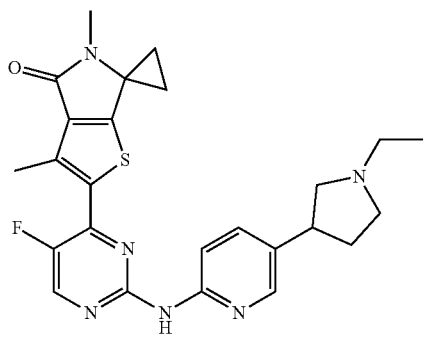 [SMILES: CCN1CCC(c2ccc(Nc3ncc(F)c(-c4sc5c(c4C)C(=O)N(C)C54CC4)n3)nc2)C1]

Step 1. tert-Butyl 3-(6-nitropyridin-3-yl)-2,5-dihydro-1H-pyrrole-1-carboxylate

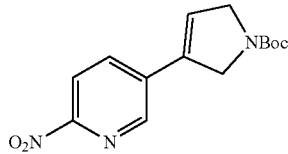 [SMILES: CC(C)(C)OC(=O)N1CC=C(c2ccc([N+](=O)[O-])nc2)C1]

The title compound was synthesized by procedures analogous to those outlined in Example 2, Step 1. LC-MS calc. for $C_{14}H_{18}N_3O_4$ [M+H]$^+$: m/z=292.1, Found 292.0.

Step 2. tert-Butyl 3-(6-aminopyridin-3-yl)pyrrolidine-1-carboxylate

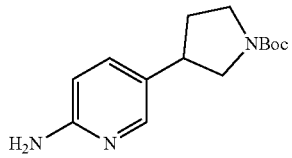 [SMILES: CC(C)(C)OC(=O)N1CCC(c2ccc(N)nc2)C1]

A mixture of tert-butyl 3-(6-nitropyridin-3-yl)-2,5-dihydro-1H-pyrrole-1-carboxylate (1.91 g, 6.52 mmol) and palladium on carbon (200 mg, 0.19 mmol, 10 wt %) in MeOH (25 mL) and THF (5.0 mL) was stirred under an atmosphere of H$_2$ for 24 h. The mixture was filtered through Celite®, and the filtrate was concentrated. The crude residue was purified by silica gel chromatography (10-30% EtOAc/heptane containing 10% MeOH) to afford the title compound (1.36 g, 5.06 mmol, 77.6% yield). LCMS calc. for $C_{14}H_{22}N_3O_2$ [M+H]$^+$: m/z=264.2, found 264.1.

Step 3. tert-Butyl 3-[6-[[4-(3',5'-dimethyl-4'-oxospiro[cyclopropane-1,6'-thieno[2,3-c]pyrrole]-2'-yl)-5-fluoropyrimidin-2-yl]amino]pyridin-3-yl]pyrrolidine-1-carboxylate

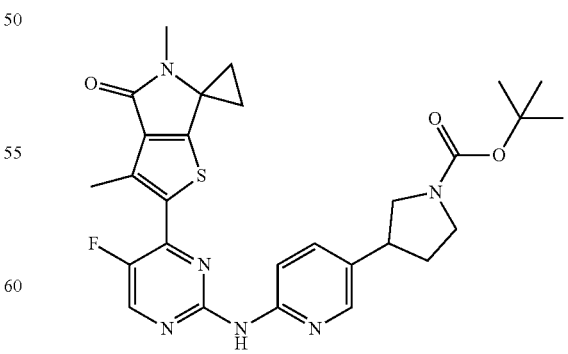

The title compound was synthesized by procedures analogous to those outlined in Example 1, Step 10. LCMS calc. for $C_{28}H_{32}FN_6O_3S$ [M+H]$^+$: m/z=551.2; Found: 551.2.

Step 4. 2'-[5-Fluoro-2-[(5-pyrrolidin-3-ylpyridin-2-yl)amino]pyrimidin-4-yl]-3',5'-dimethylspiro[cyclopropane-1,6'-thieno[2,3-c]pyrrole]-4'-one

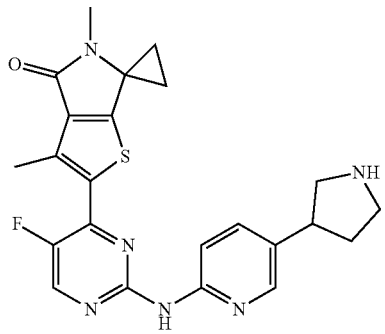 [SMILES: Cc1c(-c2nc(Nc3ccc(C4CCNC4)cn3)ncc2F)sc2c1C(=O)N(C)C21CC1]

The title compound was synthesized by procedures analogous to those outlined in Example 1, Step 7 and was purified by prep-HPLC on a C18 column (10-40%, MeCN/0.1% TFA (aq.)) to yield the title compound as a TFA salt. LCMS calc. for $C_{23}H_{24}FN_6OS$ [M+H]$^+$: m/z=451.2; Found: 451.0.

Step 5. 2'-[2-[[5-(1-Ethylpyrrolidin-3-yl)pyridin-2-yl]amino]-5-fluoropyrimidin-4-yl]-3',5'-dimethyl-spiro[cyclopropane-1,6'-thieno[2,3-c]pyrrole]-4'-one To a solution of 2'-[5-fluoro-2-[(5-pyrrolidin-3-ylpyridin-2-yl)amino]pyrimidin-4-yl]-3',5'-dimethylspiro[cyclopropane-1,6'-thieno[2,3-c]pyrrole]-4'-one (45.0 mg, 0.0999 mmol) in DCM (2 mL) was added acetaldehyde (22.0 mg, 0.499 mmol). The reaction mixture was stirred at room temperature for 30 min, and then sodium triacetoxyborohydride (63.5 mg, 0.300 mmol) was added. The resulting mixture was stirred for 30 min. The reaction was quenched with sat. NaHCO$_3$ (aq) (5 mL) The reaction mixture was stirred for 10 min and extracted with DCM (3 mL×3). The combined organic layers were dried over Na$_2$SO$_4$, filtered, and concentrated. The residue was purified by prep-HPLC on a C18 column (10-40% MeCN/0.1% TFA (aq.)) to yield the title compound as a TFA salt (17.4 mg, 0.0354 mmol, 35.4% yield), an off-white solid. $^1$H NMR (300 MHz, CD$_3$OD) δ 8.73 (d, J=3.0 Hz, 1H), 8.36-8.28 (m, 2H), 7.73 (d, J=9.6 Hz, 1H), 4.13-3.61 (m, 5H), 2.87 (s, 3H), 2.77 (d, J=2.4 Hz, 3H), 2.68-2.51 (m, 2H), 2.39-2.13 (m, 2H), 1.92 (dd, J=8.4, 6.3 Hz, 2H), 1.53 (dd, J=8.0, 6.0 Hz, 2H), 1.40 (t, J=7.5 Hz, 3H). LCMS calc. for $C_{25}H_{28}FN_6OS$ [M+H]$^+$: m/z=479.2; Found: 479.2.

Example 72. (E)-2'-(2-((5-(1-(But-2-en-1-yl)pyrrolidin-3-yl)pyridin-2-yl)amino)-5-fluoropyrimidin-4-yl)-3',5'-dimethylspiro[cyclopropane-1,6'-thieno[2,3-c]pyrrol]-4'(5'H)-one

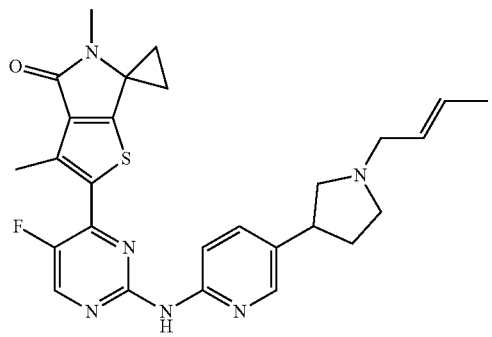 [SMILES: C/C=C/CN1CCC(c2ccc(Nc3ncc(F)c(-c4sc5c(c4C)C(=O)N(C)C54CC4)n3)nc2)C1]

The title compound was isolated as a byproduct from the procedure described in Example 71, Step 5. LCMS calc. for $C_{27}H_{30}FN_6OS$ [M+H]$^+$: 505.2; Found: 505.3.

Example 73. 2-[5-Fluoro-2-[[5-(1-methylpiperidin-4-yl)pyridin-2-yl]amino]pyrimidin-4-yl]-3-methyl-spiro[5H-thieno[2,3-c]pyrrole-6,1'-cyclopropane]-4-one

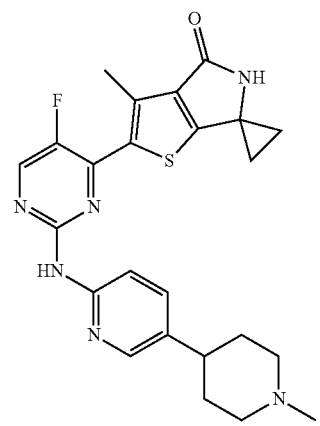 [SMILES: Cc1c(-c2nc(Nc3ccc(C4CCN(C)CC4)cn3)ncc2F)sc2c1C(=O)NC21CC1]

Step 1. 5'-[(4-Methoxyphenyl)methyl]-3'-methyl-spiro[cyclopropane-1,6'-thieno[2,3-c]pyrrole]-4'-one

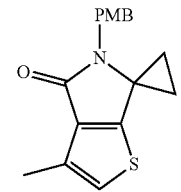

The title compound was synthesized by procedures analogous to those outlined in Example 6, Steps 1-6. LC-MS calc. for $C_{17}H_{18}NO_2S$ [M+H]$^+$: 300.1 Found: 300.1

Step 2. 2'-Bromo-5'-[(4-methoxyphenyl)methyl]-3'-methylspiro[cyclopropane-1,6'-thieno[2,3-c]pyrrole]-4'-one

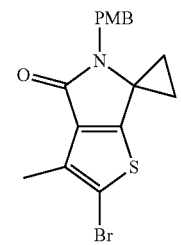

The title compound was synthesized by procedures analogous to those outlined in Example 6, Step 7. LC-MS calc. for $C_{17}H_{17}BrNO_2S$[M+H]$^+$: 378.0, 380.0; Found: 377.9, 379.9

Step 3. 2'-(2-Chloro-5-fluoropyrimidin-4-yl)-5'-[(4-methoxyphenyl)methyl]-3'-methylspiro[cyclopropane-1,6'-thieno[2,3-c]pyrrole]-4'-one

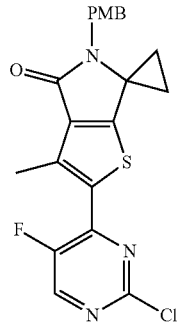

The title compound was synthesized by procedures analogous to those outlined in Example 6, Step 8. LC-MS calc. for $C_{21}H_{18}ClFN_3O_2S$ [M+H]$^+$: 430.1, 432.1; Found: 430.0, 431.9.

Step 4. 2'-[5-Fluoro-2-[[5-(1-methylpiperidin-4-yl)pyridin-2-yl]amino]pyrimidin-4-yl]-5'-[(4-methoxyphenyl)methyl]-3'-methylspiro[cyclopropane-1,6'-thieno[2,3-c]pyrrole]-4'-one

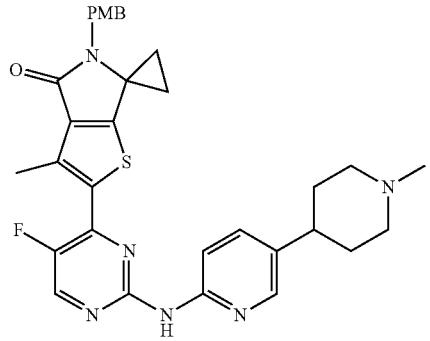

The title compound was synthesized by procedures analogous to those outlined in Example 6, Step 9. LC-MS calc. for $C_{32}H_{34}FN_6O_2S$[M+H]$^+$: 585.2; Found: 585.2.

Step 5. 2-[5-Fluoro-2-[[5-(1-methylpiperidin-4-yl)pyridin-2-yl]amino]pyrimidin-4-yl]-3-methylspiro[5H-thieno[2,3-c]pyrrole-6,1'-cyclopropane]-4-one The title compound was synthesized by procedures analogous to those outlined in Example 70, Step 6. $^1$H NMR (300 MHz, CD$_3$OD) δ 8.74 (d, J=3.0 Hz, 1H), 8.33-8.24 (m, 2H), 7.64 (d, J=9.0 Hz, 1H), 3.68 (d, J=12.3 Hz, 2H), 3.26-3.02 (m, 4H), 2.95 (s, 3H), 2.76 (d, J=2.4 Hz, 3H), 2.27-2.17 (m, 2H), 2.14-1.95 (m, 2H), 1.76 (dd, J=9.0, 6.0 Hz, 2H), 1.61-1.53 (m, 2H). LC-MS calc. for $C_{24}H_{26}FN_6OS$ [M+H]$^+$: 465.2; Found: 465.1.

Example 74. 2'-(5-Fluoro-2-((5-(1-methylpiperidin-4-yl)pyridin-2-yl)amino)pyrimidin-4-yl)-1',5'-dimethyl-5',6'-dihydrospiro[cyclopentane-1,7'-pyrrolo[3,2-c]pyridin]-4'(1'H)-one

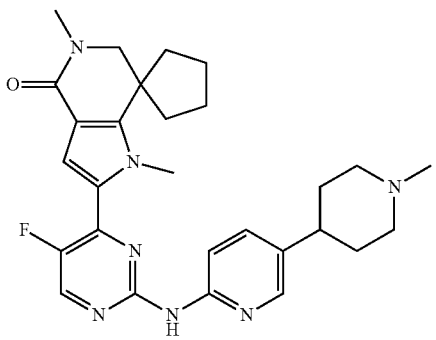 [SMILES: CN1CCC(c2ccc(Nc3ncc(F)c(-c4cc5c(n4C)C4(CCCC4)CN(C)C5=O)n3)nc2)CC1]

Step 1. Ethyl 1-(aminomethyl)cyclopentane-1-carboxylate

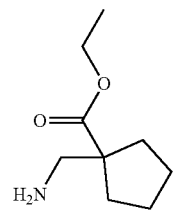

To a solution of ethyl 1-cyanocyclopentane-1-carboxylate (10.0 g, 59.8 mmol) in ethanol (30 mL) was added Raney-Nickel (1.43 g, 24.3 mmol; slurry in water; Aldrich, 221678). The mixture was stirred under an atmosphere of H$_2$ at room temperature for 48 h. The mixture was filtered through Celite and concentrated. The crude residue was dissolved in DCM, dried over Na$_2$SO$_4$, filtered, and concentrated. The residue was purified by silica gel chromatography (0-20% MeOH/DCM) to afford the title compound (7.30 g, 42.6 mmol, 71.0% yield) as a colorless oil. $^1$H NMR (300 MHz, CDCl$_3$) δ 4.13 (q, J=7.1 Hz, 2H), 2.80 (s, 2H), 2.09-1.97 (m, 2H), 1.86 (s, 2H), 1.74-1.43 (m, 6H), 1.24 (t, J=7.1 Hz, 3H). R$_f$=0.2 (10% MeOH/DCM, ninhydrin stain).

Step 2. Ethyl 1-((2,2,2-trifluoroacetamido)methyl)cyclopentane-1-carboxylate

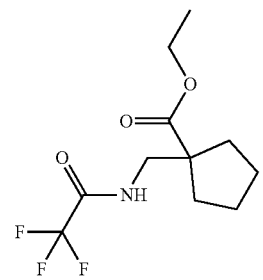 [SMILES: CCOC(=O)C1(CNC(=O)C(F)(F)F)CCCC1]

To a solution of ethyl 1-(aminomethyl)cyclopentane-1-carboxylate (2.01 g, 11.7 mmol) in ethyl trifluoroacetate (20.0 mL, 168 mmol) was triethylamine (2.44 mL, 17.5 mmol). The mixture was stirred at 50° C. for 1 h. The solvent was removed under reduced pressure. The residue was diluted with sat. NaHCO₃ (aq.) (20 mL) and extracted with DCM (20 mL×3). The combined organic layers were dried over Na₂SO₄, filtered, and concentrated to give the title compound (3.12 g, 11.7 mmol) as a colorless oil, which was used directly in the next step without any further purification. $R_f$=0.1 (30% EtOAc/hexanes).

Step 3. Ethyl 1-((2,2,2-trifluoro-N-methylacetamido)methyl)cyclopentane-1-carboxylate

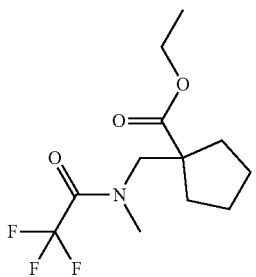 [SMILES: CCOC(=O)C1(CN(C)C(=O)C(F)(F)F)CCCC1]

To a solution of ethyl 1-[[(2,2,2-trifluoroacetyl)amino]methyl]cyclopentane-1-carboxylate (2.40 g, 8.98 mmol) in THF (30 mL) at 0° C. was added sodium hydride (1.08 g, 26.9 mmol, 60 wt % dispersion in mineral oil) and then iodomethane (1.68 mL, 26.9 mmol). The mixture was stirred at room temperature for 1 h. The reaction was quenched with sat. NH₄Cl (aq.) (30 mL) and extracted with EtOAc (30 mL×3). The combined organic layers were dried over Na₂SO₄, filtered, and concentrated to give the title compound (2.53 g, 8.98 mmol) as a colorless oil, which was used directly in the next step without any further purification. LCMS calc. for $C_{12}H_{19}F_3NO_3$ [M+H]⁺: m/z=282.1; Found 282.0.

Step 4. Ethyl 1-((methylamino)methyl)cyclopentane-1-carboxylate

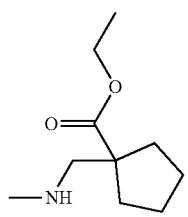

To a suspension of ethyl 1-[[methyl-(2,2,2-trifluoroacetyl)amino]methyl]cyclopentane-1-carboxylate (2.00 g, 7.10 mmol) in methanol (15 mL) and water (7.5 mL) was added Na₂CO₃ (1.51 g, 14.2 mmol). The mixture was stirred at room temperature overnight. The mixture was poured into water (20 mL) and extracted with CHCl₃ (20 mL×3). The combined organic layers were dried over Na₂SO₄, filtered, and concentrated. The crude residue was purified by silica gel chromatography (0-30% MeOH/DCM) to give the title compound (558 mg, 3.01 mmol, 42.0% yield over three steps) as a colorless oil. LCMS calc. for $C_{10}H_{20}NO_2$ [M+H]⁺: m/z=186.1; Found 185.9.

Step 5. Ethyl 1-((3-ethoxy-N-methyl-3-oxopropanamido)methyl)cyclopentane-1-carboxylate

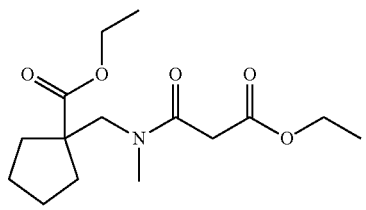 [SMILES: CCOC(=O)CC(=O)N(C)CC1(C(=O)OCC)CCCC1]

To a solution of ethyl 1-((methylamino)methyl)cyclopentane-1-carboxylate (256.8 mg, 1.386 mmol) in DCM (2 mL) was added ethyl 3-chloro-3-oxopropanoate (288 μL, 2.25 mmol). The mixture was cooled to 0° C., and triethylamine (0.63 mL, 4.5 mmol) was added dropwise. The mixture was warmed to room temperature and stirred for 2 h. The reaction mixture was diluted with H₂O (2 mL) and extracted with DCM (2 mL×3). The combined organic layers were dried over Na₂SO₄, filtered, and concentrated. The residue was purified by silica gel chromatography (0-65% EtOAc/heptane) to give the title compound (286 mg, 0.956 mmol, 69% yield) as a light green oil. ¹H NMR (300 MHz, CDCl₃) δ 4.25-4.11 (m, 4H), 3.75 (s, 2H), 3.43 (s, 2H), 2.93 (s, 3H), 2.12-1.94 (m, 2H), 1.77-1.56 (m, 6H), 1.32-1.23 (m, 6H).

Step 6. 7-Methyl-7-azaspiro[4.5]decane-8,10-dione

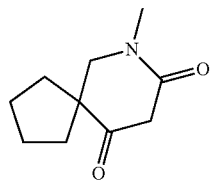

To a solution of ethyl 1-((3-ethoxy-N-methyl-3-oxopropanamido)methyl)cyclopentane-1-carboxylate (621 mg, 2.07 mmol) in toluene (10 mL) was added sodium ethoxide (1.26 mL, 3.26 mmol, 20 wt % in ethanol). The mixture was heated at 80° C. for 2 h. The mixture was cooled to room temperature, and H₂O (10 mL) was added. The aqueous layer was removed, and the organic layer was extracted with H₂O (10 mL×2). The combined aqueous layers were acidified with 4 N HCl (aq.) to pH<1 and extracted with EtOAc (20 mL×3). The combined organic layers were dried over Na₂SO₄, filtered, and concentrated. The crude residue was dissolved in MeCN containing 2% H₂O (6 mL) and stirred at 80° C. for 2 h. The solvent was evaporated, and the crude residue purified by silica gel chromatography (0-20% MeOH/DCM) to give the title compound (360 mg, 1.99 mmol, 96.1%) as an off-white solid. GCMS calc. for $C_{10}H_{15}NO_2$ [M]⁺: m/z=181.1; Found 181.1.

Step 7: 2-Chloro-4-(1-ethoxyethenyl)-5-fluoropyrimidine

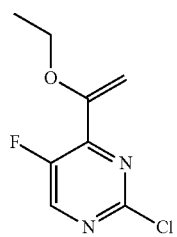

To a solution of tributyl(1-ethoxyvinyl)tin (1.34 mL, 3.97 mmol) and 2,6-dichloro-5-fluororacil (553 mg, 3.31 mmol) in toluene (6.00 mL) was added [1,1'-bis(diphenylphosphino) ferrocene]dichloropalladium(II) (194 mg, 0.265 mmol). The mixture was stirred at 100° C. for 3 h. To the mixture was added KF (1.00 g, 17.2 mmol), and the mixture was stirred at room temperature for 1 h. Then water (10 mL) was added, and the mixture was stirred overnight. The mixture filtered, and the two phases separated. The aqueous phase extracted with EtOAc (10 mL×3). The combined organic layers were dried over Na$_2$SO$_4$, filtered, and concentrated under reduced pressure. The crude residue was purified by silica gel chromatography (0%-10% EtOAc/heptane) to give the title compound (268 mg, 1.32 mmol, 39.9% yield). GC-MS calc. for C$_8$H$_8$ClFN$_2$O [M]$^+$: m/z=202.0; Found 202.1.

Step 8: 2-Bromo-1-(2-chloro-5-fluoropyrimidin-4-yl)ethan-1-one

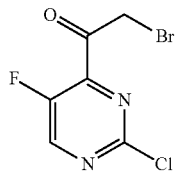

To a solution of 2-chloro-4-(1-ethoxyethenyl)-5-fluoropyrimidine (1.94 g, 9.59 mmol) in THF (15 mL) and water (6 mL) was added N-bromosuccinimide (1.71 g, 9.59 mmol). The reaction mixture was stirred at room temperature for 10 min. To the mixture was added hexane (8 mL) and EtOAc (8 mL) and then H$_2$O (6 mL). The organic layer was removed, and the aqueous layer was extracted with EtOAc (15 mL×3). The combined organic layers were dried over Na$_2$SO$_4$, filtered, and concentrated. The crude residue was purified by silica gel chromatography (0-45%, EtOAc/heptane) to afford the title compound as a colorless solid (2.40 g, 9.47 mmol, 98.7% yield). GC-MS calc. for C$_6$H$_3$BrClFN$_2$O [M]$^+$: m/z=251.9, 253.9; found 252.0, 254.0.

Step 9. 2'-(2-Chloro-5-fluoropyrimidin-4-yl)-5'-methyl-5',6'-dihydrospiro[cyclopentane-1,7'-pyrrolo[3,2-c]pyridin]-4'(1'H)-one

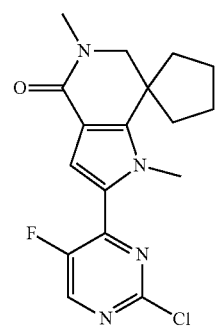 [SMILES: CN1CC2(CCCC2)c2c(cc(-c3nc(Cl)ncc3F)n2C)C1=O]

To a solution of 7-methyl-7-azaspiro[4.5]decane-8,10-dione (105 mg, 0.579 mmol) in ethanol (1 mL) was added 2-bromo-1-(2-chloro-5-fluoropyrimidin-4-yl)ethan-1-one (3.29 mL, 0.582 mmol, 1.77M in ethanol) and then NH$_4$OAc (59.7 mg, 0.775 mmol). The mixture was stirred at room temperature for 4 h. The reaction mixture was concentrated, and the crude residue was purified by prep-HPLC on a C18 column (10-55%, MeCN/0.1% TFA (aq.)) to give the title compound (47 mg, 0.14 mmol, 24% yield). LCMS calc. for C$_{16}$H$_{17}$ClFN$_4$O [M+H]$^+$ m/z=335.1; Found 334.9.

Step 10. 2'-(2-Chloro-5-fluoropyrimidin-4-yl)-1',5'-dimethyl-5',6'-dihydrospiro [cyclopentane-1,7'-pyrrolo[3,2-c]pyridin]-4'(1'H)-one To a solution of 2-(2-chloro-5-fluoropyrimidin-4-yl)-5-methylspiro[1,6-dihydropyrrolo[3,2-c]pyridine-7,1'-cyclopentane]-4-one (41.9 mg, 0.125 mmol) and K$_2$CO$_3$ (87 mg, 0.63 mmol) in acetone (3 mL) was added dimethyl sulfate (118 μL, 1.25 mmol). The mixture was stirred at room temperature for 24 h. To the mixture was added an additional portion of dimethyl sulfate (118 μL, 1.25 mmol), and the mixture was stirred for an additional 2 d. The mixture was filtered, concentrated, and purified by prep-HPLC on a C18 column (10-70% MeCN/0.1% TFA (aq.)) to afford the title compound (32.5 mg, 0.0932 mmol, 74.6% yield) as a colorless solid. LCMS calc. for C$_{17}$H$_{19}$ClFN$_4$O [M+H]$^+$ m/z=349.1; Found 348.9.

Step 10. 2'-(5-Fluoro-2-((5-(1-methylpiperidin-4-yl)pyridin-2-yl)amino)pyrimidin-4-yl)-1' 5'-dimethyl-5',6'-dihydrospiro[cyclopentane-1,7'-pyrrolo[3,2-c]pyridin]-4'(1'H)-one The title compound was synthesized by procedures analogous to those outlined in Example 1, Step 10. It was isolated as a TFA salt $^1$H NMR (400 MHz, methanol-$d_4$) δ 8.58 (d, J=3.6 Hz, 1H), 8.25-8.17 (m, 2H), 7.66 (d, J=8.8 Hz, 1H), 7.40 (d, J=4.0 Hz, 1H), 4.05 (s, 3H), 3.71-3.64 (m, 2H), 3.41 (s, 2H), 3.23-3.14 (m, 2H), 3.06 (s, 3H), 2.94 (s, 3H), 2.27-2.18 (m, 2H), 2.16-2.09 (m, 2H), 2.08-1.82 (m, 9H). LCMS calc. for $C_{28}H_{35}FN_7O$ [M+H]$^+$ m/z=504.3; Found 504.2.

Example 75. 5'-Ethyl-2'-(2-((5-(6-ethyl-2,6-diazaspiro[3.3]heptan-2-yl)pyridin-2-yl)amino)-5-fluoropyrimidin-4-yl)-5',6'-dihydro-4'H-spiro[cyclohexane-1,7'-thieno[3,2-c]pyridin]-4'-one

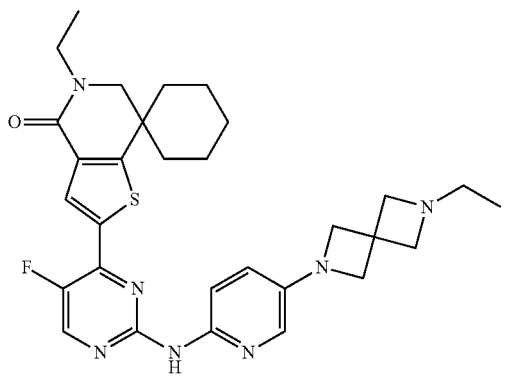 [SMILES: CCN1CC2(C1)CN(c1ccc(Nc3ncc(F)c(-c4cc5c(s4)C4(CCCCC4)CN(CC)C5=O)n3)nc1)C2]

The title compound was synthesized by procedures analogous to those outlined in Example 1, Steps 1-10. LCMS calc. for $C_{30}H_{37}FN_7OS$ [M+H]$^+$: 562.3; Found: 562.1.

Example 76. 2'''-(2-((5-(6-Ethyl-2,6-diazaspiro[3.3]heptan-2-yl)pyridin-2-yl)amino)-5-fluoropyrimidin-4-yl)-5'''-methyl-5''',6'''-dihydro-4'''H-dispiro[cyclopropane-1,1'-cyclobutane-3',7'''-thieno[3,2-c]pyridin]-4'''-one

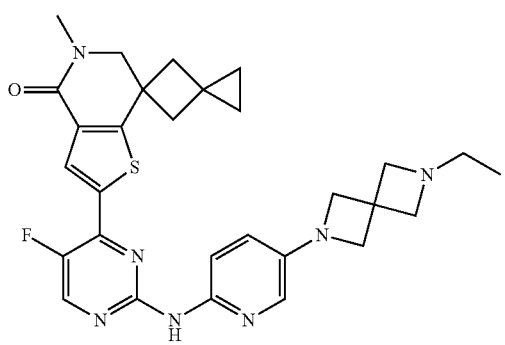 [SMILES: CCN1CC2(C1)CN(c1ccc(Nc3ncc(F)c(-c4cc5c(s4)C4(CN(C)C5=O)CC5(CC5)C4)n3)nc1)C2]

Step 1. (5-(Thiophen-2-yl)spiro[2.3]hexan-5-yl)methanamine

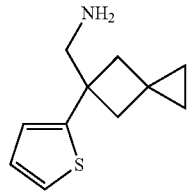 [SMILES: NCC1(c2cccs2)CC2(CC2)C1]

The title compound was synthesized by procedures analogous to those outlined in Example 28, Steps 4-5, substituting 1,1-bis(bromomethyl)cyclopropane for 1,2-dibromoethane in Step 4. LCMS calc. for $C_{11}H_{16}NS$ [M+H]$^+$: 194.1; Found: 194.2.

Step 2. 2'''-(2-((5-(6-Ethyl-2,6-diazaspiro[3.3]heptan-2-yl)pyridin-2-yl)amino)-5-fluoropyrimidin-4-yl)-5'''-methyl-5''',6'''-dihydro-4'''H-dispiro[cyclopropane-1,1'-cyclobutane-3',7'''-thieno[3,2-c]pyridin]-4'''-one The title compound was synthesized by procedures analogous to those outlined in Example 1. $^1$H NMR (400 MHz, CD$_3$OD) δ 8.56 (d, J=3.2 Hz, 1H), 8.13 (d, J=1.8 Hz, 1H), 7.56 (dd, J=9.5, 2.8 Hz, 1H), 7.39 (d, J=6.0 Hz, 1H), 7.38 (s, 1H), 4.40 (d, J=11.2 Hz, 2H), 4.26-4.13 (m, 4H), 4.08 (s, 2H), 3.78 (s, 2H), 3.17 (q, J=7.2 Hz, 2H), 3.05 (s, 3H), 2.44 (d, J=12.8 Hz, 2H), 2.32 (d, J=12.6 Hz, 2H), 1.13 (t, J=7.2 Hz, 3H), 0.54 (s, 4H). LCMS calc. for $C_{29}H_{33}FN_7OS$ [M+H]$^+$: 546.2; Found: 546.1.

Example 77. 2'-(5-Fluoro-2-((5-(1-methylpiperidin-4-yl)pyridin-2-yl)amino)pyrimidin-4-yl)-5'-methyl-2,3,5,5',6,6'-hexahydro-4'H-spiro[pyran-4,7'-thieno[3,2-c]pyridin]-4'-one

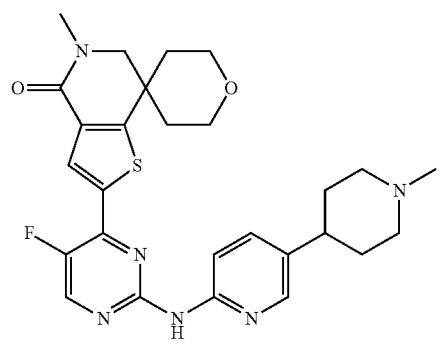 [SMILES: CN1CCC(c2ccc(Nc3ncc(F)c(-c4cc5c(s4)C4(CCOCC4)CN(C)C5=O)n3)nc2)CC1]

The title compound was synthesized by procedures analogous to those outlined in Example 28, Steps 6-11, substituting (4-(thiophen-2-yl)tetrahydro-2H-pyran-4-yl)methanamine (CombiBlock, QJ-3597) for (1-(4-methylthiophen-2-yl)cyclopropyl)methanamine in Step 6. $^1$H NMR (400 MHz, CD$_3$OD) δ 8.69 (d, J=3.1 Hz, 1H), 8.27 (d, J=1.8 Hz, 2H), 8.15 (dd, J=8.9, 2.4 Hz, 1H), 7.84 (d, J=9.0 Hz, 1H), 3.97-3.89 (m, 2H), 3.88-3.80 (m, 4H), 3.73-3.64 (m, 2H), 3.26-3.20 (m, 2H), 3.18 (s, 3H), 3.10-3.03 (m, 1H), 2.97 (s, 3H), 2.29-2.20 (m, 2H), 2.08-1.89 (m, 6H). LCMS calc. for $C_{27}H_{32}FN_6O_2S$ [M+H]$^+$: 523.2; Found: 523.1.

Example 78. 6'-(2-((5-(6-Ethyl-2,6-diazaspiro[3.3]heptan-2-yl)pyridin-2-yl)amino)-5-fluoropyrimidin-4-yl)-2'-methylspiro[cyclopentane-1,1'-isoindolin]-3'-one

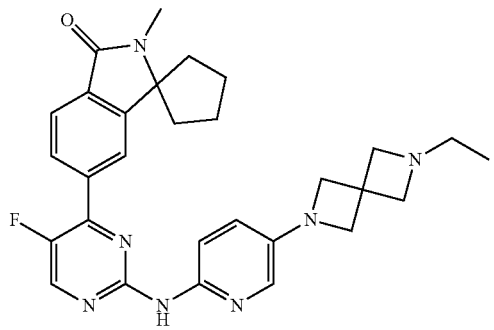 [SMILES: CCN1CC2(C1)CN(c1ccc(Nc3ncc(F)c(-c4ccc5c(c4)C4(CCCC4)N(C)C5=O)n3)nc1)C2]

Step 1. 6'-Bromo-2'-methylspiro[cyclopentane-1,1'-isoindolin]-3'-one

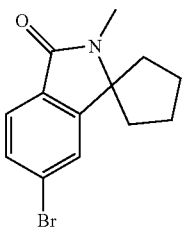 [SMILES: CN1C(=O)c2ccc(Br)cc2C12CCCC2]

Sodium hydride (80.0 mg, 2.00 mmol, 60 wt % dispersion in mineral oil) and 5-bromo-2,3-dihydro-2-methyl-1H-isoindol-1-one (90.4 mg, 0.400 mmol) were suspended in anhydrous THF (10 mL) and stirred at room temperature for 30 min. 1,4-Diiodobutane (0.260 mL, 2.00 mmol) was added, and the reaction was stirred for 24 h. The reaction was poured into sat. NH$_4$Cl (aq.) and extracted with EtOAc. The organic layer was washed with brine, dried over anhydrous Na$_2$SO$_4$, filtered, and concentrated. The crude residue was purified by silica gel column chromatography (0-30% EtOAc/hexanes) to afford the title compound as white solid (80.0 mg, 0.286 mmol, 71.4%). $^1$H NMR (400 MHz, CDCl$_3$) δ 7.68 (d, J=8.2 Hz, 1H), 7.60-7.54 (m, 2H), 3.04 (s, 3H), 2.15-1.88 (m, 8H). LCMS calc. for $C_{13}H_{15}BrNO$ [M+H]$^+$: m/z=280.0/282.0; Found: 279.9/281.9.

Step 2. 6'-(2-((5-(6-Ethyl-2,6-diazaspiro[3.3]heptan-2-yl)pyridin-2-yl)amino)-5-fluoropyrimidin-4-yl)-2'-methylspiro[cyclopentane-1,1'-isoindolin]-3'-one The title compound was synthesized by procedures analogous to those outlined in Example 1, Steps 5 and 10. $^1$H NMR (400 MHz, CD$_3$OD) δ 8.66 (d, J=3.2 Hz, 1H), 8.19 (s, 1H), 8.14 (d, J=8.1 Hz, 1H), 7.80 (d, J=8.0 Hz, 1H), 7.57 (dd, J=9.4, 2.8 Hz, 1H), 7.43-7.31 (m, 2H), 4.41 (d, J=11.3 Hz, 2H), 4.21 (d, J=10.9 Hz, 2H), 4.18 (s, 2H), 4.08 (s, 2H), 3.17 (q, J=7.3 Hz, 2H), 3.02 (s, 3H), 2.23-1.78 (m, 8H), 1.13 (t, J=7.2 Hz, 3H). LCMS calc. for $C_{29}H_{33}FN_7O$ [M+H]$^+$: m/z=514.3; Found: 514.1.

Example 79. 6'-(5-Fluoro-2-((5-(1-methylpiperidin-4-yl)pyridin-2-yl)amino)pyrimidin-4-yl)-2'-methyl-spiro[cyclopentane-1,1'-isoindolin]-3'-one

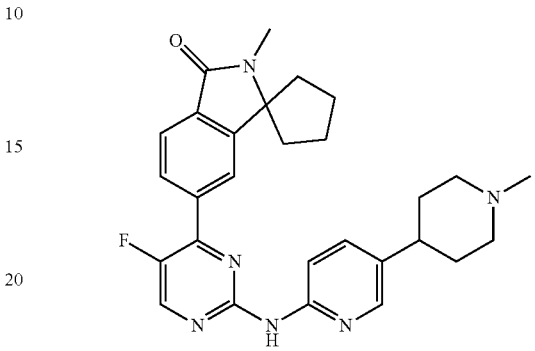

The title compound was synthesized by procedures analogous to those outlined in Example 78, Steps 1-2. $^1$H NMR (400 MHz, CD$_3$OD) δ 8.72 (d, J=3.1 Hz, 1H), 8.23-8.12 (m, 4H), 7.81 (d, J=8.0 Hz, 1H), 7.55 (d, J=9.4 Hz, 1H), 3.58 (d, J=12.4 Hz, 2H), 3.10 (t, J=12.6 Hz, 2H), 3.02 (s, 3H), 3.01-2.92 (m, 1H), 2.85 (s, 3H), 2.21-1.83 (m, 12H). LCMS calc. for $C_{28}H_{32}FN_6O$ [M+H]$^+$: m/z=487.3; Found: 487.1.

Example 80. 5'-Methyl-2'-(5-methyl-2-((5-(1-methylpiperidin-4-yl)pyridin-2-yl)amino) pyrimidin-4-yl)spiro[cyclopropane-1,6'-thieno[2,3-c]pyrrol]-4'(5'H)-one

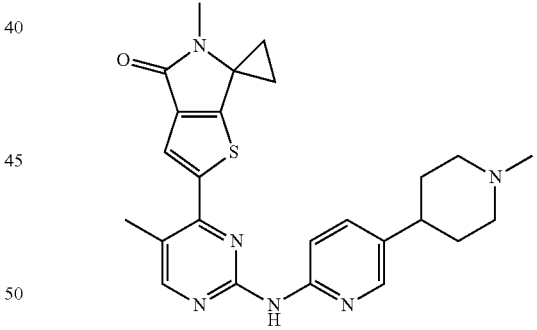

Step 1. 5'-Methylspiro[cyclopropane-1,6'-thieno[2,3-c]pyrrol]-4'(5'H)-one

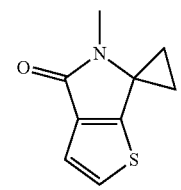

The title compound was synthesized by procedures analogous to those outlined in Example 6, Step 1-6. LC-MS calc. for C$_9$H$_{10}$NOS [M+H]$^+$: 180.1; Found: 180.0.

Step 2. 5'-Methyl-2'-(4,4,5,5-tetramethyl-1,3,2-dioxaborolan-2-yl)spiro[cyclopropane-1,6'-thieno[2,3-c]pyrrol]-4'(5'H)-one

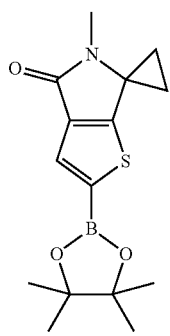 [SMILES: CN1C(=O)c2cc(B3OC(C)(C)C(C)(C)O3)sc2C12CC2]

To a solution of 5'-methylspiro[cyclopropane-1,6'-thieno[2,3-c]pyrrol]-4'(5'H)-one (94.0 mg, 0.520 mmol) and 2-isopropoxy-4,4,5,5-tetramethyl-1,3,2-dioxaborolane (0.210 mL, 1.05 mmol) in THF (1.7 mL) at −78° C. was added lithium diisopropylamide (0.79 mL, 1.57 mmol, 2.0 M in THF/heptane/ethylbenzene) slowly over 15 min. After stirring at room temperature for 90 min, sat. NH$_4$Cl (aq.) (10 mL) was added, and the mixture was extracted with EtOAc (5 mL). The title compound was observed. LC-MS calc. for C$_{15}$H$_{21}$BNO$_3$S [M+H]$^+$: 306.1; Found: 306.0. The organic layer was removed, and the aqueous layer was extracted with 1:3 isopropanol/chloroform (5 mL×4). The combined organic layers were concentrated to afford a dark oil, which was used without further purification.

Step 3. 2'-(2-Chloro-5-methylpyrimidin-4-yl)-5'-methylspiro[cyclopropane-1,6'-thieno[2,3-c]pyrrol]-4'(5'H)-one

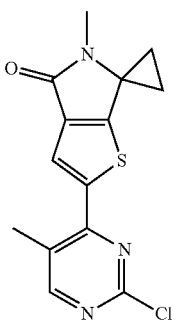 [SMILES: Cc1cnc(Cl)nc1-c1cc2c(s1)C1(CC1)N(C)C2=O]

A mixture of 5'-methyl-2'-(4,4,5,5-tetramethyl-1,3,2-dioxaborolan-2-yl)spiro[cyclopropane-1,6'-thieno[2,3-c]pyrrol]-4'(5'H)-one from step 2, 2,4-dichloro-5-methylpyrimidine (from Step 2), K$_3$PO$_4$ (334 mg, 1.58 mmol) and [1,1'-bis(diphenylphosphino) ferrocene]dichloropalladium (II) (38.4 mg, 0.0525 mmol), 1,4-dioxane (4 mL), and water (1 mL) was sparged with N$_2$ for 10 min. Next, the reaction vessel was capped, and the reaction mixture heated at 100° C. for 16 h. The reaction mixture was diluted with water (10 mL) and extracted with EtOAc (10 mL×3). The combined organic layers were dried over Na$_2$SO$_4$, filtered, and concentrated. The crude residue was purified by silica gel chromatography (0-40% EtOAc/heptanes) to afford the title compound (17.0 mg, 0.0556 mmol, 10.7% yield over 2 steps). LCMS calc. for C$_{14}$H$_{13}$ClN$_3$OS[M+H]$^+$: 306.0, 308.0; Found: 306.1, 308.1.

Step 4. 5'-Methyl-2'-(5-methyl-2-((5-(1-methylpiperidin-4-yl)pyridin-2-yl)amino) pyrimidin-4-yl)spiro[cyclopropane-1,6'-thieno[2,3-c]pyrrol]-4'(5'H)-one The title compound was synthesized by procedures analogous to those outlined in Example 6, Step 9. It was isolated as a TFA salt. LC-MS calc. for C$_{25}$H$_{29}$N$_6$OS [M+H]$^+$: 461.2; Found: 461.2.

Example 81. 2'-(2-((5-(2-Ethyl-2-azaspiro[3.3]heptan-6-yl)pyridin-2-yl)amino)-5-fluoropyrimidin-4-yl)-3',5'-dimethylspiro[cyclopropane-1,6'-thieno[2,3-c]pyrrol]-4'(5'H)-one

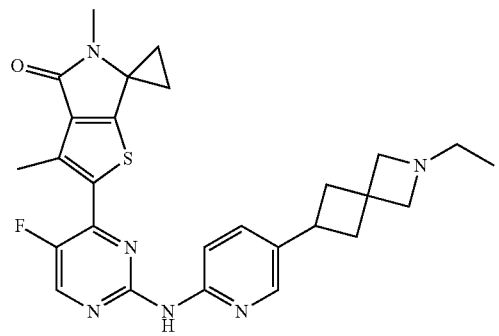 [SMILES: CCN1CC2(CC(c3ccc(Nc4ncc(F)c(-c5sc6c(c5C)C(=O)N(C)C65CC5)n4)nc3)C2)C1]

Step 1. tert-Butyl 6-iodo-2-azaspiro[3.3]heptane-2-carboxylate

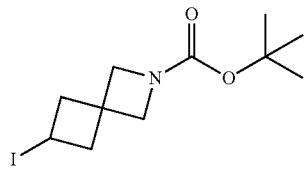

A vial was charged with tert-butyl 6-hydroxy-2-azaspiro[3.3]heptane-2-carboxylate (2.55 g, 12.0 mmol), imidazole (2.44 g, 35.9 mmol), triphenylphosphine (6.27 g, 23.9 mmol), and iodine (4.55 g, 17.9 mmol). Then toluene (40 mL) was added. The mixture was refluxed for 1 h. The mixture was cooled to room temperature, washed with H$_2$O (40 mL), dried over Na$_2$SO$_4$, filtered, and concentrated to give a colorless solid. The crude residue was purified by silica gel chromatography (0-20% EtOAc/heptanes) to afford the title compound (3.55 g, 10.9 mmol, 91.8% yield) as a colorless solid. R$_f$=0.7 (20% EtOAc/hexane).

147

Step 2. tert-Butyl 6-(6-aminopyridin-3-yl)-2-azaspiro[3.3]heptane-2-carboxylate

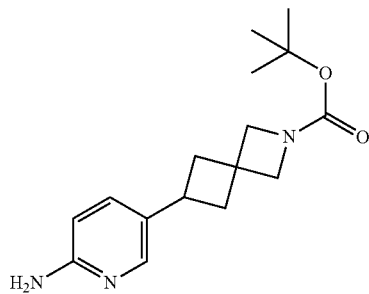 [SMILES: CC(C)(C)OC(=O)N1CC2(CC(c3ccc(N)nc3)C2)C1]

A vial was charged with 5-(4,4,5,5-tetramethyl-1,3,2-dioxaborolan-2-yl)pyridin-2-amine (82.1 mg, 0.373 mmol), tert-butyl 6-iodo-2-azaspiro[3.3]heptane-2-carboxylate (120.5 mg, 0.3729 mmol), [1,1'-bis(diphenylphosphino)ferrocene]dichloropalladium(II) (27.3 mg, 0.0373 mmol), and K$_3$PO$_4$ (237.4 mg, 1.119 mmol). Then 1,4-dioxane (3 mL) and water (1 mL) were added. The mixture was heated at 100° C. overnight. The mixture was concentrated and partitioned between DCM (10 mL) and water (10 mL). The biphasic mixture was then filtered via a syringe filter. The organic layer was separated, and the aqueous phase was extracted with DCM (10 mL×3). The combined organic layers were dried over Na$_2$SO$_4$, filtered, concentrated. The crude residue was purified by silica gel chromatography (0-10% MeOH/DCM) to afford the title compound (40.1 mg, 0.138 mmol, 37.0% yield). LCMS calc. for C$_{16}$H$_{24}$N$_3$O$_2$ [M+H]$^+$: m/z=290.2; Found: 290.0.

Step 3. tert-Butyl 6-(6-((4-(3',5'-dimethyl-4'-oxo-4',5'-dihydrospiro[cyclopropane-1,6'-thieno[2,3-c]pyrrol]-2'-yl)-5-fluoropyrimidin-2-yl)amino)pyridin-3-yl)-2-azaspiro[3.3]heptane-2-carboxylate

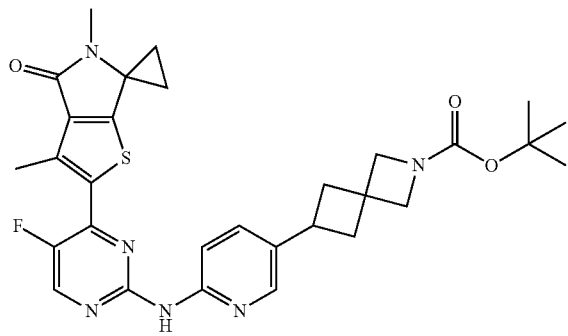 [SMILES: Cc1c(-c2nc(Nc3ccc(C4CC5(C4)CN(C(=O)OC(C)(C)C)C5)cn3)ncc2F)sc2c1C(=O)N(C)C21CC1]

The title compound was synthesized by procedures analogous to those outlined in Example 6, Step 9. LCMS calc. for C$_3$OH$_{34}$FN$_6$O$_3$S [M+H]$^+$: m/z=577.2; Found: 577.5.

148

Step 4. 2'-(2-((5-(2-Azaspiro[3.3]heptan-6-yl)pyridin-2-yl)amino)-5-fluoropyrimidin-4-yl)-3',5'-dimethylspiro[cyclopropane-1,6'-thieno[2,3-c]pyrrol]-4'(5'H)-one

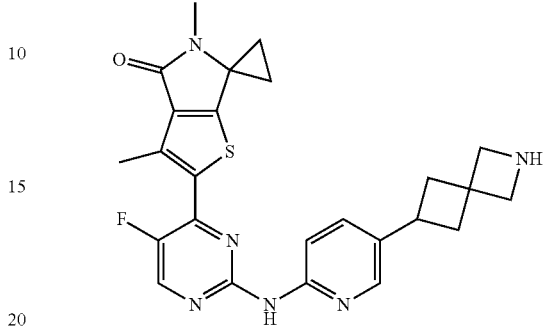

The title compound was synthesized by procedures analogous to those outlined in Example 1, Step 7. LCMS calc. for C$_{25}$H$_{26}$FN$_6$OS [M+H]$^+$: m/z=477.2; Found: 477.2.

Step 5. 2'-(2-((5-(2-Ethyl-2-azaspiro[3.3]heptan-6-yl)pyridin-2-yl)amino)-5-fluoropyrimidin-4-yl)-3',5'-dimethylspiro[cyclopropane-1,6'-thieno[2,3-c]pyrrol]-4'(5'H)-one The title compound was synthesized by procedures analogous to those outlined in Example 1, Step 8. $^1$H NMR (300 MHz, methanol-d$_4$) δ 8.73 (d, J=3.0 Hz, 1H), 8.28 (dd, J=9.0, 2.1 Hz, 1H), 8.20-8.15 (m, 1H), 7.60 (d, J=9.0 Hz, 1H), 4.46 (dd, J=10.8, 2.5 Hz, 1H), 4.21 (d, J=10.5, 2H), 4.03 (d, J=10.8 Hz, 1H), 3.62 (p, J=9.0 Hz, 1H), 3.24 (q, J=7.0 Hz, 2H), 2.86 (s, 3H), 2.84-2.80 (m, 1H), 2.77 (d, J=2.4 Hz, 3H), 2.74-2.66 (m, 1H), 2.60-2.43 (m, 2H), 1.92 (dd, J=8.7, 6.0 Hz, 2H), 1.54 (d, J=8.4, 6.0 Hz, 2H), 1.21 (t, J=7.2 Hz, 3H). LCMS calc. for C$_{27}$H$_{30}$FN$_6$OS [M+H]$^+$: m/z=505.2; Found: 505.0.

Example 82. 2-[2-[[6-(6-Ethyl-2,6-diazaspiro[3.3]heptan-2-yl)pyridazin-3-yl]amino]-5-fluoropyrimidin-4-yl]-5-methylspiro[6H-thieno[3,2-c]pyridine-7,1'-cyclopentane]-4-one

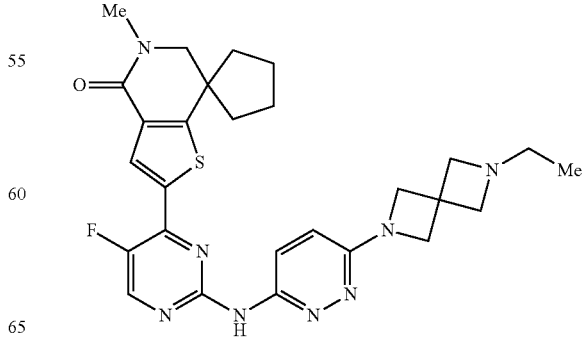

Step 1. tert-Butyl 6-(6-chloropyridazin-3-yl)-2,6-diazaspiro[3.3]heptane-2-carboxylate

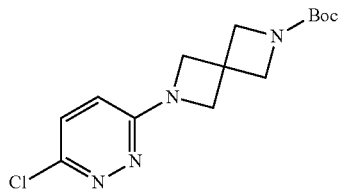 [SMILES: CC(C)(C)OC(=O)N1CC2(C1)CN(c1ccc(Cl)nn1)C2]

To a solution of 3,6-dichloropyridazine (500 mg, 3.36 mmol) in 1,4-dioxane (10 mL) was added tert-butyl 2,6-diazaspiro[3.3]heptane-2-carboxylate (665 mg, 3.36 mmol), $K_3PO_4$ (2.14 g, 10.1 mmol), and XPhos Pd G2 (264 mg, 0.340 mmol, CAS 1310584-14-5). The mixture was stirred at 100° C. for 24 h. The reaction mixture was cooled to room temperature, water (10 mL) was added, and the mixture was extracted with ethyl acetate (10 mL×3). The combined organic layers were dried over $Na_2SO_4$, filtered, and concentrated. The residue was purified by silica gel chromatography (10-90% EtOAc/heptanes) to afford the title compound (545 mg, 1.75 mmol, 52.3% yield). LCMS calc. for $C_{14}H_{20}ClN_4O_2$ [M+H]$^+$: m/z=311.1, 313.1; Found 311.1, 313.0.

Step 2. 2-(6-Chloropyridazin-3-yl)-2,6-diazaspiro[3.3]heptane

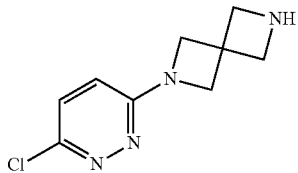 [SMILES: Clc1ccc(N2CC3(CNC3)C2)nn1]

To a solution of tert-butyl 6-(6-chloropyridazin-3-yl)-2,6-diazaspiro[3.3]heptane-2-carboxylate (545 mg, 1.75 mmol) in DCM (5 mL) was added TFA (5.0 mL, 65 mmol). The mixture was stirred at room temperature for 3 h. The solvent was removed under reduced pressure, and the crude material, which contained the title compound, was carried forward without further purification. LCMS calc. for $C_9H_{11}ClN_4$ [M+H]$^+$: m/z=211.1; Found 211.1.

Step 3. 2-(6-Chloropyridazin-3-yl)-6-ethyl-2,6-diazaspiro[3.3]heptane

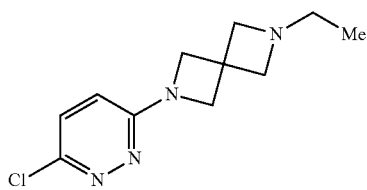 [SMILES: CCN1CC2(C1)CN(c1ccc(Cl)nn1)C2]

To a solution of 2-(6-chloropyridazin-3-yl)-2,6-diazaspiro[3.3]heptane (350 mg, 1.66 mmol) in methanol (4 mL) was added triethylamine (0.462 mL, 3.32 mmol), acetaldehyde (366 mg, 8.31 mmol), acetic acid (100 mg, 1.66 mmol), and sodium cyanoborohydride (1.04 g, 16.6 mmol). The mixture was stirred at room temperature overnight. Water (10 mL) was added, and the mixture was extracted with ethyl acetate (5 mL×3). The combined organic layers were dried over $Na_2SO_4$, filtered, and concentrated under reduced pressure to afford the title compound (300 mg, 1.26 mmol, 75.6% yield). LCMS calc. for $C_{11}H_{16}ClN_4$ [M]$^+$: m/z=239.1; Found 239.1.

Step 4. N-[6-(6-Ethyl-2,6-diazaspiro[3.3]heptan-2-yl)pyridazin-3-yl]-1,1-diphenylmethanimine

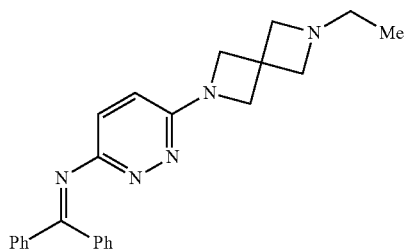 [SMILES: CCN1CC2(C1)CN(c1ccc(N=C(c3ccccc3)c3ccccc3)nn1)C2]

To a solution of 2-(6-chloropyridazin-3-yl)-6-ethyl-2,6-diazaspiro[3.3]heptane (360 mg, 1.51 mmol) in toluene (7.2 mL) was added benzophenone imine (410 mg, 2.26 mmol), tris(dibenzylideneacetone)dipalladium(0) (51.4 mg, 0.151 mmol), rac-BINAP (141 mg, 0.231 mmol, CAS 98327-87-8) and sodium tert-butoxide (435 mg, 4.52 mmol). The resulting mixture was stirred at 100° C. for 3 h. The reaction mixture was cooled to room temperature and diluted sequentially with water (30 mL) and EtOAc (30 mL). The organic layer was removed, and the aqueous layer was extracted with EtOAc (30 mL×3). The combined organic layers were dried over sodium sulfate, filtered, and concentrated. The residue was purified by silica gel chromatography (20%-100% EtOAc/heptanes, then 0%-30% MeOH/EtOAc) to afford title compound (210 mg, 0.548 mmol, 36.3% yield) as a white solid. LCMS calc. for $C_{24}H_{26}N_5$ [M+H]$^+$: m/z=384.2; Found: 384.2.

Step 5. 6-(6-Ethyl-2,6-diazaspiro[3.3]heptan-2-yl)pyridazin-3-amine

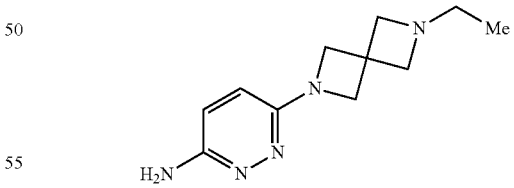

To a solution of N-[6-(6-ethyl-2,6-diazaspiro[3.3]heptan-2-yl)pyridazin-3-yl]-1,1-diphenylmethanimine (1.38 g, 3.60 mmol) in DCM (15 mL) was added trifluoroacetic acid (15.0 mL, 196 mmol) slowly. The resulting mixture was stirred at room temperature for 24 h. The mixture was concentrated under reduced pressure and then co-evaporated with toluene. The residue was purified by prep-HPLC on C18 column (0%-60% MeCN/0.1% TFA (aq)). The material was concentrated and then was partitioned between 10 mL 1:3 isopropyl alcohol/CHCl$_3$ and 10 mL of saturated sodium bicarbonate solution. The organic layer was removed, and the aqueous layer was extracted with 1:3 isopropyl alcohol/CHCl₃ (10 mL×5). The combined organic layers were dried over sodium sulfate, filtered, and concentrated under reduced pressure. The residue was further purified by silica gel chromatography (0%-40% MeOH/DCM) to afford the title compound (200 mg, 0.912 mmol, 25.3% yield) as a white solid. $^1$H NMR (300 MHz, CD₃OD) δ 6.91 (d, J=9.4 Hz, 1H), 6.80 (d, J=9.4 Hz, 1H), 4.06 (s, 4H), 3.44 (s, 4H), 2.53 (q, J=7.2 Hz, 2H), 0.99 (t, J=7.2 Hz, 3H). LCMS calc. for $C_{11}H_{18}N_5$ [M+H]⁺: m/z=220.2; Found: 220.1.

Step 6. 2-[2-[[6-(6-Ethyl-2,6-diazaspiro[3.3]heptan-2-yl)pyridazin-3-yl]amino]-5-fluoropyrimidin-4-yl]-5-methylspiro[6H-thieno[3,2-c]pyridine-7,1'-cyclopentane]-4-one To a nitrogen sparged solution of 2-(2-chloro-5-fluoropyrimidin-4-yl)-5-methylspiro[6H-thieno[3,2-c]pyridine-7,1'-cyclopentane]-4-one (50.0 mg, 0.142 mmol), 6-(6-ethyl-2,6-diazaspiro[3.3]heptan-2-yl)pyridazin-3-amine (37.4 mg, 0.171 mmol), and potassium phosphate tribasic (90.5 mg, 0.426 mmol) in 1,4-dioxane (4.75 mL) was added XPhos Pd G2 (11.2 mg, 0.0142 mmol). The reaction was sealed and stirred at 100° C. for 48 h. The reaction mixture was cooled to room temperature, filtered, diluted with MeCN, and purified via prep-HPLC on a C18 column (11-31% MeCN/0.1% TFA (aq.)) to afford the title compound as a TFA salt (21.7 mg, 0.0245 mmol, 17.2% yield), a yellow powder. $^1$H NMR (400 MHz, DMSO-d₆) δ 9.99 (s, 1H), 8.70 (d, J=3.1 Hz, 1H), 8.19 (d, J=9.7 Hz, 1H), 7.93 (d, J=1.9 Hz, 1H), 7.44 (d, J=9.8 Hz, 1H), 4.50-4.31 (m, 6H), 4.25 (dd, J=11.2, 6.5 Hz, 2H), 3.53 (s, 2H), 3.18 (p, J=7.0 Hz, 2H), 3.02 (s, 3H), 2.06-1.94 (m, 2H), 1.90-1.75 (m, 6H), 1.07 (t, J=7.2 Hz, 3H). LCMS calc. for $C_{27}H_{32}FN_8OS$ [M+H]⁺: m/z=535.2; Found: 535.1.

Example 83. 2'-(5-Fluoro-2-((6-(1-isopropylpiperidin-4-yl)pyridazin-3-yl)amino)pyrimidin-4-yl)-3',5'-dimethyl-5',6'-dihydro-4'H-spiro[cyclopropane-1,7'-thieno[3,2-c]pyridin]-4'-one

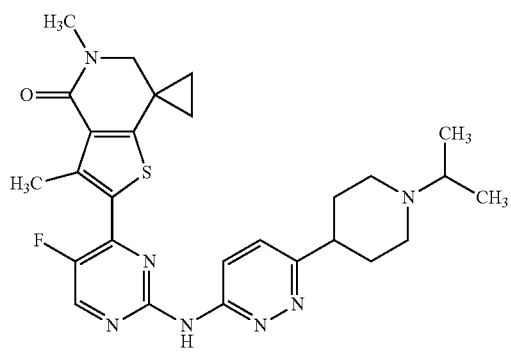 [SMILES: Cc1c(-c2nc(Nc3ccc(C4CCN(C(C)C)CC4)nn3)ncc2F)sc2c1C(=O)N(C)CC21CC1]

Step 1. tert-Butyl 4-(6-aminopyridazin-3-yl)-3,6-dihydropyridine-1(2H)-carboxylate

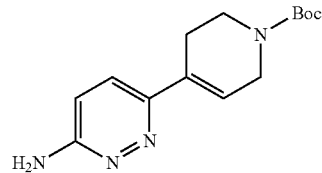

N-Boc-1,2,3,6-tetrahydropyridine-4-boronic acid pinacol ester (2.63 g, 8.49 mmol), 6-chloropyridazin-3-amine (1.00 g, 7.72 mmol), K₃PO₄ (4.92 g, 23.2 mmol), and [1,1'-bis(diphenylphosphino)ferrocene]dichloropalladium(II) (0.565 g, 0.772 mmol) were suspended in 1,4-dioxane (15.0 mL) and water (5.00 mL). The reaction mixture was heated at 100° C. for 2 h. The reaction mixture was cooled to room temperature and diluted with water (30.0 mL). The mixture was extracted with EtOAc (30.0 mL×3). The organic layers were combined, dried over sodium sulfate, filtered, and concentrated. The crude material was suspended in DCM (20.0 mL), and the solid was collected by filtration to afford the title compound (1.65 g, 5.97 mmol, 77.4% yield) as a white solid. $^1$H NMR (300 MHz, CDCl₃) δ 7.39 (d, J=9.3 Hz, 1H), 6.73 (d, J=9.3 Hz, 1H), 6.32 (s, 1H), 4.69 (s, 2H), 4.12 (q, J=3.1 Hz, 2H), 3.64 (t, J=5.7 Hz, 2H), 2.76 (s, 2H), 1.49 (s, 9H).

Step 2. tert-Butyl 4-(6-aminopyridazin-3-yl)piperidine-1-carboxylate

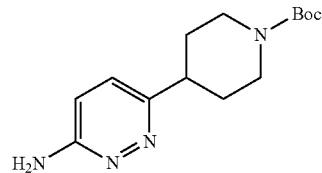

tert-Butyl 4-(6-aminopyridazin-3-yl)-3,6-dihydropyridine-1(2H)-carboxylate (1.60 g, 5.79 mmol) was dissolved in MeOH (30.0 mL). Palladium on carbon (0.800 g, 0.751 mmol, 10 wt %) and acetic acid (2.00 mL, 34.8 mmol) were added sequentially. The reaction vessel was sealed in a Parr shaker, and the vessel was charged with H₂ (60 psi). The reaction mixture was shaken overnight. The H₂ atmosphere was removed, the mixture was filtered, and the filtrate was concentrated. The crude residue was purified by silica gel chromatography (50-100% EtOAc in heptanes, then 0-30% MeOH in EtOAc) to afford the title compound (610 mg, 2.19 mmol, 37.8% yield). LCMS calc. for $C_{14}H_{23}N_4O_2$ [M+H]⁺: m/z=279.2; Found: 279.0.

Step 3. tert-Butyl 4-(6-((4-(3',5'-dimethyl-4'-oxo-5',6'-dihydro-4'H-spiro[cyclopropane-1,7'-thieno[3,2-c]pyridin]-2'-yl)-5-fluoropyrimidin-2-yl)amino)pyridazin-3-yl)piperidine-1-carboxylate

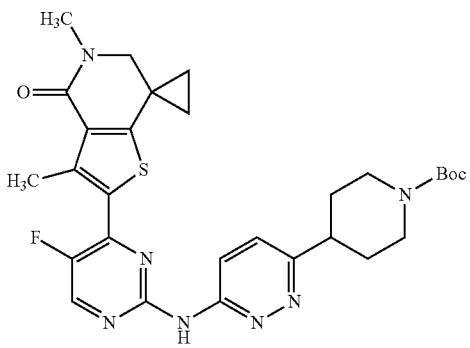 [SMILES: Cc1c(-c2nc(Nc3ccc(C4CCN(C(=O)OC(C)(C)C)CC4)nn3)ncc2F)sc2c1C(=O)N(C)CC21CC1]

The title compound was synthesized by a procedure analogous to that outlined in Example 1, Step 10. LCMS calc. for $C_{29}H_{35}FN_7O_3S$ [M+H]$^+$: m/z=580.2; Found: 580.1.

Step 4. 2'-(5-Fluoro-2-((6-(piperidin-4-yl)pyridazin-3-yl)amino)pyrimidin-4-yl)-3',5'-dimethyl-5',6'-dihydro-4'H-spiro[cyclopropane-1,7'-thieno[3,2-c]pyridin]-4'-one

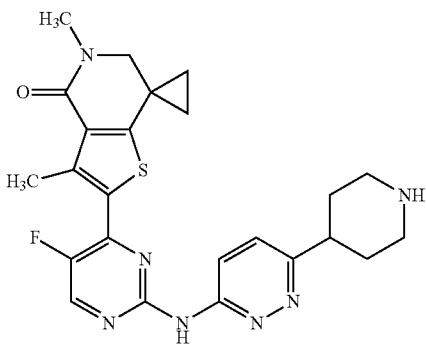 [SMILES: Cc1c(-c2nc(Nc3ccc(C4CCNCC4)nn3)ncc2F)sc2c1C(=O)N(C)CC21CC1]

The title compound was synthesized by a procedure analogous to that outlined in Example 1, Step 7. LCMS calc. for $C_{24}H_{27}FN_7OS$ [M+H]$^+$: m/z=480.2; Found: 480.1.

Step 5. 2'-(5-Fluoro-2-((6-(1-isopropylpiperidin-4-yl)pyridazin-3-yl)amino)pyrimidin-4-yl)-3',5'-dimethyl-5',6'-dihydro-4'H-spiro[cyclopropane-1,7'-thieno[3,2-c]pyridin]-4'-one Potassium carbonate (120 mg, 0.85 mmol) and 2-iodopropane (26 μL, 0.26 mmol) were added to a solution of 2'-(5-fluoro-2-((6-(piperidin-4-yl)pyridazin-3-yl)amino)pyrimidin-4-yl)-3',5'-dimethyl-5',6'-dihydro-4'H-spiro[cyclopropane-1,7'-thieno[3,2-c]pyridin]-4'-one (100 mg, 0.21 mmol) in DMF (1.10 mL) at room temperature. The mixture was stirred for 20 h. The crude reaction was diluted with methanol, filtered, and concentrated. The crude residue was purified by prep-HPLC on a C18 column (14-34% MeCN/0.1% TFA (aq.)) to afford the title compound as a TFA salt (3.9 mg, 0.0046 mmol, 2.20% yield). LCMS calc. for $C_{27}H_{33}FN_7OS$ [M+H]$^+$: m/z=522.2; Found: 522.1.

Example 84. 3,3-Difluoro-2'-(5-fluoro-2-((5-(1-methylpiperidin-4-yl)pyridin-2-yl)amino)pyrimidin-4-yl)-5'-methyl-5',6'-dihydro-4'H-spiro[cyclobutane-1,7'-thieno[3,2-c]pyridin]-4'-one

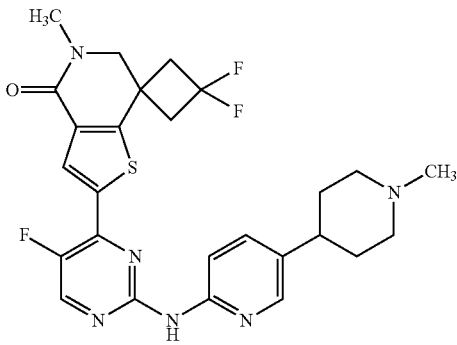 [SMILES: CN1CCC(c2ccc(Nc3ncc(F)c(-c4cc5c(s4)C4(CN(C)C5=O)CC(F)(F)C4)n3)nc2)CC1]

Step 1. 3,3-Dimethoxy-1-(thiophen-2-yl)cyclobutane-1-carbonitrile

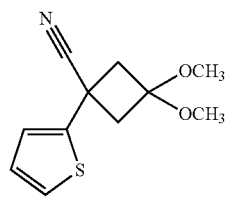 [SMILES: COC1(OC)CC(C#N)(c2cccs2)C1]

Sodium hydride (1.62 mg, 40.6 mmol, 60 wt % dispersion in mineral oil) and 1,3-dibromo-2,2-dimethoxypropane (4.68 g, 17.9 mmol) were added to a solution of 2-thiopheneacetonitrile (2.00 g, 16.2 mmol) in DMF (40.0 mL) at room temperature. The reaction mixture was heated at 60° C. for 18 h. The reaction was quenched with water (50.0 mL), and the mixture diluted with EtOAc (50.0 mL). The two phases were separated, and the aqueous layer was extracted with EtOAc (50.0 mL×2). The organic layers were combined, dried over sodium sulfate, filtered, and concentrated. The crude residue was purified by silica gel chromatography (0-40% EtOAc in hexanes) to afford the title compound (2.90 g, 13.0 mmol, 80.0% yield) as a pale yellow oil. $^1$H NMR (400 MHz, CDCl$_3$) δ 7.28 (dd, J=5.1, 1.3 Hz, 1H), 7.13 (dd, J=3.6, 1.3 Hz, 1H), 6.97 (dd, J=5.1, 3.6 Hz, 1H), 3.26 (s, 3H), 3.18 (s, 3H), 3.17-3.14 (m, 1H), 3.13-3.10 (m, 1H), 2.79-2.76 (m, 1H), 2.75-2.72 (m, 1H).

Step 2. 3,3-Dimethoxy-1-(thiophen-2-yl)cyclobutane-1-carbonitrile

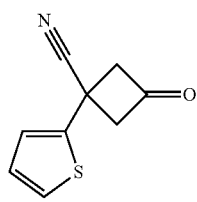 [SMILES: N#CC1(c2cccs2)CC(=O)C1]

Hydrochloric acid (aq.) (0.832 mL, 9.99 mmol, 12 M) was added to a solution of 3,3-dimethoxy-1-(thiophen-2-yl)cyclobutane-1-carbonitrile (446 mg, 2.0 mmol) in 1:1 acetone/water (6.60 mL) at room temperature. The reaction mixture was heated at 75° C. for 2 h. The reaction mixture was cooled to room temperature and diluted with water (10.0 mL) and DCM (10.0 mL). The two phases were separated, and the aqueous phase was extracted with DCM (10.0 mL×2). The organic layers were combined, dried over sodium sulfate, filtered, and concentrated under reduced pressure to afford the title compound (350 mg, 1.97 mmol, 98.9% yield) as a grey oil. $^1$H NMR (400 MHz, CDCl$_3$) δ 7.35 (dd, J=5.1, 1.2 Hz, 1H), 7.19 (dd, J=3.6, 1.2 Hz, 1H), 7.03 (dd, J=5.1, 3.6 Hz, 1H), 4.16-4.10 (m, 1H), 4.10-4.05 (m, 1H), 3.80-3.75 (m, 1H), 3.75-3.70 (m, 1H).

Step 3. 3,3-Difluoro-1-(thiophen-2-yl)cyclobutane-1-carbonitrile

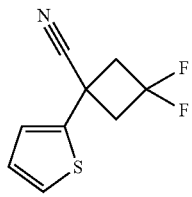 [SMILES: N#CC1(c2cccs2)CC(F)(F)C1]

Diethylaminosulfur trifluoride (0.650 mL, 4.93 mmol) was added to a solution of 3,3-dimethoxy-1-(thiophen-2-yl)cyclobutane-1-carbonitrile (349 mg, 1.97 mmol) in DCM (10.0 mL) at room temperature. The reaction mixture stirred for 18 h. The reaction mixture was poured into a sat. NaHCO$_3$ (aq.) (20.0 mL) and was diluted with DCM (10.0 mL). The two phases were separated, and the aqueous layer was extracted with DCM (10.0 mL×2). The organic layers were combined, dried over sodium sulfate, filtered, and concentrated. The crude residue was purified by silica gel chromatography (0-20% EtOAc in hexanes) to afford the title compound (313 mg, 1.57 mmol, 79.8% yield) as a colorless oil. $^1$H NMR (400 MHz, CDCl$_3$) δ 7.34 (d, J=5.2 Hz, 1H), 7.16 (d, J=3.7 Hz, 1H), 7.02 (dd, J=5.2, 3.6 Hz, 1H), 3.63-3.46 (m, 2H), 3.33-3.15 (m, 2H).

Step 5. (3,3-Difluoro-1-(thiophen-2-yl)cyclobutyl)methanamine

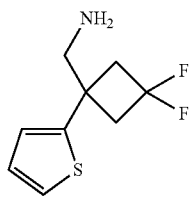 [SMILES: NCC1(c2cccs2)CC(F)(F)C1]

Lithium aluminum hydride (62.6 mg, 1.65 mmol) was added to a solution of 3,3-difluoro-1-(thiophen-2-yl)cyclobutane-1-carbonitrile (313 mg, 1.57 mmol) in THF (5.00 mL) at room temperature. After stirring 30 min, the reaction was quenched by sequential addition of water (0.070 mL) and 1 N NaOH (aq.) (0.280 mL). The suspension was diluted with EtOAc and dried with sodium sulfate. The resulting mixture was filtered and concentrated. The crude residue, containing the title compound as a colorless oil, was used without further purification. LCMS calc. for C$_9$H$_{12}$F$_2$NS [M+H]$^+$: m/z=204.1; Found 203.9.

Step 6. 2'-Bromo-3,3-difluoro-5'-methyl-5',6'-dihydro-4'H-spiro[cyclobutane-1,7'-thieno[3,2-c]pyridin]-4'-one

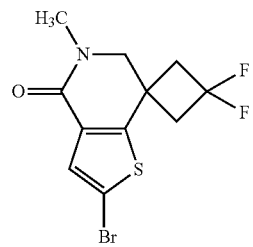 [SMILES: CN1CC2(CC(F)(F)C2)c2sc(Br)cc2C1=O]

The title compound is synthesized by procedures analogous to those outlined in Example 1, Steps 1-4. It was isolated as the major component of a mixture. $^1$H NMR (400 MHz, CDCl$_3$) δ 7.37 (s, 1H), 3.66 (d, J=1.3 Hz, 2H), 3.11 (s, 3H), 2.92-2.73 (m, 4H). LCMS calc. for C$_{11}$H$_{11}$BrF$_2$NOS [M+H]$^+$: m/z=322.0, 324.0; Found: 321.8, 323.7.

Step 7. 3,3-Difluoro-2'-(5-fluoro-2-((5-(1-methylpiperidin-4-yl)pyridin-2-yl)amino)pyrimidin-4-yl)-5'-methyl-5',6'-dihydro-4'H-spiro[cyclobutane-1,7'-thieno[3,2-c]pyridin]-4'-one The title compound was synthesized by procedures analogous to those outlined in Example 1, Steps 5 and 10. It was isolated as a TFA salt. $^1$H NMR (400 MHz, DMSO-d$_6$) δ 10.23 (s, 1H), 9.35 (s, 1H), 8.73 (d, J=3.1 Hz, 1H), 8.21 (d, J=2.5 Hz, 1H), 8.13 (d, J=8.7 Hz, 1H), 7.95 (d, J=1.9 Hz, 1H), 7.72 (dd, J=8.7, 2.5 Hz, 1H), 3.80 (s, 2H), 3.54 (d, J=12.0 Hz, 2H), 3.24-3.05 (m, 4H), 3.04 (s, 3H), 2.99-2.88 (m, 3H), 2.83 (d, J=4.7 Hz, 3H), 2.14-2.00 (m, 2H), 1.94-1.73 (m, 2H). LCMS calc. for C$_{26}$H$_{28}$F$_3$N$_6$OS [M+H]$^+$: m/z=529.2; Found: 529.0.

Example 85. 2'-(2-((5-(6-Ethyl-2,6-diazaspiro[3.3]heptan-2-yl)pyridin-2-yl)amino)-5-fluoropyrimidin-4-yl)-3,3-difluoro-5'-methyl-5',6'-dihydro-4'H-spiro[cyclobutane-1,7'-thieno[3,2-c]pyridin]-4'-one

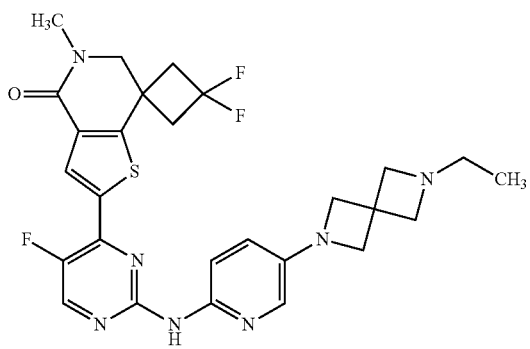 [SMILES: CCN1CC2(C1)CN(c1ccc(Nc3ncc(F)c(-c4cc5c(s4)C4(CN(C)C5=O)CC(F)(F)C4)n3)nc1)C2]

The title compound was synthesized by procedures analogous to those outlined in Example 84. It was isolated as a TFA salt. ¹H NMR (400 MHz, DMSO-d₆) δ 9.90 (s, 1H), 9.79 (s, 1H), 8.65 (d, J=3.1 Hz, 1H), 7.93 (d, J=1.8 Hz, 1H), 7.90 (d, J=9.0 Hz, 1H), 7.61 (d, J=3.0 Hz, 1H), 7.08 (dd, J=9.1, 3.0 Hz, 1H), 4.35 (dd, J=11.4, 6.3 Hz, 2H), 4.21 (dd, J=11.6, 6.0 Hz, 2H), 4.09 (s, 2H), 4.00 (s, 2H), 3.79 (s, 2H), 3.24-3.09 (m, 4H), 3.03 (s, 3H), 3.00-2.85 (m, 2H), 1.07 (t, J=7.2 Hz, 3H). LCMS calc. for $C_{27}H_{29}F_3N_7OS$ [M+H]⁺: m/z=556.2; Found: 556.0.

Example 86. 2-[2-[[5-(4-Ethyl-2-oxopiperazin-1-yl)pyridin-2-yl]amino]-5-fluoropyrimidin-4-yl]-5-methylspiro[6H-thieno[3,2-c]pyridine-7,1'-cyclopentane]-4-one

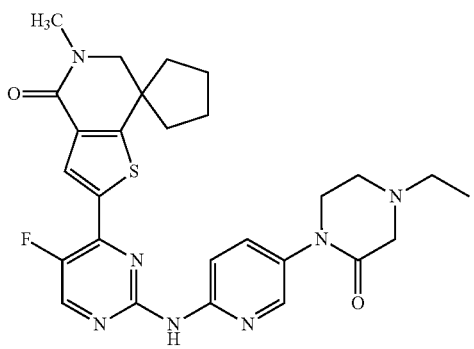 [SMILES: CCN1CCN(c2ccc(Nc3ncc(F)c(-c4cc5c(s4)C4(CCCC4)CN(C)C5=O)n3)nc2)C(=O)C1]

Step 1:
4-Ethyl-1-(6-nitropyridin-3-yl)piperazin-2-one

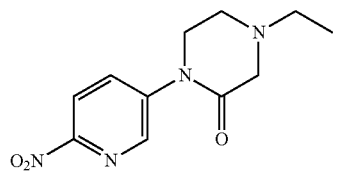

A solution of 5-bromo-2-nitropyridine (1050 mg, 5.16 mmol), 4-ethyl-2-piperazinone hydrochloride (850 mg, 5.16 mmol), and cesium carbonate (3360 mg, 10.3 mmol) in 1,4-dioxane (25 mL) was sparged with N₂ for 20 min. Tris(dibenzylideneacetone)dipalladium(0) (88.0 mg, 0.258 mmol) and 9,9-dimethyl-4,5-bis(diphenylphosphino)xanthene (257 mg, 0.444 mmol) were added, and the solution was sparged with N₂ for an additional 10 min. The reaction was stirred overnight at 105° C. The reaction mixture was cooled to room temperature, diluted with water (40 mL) and EtOAc (40 mL), and filtered through Celite. The aqueous layer was extracted with EtOAc (3×20 mL). The combined organic layers were washed with brine, dried over anhydrous magnesium sulfate, filtered, and concentrated. The crude material was purified by silica gel chromatography (0-20% MeOH/DCM) to afford the title compound (992 mg, 3.96 mmol, 76.8% yield) as an orange solid. LCMS calc. for $C_{11}H_{15}N_4O_3$ [M+H]⁺: m/z=251.1; Found: 251.0.

Step 2.
1-(6-Aminopyridin-3-yl)-4-ethylpiperazin-2-one

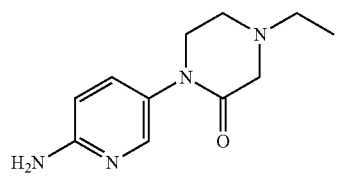 [SMILES: CCN1CCN(c2ccc([N+](=O)[O-])nc2)C(=O)C1]

The title compound was synthesized by procedures analogous to those outlined in Example 1, Step 9. LCMS calc. for $C_{11}H_{17}N_4O$ [M+H]⁺: m/z=221.1; Found 221.0.

Step 3. 2-[2-[[5-(4-Ethyl-2-oxopiperazin-1-yl)pyridin-2-yl]amino]-5-fluoropyrimidin-4-yl]-5-methylspiro[6H-thieno[3,2-c]pyridine-7,1'-cyclopentane]-4-one The title compound was synthesized by procedures analogous to those outlined in Example 1, Step 10 and isolated as a TFA salt. LCMS calc. for $C_{27}H_{31}FN_7O_2S$ [M+H]⁺: m/z=536.2; Found 536.1.

Example 87. 2-[5-Fluoro-2-[[6-(1-methylpiperidin-4-yl)pyridazin-3-yl]amino]pyrimidin-4-yl]-5-methylspiro[6H-thieno[3,2c]pyridine-7,1'-cyclopentane]-4-one

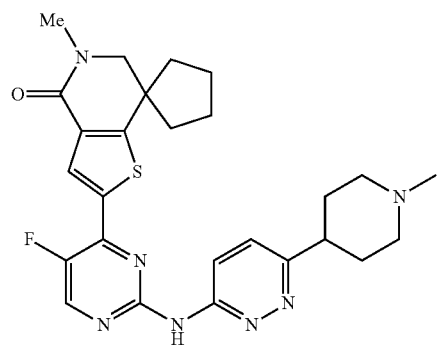 [SMILES: CN1CCC(c2ccc(Nc3ncc(F)c(-c4cc5c(s4)C4(CCCC4)CN(C)C5=O)n3)nn2)CC1]

Step 1. 2-[5-Fluoro-2-[(6-piperidin-4-ylpyridazin-3-yl)amino]pyrimidin-4-yl]-5-methylspiro[6H-thieno[3,2-c]pyridine-7,1'-cyclopentane]-4-one

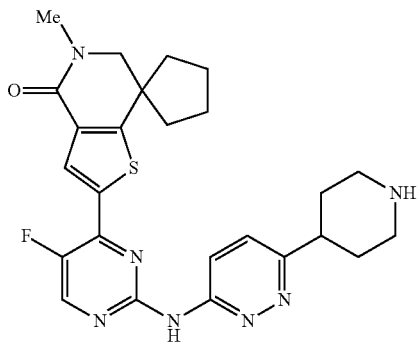 [SMILES: CN1CC2(CCCC2)c2sc(-c3nc(Nc4ccc(C5CCNCC5)nn4)ncc3F)cc2C1=O]

The title compound was synthesized by procedures analogous to those outlined in Example 83, Steps 1-4. LCMS calc. for $C_{25}H_{29}FN_7OS$ [M+H]$^+$: m/z=494.2; Found 494.0.

Step 2. 2-[5-Fluoro-2-[[6-(1-methylpiperidin-4-yl)pyridazin-3-yl]amino]pyrimidin-4-yl]-5-methylspiro[6H-thieno[3,2-c]pyridine-7,1'-cyclopentane]-4-one To a solution of 2-[5-fluoro-2-[(6-piperidin-4-ylpyridazin-3-yl)amino]pyrimidin-4-yl]-5-methylspiro[6H-thieno[3,2-c]pyridine-7,1'-cyclopentane]-4-one (165 mg, 0.340 mmol) in methanol (1.75 mL) was added acetic acid (0.110 mL, 2.01 mmol) and formaldehyde (0.16 mL, 2.01 mmol, 37 wt % in water). The reaction was stirred for 15 min at room temperature. Sodium cyanoborohydride (126 mg, 2.01 mmol) was added in portions, and the reaction mixture was stirred for 18 h. The reaction mixture was filtered through Celite, concentrated, and purified by prep-HPLC on a C18 column (14-34% MeCN/0.1% TFA (aq.)) to afford the title compound as a TFA salt (2.10 mg, 0.00257 mmol, 0.767% yield). LCMS calc. for $C_{26}H_{31}FN_7OS$ [M+H]$^+$: m/z=508.2; Found: 508.1.

Example A: Enzymatic Activity and Cytotoxicity Studies

CDK4/CyclinD1 Enzymatic Activity Assay

The inhibitory activity of compounds was evaluated in vitro using TR-FRET assay with white 384-well low volume microplate (Greiner Bio-One). CDK4/Cyclin D1 catalyzed phosphorylation of peptide in the presence and absence of compounds was measured. $IC_{50}$ determination. Recombinant protein complex CDK4/Cyclin D1, expressed from insect cell, was purchased from ProQinase. Testing compounds were dissolved in DMSO at 0.1 mM and tested in 9-dose $IC_{50}$ mode. The reaction mixture was prepared by mixing CDK4/CyclinD1 (1 nM final), ULight-4E-BP1 (100 nM final, Perkinelmer, TRF0128-D), and ATP (2 mM final) in assay buffer (20 mM of HEPES pH 7.4, 1 mM of EGTA, 0.05% BSA, 0.005% Tween 20, and 1 mM TCEP). The compound of interest in DMSO was added to each well in 3-fold serial dilution by dispenser (TECAN D300E). After 20 minutes preincubation at room temperature, MgCl$_2$ (10 mM final) was added to initiate the reaction. Following a 60 minutes incubation at 37° C., the reaction was stopped by addition of 2 μL of quenching buffer consisting of Lance detection buffer (Perkinelmer CR97-100C), 2 nM LANCE Ultra Europium-anti-P-4E-BP1 (Perkinelmer, TRF0216-D), 10 mM EDTA, and incubate at room temperature for additional 60 minutes in dark. The reaction signal was measured by Envision multimode plate reader (PerkinElmer, 2102-0010). $IC_{50}$ values were determined by fitting the data to the standard 4 parameters with Hill Slope using GraphPad Prism software. Table 1, below, shows the $IC_{50}$ values determined by this assay.

CDK6/CyclinD1 Enzymatic Activity Assay

The inhibitory activity of compounds was evaluated in vitro using TR-FRET assay with white 384-well low volume microplate (Greiner Bio-One). CDK6/Cyclin D1 catalyzed phosphorylation of peptide in the presence and absence of compounds was measured and used in $IC_{50}$ determination. Recombinant protein complex CDK6/Cyclin D1, expressed from insect cell, was purchased from ProQinase. Testing compounds were dissolved in DMSO at 0.1 mM and tested in 9-dose IC50 mode. The reaction mixture was prepared by mixing CDK6/Cyclin D1 (1 nM final), ULight-4E-BP1 (100 nM final, Perkinelmer, TRF0128-D), and ATP (250 μM final) in assay buffer (20 mM of HEPES pH 7.4, 1 mM of EGTA, 0.05% BSA, 0.005% Tween 20, and 1 mM TCEP). The compound of interest in DMSO was added to each well in 3-fold serial dilution by dispenser (TECAN D300E). After 20 minutes preincubation at room temperature, 0.1 μL MgCl$_2$ (10 mM final) was added to initiate the reaction. Following a 60 minutes incubation at 37° C., the reaction was stopped by addition of 2 μL of quenching buffer consisting of Lance detection buffer (Perkinelmer CR97-100C), 2 nM LANCE Ultra Europium-anti-P-4E-BP1 (Perkinelmer, TRF0216-D), 10 mM EDTA, and incubate at room temperature for additional 60 minutes in dark. The reaction signal was measured by Envision multimode plate reader (PerkinElmer, 2102-0010). $IC_{50}$ values were determined by fitting the data to the standard 4 parameters with Hill Slope using GraphPad Prism software. Table 1, below, shows the $IC_{50}$ values determined by this assay.

Cell Proliferation Studies in MCF7 Cells

Cell proliferation studies were conducted in MCF7 adenocarcinoma cell line. Cells were maintained in DMEM (Corning, Catalog #: 10-013-CV) supplemented with 10% v/v FBS (Gibco, Catalog #: 26140-079), 1% v/v Penicillin Streptomycin (Gibco, Catalog #15140-122) Cells were seeded in 384-well plates at a density of 100 or 200 cells/well. Compounds dissolved in DMSO were plated in quadruplicate using a digital dispenser (D300E, Tecan) and tested on a 9-point 3-fold serial dilution. Cells were incubated for 10 days in a 37° C. active humidified incubator at 5% CO$_2$. A media exchange and second compound addition were performed on day 5. Cell viability was measured using the ATP-Lite 1—Step Luminescence reagent (Perkin Elmer, Catalog #: 6016731) as per manufacturer's instructions. Luminescence signal was measured with a multimode plate reader (Envision 2105, Perkin Elmer). Raw data files were imported to Dotmatics Screening Ultra for $IC_{50}$ analysis. Luminescence values were normalized to both background and DMSO controls to obtain a percentage of viable cells relative to DMSO vehicle control. The results are shown in Table 13, below

TABLE 13

| | $IC_{50}$ Values | | |
|---|---|---|---|
| Example | CDK4_D1 $IC_{50}$ (nM) | CDK6_D1 $IC_{50}$ (nM) | PROLIFERATION_CTG_MCF7 $IC_{50}$ (nM) |
| 1 | ++++ | ++++ | +++ |
| 2 | ++++ | ++++ | +++ |
| 3 | ++++ | ++++ | +++ |
| 4 | ++++ | +++ | +++ |
| 5 | ++++ | +++ | ++++ |
| 6 | ++++ | ++++ | +++ |
| 7 | ++++ | ++++ | +++ |
| 8 | ++++ | ++++ | +++ |
| 9 | ++++ | ++++ | +++ |
| 10 | ++++ | ++++ | +++ |
| 11 | ++++ | — | +++ |
| 12 | ++++ | ++++ | ++++ |
| 13 | ++++ | ++++ | +++ |
| 14 | ++++ | — | ++++ |
| 15 | ++++ | — | +++ |
| 16 | ++++ | ++++ | +++ |
| 17 | ++++ | — | +++ |
| 18 | ++++ | — | +++ |
| 19 | ++++ | — | +++ |
| 20 | ++++ | ++++ | ++++ |
| 21 | ++++ | ++++ | +++ |
| 22 | ++++ | +++ | +++ |
| 23 | ++++ | ++++ | +++ |
| 24 | ++++ | ++++ | +++ |
| 25 | ++++ | ++++ | ++++ |

TABLE 13-continued

IC$_{50}$ Values

| Example | CDK4_D1 IC$_{50}$ (nM) | CDK6_D1 IC$_{50}$ (nM) | PROLIFERATION_CTG_MCF7 IC$_{50}$ (nM) |
|---|---|---|---|
| 26 | ++++ | ++++ | ++++ |
| 27 | ++++ | ++++ | ++++ |
| 28 | ++++ | ++++ | +++ |
| 29 | ++++ | +++ | +++ |
| 30 | ++++ | ++++ | +++ |
| 31 | ++++ | — | ++ |
| 32 | ++++ | ++++ | +++ |
| 33 | ++++ | — | +++ |
| 34 | ++++ | ++++ | ++++ |
| 35 | ++++ | ++++ | ++++ |
| 36 | ++++ | ++++ | +++ |
| 37 | ++++ | ++++ | +++ |
| 38 | ++++ | — | ++ |
| 39 | ++++ | ++++ | +++ |
| 40 | ++++ | ++++ | ++++ |
| 41 | ++++ | ++++ | ++++ |
| 42 | ++++ | — | +++ |
| 43 | ++++ | ++++ | +++ |
| 44 | ++++ | — | +++ |
| 45 | ++++ | ++++ | ++++ |
| 46 | ++++ | +++ | +++ |
| 47 | ++++ | +++ | +++ |
| 48 | ++++ | ++++ | +++ |
| 49 | ++++ | — | — |
| 50 | ++++ | ++++ | +++ |
| 51 | ++++ | — | +++ |
| 52 | ++++ | ++++ | +++ |
| 53 | ++++ | +++ | +++ |
| 54 | ++++ | ++++ | +++ |
| 55 | ++++ | ++++ | +++ |
| 56 | ++++ | — | — |
| 57 | ++++ | ++++ | +++ |
| 58 | ++++ | ++++ | ++++ |
| 59 | ++++ | ++++ | ++++ |
| 60 | ++++ | ++++ | +++ |
| 61 | ++++ | ++++ | ++++ |
| 62 | ++++ | +++ | +++ |
| 63 | ++++ | ++++ | +++ |
| 64 | ++++ | — | +++ |
| 65 | ++++ | — | — |
| 66 | ++++ | +++ | +++ |
| 67 | ++++ | +++ | +++ |
| 68 | ++++ | — | — |
| 69 | +++ | — | — |
| 70 | ++++ | ++++ | +++ |
| 71 | ++++ | ++++ | +++ |
| 72 | ++++ | — | — |
| 73 | ++++ | ++++ | ++++ |
| 74 | ++++ | +++ | +++ |
| 75 | +++ | — | — |
| 76 | ++++ | — | — |
| 77 | ++++ | +++ | +++ |
| 78 | ++++ | +++ | +++ |
| 79 | +++ | — | — |
| 80 | ++++ | +++ | ++++ |
| 81 | ++++ | ++++ | ++++ |
| 82 | ++++ | ++++ | +++ |
| 83 | ++++ | — | +++ |
| 84 | +++ | — | — |
| 85 | +++ | — | — |
| 86 | ++++ | +++ | +++ |
| 87 | +++ | — | — |

In Table 1, a "+" denotes an IC$_{50}$ value of >2000 nM;
a "++" denotes an IC$_{50}$ value of >200 nM < IC$_{50}$ ≤ 2000 nM;
a "+++" denotes an IC$_{50}$ value of 20 nM < IC$_{50}$ ≤ 200 nM; and
a "++++" denotes an IC$_{50}$ value of ≤20 nM.

Example B: Brain-to-Plasma Ratio Determination in Sprague-Dawley Rats

The brain-to-plasma ratio ($K_p$) was determined in male Sprague-Dawley rats (7-9 weeks old) four hours after a single oral dose. Rats were acclimated and given free access to standard rodent chow and water throughout the entire study. Test articles were formulated as a solution at 0.3, 0.4, 0.5, or 1.0 mg/mL in a vehicle comprised of 10:15:75 (v:v:v) dimethylacetamide (DMA):Solutol HS15:water and delivered orally at a rate of 10 mL/kg to three rats to achieve final doses of 3, 4, 5, or 10 mg/kg, respectively. At 4 hours post-dose, blood samples were collected via jugular vein cannula into tubes containing K$_2$EDTA as the anticoagulant and stored on ice. Blood samples were then centrifuged at 4° C. at 6000 rpm for 5 minutes, and the resulting plasma was placed into tubes and stored frozen at −80° C. until analysis. Whole brain samples were also collected at 4 hours post-dose. The weight of each brain was measured and recorded, and samples were immediately stored on dry ice. Brain samples were then transferred to storage at −80° C. until analysis.

Prior to analysis, brain samples were combined with water (4 mL/1 gram of brain) and homogenized. Prior to injection, plasma and brain homogenate samples and standards were prepared for analysis by precipitation with acetonitrile or 1:1 (v:v) methanol:acetonitrile. Samples were then thoroughly mixed, centrifuged at 4000 rpm for 15 minutes, and the resulting supernatant was transferred for analysis. Test article concentrations in plasma and brain homogenate were then determined by LC-MS/MS and quantified against calibration standards prepared to known concentrations in matched blank (analyte-free) biological matrix. The $K_p$ was then determined by dividing the dilution-corrected brain concentration by the plasma concentration from each rat. A brain density of 1 gram/mL was assumed for all calculations.

The results are shown in Table 14, below.

TABLE 14

$K_p$ Values

| Example | $K_p$ |
|---|---|
| 1 | ++ |
| 2 | ++ |
| 3 | +++ |
| 4 | ++ |
| 5 | n.d. |
| 6 | ++ |
| 7 | ++ |
| 12 | + |
| 14 | ++ |
| 15 | ++ |
| 16 | + |
| 18 | ++ |
| 20 | +++ |
| 24 | ++ |
| 25 | ++ |
| 26 | n.d. |
| 28 | +++ |
| 29 | ++ |
| 35 | ++ |
| 39 | ++ |
| 41 | + |
| 43 | n.d. |
| 47 | ++ |
| 48 | +++ |
| 50 | +++ |
| 55 | + |
| 59 | ++ |
| 62 | n.d. |
| 63 | +++ |
| 66 | ++ |

TABLE 14-continued

K$_p$ Values

| Example | K$_p$ |
|---|---|
| 67 | +++ |
| 71 | ++ |
| 77 | n.d. |
| 78 | ++ |
| 81 | + |
| 82 | n.d. |

In Table 14, a "+" denotes a K$_p$ value <1.0;
a "++" denotes 1.0 ≤ K$_p$ < 3.0;
a "+++" denotes K$_p$ value ≥3.0; and
n.d. denotes a brain concentration below the detectable limit.

What is claimed:

1. A compound of Formula I:

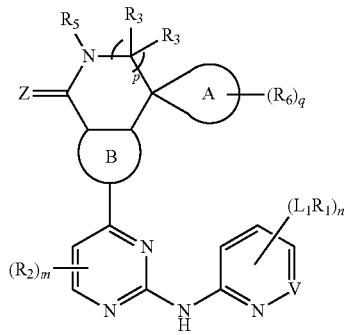

(I)

or a pharmaceutically acceptable salt, solvate, or N-oxide thereof, wherein
ring A is a 3-8-membered cycloalkyl or heterocycloalkyl ring;
ring B is a thiopheneyl group or a phenyl group, wherein ring B is optionally substituted with 1, 2 or 3 R$_4$ substituents;
Z is O, S, NR$^b$ NOR$^b$ or N—CN,
V is CL$_1$R$_1$ or N
n is 1 or 2 or 3;
m is 1 or 2;
p is 0, 1, or 2;
q is 0, 1, 2, 3, 4, 5, or 6;
each L$_1$ is independently a bond, O, —C(O), S, NR, C$_2$-C$_6$ alkylyne or C$_2$-C$_6$ alkylene, wherein R is H or C$_1$-C$_6$alkyl;
each R$_1$ is independently H, D, halogen, —OH, —CN, —NO$_2$, —C$_1$-C$_6$alkyl, C$_1$-C$_6$alkoxide, —C$_2$-C$_6$alkenyl, —C$_2$-C$_6$alkynyl, aryl, heteroaryl, cycloalkyl, cycloalkenyl, heterocycloalkyl, heterocycloalkenyl, —OR$^a$, —SR$^a$, —NR$^c$R$^d$, —NR$^a$R$^c$, —C(O)R$^b$, —OC(O)R$^b$, —C(O)OR$^b$, —C(O)NR$^c$R$^d$, —S(O)R$^b$, —S(O)$_2$NR$^c$R$^d$, —S(O)(=NR$^b$)R$^b$, —SF$_5$, —P(O)R$^b$R$^b$, —P(O)(OR$^b$)(OR$^b$), —B(OR$^c$)(OR$^d$) or —S(O)$_2$R$^b$;
each R$_2$ is independently H, D, halogen, C$_1$-C$_8$ alkoxide, C$_1$-C$_8$ alkyl, haloalkyl, or CN;
each R$_3$ is independently H, D, halogen, —OH, —CN, —NO$_2$, —C$_1$-C$_6$alkyl, —C$_2$-C$_6$alkenyl, —C$_2$-C$_6$alkynyl, C$_0$-C$_1$alk-aryl, C$_0$-C$_1$alk-heteroaryl, cycloalkyl, cycloalkenyl, heterocycloalkyl, heterocycloalkenyl, —OR$^a$, —SR$^b$, —NR$^c$R$^d$, —NR$^a$R$^c$, —C(O)R$^b$, —OC(O)R$^b$, —C(O)OR$^b$, —C(O)NR$^c$R$^d$, or —B(OR$^d$)(OR$^c$);
each R$_4$ is independently H, D, halogen, C$_1$-C$_8$ alkoxide, C$_1$-C$_8$ alkyl, haloalkyl or CN;
each R$^a$ is independently H, D, —C(O)R$^b$, —C(O)OR$^c$, —C(O)NR$^c$R$^d$, —C(=NR$^b$)NR$^b$R$^c$, —C(=NOR$^b$)NR$^b$R$^c$, —C(=NCN)NR$^b$R$^c$, —P(OR$^c$)$_2$, —P(O)OR$^c$OR$^b$, —S(O)$_2$R$^b$, —S(O)$_2$NR$^c$R$^d$, SiR$^b$$_3$, —C$_1$-C$_{10}$alkyl, —C$_2$-C$_{10}$ alkenyl, —C$_2$-C$_{10}$ alkynyl, —C$_0$-C$_1$alk-aryl, cycloalkyl, cycloalkenyl, C$_0$-C$_1$alk-heteroaryl, heterocycloalkyl, or heterocycloalkenyl;
each R$^b$, is independently H, D, —C$_1$-C$_6$ alkyl, —C$_2$-C$_6$ alkenyl, —C$_2$-C$_6$ alkynyl, C$_0$-C$_1$alk-aryl, cycloalkyl, cycloalkenyl, C$_0$-C$_1$alk-heteroaryl, heterocycloalkyl, or heterocycloalkenyl;
each R$^c$ or R$^d$ is independently H, D, —C$_1$-C$_{10}$ alkyl, —C$_2$-C$_6$ alkenyl, —C$_2$-C$_6$ alkynyl, —OC$_1$-C$_6$alkyl, —O-cycloalkyl, aryl, C$_1$alk-aryl, heteroaryl, cycloalkyl, cycloalkenyl, C$_1$alk-heteroaryl, heterocycloalkyl, or heterocycloalkenyl;
or R$^c$ or R$^d$, together with the atom to which they are both attached, form a monocyclic or multicyclic heterocycloalkyl, or a monocyclic or multicyclic heterocyclo-alkenyl group;
R$_5$ is H, D, OR$^b$, C$_{1-4}$alkyl, wherein the C$_{1-4}$alkyl may be substituted with at least one of halogen, —OH, —CN or an amine, or cycloalkyl; and
R$_6$ is independently H, D, halogen, —OH, —CN, —NO$_2$, —C$_1$-C$_6$alkyl, —C$_2$-C$_6$alkenyl, —C$_2$-C$_6$alkynyl, aryl, heteroaryl, cycloalkyl, cycloalkenyl, heterocycloalkyl, heterocycloalkenyl, —OR$^a$, —SR$^a$, —NR$^c$R$^d$, —NR$^a$R$^c$, —C(O)R$^b$, —OC(O)R$^b$, —C(O)OR$^b$, —C(O)NR$^c$R$^d$, —S(O)R$^b$, —S(O)$_2$NR$^c$R$^d$, —S(O)(=NR$^b$)R$^b$, —SF$_5$, —P(O)R$^b$R$^b$, —P(O)(OR$^b$)(OR$^b$), —B(OR$^c$)(OR$^d$) or —S(O)$_2$R$^b$.

2. The compound of claim 1, that is a compound of formula II:

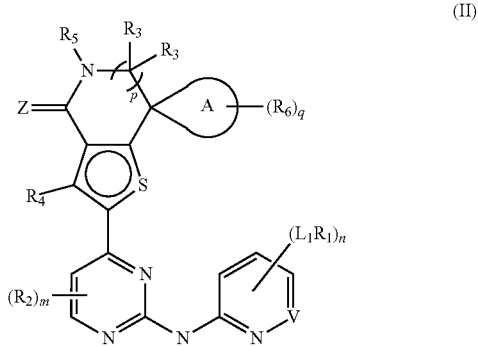

(II)

or a pharmaceutically acceptable salt, solvate, or N-oxide thereof.

3. The compound of claim 1, wherein Z is O.

4. The compound of claim 1, wherein R$_4$ is selected from the group consisting of H, Me, halogen, and haloalkyl.

5. The compound of claim 1, wherein R$_5$ is selected from the group consisting of H and C$_{1-4}$alkyl.

6. The compound of claim 1, wherein at least one R$_3$ is H or C$_{1-6}$alkyl.

7. The compound of claim 1, that is a compound of formula III:

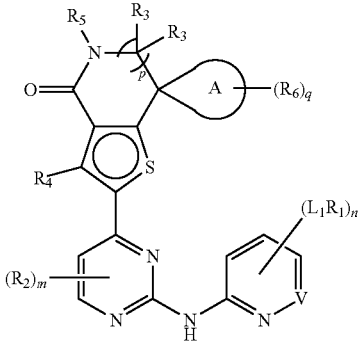
(III)

or a pharmaceutically acceptable salt, solvate, or N-oxide thereof.

8. The compound of claim 1, that is a compound of formula IV:

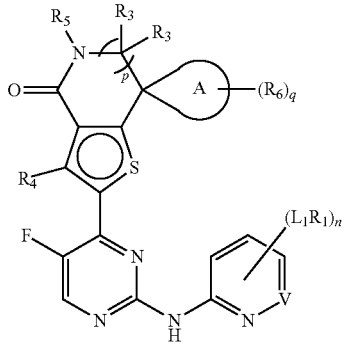
(IV)

or a pharmaceutically acceptable salt, solvate, or N-oxide thereof.

9. A compound of formula V, formula VI, formula VII, formula VIII, formula IX, formula X or formula XI:

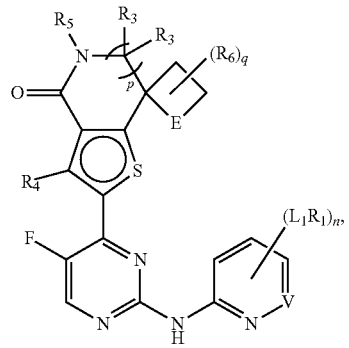
(V)

-continued

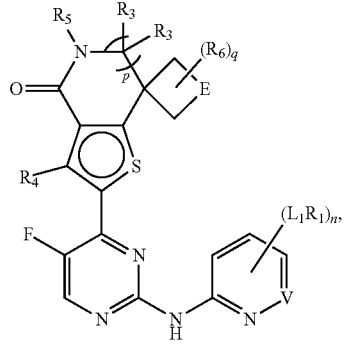
(VI)

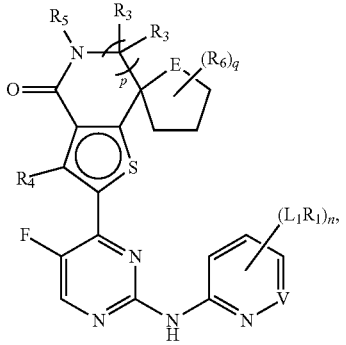
(VII)

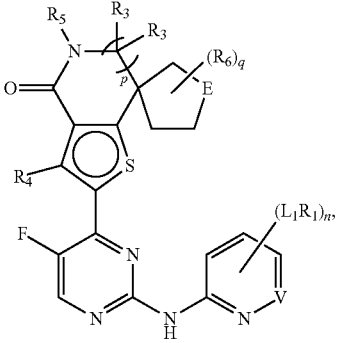
(VIII)

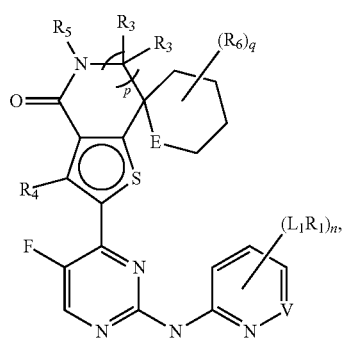
(IX)

-continued (X)

(XI)

or a pharmaceutically acceptable salt, solvate, or N-oxide thereof; wherein
V is $CL_1R_1$ or N
n is 1 or 2 or 3;
p is 0, 1, or 2;
q is 0, 1, 2, 3, 4, 5, or 6;
each $L_1$ is independently a bond, O, —C(O), S, NR, $C_2$-$C_6$ alkylyne or $C_2$-$C_6$ alkylene, wherein R is H or $C_1$-$C_6$alkyl;
each $R_1$ is independently H, D, halogen, —OH, —CN, —$NO_2$, —$C_1$-$C_6$alkyl, $C_1$-$C_6$alkoxide, —$C_2$-$C_6$alkenyl, —$C_2$-$C_6$alkynyl, aryl, heteroaryl, cycloalkyl, cycloalkenyl, heterocycloalkyl, heterocycloalkenyl, —$OR^a$, —$SR^a$, —$NR^cR^d$, —$NR^aR^c$, —$C(O)R^b$, —$OC(O)R^b$, —$C(O)OR^b$, —$C(O)NR^cR^d$, —$S(O)R^b$, —$S(O)_2NR^cR^d$, —$S(O)(=NR^b)R^b$, —$SF_5$, —$P(O)R^bR^b$, —$P(O)(OR^b)(OR^b)$, —$B(OR^c)(OR^d)$ or —$S(O)_2R^b$;
each $R_3$ is independently H, D, halogen, —OH, —CN, —$NO_2$, —$C_1$-$C_6$alkyl, —$C_2$-$C_6$alkenyl, —$C_2$-$C_6$alkenyl, $C_0$-$C_1$alk-aryl, $C_0$-$C_1$alk-heteroaryl, cycloalkyl, cycloalkenyl, heterocycloalkyl, heterocycloalkenyl, —$OR^a$, —$SR^a$, —$NR^cR^d$, —$NR^aR^c$, —$C(O)R^b$, —$OC(O)R^b$, —$C(O)OR^b$, —$C(O)NR^cR^d$, or —$B(OR^d)(OR^c)$;
$R_4$ is H, D, halogen, $C_1$-$C_8$ alkoxide, $C_1$-$C_8$ alkyl, haloalkyl or CN;
each $R^a$ is independently H, D, —$C(O)R^b$, —$C(O)OR^c$, —$C(O)NR^cR^d$, —$C(=NR^b)NR^bR^c$, —$C(=NOR^b)NR^bR^c$, —$C(=NCN)NR^bR^c$, —$P(OR^c)_2$, —$P(O)OR^cOR^b$, —$S(O)_2R^b$, —$S(O)_2NR^cR^d$, $SiR^b_3$, —$C_1$-$C_{10}$alkyl, —$C_2$-$C_{10}$ alkenyl, —$C_2$-$C_{10}$ alkynyl, —$C_0$-$C_1$alk-aryl, cycloalkyl, cycloalkenyl, $C_0$-$C_1$alk-heteroaryl, heterocycloalkyl, or heterocycloalkenyl;
each $R^b$, is independently H, D, —$C_1$-$C_6$ alkyl, —$C_2$-$C_6$ alkenyl, —$C_2$-$C_6$ alkynyl, $C_0$-$C_1$alk-aryl, cycloalkyl, cycloalkenyl, $C_0$-$C_1$alk-heteroaryl, heterocycloalkyl, or heterocycloalkenyl;

each $R^c$ or $R^d$ is independently H, D, —$C_1$-$C_{10}$ alkyl, —$C_2$-$C_6$ alkenyl, —$C_2$-$C_6$ alkynyl, —$OC_1$-$C_6$alkyl, —O-cycloalkyl, aryl, $C_1$alk-aryl, heteroaryl, cycloalkyl, cycloalkenyl, $C_1$alk-heteroaryl, heterocycloalkyl, or heterocycloalkenyl;

or $R^c$ or $R^d$, together with the atom to which they are both attached, form a monocyclic or multicyclic heterocycloalkyl, or a monocyclic or multicyclic heterocyclo-alkenyl group;

$R_5$ is H, D, $OR^b$, $C_1$-$C_4$alkyl, wherein the $C_1$-$C_4$alkyl may be substituted with at least one of halogen, —OH, —CN or an amine, or cycloalkyl;

each $R_6$ is independently H, D, halogen, —OH, —CN, —$NO_2$, —$C_1$-$C_6$alkyl, —$C_2$-$C_6$alkenyl, —$C_2$-$C_6$alkynyl, aryl, heteroaryl, cycloalkyl, cycloalkenyl, heterocycloalkyl, heterocycloalkenyl, —$OR^a$, —$SR^a$, —$NR^cR^d$, —$NR^aR^c$, —$C(O)R^b$, —$OC(O)R^b$, —$C(O)OR^b$, —$C(O)NR^cR^d$, —$S(O)R^b$, —$S(O)_2NR^cR^d$, —$S(O)(=NR^b)R^b$, —$SF_5$, —$P(O)R^bR^b$, —$P(O)(OR^b)(OR^b)$, —$B(OR^c)(OR^d)$ or —$S(O)_2R^b$; and E is a bond, —O—, —S—, $C(R^a)_2$, —(C=O)$NR^a$—, or $NR^a$.

10. A compound of formula XII, formula XIII, formula XIV, formula XV, formula XVI or formula XVII:

(XII)

(XIII)

-continued

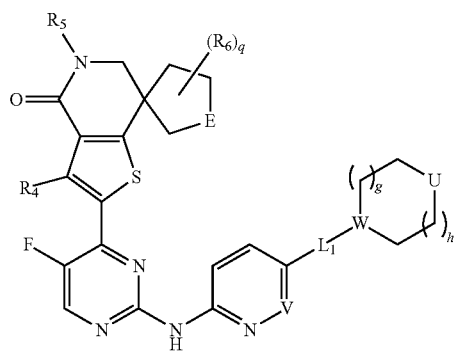
(XIV)

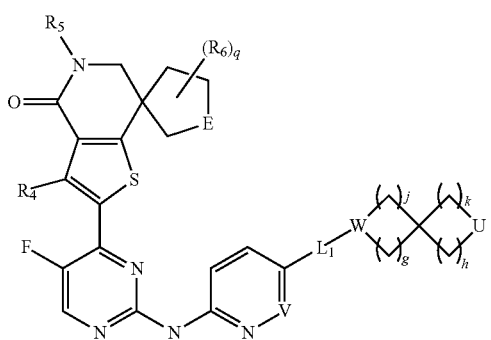
(XV)

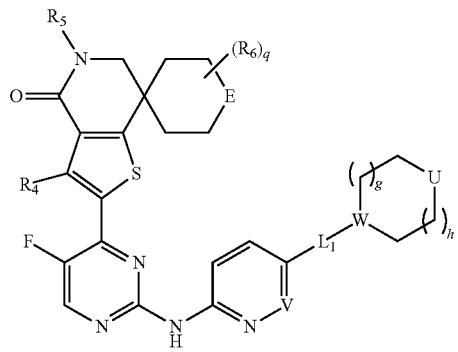
(XVI)

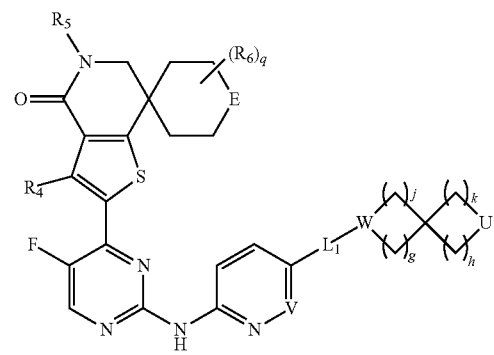
(XVII)

or a pharmaceutically acceptable salt, solvate, or N-oxide thereof; wherein
E is a bond, —O—, —S—, C(R$^a$)$_2$, —(C=O)NR$^a$—, or NR$^a$;
L$_1$ is a bond, —CH$_2$—, or C=O;
V is CR$_{11}$ or N;
W is CR$_{11}$ or N;
U is C(R$_{11}$)$_2$, NR$_{10}$, or O;

R$_{11}$ is H, D, fluoro, C$_{1-6}$alkyl, or C$_{1-6}$alkoxide;
R$_4$ is H, D, Methyl, or haloalkyl;
R$_5$ is H, D, Methyl, or haloalkyl;
R$_{10}$ is H, D, C$_{1-6}$alkyl, or haloalkyl; and
each g, h, j and k is independently 0, 1, 2 or 3;
q is 0, 1, 2, 3, 4, 5, or 6;
each R$_6$ is independently H, D, halogen, —OH, —CN, —NO$_2$, —C$_1$-C$_6$alkyl, —C$_2$-C$_6$alkenyl, —C$_2$-C$_6$alkynyl, aryl, heteroaryl, cycloalkyl, cycloalkenyl, heterocycloalkyl, heterocycloalkenyl, —OR$^a$, —SR$^a$, —NR$^c$R$^d$, —NR$^a$R$^c$, —C(O)R$^b$, —OC(O)R$^b$, —C(O)OR$^b$, —C(O)NR$^c$R$^d$, —S(O)R$^b$, —S(O)$_2$NR$^c$R$^d$, —S(O)(=NR$^b$)R$^b$, —SF$_5$, —P(O)R$^b$R$^b$, —P(O)(OR$^b$)(OR$^b$), —B(OR$^c$)(OR$^d$) or —S(O)$_2$R$^b$;

each R$^a$ is independently H, D, —C(O)R$^b$, —C(O)OR$^c$, —C(O)NR$^c$R$^d$, —C(=NR$^b$)R$^b$R$^c$, —C(=NOR$^b$)NR$^b$R$^c$, —C(=NCN)NR$^b$R$^c$, —P(OR$^c$)$_2$, —P(O)OR$^c$OR$^b$, —S(O)$_2$R$^b$, —S(O)$_2$NR$^c$R$^d$, SiR$^b$$_3$, —C$_1$-C$_{10}$alkyl, —C$_2$-C$_{10}$ alkenyl, —C$_2$-C$_{10}$ alkynyl, —C$_0$-C$_1$alk-aryl, cycloalkyl, cycloalkenyl, C$_0$-C$_1$alk-heteroaryl, heterocycloalkyl, or heterocycloalkenyl;

each R$^b$, is independently H, D, —C$_1$-C$_6$ alkyl, —C$_2$-C$_6$ alkenyl, —C$_2$-C$_6$ alkynyl, C$_0$-C$_1$alk-aryl, cycloalkyl, cycloalkenyl, C$_0$-C$_1$alk-heteroaryl, heterocycloalkyl, or heterocycloalkenyl; and each R$^c$ or R$^d$ is independently H, D, —C$_1$-C$_{10}$ alkyl, —C$_2$-C$_6$ alkenyl, —C$_2$-C$_6$ alkynyl, —OC$_1$-C$_6$alkyl, —O-cycloalkyl, aryl, C$_1$alk-aryl, heteroaryl, cycloalkyl, cycloalkenyl, C$_1$alk-heteroaryl, heterocycloalkyl, or heterocycloalkenyl;

or R$^c$ or R$^d$, together with the atom to which they are both attached, form a monocyclic or multicyclic heterocycloalkyl, or a monocyclic or multicyclic heterocyclo-alkenyl group.

11. The compound of claim 10, that is a compound of formula XVIII, formula XIX, formula XX, formula XXI, formula XXII or formula XXIII:

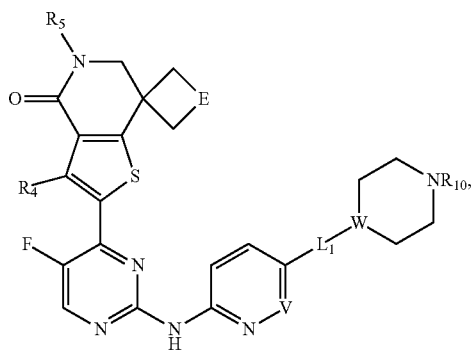
(XVIII)

or a pharmaceutically acceptable salt, solvate, or N-oxide thereof.

12. The compound of claim 1, wherein V is N or CH.

13. The compound of claim 1, wherein $L_1$ is selected from the group consisting of bond, $CH_2$, and C=O.

14. The compound of claim 1, wherein at least one $R_1$ is a group of formula Y:

(Y)

wherein

∿ is a point of attachment to $L_1$;

W is $CR_{11}$ or N;

U is $C(R_{11})_2$, $NR_{10}$, or O;

$R_{10}$ is H, D, $C_{1-6}$alkyl or haloalkyl;

$R_{11}$ is H, D, fluoro, $C_{1-6}$alkyl, or $C_{1-6}$alkoxide;

$R_{12}$ is H, D, fluoro, $C_{1-6}$alkyl, or $C_{1-6}$alkoxide;

t is 0, 1, 2, 3, 4, 5, or 6; and each g and h is independently 0, 1, 2 or 3.

15. The compound of claim 1, wherein at least one $R_1$ is a group chosen from:

-continued wherein $R_{10}$ is H or $C_{1-6}$alkyl and ⌇ is a point of attachment to $L_1$.

16. The compound of claim 1, wherein $R_1$ is a piperazine or a piperidine.

17. A compound of Formula I:

(I)

or a pharmaceutically acceptable salt, solvate, or N-oxide thereof, wherein
ring A is a 3-8-membered cycloalkyl or heterocycloalkyl ring;
ring B is a thiopheneyl group or a phenyl group, wherein ring B is optionally substituted with 1, 2 or 3 $R_4$ substituents;
Z is O, S, $NR^b$, $NOR^b$ or N—CN,
V is $CL_1R_1$ or N
n is 1 or 2 or 3;
m is 1 or 2;
p is 0, 1, or 2;
q is 0, 1, 2, 3, 4, 5, or 6;
each $L_1$ is independently a bond, O, —C(O), S, NR, $C_2$-$C_6$ alkylyne or $C_2$-$C_6$ alkylene, wherein R is H or $C_1$-$C_6$alkyl;
each $R_1$ is independently H, D, halogen, —OH, —CN, —NO$_2$, —C$_1$-C$_6$alkyl, C$_1$-C$_6$alkoxide, —C$_2$-C$_6$alkenyl, —C$_2$-C$_6$alkynyl, aryl, heteroaryl, cycloalkyl, cycloalkenyl, heterocycloalkyl, heterocycloalkenyl, —OR$^a$, —SR$^a$, —NR$^c$R$^d$, —NR$^a$R$^c$, —C(O)R$^b$, —OC(O)R$^b$, —C(O)OR$^b$, —C(O)NR$^c$R$^d$, —S(O)R$^b$, —S(O)$_2$NR$^c$R$^d$, —S(O)(=NR$^b$)R$^b$, —SF$_5$, —P(O)R$^b$R$^b$, —P(O)(OR$^b$)(OR$^b$), —B(OR$^c$)(OR$^d$) or —S(O)$_2$R$^b$;
each $R_2$ is independently H, D, halogen, $C_1$-$C_8$ alkoxide, $C_1$-$C_8$ alkyl, haloalkyl, or CN;
each $R_3$ is independently H, D, halogen, —OH, —CN, —NO$_2$, —C$_1$-C$_6$alkyl, —C$_2$-C$_6$alkenyl, —C$_2$-C$_6$alkynyl, C$_0$-C$_1$alk-aryl, C$_0$-C$_1$alk-heteroaryl, cycloalkyl, cycloalkenyl, heterocycloalkyl, heterocycloalkenyl, —OR$^a$, —SR$^b$, —NR$^c$R$^d$, —NR$^a$R$^c$, —C(O)R$^b$, —OC(O)R$^b$, —C(O)OR$^b$, —C(O)NR$^c$R$^d$, or —B(OR$^d$)(OR$^c$);
each $R_4$ is independently H, D, halogen, $C_1$-$C_8$ alkoxide, $C_1$-$C_8$ alkyl, haloalkyl or CN;
each $R^a$ is independently H, D, —C(O)R$^b$, —C(O)OR$^c$, —C(O)NR$^c$R$^d$, —C(=NR$^b$)NR$^b$R$^c$, —C(=NOR$^b$)NR$^b$R$^c$, —C(=NCN)NR$^b$R$^c$, —P(OR$^c$)$_2$, —P(O)OR$^c$OR$^b$, —S(O)$_2$R$^b$, —S(O)$_2$NR$^c$R$^d$, SiR$^b$$_3$, —C$_1$-C$_{10}$alkyl, —C$_2$-C$_{10}$ alkenyl, —C$_2$-C$_{10}$ alkynyl, —C$_0$-C$_1$alk-aryl, cycloalkyl, cycloalkenyl, C$_0$-C$_1$alk-heteroaryl, heterocycloalkyl, or heterocycloalkenyl;
each $R^b$, is independently H, D, —C$_1$-C$_6$ alkyl, —C$_2$-C$_6$ alkenyl, —C$_2$-C$_6$ alkynyl, C$_0$-C$_1$alk-aryl, cycloalkyl, cycloalkenyl, C$_0$-C$_1$alk-heteroaryl, heterocycloalkyl, or heterocycloalkenyl;
each $R^c$ or $R^d$ is independently H, D, —C$_1$-C$_{10}$ alkyl, —C$_2$-C$_6$ alkenyl, —C$_2$-C$_6$ alkynyl, —OC$_1$-C$_6$alkyl, —O-cycloalkyl, aryl, C$_1$alk-aryl, heteroaryl, cycloalkyl, cycloalkenyl, C$_1$alk-heteroaryl, heterocycloalkyl, or heterocycloalkenyl;
or $R^c$ or $R^d$, together with the atom to which they are both attached, form a monocyclic or multicyclic heterocycloalkyl, or a monocyclic or multicyclic heterocyclo-alkenyl group;
$R_5$ is H, D, OR$^b$, $C_{1-4}$alkyl, wherein the $C_{1-4}$alkyl may be substituted with at least one of halogen, —OH, —CN or an amine, or cycloalkyl; and
$R_6$ is independently H, D, halogen, —OH, —CN, —NO$_2$, —C$_1$-C$_6$alkyl, —C$_2$-C$_6$alkenyl, —C$_2$-C$_6$alkynyl, aryl, heteroaryl, cycloalkyl, cycloalkenyl, heterocycloalkyl, heterocycloalkenyl, —OR$^a$, —SR$^a$, —NR$^c$R$^d$, —NR$^a$R$^c$, —C(O)R$^b$, —OC(O)R$^b$, —C(O)OR$^b$, —C(O)NR$^c$R$^d$, —S(O)R$^b$, —S(O)$_2$NR$^c$R$^d$, —S(O)(=NR$^b$)R$^b$, —SF$_5$, —P(O)R$^b$R$^b$, —P(O)(OR$^b$)(OR$^b$), —B(OR$^c$)(OR$^d$) or —S(O)$_2$R$^b$;
wherein at least one $R_1$ is a group of formula Z:

(Z)

wherein
⌇ is a point of attachment to $L_1$;
W is CH or N;
U is C($R_{11}$)$_2$, NR$_{10}$, or O;
$R_{10}$ is H, D, $C_{1-6}$alkyl or haloalkyl;
$R_{11}$ is H, D, fluoro, $C_{1-6}$alkyl, or $C_{1-6}$alkoxide;
$R_{12}$ is H, D, fluoro, $C_{1-6}$alkyl, or $C_{1-6}$alkoxide;
t is 0, 1, 2, 3, 4, 5, or 6; and
each g, h, j and k is independently 0, 1, 2 or 3.

18. The compound of claim 17, wherein at least one $R_1$ is a group chosen from:

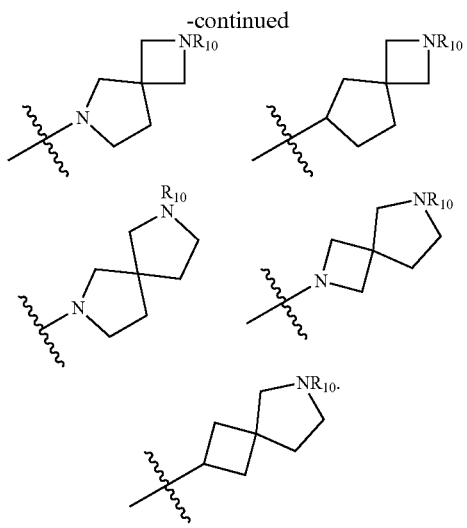

19. A compound that is:
2'-(2-((5-(6-Ethyl-2,6-diazaspiro[3.3]heptan-2-yl)pyridin-2-yl)amino)-5-fluoropyrimidin-4-yl)-5'-methyl-5',6'-dihydro-4'H-spiro[cyclopentane-1,7'-thieno[3,2-c]pyridin]-4'-one;
2'-(5-Fluoro-2-((5-(1-methylpiperidin-4-yl)pyridin-2-yl)amino)pyrimidin-4-yl)-5'-methyl-5',6'-dihydro-4'H-spiro[cyclopentane-1,7'-thieno[3,2-c]pyridin]-4'-one;
2'-(2-((5-(4-Ethylpiperazin-1-yl)pyridin-2-yl)amino)-5-fluoropyrimidin-4-yl)-5'-methyl-5',6'-dihydro-4'H-spiro[cyclopentane-1,7'-thieno[3,2-c]pyridin]-4'-one;
2'-(2-((5-(6-Ethyl-2,6-diazaspiro[3.3]heptan-2-yl)pyridin-2-yl)amino)-5-fluoropyrimidin-4-yl)-5'-methyl-5',6'-dihydro-4'H-spiro[cyclohexane-1,7'-thieno[3,2-c]pyridin]-4'-one 2'-(5-Fluoro-2-((5-(1-methylpiperidin-4-yl)pyridin-2-yl)amino)pyrimidin-4-yl)-5'-methyl-5',6'-dihydro-4'H-spiro[cyclohexane-1,7'-thieno[3,2-c]pyridin]-4'-one;

or a pharmaceutically acceptable salt thereof.

20. A compound that is:
2'-(5-Fluoro-2-((5-(1-methylpiperidin-4-yl)pyridin-2-yl)amino) pyrimidin-4-yl)-3',5'-dimethylspiro[cyclopropane-1,6'-thieno[2,3-c]pyrrol]-4'(5'H)-one;
5'-Ethyl-2'-(5-fluoro-2-((5-(1-methylpiperidin-4-yl)pyridin-2-yl)amino) pyrimidin-4-yl)-3'-methylspiro[cyclopropane-1,6'-thieno[2,3-c]pyrrol]-4'(5'H)-one;
2'-(5-Fluoro-2-((5-(1-methylpiperidin-4-yl)pyridin-2-yl)amino) pyrimidin-4-yl)-5'-methyl-spiro[cyclopropane-1,6'-thieno[2,3-c]pyrrol]-4'(5'H)-one;
3'-chloro-2'-(5-Fluoro-2-((5-(1-methylpiperidin-4-yl) pyridin-2-yl) amino)pyrimidin-4-yl)-5'-methylspiro [cyclopropane-1,6'-thieno[2,3-c]pyrrol]-4'(5'H)-one;
2'-(5-Fluoro-2-((5-(1-methyl-piperidin-4-yl)pyridin-2-yl) amino) pyrimidin-4-yl)-5'-methyl-3'-(trifluoromethyl) spiro [cyclopropane-1,6'-thieno[2,3-c] pyrrol]-4'(5'H)-one;
2'-(5-Chloro-2-((5-(1-methyl-piperidin-4-yl)pyridin-2-yl) amino) pyrimidin-4-yl)-5'-ethyl-3'-methylspiro[cyclopropane-1,6'-thieno[2,3-c]pyrrol]-4'(5'H)-one;
2'-(2-((5-(6-Ethyl-2,6-diazaspiro[3.3]heptan-2-yl)pyridin-2-yl)amino)-5-fluoropyrimidin-4-yl)-3',5'-dimethylspiro [cyclopropane-1,6'-thieno [2,3-c]pyrrol]-4'(5'H)-one;
2'-(2-((5-((4-Ethylpiperazin-1-yl)methyl)pyridin-2-yl) amino)-5-fluoro-pyrimidin-4-yl)-3',5'-dimethylspiro [cyclopropane-1,6'-thieno[2,3-c] pyrrol]-4'(5'H)-one;
2'-(5-Fluoro-2-((5-(6-methyl-2,6-diazaspiro[3.4]octan-2-yl)pyridin-2-yl)amino)pyrimidin-4-yl)-3',5'-dimethyl-spiro[cyclopropane-1,6'-thieno [2,3-c]pyrrol]-4'(5'H)-one;
2'-(5-Fluoro-2-((5-(1-methylpiperidin-3-yl)pyridin-2-yl) amino) pyrimidin-4-yl)-3',5'-dimethylspiro[cyclopropane-1,6'-thieno[2,3-c] pyrrol]-4'(5'H)-one;
2'-(5-Fluoro-2-((5-(1-isopropylpyrrolidin-3-yl)pyridin-2-yl)amino) pyrimidin-4-yl)-3',5'-dimethylspiro[cyclopropane-1,6'-thieno[2,3-c] pyrrol]-4'(5'H)-one;
5'-Ethyl-2'-(5-methyl-2-((5-((3aR,6aS)-5-methylhexahydropyrrolo[3,4-c]pyrrol-2(1H)-yl)pyridin-2-yl)amino) pyrimidin-4-yl)spiro [cyclopropane-1,6'-thieno[2,3-c] pyrrol]-4'(5'H)-one;
5'-Ethyl-2'-[5-methyl-2-[[5-(1-methylpiperidin-3-yl)pyridin-2-yl] amino]pyrimidin-4-yl]spiro[cyclopropane-1,6'-thieno[2,3-c]pyrrole]-4'-one;
5'-Ethyl-2'-[5-methyl-2-[[5-(1-methylpiperidin-4-yl)pyridin-2-yl] amino]pyrimidin-4-yl]spiro[cyclopropane-1,6'-thieno[2,3-c]pyrrole]-4'-one;
2'-(5-Fluoro-2-((5-(1-methylpiperidin-4-yl)pyridin-2-yl) amino) pyrimidin-4-yl)-5'-methyl-spiro[cyclopentane-1,6'-thieno[2,3-c]pyrrol]-4'(5'H)-one;
5'-Ethyl-2'-(2-((5-(6-ethyl-2,6-diazaspiro[3.3]heptan-2-yl)pyridin-2-yl)amino)-5-fluoro-pyrimidin-4-yl)spiro [cyclopentane-1,6'-thieno[2,3-c]pyrrol]-4'(5'H)-one;
5'-Ethyl-2'-(5-fluoro-2-((5-(1-methylpiperidin-4-yl)pyridin-2-yl)amino) pyrimidin-4-yl)spiro [cyclopentane-1,6'-thieno[2,3-c]pyrrol]-4'(5'H)-one;
2'-(2-((5-(1-Ethylpiperidin-4-yl)pyridin-2-yl)amino)-5-fluoro-pyrimidin-4-yl)-5'-methylspiro [cyclopentane-1,6'-thieno[2,3-c]pyrrol]-4'(5'H)-one;
2'-(2-((5-(6-Ethyl-2,6-diazaspiro [3.3]heptan-2-yl)pyridin-2-yl)amino)-5-fluoropyrimidin-4-yl)-5'-methyl-spiro[cyclopentane-1,6'-thieno[2,3-c]pyrrol]-4'(5'H)-one;
2'-(5-Fluoro-2-((5-(1-methylpiperidin-4-yl)pyridin-2-yl) amino) pyrimidin-4-yl)-3',5'-dimethylspiro[cyclopentane-1,6'-thieno[2,3-c]pyrrol]-4'(5'H)-one;
2'-(5-Fluoro-2-((5-(1-methylpiperidin-4-yl)pyridin-2-yl) amino) pyrimidin-4-yl)-5'-methyl-3'-(trifluoromethyl) spiro [cyclopentane-1,6'-thieno[2,3-c]pyrrol]-4'(5'H)-one;
3'-Chloro-2'-(5-fluoro-2-((5-(1-methylpiperidin-4-yl) pyridin-2-yl)amino)pyrimidin-4-yl)-5'-methylspiro[cyclopentane-1,6'-thieno[2,3-c]pyrrol]-4'(5'H)-one;
2'-(5-Fluoro-2-((5-(1-methylpiperidin-4-yl)pyridin-2-yl) amino) pyrimidin-4-yl)-3',5'-dimethyl-5',6'-dihydro-4'H-spiro[cyclopropane-1,7'-thieno[3,2-c]pyridin]-4'-one;
2'-(5-Fluoro-2-((5-(1-methyl-piperidin-4-yl)pyridin-2-yl) amino) pyrimidin-4-yl)-5'-methyl-5',6'-dihydro-4'H-spiro[cyclo-propane-1,7'-thieno[3,2-c]pyridin]-4'-one;
2'-(5-Fluoro-2-((5-(1-methyl-piperidin-3-yl)pyridin-2-yl) amino) pyrimidin-4-yl)-3',5'-dimethyl-5',6'-dihydro-4'H-spiro [cyclopropane-1,7'-thieno[3,2-c] pyridin]-4'-one;
2'-(2-((5-(1-Ethylpyrrolidin-3-yl)pyridin-2-yl)amino)-5-fluoro-pyrimidin-4-yl)-5'-methyl-5',6'-dihydro-4'H-spiro[cyclo-propane-1,7'-thieno[3,2-c]pyridin]-4'-one;
2'-(5-Fluoro-2-((5-(1-(tetrahydrofuran-3-yl)piperidin-4-yl)pyridin-2-yl)amino)pyrimidin-4-yl)-3',5'-dimethyl-5',6'-dihydro-4'H-spiro [cyclopropane-1,7'-thieno[3,2-c]pyridin]-4'-one;
2'-(5-Fluoro-2-((5-(6-methyl-3,6-diazabicyclo[3.1.1]heptan-3-yl) pyridin-2-yl)amino) pyrimidin-4-yl)-3', 5'-dimethyl-5',6'-dihydro-4'H-spiro[cyclopropane-1,7'-thieno[3,2-c]pyridin]-4'-one;

2'-(5-Fluoro-2-((5-(6-isopropyl-2,6-diazaspiro[3.3]heptan-2-yl)pyridin-2-yl)amino) pyrimidin-4-yl)-3',5'-dimethyl-5',6'-dihydro-4'H-spiro [cyclopropane-1,7'-thieno[3,2-c]pyridin]-4'-one;

2'-(5-Fluoro-2-((5-(6-methyl-2,6-diazaspiro[3.4]octan-2-yl)pyridin-2-yl)amino)pyrimidin-4-yl)-3',5'-dimethyl-5',6'-dihydro-4'H-spiro [cyclopropane-1,7'-thieno[3,2-c]pyridin]-4'-one;

2'-(5-Fluoro-2-((5-(2-methyl-2,7-diazaspiro[3.5]nonan-7-yl)pyridin-2-yl)amino)pyrimidin-4-yl)-3',5'-dimethyl-5',6'-dihydro-4'H-spiro [cyclopropane-1,7'-thieno[3,2-c]pyridin]-4'-one;

2'-(5-Fluoro-2-((5-(7-methyl-2,7-diazaspiro[4.4]nonan-2-yl)pyridin-2-yl)amino)pyrimidin-4-yl)-3',5'-dimethyl-5',6'-dihydro-4'H-spiro [cyclopropane-1,7'-thieno[3,2-c]pyridin]-4'-one;

2'-(2-((5-((4-Ethylpiperazin-1-yl)methyl)pyridin-2-yl) amino)-5-fluoropyrimidin-4-yl)-3',5'-dimethyl-5',6'-dihydro-4'H-spiro [cyclopropane-1,7'-thieno[3,2-c]pyridin]-4'-one;

2'-(2-((5-((3aS,6aS)-5-Ethylhexahydropyrrolo[3,4-c]pyrrol-2(1H)-yl)pyridin-2-yl)amino)-5-fluoropyrimidin-4-yl)-3',5'-dimethyl-5',6'-dihydro-4'H-spiro[cyclopropane-1,7'-thieno[3,2-c] pyridin]-4'-one;

5-Methyl-2-[4-[[5-(1-methylpiperidin-4-yl)pyridin-2-yl] amino]-5-(trifluoromethyl) pyrimidin-2-yl]spiro[6H-thieno[3,2-c]pyridine-7,1'-cyclopropane]-4-one;

2-[2-[[5-(6-Ethyl-2,6-diazaspiro[3.3]heptan-2-yl)pyridin-2-yl]amino]-5-methylpyrimidin-4-yl]-5-methylspiro [6H-thieno[3,2-c]pyridine-7,1'-cyclopropane]-4-one;

2-[2-[[5-(6-Ethyl-2,6-diazaspiro[3.3]heptan-2-yl)pyridin-2-yl]amino]-5-methylpyrimidin-4-yl]-3,5-dimethyl-spiro[6H-thieno [3,2-c]pyridine-7,1'-cyclopropane]-4-one;

5-methyl-2-[5-Methyl-2-[[5-(2-methyl-2,7-diazaspiro [3.5]nonan-7-yl)pyridin-2-yl]amino] pyrimidin-4-yl] spiro[6H-thieno[3,2-c]pyridine-7,1'-cyclopropane]-4-one;

2-[5-Chloro-2-[[5-(6-ethyl-2,6-diazaspiro[3.3]heptan-2-yl)pyridin-2-yl]amino]pyrimidin-4-yl]-3,5-dimethylspiro[6H-thieno[3,2-c]pyridine-7,1'-cyclopropane]-4-one;

2-[5-Chloro-2-[[5-(6-ethyl-2,6-diazaspiro[3.3]heptan-2-yl)pyridin-2-yl]amino]pyrimidin-4-yl]-5-methylspiro [6H-thieno[3,2-c]pyridine-7,1'-cyclopropane]-4-one;

2'-(5-Fluoro-2-((5-(6-methyl-3,6-diazabicyclo[3.1.1]heptan-3-yl) pyridin-2-yl)amino) pyrimidin-4-yl)-5'-methyl-5',6'-dihydro-4'H-spiro[cyclobutane-1,7'-thieno [3,2-c]pyridin]-4'-one;

2'-(5-Fluoro-2-((5-(1-methyl-piperidin-4-yl)pyridin-2-yl) amino) pyrimidin-4-yl)-5'-methyl-5',6'-dihydro-4'H-spiro[cyclobutane-1,7'-thieno[3,2-c]pyridin]-4'-one;

2'-(5-Fluoro-2-((5-(1-methyl-piperidin-4-yl)pyridin-2-yl) amino) pyrimidin-4-yl)-3',5'-dimethyl-5',6'-dihydro-4'H-spiro[cyclobutane-1,7'-thieno[3,2-c]pyridin]-4'-one;

2'-(2-((5-(1-(2,2-difluoroethyl) piperidin-4-yl)pyridin-2-yl)amino)-5-fluoropyrimidin-4-yl)-5'-methyl-5',6'-dihydro-4'H-spiro[cyclobutane-1,7'-thieno[3,2-c]pyridin]-4'-one;

2'-(5-Fluoro-2-((5-(4-methyl-piperazin-1-yl)pyridin-2-yl) amino) pyrimidin-4-yl)-5'-methyl-5',6'-dihydro-4'H-spiro[cyclobutane-1,7'-thieno[3,2-c]pyridin]-4'-one;

2'-(2-((5-(1-Ethyl-1,6-diazaspiro [3.3]heptan-6-yl)pyridin-2-yl) amino)-5-fluoropyrimidin-4-yl)-5'-methyl-5',6'-dihydro-4'H-spiro [cyclobutane-1,7'-thieno[3,2-c] pyridin]-4'-one;

2'-(2-((5-(6-Ethyl-2,6-diazaspiro [3.3]heptan-2-yl)pyridin-2-yl) amino)-5-fluoropyrimidin-4-yl)-3',5'-dimethyl-5',6'-dihydro-4'H-spiro[cyclobutane-1,7'-thieno [3,2-c]pyridin]-4'-one;

2'-(2-((5-(1,4-diazabicyclo [3.2.2]nonan-4-yl)pyridin-2-yl)amino)-5-fluoropyrimidin-4-yl)-5'-methyl-5',6'-dihydro-4'H-spiro [cyclobutane-1,7'-thieno[3,2-c] pyridin]-4'-one;

2'-(5-Fluoro-2-((5-(6-methyl-2,6-diazaspiro[3.4]octan-2-yl)pyridin-2-yl)amino)pyrimidin-4-yl)-3',5'-dimethyl-5',6'-dihydro-4'H-spiro [cyclobutane-1,7'-thieno[3,2-c] pyridin]-4'-one;

2'-(5-Fluoro-2-((5-(7-methyl-2,7-diazaspiro[4.4]nonan-2-yl)pyridin-2-yl)amino)pyrimidin-4-yl)-3',5'-dimethyl-5',6'-dihydro-4'H-spiro [cyclobutane-1,7'-thieno[3,2-c] pyridin]-4'-one;

2'-(2-((5-((4-Ethylpiperazin-1-yl)methyl)pyridin-2-yl) amino)-5-fluoropyrimidin-4-yl)-3',5'-dimethyl-5',6'-dihydro-4'H-spiro [cyclobutane-1,7'-thieno[3,2-c]pyridin]-4'-one;

2'-(5-Fluoro-2-((5-((3aR,6aS)-5-methylhexahydropyrrolo [3,4-c]pyrrol-2(1H)-yl)pyridin-2-yl)amino)pyrimidin-4-yl)-3',5'-dimethyl-5',6'-dihydro-4'H-spiro[cyclobutane-1,7'-thieno[3,2-c]pyridin]-4'-one;

5-Methyl-2-[4-[[5-(1-methylpiperidin-4-yl)pyridin-2-yl] amino]-5-(trifluoromethyl) pyrimidin-2-yl]spiro[6H-thieno[3,2-c]pyridine-7,1'-cyclobutane]-4-one;

5-Methyl-2-[5-methyl-2-[[5-(1-methylpiperidin-4-yl) pyridin-2-yl] amino]pyrimidin-4-yl]spiro[6H-thieno[3,2-c]pyridine-7,1'-cyclobutane]-4-one;

2-[5-Chloro-2-[[5-(1-methyl-piperidin-4-yl)pyridin-2-yl] amino] pyrimidin-4-yl]-3,5-dimethylspiro [6H-thieno[3,2-c]pyridine-7,1'-cyclobutane]-4-one;

2'-(5-Fluoro-2-((5-(6-(methyl-d3)-2,6-diazaspiro[3.3] heptan-2-yl) pyridin-2-yl)amino) pyrimidin-4-yl)-5'-(methyl-d3)-5',6'-dihydro-4'H-spiro[cyclopentane-1,7'-thieno[3,2-c]pyridin]-4'-one;

2'-(5-Fluoro-2-((5-morpholino-pyridin-2-yl)amino)pyrimidin-4-yl)-5'-methyl-5',6'-dihydro-4'H-spiro [cyclopentane-1,7'-thieno[3,2-c] pyridin]-4'-one;

2'-(5-Fluoro-2-((5-(1-methyl-piperidin-4-yl)pyridin-2-yl) amino) pyrimidin-4-yl)-3',5'-dimethyl-5',6'-dihydro-4'H-spiro [cyclopentane-1,7'-thieno[3,2-c] pyridin]-4'-one;

2-[2-[[5-(1,4-diazabicyclo [3.2.2]nonan-4-yl)pyridin-2-yl] amino]-5-fluoropyrimidin-4-yl]-5-methylspiro[6H-thieno[3,2-c] pyridine-7,1'-cyclopentane]-4-one;

2-[5-Fluoro-2-[[5-[4-methyl-2-(trifluoromethyl)piperazin-1-yl]pyridin-2-yl]amino]pyrimidin-4-yl]-5-methylspiro[6H-thieno[3,2-c]pyridine-7,1'-cyclopentane]-4-one;

2'-[5-Fluoro-2-[[5-(1-methylpiperidin-4-yl)pyridin-2-yl] amino] pyrimidin-4-yl]-3'-methyl-5'-(trideuteriomethyl)spiro[cyclopropane-1,6'-thieno[2,3-c]pyrrole]-4'-one;

2'-[2-[[5-(1-Ethylpyrrolidin-3-yl)pyridin-2-yl]amino]-5-fluoropyrimidin-4-yl]-3',5'-dimethylspiro[cyclopropane-1,6'-thieno [2,3-c]pyrrole]-4'-one;

(E)-2'-(2-((5-(1-(But-2-en-1-yl)pyrrolidin-3-yl)pyridin-2-yl)amino)-5-fluoropyrimidin-4-yl)-3',5'-dimethylspiro [cyclopropane-1,6'-thieno [2,3-c]pyrrol]-4'(5'H)-one;

2-[5-Fluoro-2-[[5-(1-methylpiperidin-4-yl)pyridin-2-yl]amino] pyrimidin-4-yl]-3-methyl-spiro[5H-thieno[2,3-c]pyrrole-6,1'-cyclopropane]-4-one;

5'-Ethyl-2'-(2-((5-(6-ethyl-2,6-diazaspiro[3.3]heptan-2-yl)pyridin-2-yl)amino)-5-fluoropyrimidin-4-yl)-5',6'-dihydro-4'H-spiro [cyclohexane-1,7'-thieno[3,2-c]pyridin]-4'-one;

2'''-(2-((5-(6-Ethyl-2,6-diazaspiro[3.3]heptan-2-yl)pyridin-2-yl)amino)-5-fluoropyrimidin-4-yl)-5''-methyl-5'',6''-dihydro-4''H-dispiro [cyclopropane-1,1'-cyclobutane-3',7''-thieno[3,2-c]pyridin]-4''-one;

2'-(5-Fluoro-2-((5-(1-methylpiperidin-4-yl)pyridin-2-yl)amino) pyrimidin-4-yl)-5'-methyl-2,3,5,5',6,6'-hexahydro-4'H-spiro[pyran-4,7'-thieno[3,2-c]pyridin]-4'-one;

5'-Methyl-2'-(5-methyl-2-((5-(1-methylpiperidin-4-yl)pyridin-2-yl) amino)pyrimidin-4-yl)spiro[cyclopropane-1,6'-thieno[2,3-c]pyrrol]-4'(5'H)-one;

2'-(2-((5-(2-Ethyl-2-azaspiro[3.3]heptan-6-yl)pyridin-2-yl)amino)-5-fluoropyrimidin-4-yl)-3',5'-dimethylspiro [cyclopropane-1,6'-thieno [2,3-c]pyrrol]-4'(5'H)-one;

2-[2-[[6-(6-Ethyl-2,6-diazaspiro[3.3]heptan-2-yl) pyridazin-3-yl]amino]-5-fluoropyrimidin-4-yl]-5-methylspiro[6H-thieno[3,2-c]pyridine-7,1'-cyclopentane]-4-one;

2'-(5-Fluoro-2-((6-(1-isopropylpiperidin-4-yl)pyridazin-3-yl)amino) pyrimidin-4-yl)-3',5'-dimethyl-5',6'-dihydro-4'H-spiro[cyclopropane-1,7'-thieno[3,2-c]pyridin]-4'-one;

3,3-Difluoro-2'-(5-fluoro-2-((5-(1-methylpiperidin-4-yl) pyridin-2-yl)amino) pyrimidin-4-yl)-5'-methyl-5',6'-dihydro-4'H-spiro [cyclobutane-1,7'-thieno[3,2-c]pyridin]-4'-one;

2'-(2-((5-(6-Ethyl-2,6-diazaspiro[3.3]heptan-2-yl)pyridin-2-yl)amino)-5-fluoropyrimidin-4-yl)-3,3-difluoro-5'-methyl-5',6'-dihydro-4'H-spiro[cyclobutane-1,7'-thieno[3,2-c]pyridin]-4'-one 2-[2-[[5-(4-Ethyl-2-oxopiperazin-1-yl)pyridin-2-yl]amino]-5-fluoropyrimidin-4-yl]-5-methylspiro[6H-thieno[3,2-c] pyridine-7,1'-cyclopentane]-4-one;

2-[5-Fluoro-2-[[6-(1-methylpiperidin-4-yl)pyridazin-3-yl]amino] pyrimidin-4-yl]-5-methylspiro[6H-thieno[3,2-c]pyridine-7,1'-cyclopentane]-4-one; or a pharmaceutically acceptable salt thereof.

21. The compound of claim 1 in the form of a pharmaceutically acceptable salt.

22. A pharmaceutical composition comprising a compound according to claim 1, or a pharmaceutically acceptable salt thereof, and a pharmaceutically acceptable excipient.

23. A method of inhibiting CDK4 and CDK6 comprising administering to a patient a compound according to claim 1, or a pharmaceutically acceptable salt thereof, or a pharmaceutical composition comprising the compound according to claim 1 or a pharmaceutically acceptable salt thereof, and a pharmaceutically acceptable excipient.

24. A method for treating cancer in a patient in need thereof, comprising administering to said patient a compound according to claim 1, or a pharmaceutically acceptable salt thereof, or a pharmaceutical composition comprising the compound according to claim 1 or a pharmaceutically acceptable salt thereof, and a pharmaceutically acceptable excipient.

25. The method according to claim 24, wherein the CDK4-mediated and CDK6-mediated disorder is a cancer; optionally wherein the cancer is breast cancer, malignant brain tumors, colon cancer, small-cell lung cancer, non-small-cell lung cancer, bladder cancer, ovarian cancer, prostate cancer, chronic lymphoid leukemia, lymphoma, myeloma, acute myeloid leukemia, secondary pancreatic cancer or secondary brain metastases; and optionally wherein the breast cancer is HR+/HER2− or HR+/HER2+ advanced or metastatic breast cancer; and the malignant brain tumors are glioblastoma, astrocytoma, or pontine glioma.

26. The method according to claim 24, wherein the patient is administered a pharmaceutical composition of claim 22; optionally wherein the administration is oral administration.

27. The method according to claim 24, further comprising administering an additional therapeutic agent to the patient; optionally wherein the additional therapeutic agent is a PRMT5 inhibitor, a HER2 kinase inhibitor, an aromatase inhibitor, an estrogen receptor antagonist or an alkylating agent; and optionally wherein the aromatase inhibitor is letrozole; optionally wherein estrogen receptor antagonist is fulvestrant; optionally wherein the alkylating agent is temozolomide.

28. The compound of claim 1 that is:

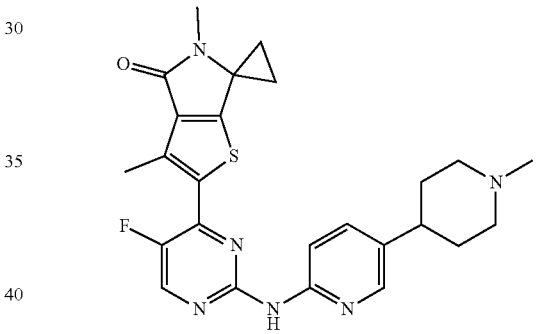

or a pharmaceutically acceptable salt thereof.

29. The compound of claim 28 that is:

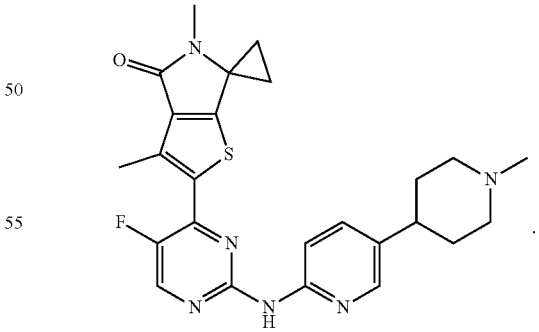

* * * * *